(12) United States Patent
Jacobsen et al.

(10) Patent No.: US 9,505,765 B2
(45) Date of Patent: Nov. 29, 2016

(54) 4-ALKOXY/ARALKOXY-5-SUBSTITUTED-PYRROLOPYRIMIDINE COMPOUNDS AS TAK1 INHIBITORS IN DISEASE TREATMENT

(71) Applicant: Confluence Life Sciences Inc., St. Louis, MO (US)

(72) Inventors: Eric Jonathan Jacobsen, Chesterfield, MO (US); John Robert Springer, Wentzville, MO (US); James Robert Blinn, O'Fallon, MO (US); Balekudru Devadas, Chesterfield, MO (US)

(73) Assignee: CONFLUENCE LIFE SCIENCES INC., St. Louis, MO (US)

( * ) Notice: Subject to any disclaimer, the term of this patent is extended or adjusted under 35 U.S.C. 154(b) by 0 days.

(21) Appl. No.: 14/417,518

(22) PCT Filed: Jul. 26, 2013

(86) PCT No.: PCT/US2013/052326
§ 371 (c)(1),
(2) Date: Jan. 26, 2015

(87) PCT Pub. No.: WO2014/018888
PCT Pub. Date: Jan. 30, 2014

(65) Prior Publication Data
US 2015/0203499 A1 Jul. 23, 2015

Related U.S. Application Data

(60) Provisional application No. 61/676,240, filed on Jul. 26, 2012.

(51) Int. Cl.
| | | |
|---|---|---|
| C07D 487/04 | (2006.01) | |
| A61K 31/519 | (2006.01) | |
| A61K 45/06 | (2006.01) | |
| A61K 31/53 | (2006.01) | |
| A61P 35/00 | (2006.01) | |

(52) U.S. Cl.
CPC ........... C07D 487/04 (2013.01); A61K 31/519 (2013.01); A61K 31/53 (2013.01); A61K 45/06 (2013.01)

(58) Field of Classification Search
CPC .......................... C07D 487/04; A61K 31/519
See application file for complete search history.

(56) References Cited

U.S. PATENT DOCUMENTS

| | | | | |
|---|---|---|---|---|
| 5,663,346 A | 9/1997 | Buzzetti et al. | ............... | 546/113 |
| 5,760,068 A | 6/1998 | Talley et al. | .................. | 514/403 |
| 8,143,237 B2 | 3/2012 | Gokaraju et al. | ............. | 514/151 |
| 2005/0009703 A1* | 1/2005 | Wachendorff-Neumann | ............... | A01N 37/50 504/138 |
| 2005/0239806 A1 | 10/2005 | Mehta et al. | ............... | 514/260.1 |
| 2009/0286782 A1 | 11/2009 | Ibrahim et al. | ............. | 514/234.2 |
| 2011/0152258 A1 | 6/2011 | Ibrahim et al. | ............. | 514/234.2 |

FOREIGN PATENT DOCUMENTS

| | | | | |
|---|---|---|---|---|
| WO | WO 2010/003133 | 1/2010 | ........... | A61K 31/437 |
| WO | WO 2010/129053 | 11/2010 | ........... | C07D 473/16 |
| WO | WO 2011/063159 | 5/2011 | ............. | A01N 43/90 |
| WO | WO 2011/133637 | 10/2011 | ........... | C07D 471/04 |

OTHER PUBLICATIONS

Carie, et al. (2011) "IT-141, a polymer micelle encapsulating SN-38, induces tumor regression in multiple colorectal cancer models." *J. Drug Delivery* 2011, Article ID 869027, 9 pages.
Ebenreth, et al. (1992) "Neue pyrrolderivate." *Pharmazie*, 47(8):571-3.
Eda, et al. (2011) "Interleukin-1β-induced interleukin-6 production in A549 cells is mediated by both phosphatidylinositol 3-kinase and interleukin-1 receptor-associated kinases-4." *Cell Biol. Int.*, 35:355-358.
Hida, et al. (2000) "Cyclooxygense-2 inhibitor induces apoptosis and enhances cytotoxicity of various anticancer agents in non-small cell lung cancer cell lines[1]." *Clin. Cancer Res.*, 6:2006-2011.
Kiguchi, et al. (2007) "Therapeutic effect of CS-706, a specific cyclooxygenase-2 inhibitor, on gallbladder carcinoma in BK5.ErbB-2 mice." *Mol. Cancer Ther*, 6(6):1709-1717.
Melisi, et al. (2011) "Modulation of pancreatic cancer chemoresistance by inhibition of TAK1." *J. Natl. Cancer Inst.*, 103(15):1190-1204.
Park, et al. (2010) "Suppression of A549 lung cancer cell migration by precursor let-7g microRNA." *Molecular Medicine Reports*, 3:1007-1013.
Rao, et al. (2006) "Nitric oxide-releasing aspirin and indomethacin are potent inhibitors against colon cancer in azoxymethane-treated rats: effects on molecular targets." *Mol. Cancer Ther.*, 5(6):1530-1538.

(Continued)

*Primary Examiner* — Susanna Moore
(74) *Attorney, Agent, or Firm* — Harness, Dickey & Pierce, P.L.C.

(57) ABSTRACT

4-alkoxy/aralkoxy-5-substituted-pyrrolopyrimidine compounds, pharmaceutically acceptable salts, solvates and pharmaceutical compositions of compounds embraced by Formula (I), provide a therapeutic benefit to subjects with disease conditions, especially cancer, wherein $R^1$ and $R^2$ are as defined in the detailed description.

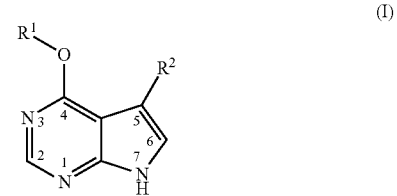

(I)

24 Claims, No Drawings

(56) References Cited

OTHER PUBLICATIONS

Vo, G.D. and Hartwig, J.F. (2009) "Palladium-catalyzed coupling of ammonia with aryl chlorides bromides, Iodides and sulfonates: a general method for the preparation of primary arylamines." *J. Am. Chem. Soc.*, 131(31)11049-11061.

Wheeler, et al. (2004) : Epigallocatechin-3-gallate, a green tea-derived polyphenol, inhibits IL-1β-dependent proinflammatory signal transduction in cultured respiratory epithelial cells. *J. Nutrition*, 134:1039-1044.

Williams, et al. (2001) "Squalamine treatment of human tumors in nu/nu mice enhances platinum-based chemotherapies." *Clin. Cancer Res.*, 7:724-733.

Zhao, et al. (2011) "An essential role for TAK1 in the contact hypersensitivity response." *Cellular & Molecular Immunology*, 8:315-324.

International Search Report (ISR) and Written Opinion (WO) in PCT/US2013/052326 dated Dec. 6, 2013.

* cited by examiner

4-ALKOXY/ARALKOXY-5-SUBSTITUTED-PYRROLOPYRIMIDINE COMPOUNDS AS TAK1 INHIBITORS IN DISEASE TREATMENT

CROSS-REFERENCE TO RELATED APPLICATIONS

This application is a national phase application of PCT Application No. PCT/US2013/052326 filed on 26 Jul. 2013, which claims the benefit and priority to U.S. Provisional Application No. 61/676,240 filed 26 Jul. 2012. The entire disclosures of the applications identified in this paragraph are incorporated herein by references.

FIELD

Substituted pyrrolopyrimidine compounds, and pharmaceutical compositions comprising such compounds, are useful for treating disease conditions in a subject. Of particular interest are 4-alkoxy/aralkoxy-5-substituted-pyrrolopyrimidine compounds and pharmaceutical compositions useful for treating cancer.

BACKGROUND

Transforming growth factor β-activated kinase 1 (TAK1, also known as MAP3K7) is an intracellular enzyme that sits at the crossroads of several disease pathways. TAK1 is a member of the mitogen-activated protein kinase kinase kinase (MAPKKK or MAP3K) class of serine/threonine kinases.

TAK1 in Cancer: Transforming growth factor beta (TGF-β) is a multifunctional secreted polypeptide involved in the regulation of cell proliferation, differentiation and survival (related to apoptosis) and is implicated in multiple aspects of tumor pathogenesis. TGF-β receptors act through several intracellular signaling cascades that include the canonical SMAD pathway as well as the non-canonical Rho GTPase and TAK1 signaling pathways. TGF-β can directly promote tumor invasiveness and metastasis in addition to induction of angiogenesis and suppression of lymphocyte and macrophage proliferation and differentiation, thereby suppressing immune surveillance of the developing tumor. Reduction of TGF-β activity may therefore be a promising target of therapeutic strategies to control tumor growth.

TAK1, a key downstream effector of TGF-β, has been implicated in transformation and metastasis of cancer cells as well as in the development of resistance to chemotherapeutic drugs and ionizing radiation. TAK1 is required for TGF-β initiated R-Ras mediated transformation of mammary epithelial cells, a process that is independent of SMAD signaling but requires TAK1 directed activation of p38 and c-Jun N-terminal kinase (JNK) pathways. It has been shown that TAK1 activation is involved in metastasis and bone destruction by breast carcinoma cells, as well as in the metastasis and lung invasion of colon cancer cells. The TAK1-dependent activation of p38, JNK and nuclear factor κB (NF-κB) pathways was central to promoting these cancer phenotypes. Multiple genotoxic anti-cancer drugs and ionizing radiation have been shown to activate NF-κB and thereby protect cancer cells from DNA damage-induced apoptosis. For example, two anticancer drugs, doxorubicin and etoposide, when tested in multiple cancer cell lines, promoted TAK1-mediated DNA-damage response-pathway that involved the downstream activation of NF-κB, p38 and MK2, conferring chemoresistance and promoting cancer cell survival. The role of TAK1, as a potential mediator of the extreme drug resistance displayed by pancreatic cancer, was studied using an orally, bioavailable small molecule inhibitor of TAK1, LYTAK1. Results demonstrated an increased sensitivity of pancreatic cancer cells to chemotherapeutic drugs gemcitabine and oxaliplatin (Melisi, et al. J. Natl. Cancer Inst. 103, 1190-1204 (2011)).

TAK1 in Inflammation and Autoimmune Disease: TAK1 is also a key mediator of pro-inflammatory and stress signals. Cellular activation of TAK1 activity is promoted by pro-inflammatory cytokines such as tumor necrosis factor-α (TNF-α) and interleukin-1β (IL-1β) as well as by the engagement of T cell, B cell and toll-like receptors. TAK1 activation induces the downstream nuclear translocation of NF-κB and activation of the JNK and p38 pathways that are central to driving inflammatory and immune responses as well as T cell and B cell development, activation and survival.

Protein-based (biologics) and small molecule drugs that block TNF-α (ENBREL, HUMIRA, REMICADE, SIMPONI) or IL-1β (KINERET) signaling or that limit T cell (ORENCIA, TYSABRI) or B cell (RITUXAN) function have been used to treat a number of autoimmune diseases such as rheumatoid arthritis, psoriatic arthritis, juvenile idiopathic arthritis, ankylosing spondylitis, cryopyrin associated periodic syndromes and inflammatory bowel disease (IBD). The essential role of TAK1 in modulating TNF-α and IL-1β production and signaling and T cell and B cell function make it important in autoimmune chronic inflammatory and autoinflammatory diseases.

TAK1 plays a pivotal role in JNK-mediated activation of metalloproteinase (MMP) gene expression and joint destruction in inflammatory arthritis. In animal models of autoimmune arthritis, the targeted knockdown of TAK1 with small interfering RNA (siRNA) provides disease-modifying benefit, both prophylactically and therapeutically. At the molecular and cellular levels, TAK1 knockdown severely impairs JNK and NF-κB signaling, down-regulated expression of pro-inflammatory mediators and constrains the expansion of IL-17A producing T cells that contribute to the pathogenesis of rheumatoid arthritis and other autoimmune diseases. The immunosuppressive impact of TAK1 deletion has also been studied in an animal model of contact hypersensitivity (CHS), a classic T cell-mediated immune response. Both dendritic cells (innate immunity) and T cells (adaptive immunity) play critical roles in the onset of CHS. By specifically deleting TAK1 in dendritic cells in a mouse model, it was shown that TAK1 is essential in dendritic cell-mediated T cell activation and the development of CHS (Zhao, et al. Cell. Mol. Immunol. 8, 315-324 (2011)).

Compounds useful as protein kinase inhibitors for treatment of proliferative diseases including cancer are reported in WO 2011/133637 (pub. 27 Oct. 2011). A compound described therein is 4-((5-(6-((4,4-difluorocyclohexyl)amino)-2-fluoronicotinoyl)-7H-pyrrolo[2,3-d]pyrimidin-4-yl)amino)pyrrolidin-2-one.

Compounds useful as epidermal growth factor receptor (EGFR) inhibitors for treatment of proliferative diseases including cancer are reported in WO 2010/129053 (pub. 11 Nov. 2010). A compound described therein is N-(3-((5-(pyridin-3-yl)-7H-pyrrolo[2,3-d]pyrimidin-4-yl)oxy)phenyl)acrylamide.

Compounds useful as Raf inhibitors for treatment of proliferative diseases including cancer are reported in WO 2011/063159 (pub. 26 May 2011). A compound described therein is N-(2,4-difluoro-3-(4-isobutoxy-7H-pyrrolo[2,3-d]pyrimidine-5-carbonyl)phenyl)-4-(trifluoromethyl)benzenesulfonamide.

Compounds useful as PDK1 inhibitors for cancer treatment are reported in WO 2010/003133 (pub. 7 Jan. 2012). A compound described therein is 4-(4-methoxy-7H-pyrrolo[2,3-d]pyrimidin-5-yl)pyridin-2-amine.

S-(4-substituted-5-cyano-2-methyl-7H-pyrrolo[2,3-d]-pyrimidin-6-yl)thioacetic acid derivatives are reported as intermediate compounds for the syntheses of S-(5-carbamoyl-2-methyl-4-oxo-3,4-dihydropyrrolo[2,3-d]pyrimidin-6-yl) thioacetic acid ester product compounds (A. Ebenereth, et al, *Pharmazie* (1992), 47(8), 571-3). These amido-derivative product compounds are described as proving to be of particular interest as chemotherapeutic agents.

SUMMARY

The present invention comprises a class of 4-alkoxy/aralkoxy-5-substituted-pyrrolopyrimidine compounds, or pharmaceutically acceptable salts, or solvates of compounds or salts, and pharmaceutical compositions of compounds embraced by Formula (I), and providing a therapeutic benefit to subjects with disease conditions, especially cancer, wherein $R^1$ and $R^2$ are as defined in the detailed description.

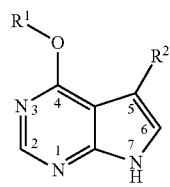

(I)

Compounds of the present invention can exist in tautomeric, geometric or stereoisomeric forms. Ester, metabolite, oxime, prodrug, onium, hydrate, solvate and N-oxide forms of a compound of Formula (I) are also embraced by the invention. The present invention considers all such compounds, including, but not limited to, cis- and trans-geometric isomers (Z- and E-geometric isomers), R- and S-enantiomers, diastereomers, d-isomers, l-isomers, atropisomers, epimers, conformers, rotamers, mixtures of isomers and racemates thereof, as falling within the scope of the invention.

In another embodiment, there is provided a pharmaceutical composition comprising a compound of Formula (I) and a pharmaceutically-acceptable carrier.

In another embodiment, a compound of Formula (I) further comprises one or more additional pharmaceutically active compounds.

In another embodiment, there is provided a method for treating a disease condition comprising administering to a subject a therapeutically effective amount of a compound of Formula (I), wherein the disease condition to be treated includes a proliferative disease, cancer, inflammatory disorder, or a disease condition for which a TAK1 inhibitor is effective.

In another embodiment, the method for treating a disease condition comprises administering a combination of a compound of Formula (I) and at least one additional pharmaceutically active compound.

In another embodiment, there is provided a use of a compound of Formula (I) for the manufacture of a medicament for the treatment of a disease condition in a subject.

In another embodiment, there is provided a method for preparing a compound of Formula (I).

In another embodiment, there is provided an intermediate useful in making a compound of Formula (I).

DETAILED DESCRIPTION

A. Compounds

The present invention provides 4-alkoxy/aralkoxy-5-substituted pyrrolopyrimidine compounds, or pharmaceutically acceptable salts, or solvates of compounds or salts, of Formula (I):

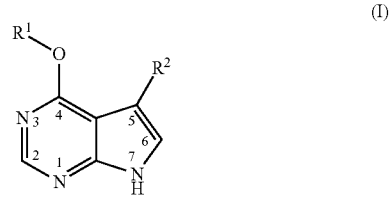

(I)

wherein:
$R^1$ is selected from the group consisting of alkyl, cycloalkyl, aryl, aralkyl, fully or partially saturated heterocyclylalkyl, heteroaryl and heteroaralkyl, wherein alkyl, cycloalkyl, aryl, aralkyl, fully or partially saturated heterocyclylalkyl, heteroaryl or heteroaralkyl may be optionally substituted, on any substitutable carbon, with one or more $R^3$ radicals;
$R^2$ is selected from the group consisting of cyano, alkenyl, alkynyl,

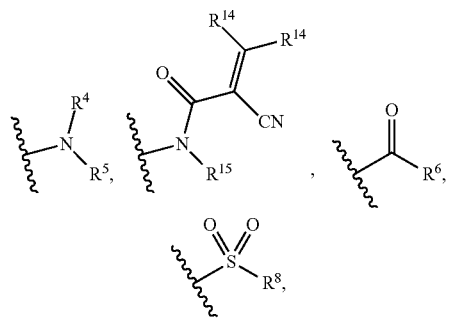

cycloalkenyl, heterocycloalkenyl and heteroaryl, wherein each alkenyl moiety is optionally substituted on any substitutable carbon with one or more $R^7$ or $R^{17}$ radicals, wherein alkynyl is optionally substituted on any substitutable carbon with one or more $R^{117}$ radicals, wherein cycloalkenyl is optionally substituted on any substitutable carbon with one or more $R^9$ radicals, wherein heterocycloalkenyl is optionally substituted on any substitutable carbon with one or more $R^{119}$ radicals, and wherein heteroaryl is optionally substituted on any substitutable carbon with one or more $R^{19}$ radicals; $R^3$ is selected from the group consisting of alkyl, hydroxy, alkoxy, aryloxy, oxo, acyl, carboxy, hydroxyalkyl, halo, haloalkyl, cyano, amino, monoalkylamino, dialkylamino, acylamino, aminoalkyl, monoalkylaminoalkylene, dialkylaminoalkylene, cycloalkyl, alkylsulfonyl, alkylsulfonylamino, aminosulfonyl, aminocarbonyl, cyanoalkylcarbonyl, alkoxycarbonyl, alkoxycarbonyloxy, alkoxycarbonylamino, alkoxycarbonylaminoalkylene, alkylureido, alkylureidoalkylene, dialkylaminosulfonyl and monoalkylaminosulfonyl; $R^4$ is selected from the group consisting of cyano, haloacyl, alkenylcarbonyl, hydroxyalkenylcarbonyl, aminoalkenylcarbonyl, monoalkylaminoalkenylcarbonyl, dialkylaminoalkenylcarbonyl, haloalkenylcarbonyl, cyanoalkenylcarbonyl, alkoxycarbonylalkenylcarbonyl, alkynylcarbonyl, hydroxyalkynylcarbonyl, alkylcarbonylalkenylcarbonyl, arylcarbonylalkenylcarbonyl, cycloalkylcarbonylalkenylcarbonyl, aminocarbonylalkenylcarbonyl, monoalkylaminocarbonylalkenylcarbonyl, dialkylaminocarbonylalkenylcarbonyl and alkenylsulfonyl; $R^{14}$ is selected from the group consisting of H, alkyl, cycloalkyl and aryl; $R^5$ is selected from the group consisting of H, alkyl and cycloalkyl; $R^{15}$ is selected from the group consisting of H, alkyl and cycloalkyl; $R^6$ is selected from the group consisting of alkyl, haloalkyl, alkenyl, hydroxyalkenyl, cyanoalkenyl, haloalkenyl, aminoalkenyl, monoalkylaminoalkenyl, dialkylaminoalkenyl, cyanoalkylamino, aminocarbonylalkenyl, monoalkylaminocarbonylalkenyl, dialkylaminocarbonylalkenyl, alkoxycarbonylalkenyl, alkylcarbonylalkenyl, arylcarbonylalkenyl, heteroarylcarbonylalkenyl, cycloalkylcarbonylalkenyl and cyanocycloalkylamino; each of $R^7$, $R^{17}$ and $R^{117}$ is independently selected from the group consisting of alkyl, acyl, cyano, halo, aminocarbonyl, monoalkylaminocarbonyl, dialkylaminocarbonyl, mono(hydroxyalkyl)aminocarbonyl, aroyl and heterocyclocarbonyl; $R^8$ is selected from the group consisting of alkenyl, hydroxyalkenyl and cycloalkenyl; each of $R^9$ and $R^{119}$ is independently selected from the group consisting of alkyl, oxo, cyano and halo; and $R^{19}$ is selected from the group consisting of alkyl, cyano and halo.

In another family of compounds of Formula (I), $R^1$ is selected from the group consisting of iso-butyl, benzyl,

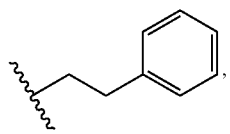 [SMILES: *CCc1ccccc1 ; ","]

sec-butyl, iso-propyl, propyl, phenyl, 2,2,2-trifluoroethyl, neopentyl, 2-hydroxy-2-methylpropyl, 3-fluorobenzyl, tert-butyl, 4,4-difluorocyclohexyl, 2-cyano-2-methylpropyl, cyclopropyl, cyclopentyl, 1-hydroxypropan-2-yl, 2-(azetidin-1 yl)ethyl, 2-(oxetan-3-yl)ethyl, 4-cyanobutan-2-yl, 1-cyanopropan-2-yl, 3-cyano-2-methylpropyl, 3-cyano-2,2-dimethylpropyl, cyclobutyl, 3-hydroxy-2,2-dimethylpropyl, 3-hydroxy-3-methylbutan-2-yl, 4-hydroxybutan-2-yl, 3-hydroxy-2-methylpropyl, 2-(1-methyl-1H-pyrazol-4-yl)ethyl, and 3-fluorophenyl; $R^2$ is selected from the group consisting of alkynyl, alkenyl,

and heteroaryl, wherein each alkenyl moiety is optionally substituted on any substitutable carbon with one or more $R^7$ or $R^{17}$ radicals, wherein alkynyl is optionally substituted on any substitutable carbon with one or more $R^{117}$ radicals, and wherein heteroaryl is optionally substituted on any substitutable carbon with one or more $R^{19}$ radicals; $R^4$ is selected from the group consisting of cyano, haloacyl, alkenylcarbonyl, hydroxyalkenylcarbonyl, aminoalkenylcarbonyl, monoalkylaminoalkenylcarbonyl, dialkylaminoalkenylcarbonyl, haloalkenylcarbonyl, cyanoalkenylcarbonyl, alkoxycarbonylalkenylcarbonyl, alkynylcarbonyl, hydroxyalkynylcarbonyl, alkylcarbonylalkenylcarbonyl, arylcarbonylalkenylcarbonyl, cycloalkylcarbonylalkenylcarbonyl, aminocarbonylalkenylcarbonyl, monoalkylaminocarbonylalkenylcarbonyl, dialkylaminocarbonylalkenylcarbonyl and alkenylsulfonyl; $R^5$ is selected from the group consisting of H, alkyl and cycloalkyl; $R^6$ is selected from the group consisting of alkyl, haloalkyl, alkenyl, hydroxyalkenyl, cyanoalkenyl, haloalkenyl, aminoalkenyl, monoalkylaminoalkenyl, dialkylaminoalkenyl, cyanoalkylamino, aminocarbonylalkenyl, monoalkylaminocarbonylalkenyl, dialkylaminocarbonylalkenyl, alkoxycarbonylalkenyl, alkylcarbonylalkenyl, arylcarbonylalkenyl, heteroarylcarbonylalkenyl, cycloalkylcarbonylalkenyl and cyanocycloalkylamino; each of $R^7$, $R^{17}$ and $R^{117}$ is independently selected from the group consisting of alkyl, acyl, cyano, halo, aminocarbonyl, monoalkylaminocarbonyl, dialkylaminocarbonyl,

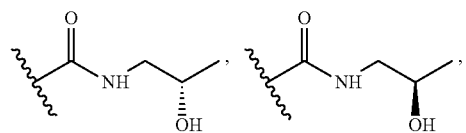

aroyl and heterocyclocarbonyl; $R^8$ is selected from the group consisting of alkenyl, hydroxyalkenyl and cycloalkenyl; and $R^{19}$ is selected from the group consisting of alkyl, cyano and halo.

In another family of compounds of Formula (I), $R^1$ is selected from the group consisting of isobutyl, benzyl, 3-fluorobenzyl, sec-butyl, isopropyl, propyl, phenyl, 2,2,2-trifluoroethyl, neopentyl, 2-hydroxy-2-methylpropyl, tert-butyl, 4,4-difluorocyclohexyl, 2-cyano-2-methylpropyl, 1-hydroxypropan-2-yl, 4-cyanobutan-2-yl, 1-cyanopropan-2-yl, 3-hydroxy-2,2-dimethylpropyl and 4-hydroxybutan-2-yl; $R^2$ is selected from the group consisting of

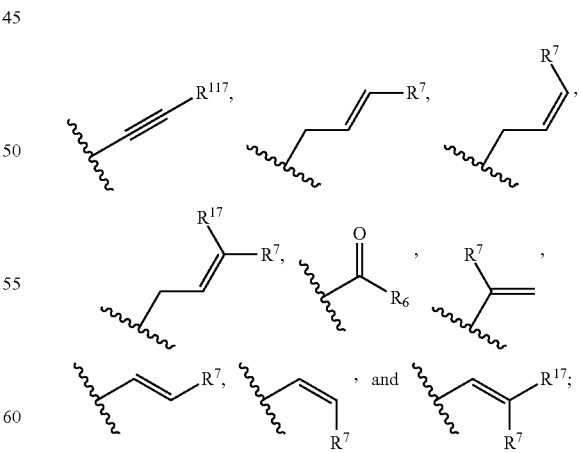

$R^6$ is methyl or chloromethyl; each of $R^7$ and $R^{17}$ is independently selected from the group consisting of cyano, acetyl, aminocarbonyl, methylaminocarbonyl, ethylaminocarbonyl, methoxycarbonyl,

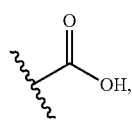

cyclopropylaminocarbonyl, cyclopropylmethylaminocarbonyl,

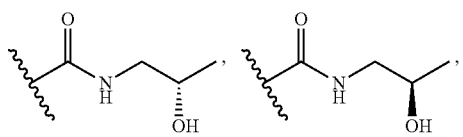

dimethylaminocarbonyl, chloro, fluoro, and methyl; and $R^{117}$ is

aminocarbonyl, methylaminocarbonyl, ethylaminocarbonyl or dimethylaminocarbonyl.

In another family of compounds of Formula (I), $R^1$ is selected from the group consisting of isobutyl, sec-butyl, isopropyl, propyl, phenyl, 2,2,2-trifluoroethyl, 2-cyano-2-methylpropyl, 1-hydroxypropan-2-yl, 4-cyanobutan-2-yl, 1-cyanopropan-2-yl, 3-hydroxy-2,2-dimethylpropyl, 4-hydroxybutan-2-yl, 4,4-difluorocyclohexyl and neopentyl; $R^2$ is

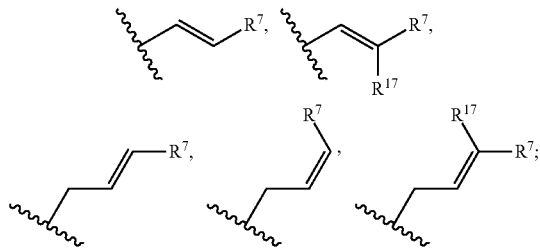

$R^7$ is selected from the group consisting of cyano, aminocarbonyl, methylaminocarbonyl, ethylaminocarbonyl, cyclopropylaminocarbonyl, and dimethylaminocarbonyl; and $R^{17}$ is cyano, methylaminocarbonyl, or ethylaminocarbonyl. Non-limiting examples include: (E)-3-(4-(sec-butoxy)-7H-pyrrolo[2,3-d]pyrimidin-5-yl)acrylamide (Compound 187); (E)-3-(4-(isopropoxy-7H-pyrrolo[2,3-d]pyrimidin-5-yl)acrylamide (Compound 188); (E)-3-(4-propoxy-7H-pyrrolo[2,3-d]pyrimidin-5-yl)acrylamide (Compound 189); (E)-3-(4-(2,2,2-trifluoroethoxy)-7H-pyrrolo[2,3-d]pyrimidin-5-yl)acrylamide (Compound 191); (E)-3-(4-(neopentyloxy)-7H-pyrrolo[2,3-d]pyrimidin-5-yl)acrylamide (Compound 192); 3-[4-(4,4-difluoro-cyclohexyloxy)-7H-pyrrolo[2,3-d]pyrimidin-5-yl]-acrylamide (Compound 199); (E)-3-(4-(2-cyano-2-methylpropoxy)-7H-pyrrolo[2,3-d]pyrimidin-5-yl)acrylamide (Compound 433); (E)-3-(4-((1-hydroxypropan-2-yl)oxy)-7H-pyrrolo[2,3-d]pyrimidin-5-yl)acrylamide (Compound 436); (E)-3-(4-((4-cyanobutan-2-yl)oxy)-7H-pyrrolo[2,3-d]pyrimidin-5-yl)acrylamide (Compound 439); (E)-3-(4-((1-cyanopropan-2-yl)oxy)-7H-pyrrolo[2,3-d]pyrimidin-5-yl)acrylamide (Compound 440); (E)-3-(4-(3-hydroxy-2,2-dimethylpropoxy)-7H-pyrrolo[2,3-d]pyrimidin-5-yl)acrylamide (Compound 444); and (E)-3-(4-((4-hydroxybutan-2-yl)oxy)-7H-pyrrolo[2,3-d]pyrimidin-5-yl)acrylamide (Compound 446).

In another family of compounds of Formula (I), $R^1$ is isobutyl; $R^2$ is

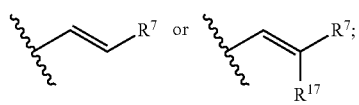

and $R^7$ is selected from the group consisting of aminocarbonyl, methylaminocarbonyl, ethylaminocarbonyl, cyclopropylaminocarbonyl, and dimethylaminocarbonyl. Non-limiting examples include: (E)-3-(4-isobutoxy-7H-pyrrolo[2,3-d]pyrimidin-5-yl)acrylamide (Compound 38); (E)-3-(4-isobutoxy-7H-pyrrolo[2,3-d]pyrimidin-5-yl)-N-methylacrylamide (Compound 39); (E)-N-ethyl-3-(4-isobutoxy-7H-pyrrolo[2,3-d]pyrimidin-5-yl)acrylamide (Compound 179); (E)-N-cyclopropyl-3-(4-isobutoxy-7H-pyrrolo[2,3-d]pyrimidin-5-yl)acrylamide (Compound 181); and (E)-3-(4-isobutoxy-7H-pyrrolo[2,3-d]pyrimidin-5-yl)-N,N-dimethylacrylamide (Compound 184).

In another family of compounds of Formula (I), $R^1$ is selected from the group consisting of isobutyl, 3-fluorobenzyl, phenyl, 2-hydroxy-2-methylpropyl, tert-butyl, 2-cyano-2-methylpropyl, 1-hydroxypropan-2-yl, 4-cyanobutan-2-yl, 1-cyanopropan-2-yl, 3-hydroxy-2,2-dimethylpropyl, 4,4-difluorocyclohexyl and 4-hydroxybutan-2-yl; $R^2$ is selected from the group consisting of

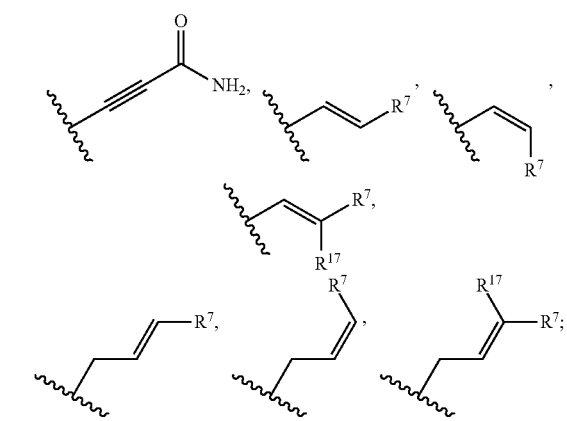

$R^7$ is selected from the group consisting of cyano, acetyl, and aminocarbonyl; and $R^{17}$ is cyano, methylaminocarbonyl, or ethylaminocarbonyl. Non-limiting examples include: (Z)-3-(4-isobutoxy-7H-pyrrolo[2,3-d]pyrimidin-5-yl)acrylonitrile (Compound 36); (E)-4-(4-isobutoxy-7H-pyrrolo[2,3-d]pyrimidin-5-yl)but-3-en-2-one (Compound 37); 3-(4-isobutoxy-7H-pyrrolo[2,3-d]pyrimidin-5-yl)propionamide (Compound 186); (E)-3-(4-phenoxy-7H-pyrrolo[2,3-d]pyrimidin-5-yl)acrylamide (Compound 190); (E)-3-(4-(2-hydroxy-2-methylpropoxy)-7H-pyrrolo[2,3-d]pyrimidin-5-yl)acrylamide (Compound 193); (E)-3-(4-((3-fluorobenzyl)oxy)-7H-pyrrolo[2,3-d]pyrimidin-5-yl)acrylamide (Compound 194); and (E)-3-(4-(tert-butoxy)-7H-pyrrolo[2,3-d]pyrimidin-5-yl)acrylamide (Compound 195).

In another family of compounds, $R^1$ is selected from the group consisting of alkyl, cycloalkyl, aryl, heterocyclylalkyl and aralkyl, wherein alkyl, cycloalkyl, aryl, heterocyclylalkyl and aralkyl may be optionally substituted, on any substitutable carbon, with one or more $R^3$ radicals; $R^2$ is selected from the group consisting of

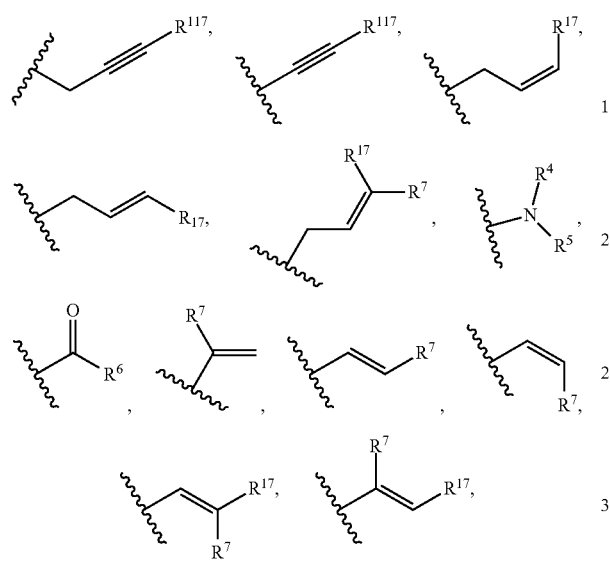

cycloalkenyl, heterocycloalkenyl, and heteroaryl; $R^3$ is selected from the group consisting of hydroxyl, halo, and cyano; $R^4$ is selected from the group consisting of cyano, haloacyl, alkenylcarbonyl, hydroxyalkenylcarbonyl, aminoalkenylcarbonyl, monoalkylaminoalkenylcarbonyl, haloalkenylcarbonyl, alkynylcarbonyl, hydroxyalkynylcarbonyl and alkenylsulfonyl; $R^5$ is H or methyl; $R^6$ is selected from the group consisting of methyl, fluoromethyl, chloromethyl, chloroethyl, trifluoromethyl,

each of $R^7$ and $R^{17}$ is independently selected from the group consisting of cyano, chloro, fluoro, methyl, acetyl, ethylcarbonyl, isopropylcarbonyl, methoxycarbonyl, aminocarbonyl, methylaminocarbonyl, ethylaminocarbonyl, dimethylaminocarbonyl, benzoyl,

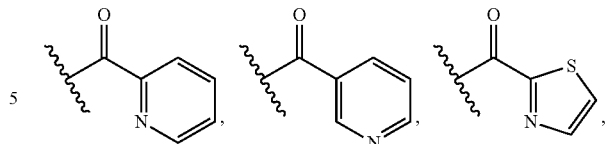

cyclopropylaminocarbonyl,

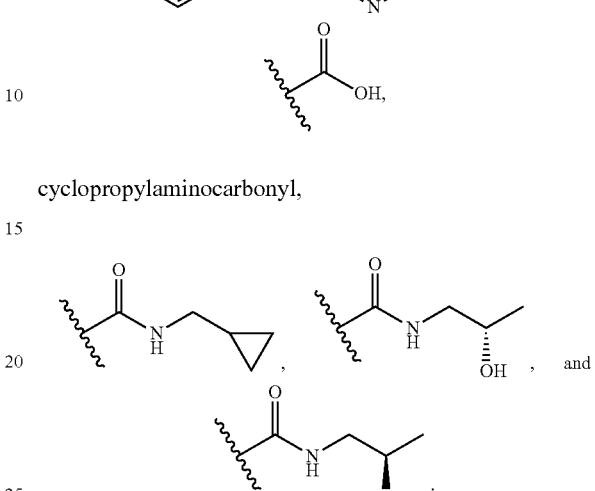

and $R^{117}$ is selected from the group consisting of

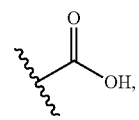

aminocarbonyl, and methylaminocarbonyl.

In another family of compounds of Formula (I), $R^1$ is selected from the group consisting of alkyl, cycloalkyl, aryl, and aralkyl, wherein alkyl, cycloalkyl, aryl, and aralkyl may be optionally substituted, on any substitutable carbon, with one or more $R^3$ radicals; $R^2$ is

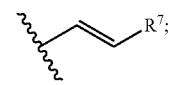

$R^3$ is selected from the group consisting of hydroxyl, fluoro, and cyano; and $R^7$ is selected from the group consisting of aminocarbonyl, methylaminocarbonyl, ethylaminocarbonyl, cyclopropylaminocarbonyl, and dimethylaminocarbonyl. Non-limiting examples include: (E)-3-(4-isopropoxy-7H-pyrrolo[2,3-d]pyrimidin-5-yl)-N-methylacrylamide (Compound 202); (E)-N-ethyl-3-(4-isopropoxy-7H-pyrrolo[2,3-d]pyrimidin-5-yl)acrylamide (Compound 203); (E)-3-(4-isopropoxy-7H-pyrrolo[2,3-d]pyrimidin-5-yl)-N,N-dimethylacrylamide (Compound 204); (E)-N-cyclopropyl-3-(4-isopropoxy-7H-pyrrolo[2,3-d]pyrimidin-5-yl) acrylamide (Compound 205); (E)-N-methyl-3-(4-(neopentyloxy)-7H-pyrrolo[2,3-d]pyrimidin-5-yl) acrylamide (Compound 244); (E)-N-ethyl-3-(4-(neopentyloxy)-7H-pyrrolo[2,3-d]pyrimidin-5-yl) acrylamide (Compound 245); (E)-N,N-dimethyl-3-(4-(neopentyloxy)-7H-pyrrolo[2,3-d]pyrimidin-5-yl) acrylamide (Compound 246); (E)-N-cyclopropyl-3-(4-(neopentyloxy)-7H-pyrrolo[2,3-d]pyrimidin-5-yl) acrylamide (Compound 247); (E)-3-(4-(2- hydroxy-2-methylpropoxy)-7H-pyrrolo[2,3-d]pyrimidin-5-yl)-N-methylacrylamide (Compound 272); (E)-N-ethyl-3-(4-(2-hydroxy-2-methylpropoxy)-7H-pyrrolo[2,3-d]pyrimidin-5-yl) acrylamide (Compound 273); (E)-3-(4-(2-hydroxy-2-methylpropoxy)-7H-pyrrolo[2,3-d]pyrimidin-5-yl)-N,N-dimethylacrylamide (Compound 274); and (E)-N-cyclopropyl-3-(4-(2-hydroxy-2-methylpropoxy)-7H-pyrrolo[2,3-d]pyrimidin-5-yl)acrylamide (Compound 275).

In another family of compounds of Formula (I), $R^1$ is selected from the group consisting of alkyl, cycloalkyl, aryl, and aralkyl, wherein alkyl, cycloalkyl, aryl, and aralkyl may be optionally substituted, on any substitutable carbon, with one or more $R^3$ radicals; $R^2$ is selected from the group consisting of

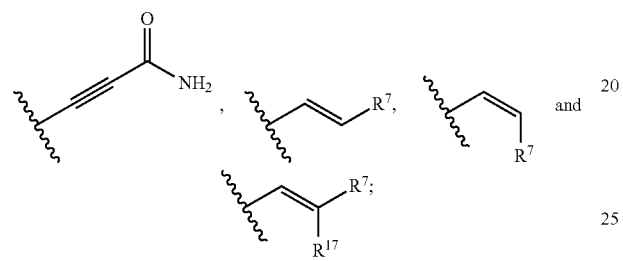

$R^3$ is selected from the group consisting of hydroxyl, fluoro, and cyano; $R^7$ is selected from the group consisting of acetyl, cyano, aminocarbonyl, methylaminocarbonyl and ethylaminocarbonyl; and $R^{17}$ is selected from the group consisting of cyano, methylaminocarbonyl, and ethylaminocarbonyl.

In another family of compounds of Formula (I), $R^1$ is selected from the group consisting of alkyl, cycloalkyl, aryl, and aralkyl, wherein alkyl, cycloalkyl, aryl, and aralkyl may be optionally substituted, on any substitutable carbon, with one or more $R^3$ radicals; $R^2$ is selected from the group consisting of

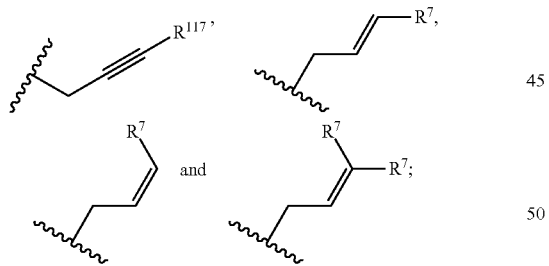

$R^3$ is selected from the group consisting of hydroxyl, fluoro, and cyano; $R^7$ is selected from the group consisting of acetyl, cyano, aminocarbonyl, methylaminocarbonyl and ethylaminocarbonyl; and $R^{17}$ is selected from the group consisting of cyano, methylaminocarbonyl, and ethylaminocarbonyl. Non-limiting examples include: (E)-4-(4-isopropoxy-7H-pyrrolo[2,3-d]pyrimidin-5-yl)but-2-enamide (Compound 211); (E)-4-(4-isopropoxy-7H-pyrrolo[2,3-d]pyrimidin-5-yl)-N-methylbut-2-enamide (Compound 212); (E)-5-(4-isopropoxy-7H-pyrrolo[2,3-d]pyrimidin-5-yl)pent-3-en-2-one (Compound 214); (E)-4-(4-isopropoxy-7H-pyrrolo[2,3-d]pyrimidin-5-yl)but-2-enenitrile (Compound 217); (Z)-4-(4-isopropoxy-7H-pyrrolo[2,3-d]pyrimidin-5-yl)but-2-enenitrile (Compound 218); 2-(2-(4-isopropoxy-7H-pyrrolo[2,3-d]pyrimidin-5-yl)ethylidene)malononitrile (Compound 219); (E)-2-cyano-4-(4-isopropoxy-7H-pyrrolo[2,3-d]pyrimidin-5-yl)but-2-enamide (Compound 220); and 4-(4-isopropoxy-7H-pyrrolo[2,3-d]pyrimidin-5-yl)but-2-ynamide (Compound 221).

In another family of compounds of Formula (I), $R^1$ is selected from the group consisting of alkyl, cycloalkyl, aryl, heterocyclylalkyl and aralkyl, wherein alkyl, cycloalkyl, aryl, heterocyclylalkyl and aralkyl may be optionally substituted, on any substitutable carbon, with one or more $R^3$ radicals; $R^2$ is heteroaryl; and $R^3$ is selected from the group consisting of hydroxyl, halo, and cyano.

In another family of compounds of Formula (I), $R^1$ is selected from the group consisting of alkyl, cycloalkyl, aryl, heterocyclylalkyl and aralkyl, wherein alkyl, cycloalkyl, aryl, heterocyclylalkyl and aralkyl may be optionally substituted, on any substitutable carbon, with one or more $R^3$ radicals; $R^2$ is selected from the group consisting of

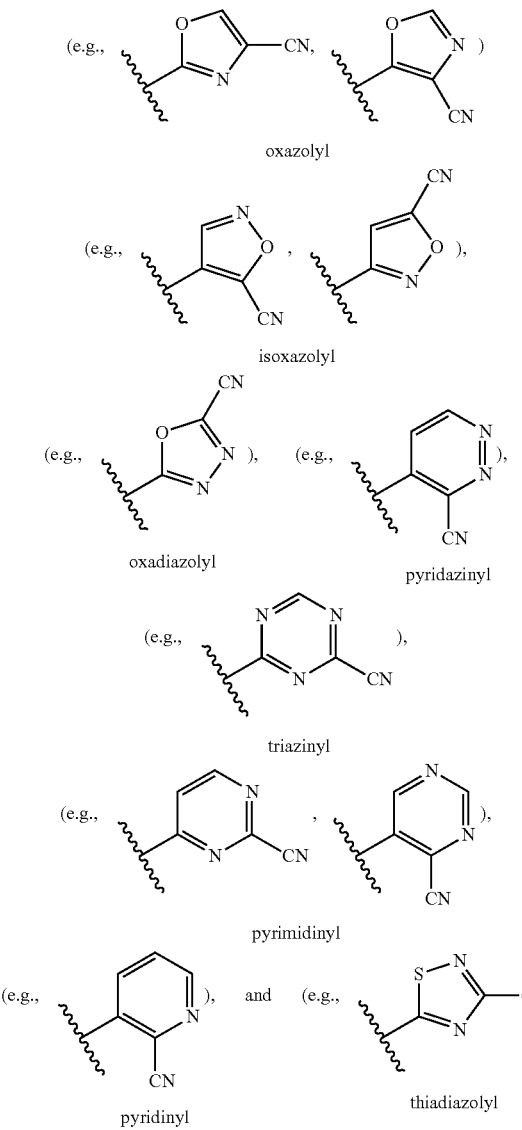

and $R^3$ is selected from the group consisting of hydroxyl, halo and cyano.

In another family of compounds of Formula (I), $R^1$ is selected from the group consisting of alkyl, cycloalkyl, aryl, heterocyclylalkyl and aralkyl, wherein alkyl, cycloalkyl, aryl, heterocyclylalkyl and aralkyl may be optionally substituted, on any substitutable carbon, with one or more R³ radicals; R² is

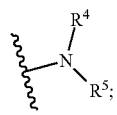

R³ is selected from the group consisting of hydroxyl, halo, and cyano; R⁴ is selected from the group consisting of cyano, haloacyl, alkenylcarbonyl, hydroxyalkenylcarbonyl, aminoalkenylcarbonyl, monoalkylaminoalkenylcarbonyl, haloalkenylcarbonyl, alkynylcarbonyl, hydroxyalkynylcarbonyl and alkenylsulfonyl; and R⁵ is H or methyl.

In another family of compounds of Formula (I), R¹ is selected from the group consisting of alkyl, cycloalkyl, aryl, heterocyclylalkyl and aralkyl, wherein alkyl, cycloalkyl, aryl, heterocyclylalkyl and aralkyl may be optionally substituted, on any substitutable carbon, with one or more R³ radicals; R² is

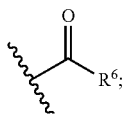

R³ is selected from the group consisting of hydroxyl, halo and cyano; and

R⁶ is selected from the group consisting of methyl, fluoromethyl, chloromethyl, chloroethyl, trifluoromethyl,

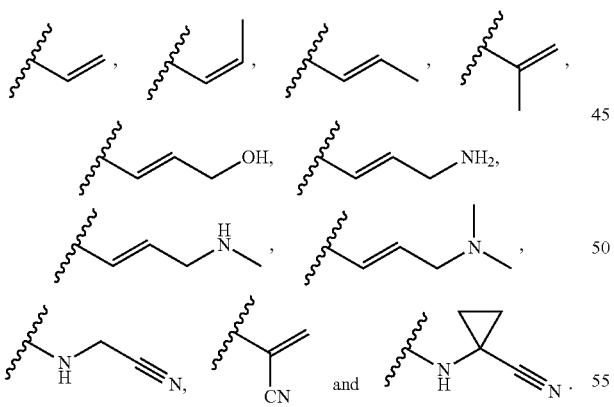

Non-limiting examples include 2-chloro-1-(4-isopropoxy-7H-pyrrolo[2,3-d]pyrimidin-5-yl)ethanone (Compound 223).

In another family of compounds of Formula (I), R¹ is selected from the group consisting of alkyl, cycloalkyl, aryl, heterocyclylalkyl and aralkyl, wherein alkyl, cycloalkyl, aryl, heterocyclylalkyl and aralkyl may be optionally substituted, on any substitutable carbon, with one or more R³ radicals; R² is

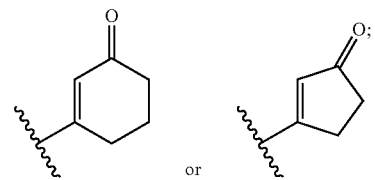 [SMILES: *C1=CC(=O)CCC1 ; *C1=CC(=O)CC1]

and R³ is selected from the group consisting of hydroxyl, halo and cyano.

In another family of compounds of Formula (I), R¹ is selected from the group consisting of alkyl, cycloalkyl, aryl, heterocyclylalkyl and aralkyl, wherein alkyl, cycloalkyl, aryl, heterocyclylalkyl and aralkyl may be optionally substituted, on any substitutable carbon, with one or more R³ radicals; R² is

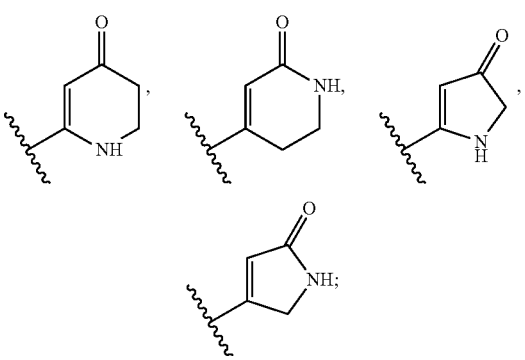

and R³ is selected from the group consisting of hydroxyl, halo and cyano.

The present invention further provides a pharmaceutical composition comprising a therapeutically effective amount of a compound of Formula (I) or a pharmaceutically acceptable salt thereof, and a pharmaceutically acceptable carrier.

The present invention further provides a pharmaceutical composition comprising a therapeutically effective amount of an active pharmaceutical ingredient selected from the group consisting of an anti-cancer drug, anti-proliferative agent and an anti-inflammatory drug.

The present invention provides 4-alkoxy/aralkoxy-5-substituted pyrrolopyrimidine compounds, or pharmaceutically acceptable salts, or solvates of compounds or salts, of Formula (II):

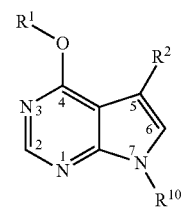

(II)

wherein:

R¹ is selected from the group consisting of iso-butyl, benzyl,

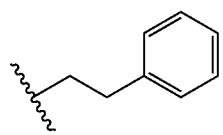

sec-butyl, iso-propyl, propyl, phenyl, 2,2,2-trifluoroethyl, neopentyl, 2-hydroxy-2-methylpropyl, 3-fluorobenzyl, tert-butyl, 4,4-difluorocyclohexyl, 2-cyano-2-methylpropyl, cyclopropyl, cyclopentyl, 1-hydroxypropan-2-yl, 2-(azetidin-1yl)ethyl, 2-(oxetan-3-yl)ethyl, 4-cyanobutan-2-yl, 1-cyanopropan-2-yl, 3-cyano-2-methylpropyl, 3-cyano-2,2-dimethylpropyl, cyclobutyl, 3-hydroxy-2,2-dimethylpropyl, 3-hydroxy-3-methylbutan-2-yl, 4-hydroxybutan-2-yl, 3-hydroxy-2-methylpropyl, 2-(1-methyl-1H-pyrazol-4-yl)ethyl, and 3-fluorophenyl; $R^2$ is Cl or I; and $R^{10}$ is selected from the group consisting of H, acetyl, acylal, benzoyl, benzyl, benzyloxy carbonyl, carbobenzyloxy, dimethoxytrityl, dithianyl, ethoxyethyl ether, methoxymethyl ether, methoxytrityl, methyl ether, methyl, methyloxy carbonyl, methylthiomethyl ether, trialkoxymethyl, oxazoline, pivaloyl, phthalimido, p-methoxybenzyl carbonyl, p-methoxyphenyl, trimethyl silyl, tert-butyldimethylsilyl, tri-iso-propylsilyloxymethyl, triisopropylsilyl, silyloxy carbonyl, tert-butoxy carbonyl, tert-butyloxy carbonyl, tetrahydropyranyl, tosyl, trimethylsilylethoxymethyl, trityl, β-methoxyethoxymethyl ether, (4-nitrophenyl)sulfonyl, (4-nitrophenyl)(dioxido)-lambda(6)-sulfanyl), 2-cyanoethyl, 2-nitrophenylsulfenyl, 3,4-dimethoxybenzyl, and 9-fluorenylmethyloxycarbonyl.

In another family of compounds of Formula (II), $R^1$ is selected from the group consisting of iso-butyl, sec-butyl, iso-propyl, propyl, phenyl, 2,2,2-trifluoroethyl, neopentyl, 2-hydroxy-2-methylpropyl, 3-fluorobenzyl, tert-butyl; $R^2$ is Cl or I; and $R^{10}$ is selected from the group consisting of H, tert-butyloxy carbonyl and tosyl. Non-limiting examples include: 5-chloro-4-isobutoxy-7H-pyrrolo[2,3-d]pyrimidine (Intermediate 1); 5-iodo-4-isobutoxy-7H-pyrrolo[2,3-d]pyrimidine (Intermediate 2); and 4-(sec-butoxy)-5-iodo-7H-pyrrolo[2,3-d]pyrimidine (Intermediate 3).

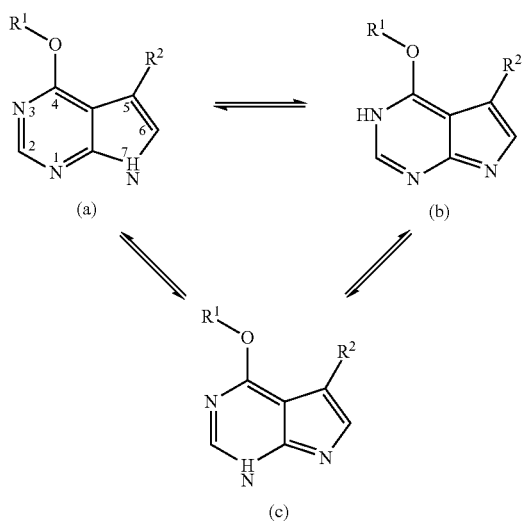

The molecular scaffold of Formula (I) may exist in several tautomeric forms, for example, tautomers (a), (b) and (c) shown above. The present claimed invention comprises all tautomeric forms of Formula (I). It is presumed that tautomeric form (a) of Formula (I) is the favored tautomeric form because some intermediate compounds herein comprise protecting group substitution at the nitrogen at ring position 7.

B. Definitions

The terms "substituent", "radical", "group", "moiety" and "fragment" may be used interchangeably.

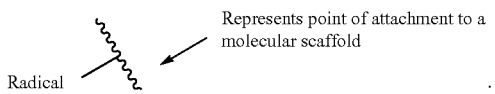

Singular forms "a" and "an" may include plural reference unless the context clearly dictates otherwise.

The term "substitutable carbon" embraces a carbon atom chemically capable of accepting a radical and forming a chemically- or biologically-stable moiety when attached to a molecular scaffold.

For clarity, the pyrrolopyrimidine ring numbering of many compounds herein is as follows:

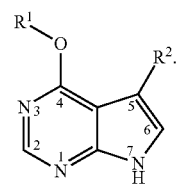

The term "hydrido" embraces a single —H atom and may be used interchangeably with the symbol "H". Hydrido may be attached, for example, to an oxygen atom to form a "hydroxy" radical (i.e., —OH), or two hydrido radicals may be attached to a carbon atom to form a "methylene" (—$CH_2$—) group.

The terms "hydroxyl" and "hydroxy" may be used interchangeably.

If a substituent is described as being "optionally substituted," the substituent may be either (1) not substituted or (2) substituted on a substitutable position. If a substitutable position is not substituted, the default substituent is H.

The number of carbon atoms in a substituent can be indicated by the prefix "$C_{A-B}$" where A is the minimum and B is the maximum number of carbon atoms in the substituent.

The term "halo" refers to fluoro (—F), chloro (—Cl), bromo (—Br), or iodo (—I).

The term "alkyl", either alone or within other terms such as "haloalkyl" and "alkylaryl", embraces a linear or branched acyclic alkyl radical containing from 1 to about 15 carbon atoms. In some embodiments, alkyl is a $C_{1-10}$alkyl, $C_{1-7}$alkyl or $C_{1-5}$alkyl radical. Examples of alkyl include methyl, ethyl, propyl, isopropyl, butyl, isobutyl, tert-butyl, sec-butyl, pentan-3-yl (i.e., 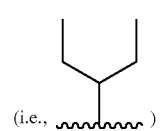 [SMILES: *C(CC)CC] )

and the like.

The term "hydroxyalkyl" embraces a hydroxy radical attached to alkyl, wherein any one or more of the alkyl carbon atoms are substituted with hydroxy. Examples of hydroxyalkyl include monohydroxyalkyl, dihydroxyalkyl and trihydroxyalkyl. More specific examples of hydroxyalkyl include hydroxymethyl, hydroxyethyl and hydroxypropyl.

The term "haloalkyl" embraces a halo radical attached to alkyl, wherein any one or more of the alkyl carbon atoms are substituted with halo. Non-limiting examples of haloalkyl include monohaloalkyl, dihaloalkyl and trihaloalkyl. More specifically, a monohaloalkyl group may have, for example, either a bromo, chloro or a fluoro atom within the radical. Dihalo radicals may have two of the same halo groups or a combination of different halo groups. A trihaloalkyl radical may have three of the same halo groups or a combination of different halo groups. More specific non-limiting examples of haloalkyl include chloroethyl, chloromethyl, dichloroethyl, dichlorofluoromethyl, dichloromethyl, dichloropropyl, difluorochloromethyl, difluoroethyl, difluoromethyl, difluoropropyl, diiodomethyl fluoroethyl, fluoromethyl, heptafluoropropyl, iodomethyl, pentafluoroethyl, trichloromethyl, trifluoroethyl, trifluoromethyl and triiodomethyl.

The term "haloacyl" embraces a halo radical attached to acyl, on a substitutable carbon, wherein any one or more of the acyl carbon atoms are substituted with halo. A non-limiting example of haloacyl includes haloacetyl. More specific non-limiting examples of haloacyl include fluoroacetyl, chloroacetyl and trifluoroacetyl.

The term "alkylene" embraces a linear or branched divalent alkyl radical. The terms "alkylene" and "alkylenyl" may be used interchangeably. Non-limiting examples of alkylene include methylene,

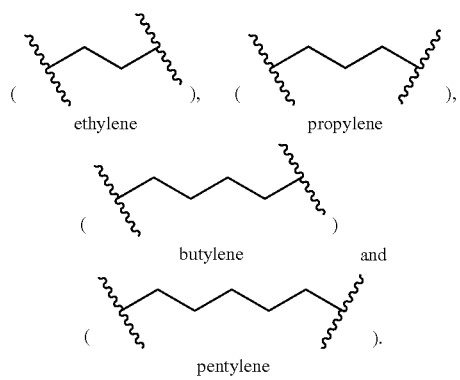

ethylene, propylene, butylene and pentylene.

The term "alkoxy" is RO— where R is alkyl. Non-limiting examples of alkoxy include methoxy, ethoxy, propoxy, isopropoxy and isobutoxy. The terms "alkyloxy" and "alkoxy" may be used interchangeably.

The term "alkoxyalkylene" embraces alkoxy attached to a molecular scaffold through divalent alkyl. Examples of alkoxyalkylene include methoxymethyl, methoxyethyl, methoxypropyl and ethoxyethyl.

The term "alkenyl" embraces an unsaturated, acyclic hydrocarbon radical with at least one double bond. Alkenyl contains from 2 to about 15 carbon atoms. Examples of alkenyl include vinyl, propenyl, butenyl and pentenyl. The terms "vinyl" and "ethenyl" may be used interchangeably. When cis/trans (or Z/E) configuration is not expressly defined for an alkenyl radical, both cis/trans isomers are embraced. For example, the term "propenyl" embraces both (E)-propenyl and (Z)-propenyl and the term "butenyl" embraces both (E)-butenyl and (Z)-butenyl.

$R^7$ or $R^{17}$

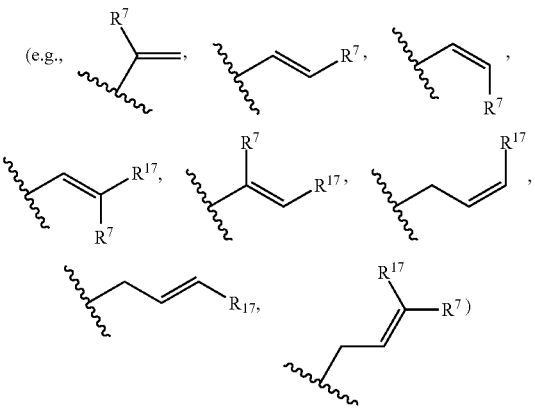

may be attached to alkenyl, where $R^7$ may be, for example, acyl (e.g., acetyl), alkyl (e.g., methyl), cyano, halo (e.g., fluoro), aminocarbonyl, monoalkylaminocarbonyl, dialkylaminocarbonyl, aroyl or heterocyclocarbonyl; and $R^{17}$ may be, for example, acyl (e.g., acetyl), cyano, halo (e.g., fluoro), aminocarbonyl, monoalkylaminocarbonyl, dialkylaminocarbonyl, aroyl or heterocyclocarbonyl.

The term "allyl" embraces a radical having the structural formula

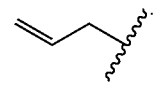

The term "alkynyl" embraces a hydrocarbon radical with at least one triple bond. Alkynyl contains from 2 to about 15 carbon atoms. A non-limiting example of alkynyl is propargyl.

$R^{117}$

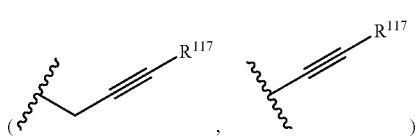

may be attached to alkynyl, where $R^{117}$ may be, for example, acyl (e.g., acetyl), alkyl (e.g., methyl), cyano, halo (e.g., fluoro), aminocarbonyl, monoalkylaminocarbonyl, dialkylaminocarbonyl, aroyl or heterocyclocarbonyl.

The term "haloalkenyl" embraces a halo radical attached to alkenyl, wherein any one or more of the alkenyl carbon atoms is substituted with halo. Non-limiting examples of haloalkenyl include fluorovinyl and fluoropropenyl.

The term "haloalkenylcarbonyl" embraces haloalkenyl attached to a molecular scaffold through carbonyl

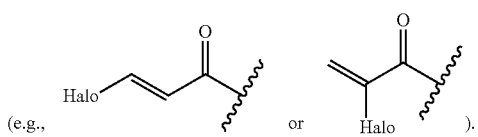

(e.g., Halo or Halo).

Non-limiting examples of haloalkenylcarbonyl include fluorovinylcarbonyl and fluoropropenylcarbonyl.

The term "alkenylsulfonyl" embraces alkenyl attached to a molecular scaffold through a sulfonyl radical. Non-limiting examples of alkenylsulfonyl include ethenylsulfonyl and propenylsulfonyl.

The term "alkenylcarbonyl" embraces alkenyl attached to a molecular scaffold through carbonyl. Non-limiting examples of alkenylcarbonyl include butenylcarbonyl and propenylcarbonyl.

The term "acyl" embraces, for example, H, alkyl, or aryl attached to carbonyl. More specific examples of acyl include formyl, acetyl and benzoyl. When alkyl is attached to carbonyl, the term "alkylcarbonyl" may be used.

The term "alkylcarbonylalkenyl" embraces alkylcarbonyl attached to a molecular scaffold through alkenyl, or having a terminal alkenyl. An example of alkylcarbonylalkenyl includes hexenyl-3-one and pentenyl-3-one.

The term "alkylcarbonylalkenylcarbonyl" embraces alkylcarbonylalkenyl attached to a molecular scaffold through carbonyl. Examples of alkylcarbonylalkenylcarbonyl include hexenyldione and pentenyldione.

The term "arylcarbonylalkenyl" embraces arylcarbonyl attached to a molecular scaffold through alkenyl, or having a terminal alkenyl. An example of arylcarbonylalkenyl includes phenylcarbonylalkenyl. A more specific example of arylcarbonylalkenyl includes phenylprop-1-enyl-3-one.

The term "arylcarbonylalkenylcarbonyl" embraces arylcarbonylalkenyl attached to a molecular scaffold through carbonyl. An example of arylcarbonylalkenylcarbonyl includes phenylcarbonylalkenylcarbonyl. A more specific example of arylcarbonylalkenylcarbonyl includes phenylbut-2-enyl-1,4-dione.

The term "cycloalkylcarbonylalkenyl" embraces cycloalkylcarbonyl attached to a molecular scaffold through alkenyl, or having a terminal alkenyl. Examples of cycloalkylcarbonylalkenyl include cyclopropylbutenyl-4-one and cyclopropylpropenyl-3-one.

The term "cycloalkylcarbonylalkenylcarbonyl" embraces cycloalkylcarbonylalkenyl attached to a molecular scaffold through carbonyl. An example of cycloalkylcarbonylalkenylcarbonyl includes cyclopropylbut-2-enyl-1,4-dione.

The term "aminocarbonylalkenyl" embraces aminocarbonyl attached to a molecular scaffold through alkenyl, or having a terminal alkenyl. Examples of aminocarbonylalkenyl include 3-amino-3-oxo-propenyl and 4-amino-4-oxobutenyl.

The term "aminocarbonylalkenylcarbonyl" embraces aminocarbonylalkenyl attached to a molecular scaffold through carbonyl. An example of aminocarbonylalkenylcarbonyl includes 4-amino-4-oxo-butenyl-1-one.

The term "monoalkylaminocarbonylalkenyl" embraces monoalkylaminocarbonyl attached to a molecular scaffold through alkenyl, or having a terminal alkenyl. Examples of monoalkylaminocarbonylalkenyl include N-ethyl-4-amino-4-oxobutenyl and N-methyl-3-amino-3-oxopropenyl.

The term "dialkylaminocarbonylalkenyl" embraces dialkylaminocarbonyl attached to a molecular scaffold through alkenyl, or having a terminal alkenyl. Examples of dialkylaminocarbonylalkenyl include N-ethyl-N-methyl-4-amino-4-oxobutenyl and N,N-dimethyl-3-amino-3-oxopropenyl.

The term "monoalkylaminocarbonylalkenylcarbonyl" embraces monoalkylaminocarbonylalkenyl attached to a molecular scaffold through carbonyl. An example of monoalkylaminocarbonylalkenylcarbonyl includes N-ethyl-4-amino-4-oxobutenyl-1-one.

The term "dialkylaminocarbonylalkenylcarbonyl" embraces dialkylaminocarbonylalkenyl attached to a molecular scaffold through carbonyl. Examples of dialkylaminocarbonylalkenylcarbonyl include N-ethyl-N-methyl-4-amino-4-oxobutenyl-1-one and N,N-dimethyl-3-amino-3-oxopropenyl-1-one.

The term "heteroarylcarbonyl" embraces heteroaryl attached to a molecular scaffold through carbonyl. Examples of heteroarylcarbonyl include pyridylcarbonyl and thiazolylcarbonyl.

The term "heteroarylcarbonylalkenyl" embraces heteroarylcarbonyl attached to a molecular scaffold through alkenyl, or having a terminal alkenyl. An example of heteroarylcarbonylalkenyl includes oxazolyl-propenylone.

The term "aminoalkenyl" embraces a primary-amino substituted alkenyl radical. A non-limiting example of aminoalkenyl includes aminopropenyl.

The term "hydroxyalkenyl" embraces a hydroxy radical attached to alkenyl, wherein any one or more of the carbon atoms are substituted with hydroxy. Examples of hydroxyalkenyl include hydroxypropenyl and hydroxylbutenyl.

The term "hydroxyalkenylcarbonyl" embraces hydroxyalkenyl attached to a molecular scaffold through carbonyl. Non-limiting examples of hydroxyalkenylcarbonyl include hydroxypropenylcarbonyl and hydroxymethylacryl.

The term "alkynylcarbonyl" embraces alkynyl attached to a molecular scaffold through carbonyl. Non-limiting examples of alkynylcarbonyl include ethynylcarbonyl and propynylcarbonyl.

The term "hydroxyalkynyl" embraces a hydroxy radical attached to substitutable alkynyl carbon atom, wherein any one or more of the carbon atoms are substituted with hydroxy. An example of hydroxyalkynyl includes hydroxypropynyl.

The term "hydroxyalkynylcarbonyl" embraces hydroxyalkynyl attached to molecular scaffold through carbonyl. A non-limiting example of hydroxyalkynylcarbonyl includes hydroxypropynylcarbonyl.

The term "amino" embraces any primary, secondary or tertiary amine-containing radical. An example of an amino radical is $NH_2$—.

An amino radical may be substituted with $R^4$ or $R^5$

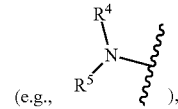

(e.g., $R^5 \diagdown N \diagup R^4$ ), where $R^4$ may be, for example, cyano, haloacyl, alkenylcarbonyl, hydroxyalkenylcarbonyl, aminoalkenylcarbonyl, monoalkylaminoalkenylcarbonyl, dialkylaminoalkenylcarbonyl, haloalkenylcarbonyl, cyanoalkenylcarbonyl, alkoxycarbonylalkenylcarbonyl, alkynylcarbonyl, hydroxyalkynylcarbonyl, alkylcarbonylalkenylcarbonyl, arylcarbonylalkenylcarbonyl, cycloalkylcarbonylalkenylcarbonyl, aminocarbonylalkenylcarbonyl, monoalkylaminocarbonylalkenylcarbonyl, dialkylaminocarbonylalkenylcarbonyl or alkenylsulfonyl; and $R^5$ may be, for example, H, alkyl or cycloalkyl.

An amino radical may substituted with $R^{14}$-vinylcyanocarbonyl and $R^{15}$

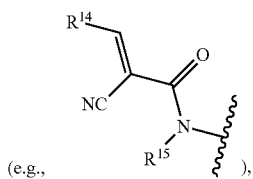
(e.g., ), where $R^{14}$ may be, for example, alkyl, cycloalkyl or aryl; and $R^{15}$ may be, for example, H, alkyl, or cycloalkyl.

The term "cyano" embraces a carbon radical having three of four covalent bonds shared by a single nitrogen atom. The terms "cyano" and "carbonitrile" may be used interchangeably.

The term "cyanoalkyl" embraces alkyl, wherein one of the alkyl carbon atoms is substituted with a cyano radical.

The term "cyanoalkylamino" embraces cyanoalkyl attached to a molecular scaffold through amino. Non-limiting examples of cyanoalkylamino include N-cyanomethylamino

(e.g., ),

N-cyanoethylamino and N-cyanopropylamino.

The term "cyanoalkylcarbonyl" embraces cyanoalkyl attached to a molecular scaffold through carbonyl. An example of cyanoalkylcarbonyl is N-cyanomethylaminocarbonyl.

The term "cyanoalkenyl" embraces cyano attached to a molecular scaffold through alkenyl, or by terminal alkenyl. A non-limiting example of cyanoalkenyl includes cyanovinyl.

The term "cyanoalkenylcarbonyl" embraces cyanoalkenyl attached to a molecular scaffold through carbonyl. Non-limiting examples of cyanoalkenylcarbonyl include cyanovinylcarbonyl and cyanopropenylcarbonyl.

The term "cycloalkylamino" embraces cycloalkyl attached to a molecular scaffold through amino. A non-limiting example of cycloalkylamino includes cyclopropylamino.

The term "cyanocycloalkylamino" embraces cyano attached to a molecular scaffold through a cycloalkylamino radical. A non-limiting example of cyanocycloalkylamino includes N-(1-cyanocyclopropyl)amino

(e.g., ).

The term "carbonyl" embraces a carbon radical having two of four covalent bonds shared with a single oxygen atom.

Carbonyl may be attached to $R^6$

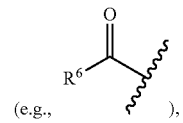
(e.g., ), where $R^6$ may be, for example, alkyl, haloalkyl, alkenyl, hydroxyalkenyl, cyanoalkenyl, haloalkenyl, aminoalkenyl, monoalkylaminoalkenyl, dialkylaminoalkenyl, cyanoalkylamino, aminocarbonylalkenyl, monoalkylaminocarbonylalkenyl, dialkylaminocarbonylalkenyl, alkoxycarbonylalkenyl, alkylcarbonylalkenyl, arylcarbonylalkenyl, heteroarylcarbonylalkenyl, cycloalkylcarbonylalkenyl and cyanocycloalkylamino.

The term "oxo" embraces a radical having the structural formula

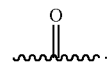

The term "alkoxycarbonyloxy" embraces alkoxycarbonyl attached to a molecular scaffold through an oxygen atom

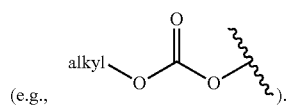
(e.g., ).

The term "alkoxycarbonylalkenyl" embraces alkoxycarbonyl attached to a molecular scaffold through alkenyl, or having a terminal alkenyl

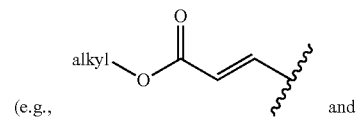
(e.g., and )

The term "alkoxycarbonylalkenylcarbonyl" embraces alkoxycarbonylalkenyl attached to a molecular scaffold through carbonyl

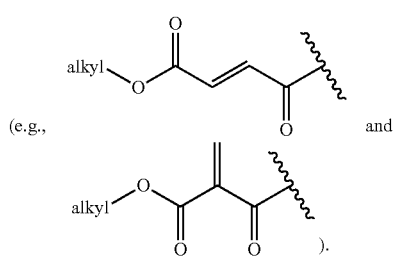
(e.g., and ).

The term "alkoxycarbonylamino" embraces alkoxycarbonyl attached to a molecular scaffold through amino (e.g., 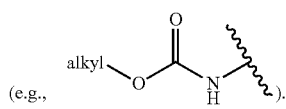).

The term "carbamate" embraces a radical containing a group having the formula —CO₂NH— or —NHCO₂—.

The term "alkoxycarbonylaminoalkylene" embraces alkoxycarbonylamino attached to a molecular scaffold through divalent alkyl (e.g., 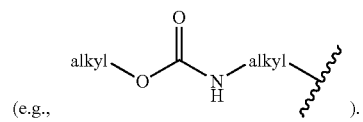).

The term "carboxy" embraces a hydroxy radical attached to one of two unshared bonds in carbonyl (e.g., 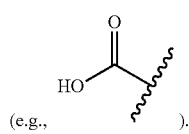).

The term "alkoxycarbonyl" embraces alkoxy attached to molecular scaffold through carbonyl (e.g., 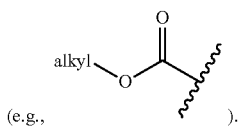).

The term "acylamino" is

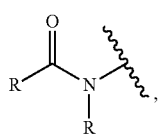, where R may be, for example, H, alkyl, aryl or aralkyl. A more specific example of acylamino is acetylamino.

The term "aminocarbonyl" embraces an amino radical attached to a molecular scaffold through carbonyl. The terms "amido" and "aminocarbonyl" may be used interchangeably.

The term "monoalkylaminocarbonyl" embraces monoalkylamino attached to a molecular scaffold through carbonyl. Examples of monoalkylaminocarbonyl include N-methylaminocarbonyl and N-ethylaminocarbonyl.

The term "dialkylaminocarbonyl" embraces dialkylamino attached to a molecular scaffold through carbonyl. An example of dialkylaminocarbonyl is N,N-dimethylaminocarbonyl, N,N-diethylaminocarbonyl and N-isopropyl-N-methylaminocarbonyl.

The term "ureido" denotes

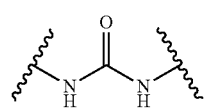 [SMILES: *NC(=O)N*]

and may be used interchangeably with the term "carbamido."

The term "alkylureido" embraces alkyl attached to a molecular scaffold through ureido (e.g., 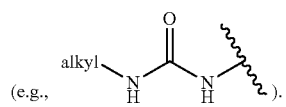).

The term "alkylureidoalkylene" embraces alkylureido attached to a molecular scaffold through divalent alkyl (e.g., 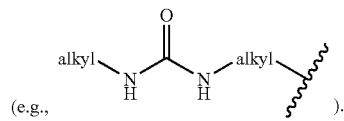).

The term "cyclic ring" embraces any aromatic or non-aromatic cyclized ring system (e.g., aryl and cycloalkyl) that may contain one or more ring heteroatoms (e.g., heteroaryl and heterocyclyl).

The term "cycloalkyl" embraces any monocyclic, bicyclic or tricyclic cyclized ring system of 3 to about 15 carbon atoms that is fully or partially saturated. Cycloalkyl may be attached to, for example, aryl, cycloalkyl or heterocyclyl in a fused or pendant manner. An example of cycloalkyl includes cyclopropyl.

The term "cycloalkenyl" embraces a cycloalkyl radical having at least one carbon-carbon double bound located in the cyclized ring system. Non-limiting examples of cycloalkenyl include cyclopentenyl (i.e., 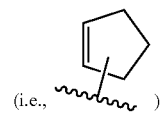)

and cyclohexenyl (i.e., 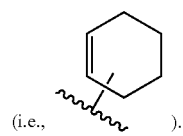).

Cycloalkenyl may be substituted with one or more $R^9$ radicals, where $R^9$ may be, for example, alkyl, oxo, cyano or halo. More specific examples of cycloalkenyl substituted with $R^9$ include cyclopentenyl and cyclohexenyl substituted with oxo, yielding cyclopentenylone and cyclohexenylone, respectively.

The term "aryl" embraces a cyclized aromatic hydrocarbon radical. Aryl may be a monocyclic, bicyclic or tricyclic ring system. Aryl may be attached to cycloalkyl, aryl or heterocyclyl in a fused or pendant manner. Examples of aryl include phenyl and naphthyl.

The term "arylcarbonyl" embraces aryl attached to a molecular scaffold through carbonyl. Examples of arylcarbonyl include benzoyl and toluoyl. The terms "arylcarbonyl" and "aroyl" may be used interchangeably.

The term "arylalkyl" embraces an aryl-substituted alkyl radical and may be used interchangeably with the term "aralkyl". Examples of aralkyl include benzyl, diphenylmethyl, triphenylmethyl, phenylethyl and diphenylethyl. The terms "benzyl" and "phenylmethyl" may be used interchangeably.

The term "heterocyclyl" embraces a radical composed of a monocyclic, bicyclic or tricyclic cyclized ring system having from 3 to about 15 ring members selected from carbon, nitrogen, sulfur and oxygen, wherein at least one ring member is a heteroatom. Heterocyclyl embraces a fully saturated (e.g., heterocyclylalkyl), partially saturated (e.g., heterocycloalkenyl) and a fully unsaturated radical (e.g., heteroaryl). Heterocyclyl may be fused or attached in a pendant manner to an additional heterocyclyl, aryl or cycloalkyl radical. Heterocyclyl embraces combinations of different heteroatoms within the same cyclized ring system. Non-limiting examples of fully saturated five- and six-membered heterocyclyl include pyrrolidinyl, imidazolidinyl, piperidinyl, piperazinyl, tetrahydrofuranyl, morpholinyl and thiazolidinyl.

The term "heterocyclylalkyl" embraces a fully saturated, partially saturated, or fully unsaturated heterocyclic ring with an alkyl moiety attached to the heterocyclic ring, wherein the alkyl moiety is further attached to a molecular scaffold. Non-limiting examples of heterocyclylalkyl include

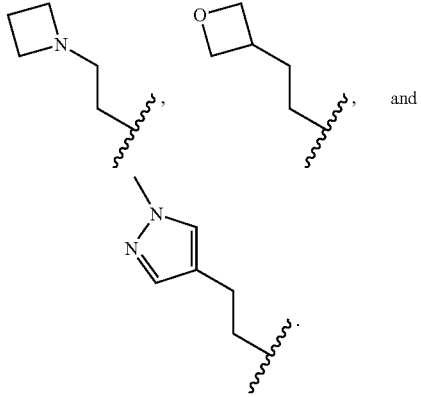

The terms "heterocycloalkyl" and "heterocyclylalkyl" may be used interchangeably.

The term "heterocycloalkenyl" embraces a partially saturated, non-aromatic heterocyclyl radical with at least one carbon-carbon double bond within the cyclized ring system. Non-limiting examples of heterocycloalkenyl include dihydropyrrolyl, dihydropyridinyl, dihydrothiophenyl

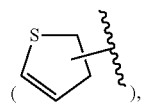

dihydropyranyl, dihydrofuranyl, dihydrothiazolyl and tetrahydropyridinyl.

Heterocycloalkenyl may be substituted with one or more $R^{119}$ radicals, where $R^{119}$ may be, for example, alkyl, oxo, cyano or halo. More specific examples include dihydropyrrolyl and dihydropyridinyl substituted with oxo, yielding pyrrolylone and dihydropyridinylone.

The term "heterocycloalkenylalkenyl" embraces a heterocycloalkenyl radical attached to a molecular scaffold through alkenyl, or having a terminal alkenyl. A non-limiting example of heterocycloalkenylalkenyl includes dihydropyrrolylpropenyl

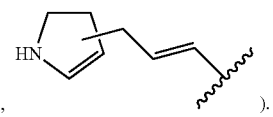

The term "heteroaryl" embraces an aromatic heterocyclyl radical. Heteroaryl may be fused or attached in a pendant manner to an additional heteroaryl, heterocyclyl, aryl or cycloalkyl radical. Heteroaryl embraces combinations of different heteroatoms within the same cyclized ring system. Non-limiting examples of heteroaryl include pyridinyl, thienyl, furanyl, pyrimidinyl, imidazolyl, pyrazolyl, thiazolyl, thiadiazolyl, isothiazolyl, oxazolyl, isoxazolyl, oxadiazolyl, pyrrolyl, pyridazinyl, pyrazinyl, quinolinyl, isoquinolinyl, benzofuranyl, benzothienyl, triazinyl, indolyl, benzothiazolyl, benzooxazolyl, benzimidazolyl, isoindolyl, benzotriazolyl

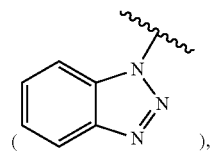

purinyl and thianaphthenyl. The term "heteroaryl" is also understood to include the N-oxide derivative of any nitrogen containing heteroaryl.

Heteroaryl may be substituted with one or more $R^{19}$ radicals, where $R^{19}$ may be, for example alkyl, cyano or halo. Examples of cyano-substituted 6-membered heteroaryl include cyanopyridazinyl, cyanopyridinyl, cyanopyrimidinyl and cyanotriazinyl. Examples of cyano- or chloro-substituted 5-membered heteroaryl include cyanooxazolyl, cyanoisoxazolyl, cyanooxadiazolyl, cyanothiadiazolyl and chlorothiadiazolyl.

The term "monoalkylamino" embraces a single alkyl radical attached to a molecular scaffold through amino (e.g., alkyl-NH-molecular scaffold). A specific non-limiting example of monoalkylamino includes N-methylamino.

The term "dialkylamino" embraces two alkyl radicals attached to a molecular scaffold through amino

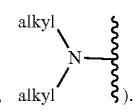

Non-limiting examples of dialkylamino include N,N-dimethylamino and N-isopropyl-N-methylamino.

The term "aminoalkyl" embraces a primary amino substituted alkyl radical (e.g., NH$_2$-alkyl-molecular scaffold).

The term "monoalkylaminoalkenyl" embraces monoalkylamino attached to molecular scaffold through alkenyl, or having a terminal alkenyl. A non-limiting example of monoalkylaminoalkenyl includes N-methylaminopropenyl.

The term "dialkylaminoalkenyl" embraces dialkylamino attached to a molecular scaffold through alkenyl, or having a terminal alkenyl. A non-limiting example of dialkylaminoalkenyl includes N,N-dimethylaminopropenyl.

The term "monoalkylaminoalkylene" embraces monoalkylamino attached to a molecular scaffold through divalent alkyl. Non-limiting examples of monoalkylaminoalkylene include N-methylaminopropyl and N-ethylaminopropyl.

The term "dialkylaminoalkylene" embraces dialkylamino attached to a molecular scaffold through divalent alkyl. Non-limiting examples of dialkylaminoalkylene include N,N-dimethylaminopropyl and N,N-diethylaminopropyl.

The term "aminoalkenylcarbonyl" embraces aminoalkenyl attached to a molecular scaffold through carbonyl. Non-limiting examples of aminoalkenylcarbonyl include aminopropenylcarbonyl and aminoethenylcarbonyl.

The term "alkylaminoalkenylcarbonyl" embraces alkylaminoalkenyl attached to a molecular scaffold through carbonyl. Non-limiting examples of alkylaminoalkenylcarbonyl include N-methylaminopropenylcarbonyl and N-ethylaminopropenylcarbonyl.

The term "dialkylaminoalkenylcarbonyl" embraces dialkylaminoalkenyl attached to a molecular scaffold through carbonyl. Examples of dialkylaminoalkenylcarbonyl include N,N-dimethylaminopropenylcarbonyl and N,N-diethylaminopropenylcarbonyl.

The term "aralkoxy" embraces arylalkyl attached to a molecular scaffold through an oxygen atom. The terms "arylalkoxy" and "aralkoxy" may be used interchangeably.

The term "aryloxy" embraces aryl attached to a molecular scaffold through an oxygen atom.

The term "aryloxyalkylene" embraces aryloxy attached to a molecular scaffold through divalent alkyl.

The term "sulfonyl" embraces a divalent radical having the structural formula

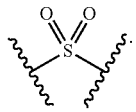

Sulfonyl may be attached to R$^8$ (e.g., 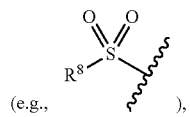), where R$^8$ may be, for example, alkenyl, hydroxyalkenyl or cycloalkenyl. More specific examples of sulfonyl substituted with R$^8$ include, vinylsulfonyl, propenylsulfonyl, hydroxypropenylsulfonyl, cyclopentenylsulfonyl and cyclohexenylsulfonyl.

The term "alkylsulfonyl" embraces alkyl attached to a molecular scaffold through sulfonyl.

The term "alkylsulfonylamino" embraces alkylsulfonyl attached to a molecular scaffold through amino.

The term "monoalkylaminosulfonyl" embraces monoalkylamino attached to a molecular scaffold through sulfonyl.

The term "dialkylaminosulfonyl" embraces dialkylamino attached to a molecular scaffold through sulfonyl.

The term "arylsulfonyl" embraces aryl attached to a molecular scaffold through sulfonyl.

The term "heteroarylsulfonyl" embraces heteroaryl attached to a molecular scaffold through sulfonyl.

The term "alkylsulfonylalkylene" embraces alkylsulfonyl attached to a molecular scaffold through divalent alkyl.

The phrase "attached to a molecular scaffold through alkenyl, or having a terminal alkenyl" embraces the following attachment orientations:

A)

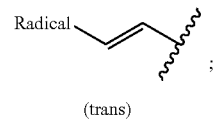

(trans)

B)

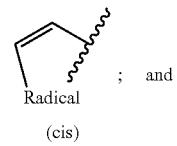

(cis)

C)

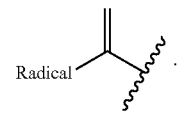

The term "methenyl" embraces a radical having the structural formula

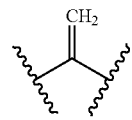

The terms "methylidyne" and "methenyl" may be used interchangeably.

The term "pharmaceutically-acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals, and more particularly in humans.

The term "pharmaceutically-acceptable salt" refers to a salt which may enhance desired pharmacological activity or may enhance stability of a compound. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, hydriodic acid, sulfuric acid, nitric acid and phosphoric acid. Examples of acid addition salts formed with organic acids include acetic acid, trifluoroacetic acid, propionic acid, hexanoic acid, heptanoic acid, cyclopentanepropionic acid, glycolic acid, pyruvic acid, lactic acid, citric acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, glucoheptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxynaphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases (e.g., cytosine, thymine, uracil and guanine).

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "solvate" embraces a molecular or ionic complex of molecules or ions of solvent with those of a compound of the present invention. The term "solvate" embraces the term "hydrate".

The term "hydrate" embraces a compound of the present invention containing water combined in the molecular form.

Some of the compounds described herein contain one or more stereocenters and are meant to include R, S and mixtures of R and S forms for each stereocenter present.

List of Abbreviations:
ACN acetonitrile
Boc tert-butyloxycarbonyl
DCI dicyclohexylcarbodiimide
DCM dichloromethane or methylenedichloride
DIEA diisopropylethylamine
DMAP 4-dimethylaminopyridine or NN-dimethylaminopyridine
DMA (PhNMe$_2$) dimethylaminobenzene or dimethylaniline
DMF N,N-dimethylformamide
DME 1,2-dimethoxyethane
DMSO dimethylsulfoxide
eq. equivalents
EtOAC ethyl acetate
EtOH ethanol
Fmoc fluorenylmethyloxycarbonyl chloride
HATU O-(7-azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HOBT hydroxybenzotriazole
HPLC high performance liquid chromatography
h hour(s)
KOH potassium hydroxide
K$_2$CO$_3$ potassium carbonate
L liter
LiOH lithium hydroxide
LC/MS liquid chromatography mass spectrometry
LC/MS/MS liquid chromatography tandem mass spectrometry
LLOD lower limit of detection
MeOH methanol
MgSO$_4$ magnesium sulfate
MSD Meso Scale Discovery
min. minute(s)
mL milliliter
mmol millimole
Na$_2$S$_2$O$_3$ sodium thiosulfate
Na$_2$SO$_4$ sodium sulfate
NaH sodium hydride
NaHCO$_3$ sodium bicarbonate
NaI sodium iodide
NaIO$_4$ sodium periodate
NaOCH$_3$ sodium methoxide
NBS N-bromosuccinimide
NIS N-iodosuccinimide
NMR nuclear magnetic resonance
NO nitric oxide
Pd(dppf)Cl$_2$ [1,1'-Bis(diphenylphosphino)ferrocene]dichloropalladium(II)
POCl$_3$ phosphorus oxychloride
psi pounds per square inch
RuCl$_3$ ruthenium trichloride hydrate
TEA triethylamine
TFA trifluoroacetic acid
THF tetrahydrofuran
TLC thin layer chromatography
TSA p-toluenesulfonic acid Non-limiting examples of compounds of the present invention include:

| Ex. # | Structure | Name |
|---|---|---|
| 1 | 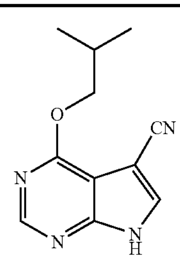 | 4-isobutoxy-7H-pyrrolo[2,3-d]pyrimidine-5-carbonitrile |

| Ex. # | Structure | Name |
|---|---|---|
| 2 | 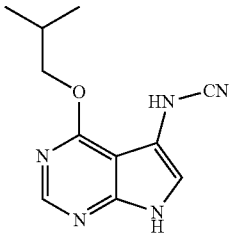 [SMILES: CC(C)COc1ncnc2[nH]cc(NC#N)c12] | N-(4-isobutoxy-7H-pyrrolo[2,3-d]pyrimidin-5-yl)cyanamide |
| 3 | 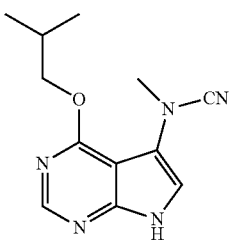 | N-(4-isobutoxy-7H-pyrrolo[2,3-d]pyrimidin-5-yl)-N-methylcyanamide |
| 4 | 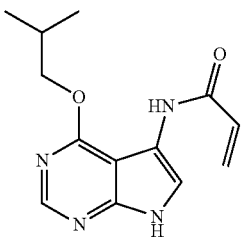 [SMILES: C=CC(=O)Nc1c[nH]c2ncnc(OCC(C)C)c12] | N-(4-isobutoxy-7H-pyrrolo[2,3-d]pyrimidin-5-yl)acrylamide |
| 5 | 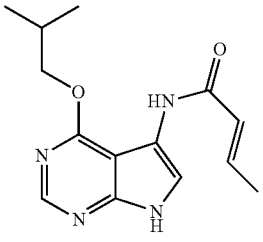 [SMILES: C/C=C/C(=O)Nc1c[nH]c2ncnc(OCC(C)C)c12] | (E)-N-(4-isobutoxy-7H-pyrrolo[2,3-d]pyrimidin-5-yl)but-2-enamide |
| 6 | 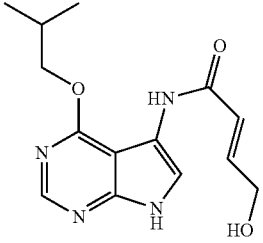 [SMILES: CC(C)COc1ncnc2[nH]cc(NC(=O)/C=C/CO)c12] | (E)-4-hydroxy-N-(4-isobutoxy-7H-pyrrolo[2,3-d]pyrimidin-5-yl)but-2-enamide |
| 7 | 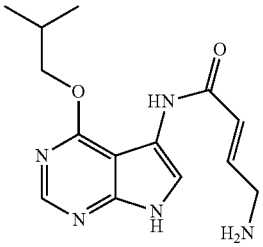 [SMILES: CC(C)COc1ncnc2[nH]cc(NC(=O)/C=C/CN)c12] | (E)-4-amino-N-(4-isobutoxy-7H-pyrrolo[2,3-d]pyrimidin-5-yl)but-2-enamide |

-continued

| Ex. # | Structure | Name |
|---|---|---|
| 8 | 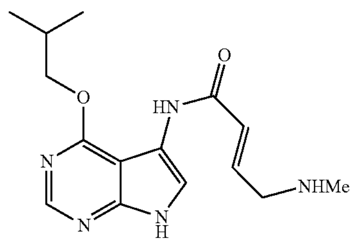 [SMILES: CNC/C=C/C(=O)Nc1c[nH]c2ncnc(OCC(C)C)c12] | (E)-N-(4-isobutoxy-7H-pyrrolo[2,3-d]pyrimidin-5-yl)-4-(methylamino)but-2-enamide |
| 9 | 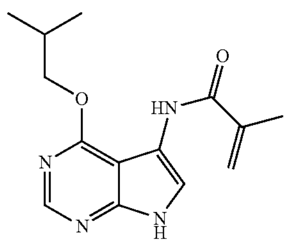 [SMILES: C=C(C)C(=O)Nc1c[nH]c2ncnc(OCC(C)C)c12] | N-(4-isobutoxy-7H-pyrrolo[2,3-d]pyrimidin-5-yl)methacrylamide |
| 10 | 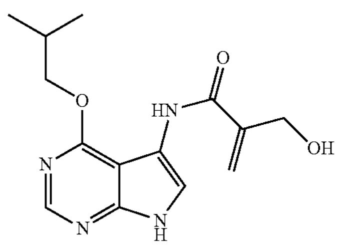 [SMILES: C=C(CO)C(=O)Nc1c[nH]c2ncnc(OCC(C)C)c12] | 2-(hydroxymethyl)-N-(4-isobutoxy-7H-pyrrolo[2,3-d]pyrimidin-5-yl)acrylamide |
| 11 | 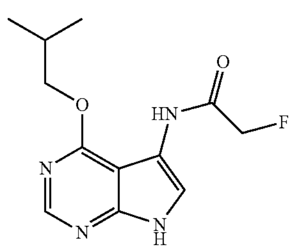 [SMILES: CC(C)COc1ncnc2[nH]cc(NC(=O)CF)c12] | 2-fluoro-N-(4-isobutoxy-7H-pyrrolo[2,3-d]pyrimidin-5-yl)acetamide |
| 12 | 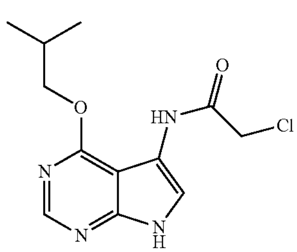 [SMILES: CC(C)COc1ncnc2[nH]cc(NC(=O)CCl)c12] | 2-chloro-N-(4-isobutoxy-7H-pyrrolo[2,3-d]pyrimidin-5-yl)acetamide |
| 13 | 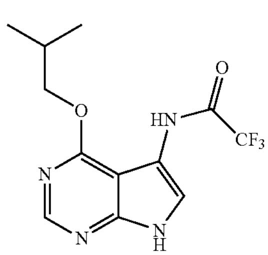 [SMILES: CC(C)COc1ncnc2[nH]cc(NC(=O)C(F)(F)F)c12] | 2,2,2-trifluoro-N-(4-isobutoxy-7H-pyrrolo[2,3-d]pyrimidin-5-yl)acetamide |

-continued

| Ex. # | Structure | Name |
|---|---|---|
| 14 | 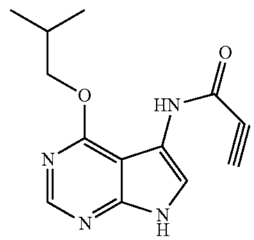 [SMILES: C#CC(=O)Nc1c[nH]c2ncnc(OCC(C)C)c12] | N-(4-isobutoxy-7H-pyrrolo[2,3-d]pyrimidin-5-yl)propiolamide |
| 15 | 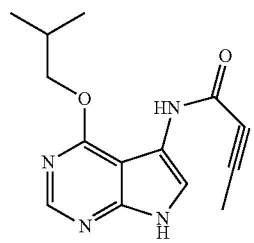 [SMILES: CC#CC(=O)Nc1c[nH]c2ncnc(OCC(C)C)c12] | N-(4-isobutoxy-7H-pyrrolo[2,3-d]pyrimidin-5-yl)but-2-ynamide |
| 16 | 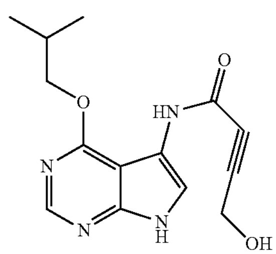 [SMILES: CC(C)COc1ncnc2[nH]cc(NC(=O)C#CCO)c12] | 4-hydroxy-N-(4-isobutoxy-7H-pyrrolo[2,3-d]pyrimidin-5-yl)but-2-ynamide |
| 17 | 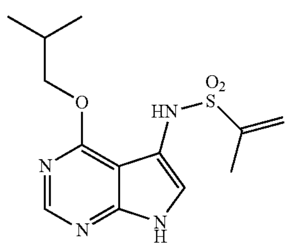 [SMILES: C=C(C)S(=O)(=O)Nc1c[nH]c2ncnc(OCC(C)C)c12] | N-(4-isobutoxy-7H-pyrrolo[2,3-d]pyrimidin-5-yl)prop-1-ene-2-sulfonamide |
| 18 | 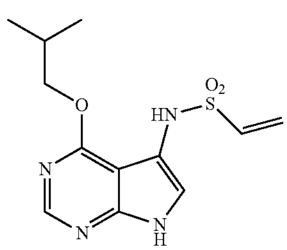 [SMILES: C=CS(=O)(=O)Nc1c[nH]c2ncnc(OCC(C)C)c12] | N-(4-isobutoxy-7H-pyrrolo[2,3-d]pyrimidin-5-yl)ethenesulfonamide |
| 19 | 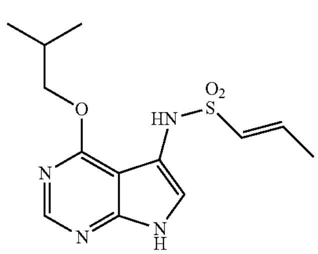 [SMILES: C/C=C/S(=O)(=O)Nc1c[nH]c2ncnc(OCC(C)C)c12] | (E)-N-(4-isobutoxy-7H-pyrrolo[2,3-d]pyrimidin-5-yl)prop-1-ene-1-sulfonamide |

| Ex. # | Structure | Name |
|---|---|---|
| 20 | 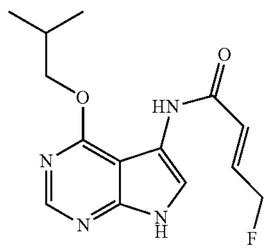 [SMILES: CC(C)COc1ncnc2[nH]cc(NC(=O)/C=C/CF)c12] | (E)-4-fluoro-N-(4-isobutoxy-7H-pyrrolo[2,3-d]pyrimidin-5-yl)but-2-enamide |
| 21 | 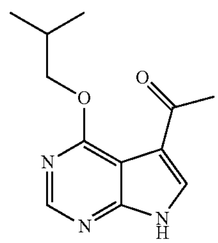 [SMILES: CC(=O)c1c[nH]c2ncnc(OCC(C)C)c12] | 1-(4-isobutoxy-7H-pyrrolo[2,3-d]pyrimidin-5-yl)ethanone |
| 22 | 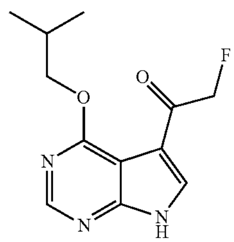 [SMILES: CC(C)COc1ncnc2[nH]cc(C(=O)CF)c12] | 2-fluoro-1-(4-isobutoxy-7H-pyrrolo[2,3-d]pyrimidin-5-yl)ethanone |
| 23 | 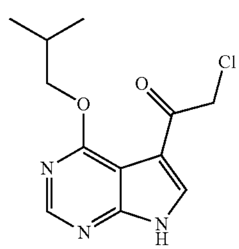 [SMILES: CC(C)COc1ncnc2[nH]cc(C(=O)CCl)c12] | 2-chloro-1-(4-isobutoxy-7H-pyrrolo[2,3-d]pyrimidin-5-yl)ethanone |
| 24 | 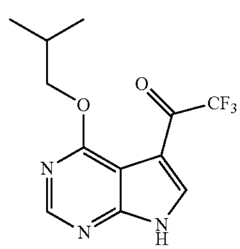 [SMILES: CC(C)COc1ncnc2[nH]cc(C(=O)C(F)(F)F)c12] | 2,2,2-trifluoro-1-(4-isobutoxy-7H-pyrrolo[2,3]pyrimidin-5-yl)ethanone |
| 25 | 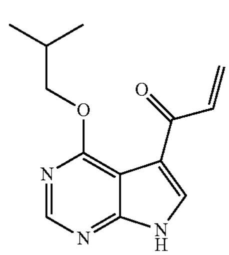 [SMILES: C=CC(=O)c1c[nH]c2ncnc(OCC(C)C)c12] | 1-(4-isobutoxy-7H-pyrrolo[2,3-d]pyrimidin-5-yl)prop-2-en-1-one |

| Ex. # | Structure | Name |
|---|---|---|
| 26 | 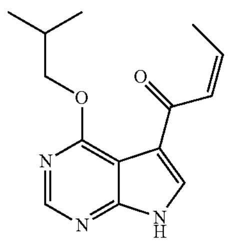 [SMILES: C/C=C\C(=O)c1c[nH]c2ncnc(OCC(C)C)c12] | (Z)-1-(4-isobutoxy-7H-pyrrolo[2,3-d]pyrimidin-5-yl)but-2-en-1-one |
| 27 | 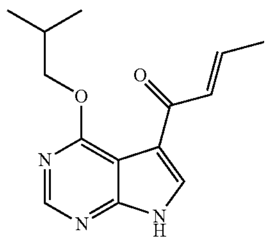 [SMILES: C/C=C/C(=O)c1c[nH]c2ncnc(OCC(C)C)c12] | (E)-1-(4-isobutoxy-7H-pyrrolo[2,3]pyrimidin-5-yl)but-2-en-1-one |
| 28 | 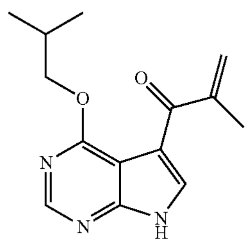 [SMILES: C=C(C)C(=O)c1c[nH]c2ncnc(OCC(C)C)c12] | 1-(4-isobutoxy-7H-pyrrolo[2,3-d]pyrimidin-5-yl)-2-methylprop-2-en-1-one |
| 29 | 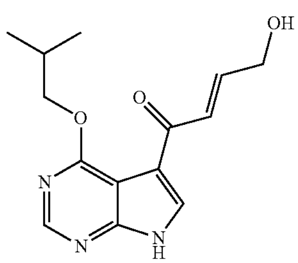 [SMILES: CC(C)COc1ncnc2[nH]cc(C(=O)/C=C/CO)c12] | (E)-4-hydroxy-1-(4-isobutoxy-7H-pyrrolo[2,3-d]pyrimidin-5-yl)but-2-en-1-one |
| 30 | 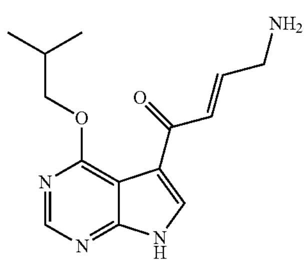 [SMILES: CC(C)COc1ncnc2[nH]cc(C(=O)/C=C/CN)c12] | (E)-4-amino-1-(4-isobutoxy-7H-pyrrolo[2,3-d]pyrimidin-5-yl)but-2-en-1-one |
| 31 | 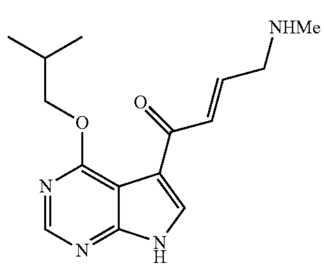 [SMILES: CNC/C=C/C(=O)c1c[nH]c2ncnc(OCC(C)C)c12] | (E)-1-(4-isobutoxy-7H-pyrrolo[2,3-d]pyrimidin-5-yl)-4-(methylamino)but-2-en-1-one |

| Ex. # | Structure | Name |
|---|---|---|
| 32 | 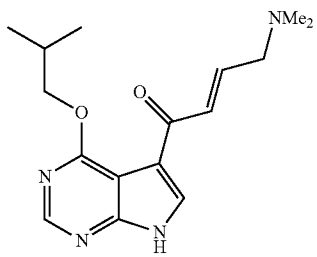 [SMILES: CC(C)COc1ncnc2[nH]cc(C(=O)/C=C/CN(C)C)c12] | (E)-4-(dimethylamino)-1-(4-isobutoxy-7H-pyrrolo[2,3-d]pyrimidin-5-yl)but-2-en-1-one |
| 33 | 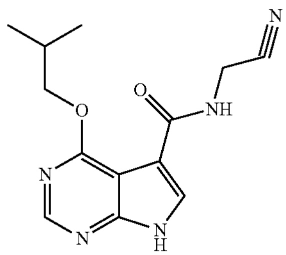 [SMILES: CC(C)COc1ncnc2[nH]cc(C(=O)NCC#N)c12] | N-(cyanomethyl)-4-isobutoxy-7H-pyrrolo[2,3-d]pyrimidine-5-carboxamide |
| 34 | 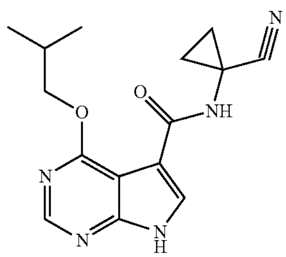 [SMILES: CC(C)COc1ncnc2[nH]cc(C(=O)NC3(C#N)CC3)c12] | N-(1-cyanocyclopropyl)-4-isobutoxy-7H-pyrrolo[2,3-d]pyrimidine-5-carboxamide |
| 35 | 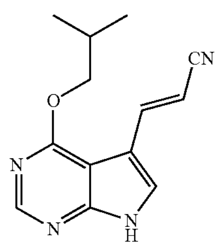 [SMILES: CC(C)COc1ncnc2[nH]cc(/C=C/C#N)c12] | (E)-3-(4-isobutoxy-7H-pyrrolo[2,3-d]pyrimidin-5-yl)acrylonitrile |
| 36 | 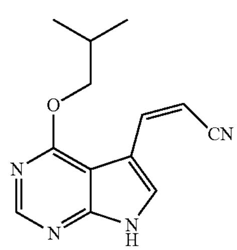 [SMILES: CC(C)COc1ncnc2[nH]cc(/C=C\C#N)c12] | (Z)-3-(4-isobutoxy-7H-pyrrolo[2,3-d]pyrimidin-5-yl)acrylonitrile |
| 37 | 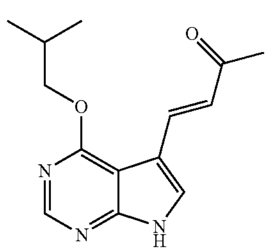 [SMILES: CC(=O)/C=C/c1c[nH]c2ncnc(OCC(C)C)c12] | (E)-4-(4-isobutoxy-7H-pyrrolo[2,3-d]pyrimidin-5-yl)but-3-en-2-one |

-continued

| Ex. # | Structure | Name |
|---|---|---|
| 38 | 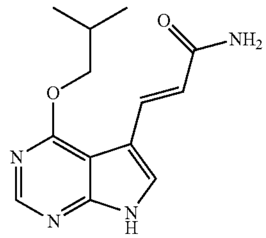 [SMILES: CC(C)COc1ncnc2[nH]cc(/C=C/C(N)=O)c12] | (E)-3-(4-isobutoxy-7H-pyrrolo[2,3-d]pyrimidin-5-yl)acrylamide |
| 39 | 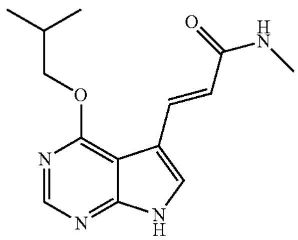 [SMILES: CNC(=O)/C=C/c1c[nH]c2ncnc(OCC(C)C)c12] | (E)-3-(4-isobutoxy-7H-pyrrolo[2,3-d]pyrimidin-5-yl)-N-methylacrylamide |
| 40 | 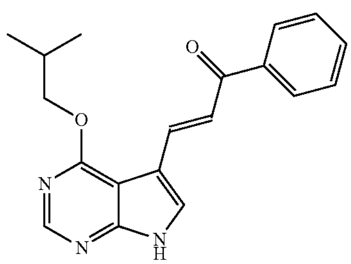 [SMILES: CC(C)COc1ncnc2[nH]cc(/C=C/C(=O)c3ccccc3)c12] | (E)-3-(4-isobutoxy-7H-pyrrolo[2,3-d]pyrimidin-5-yl)-1-phenylprop-2-en-1-one- |
| 41 | 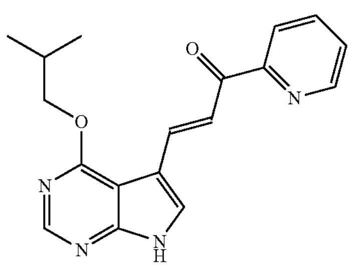 [SMILES: CC(C)COc1ncnc2[nH]cc(/C=C/C(=O)c3ccccn3)c12] | (E)-3-(4-isobutoxy-7H-pyrrolo[2,3-d]pyrimidin-5-yl)-1-(pyridin-2-yl)prop-2-en-1-one |
| 42 | 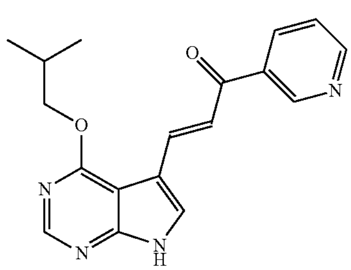 [SMILES: CC(C)COc1ncnc2[nH]cc(/C=C/C(=O)c3cccnc3)c12] | (E)-3-(4-isobutoxy-7H-pyrrolo[2,3-d]pyrimidin-5-yl)-1-(pyridin-3-yl)prop-2-en-1-one |
| 43 | 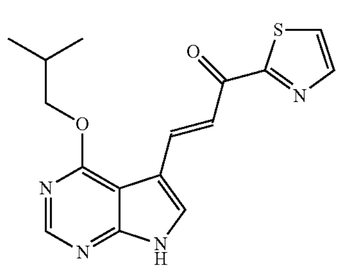 [SMILES: CC(C)COc1ncnc2[nH]cc(/C=C/C(=O)c3nccs3)c12] | (E)-3-(4-isobutoxy-7H-pyrrolo[2,3-d]pyrimidin-5-yl)-1-(thiazol-2-yl)prop-2-en-1-one |

-continued
| Ex. # | Structure | Name |
|---|---|---|
| 44 | 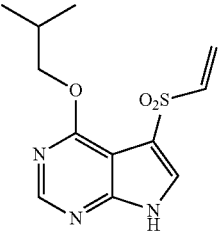 [SMILES: C=CS(=O)(=O)c1c[nH]c2ncnc(OCC(C)C)c12] | 4-isobutoxy-5-(vinylsulfonyl)-7H-pyrrolo[2,3]pyrimidine |
| 45 | 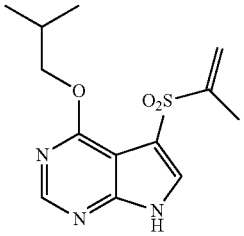 [SMILES: C=C(C)S(=O)(=O)c1c[nH]c2ncnc(OCC(C)C)c12] | 4-isobutoxy-5-(prop-1-en-2-ylsulfonyl)-7H-pyrrolo[2,3-d]pyrimidine |
| 46 | 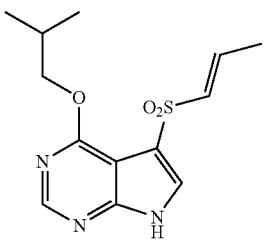 [SMILES: C/C=C/S(=O)(=O)c1c[nH]c2ncnc(OCC(C)C)c12] | (E)-4-isobutoxy-5-(prop-1-en-1-ylsulfonyl)-7H-pyrrolo[2,3-d]pyrimidine |
| 47 | 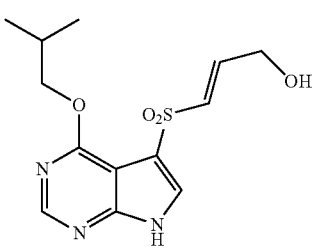 [SMILES: CC(C)COc1ncnc2[nH]cc(S(=O)(=O)/C=C/CO)c12] | (E)-3-((4-isobutoxy-7H-pyrrolo[2,3-d]pyrimidin-5-yl)sulfonyl)prop-2-en-1-ol |
| 48 | 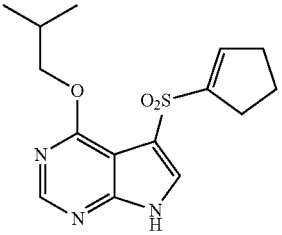 [SMILES: CC(C)COc1ncnc2[nH]cc(S(=O)(=O)C3=CCCC3)c12] | 5-(cyclopent-1-en-1-ylsulfonyl)-4-isobutoxy-7H-pyrrolo[2,3-d]pyrimidine |
| 49 | 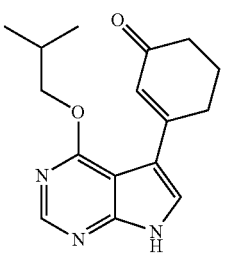 [SMILES: CC(C)COc1ncnc2[nH]cc(C3=CC(=O)CCC3)c12] | 3-(4-isobutoxy-7H-pyrrolo[2,3-d]pyrimidin-5-yl)cyclohex-2-enone |

| Ex. # | Structure | Name |
|---|---|---|
| 50 | 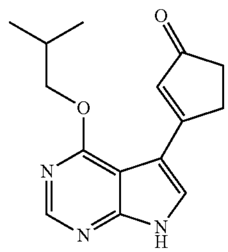 [SMILES: CC(C)COc1ncnc2[nH]cc(C3=CC(=O)CC3)c12] | 3-(4-isobutoxy-7H-pyrrolo[2,3-d]pyrimidin-5-yl)cyclopent-2-enone |
| 51 | 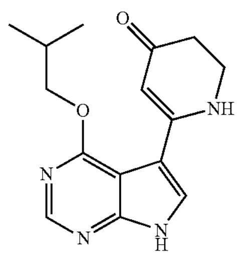 [SMILES: CC(C)COc1ncnc2[nH]cc(C3=CC(=O)CCN3)c12] | 6-(4-isobutoxy-7H-pyrrolo[2,3-d]pyrimidin-5-yl)-2,3-dihydropyridin-4(1H)-one |
| 52 | 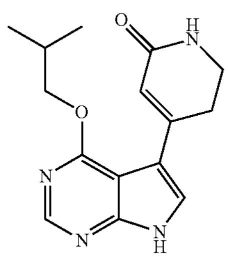 [SMILES: CC(C)COc1ncnc2[nH]cc(C3=CC(=O)NCC3)c12] | 4-(4-isobutoxy-7H-pyrrolo[2,3-d]pyrimidin-5-yl)-5,6-dihydropyridin-2(1H)-one |
| 53 | 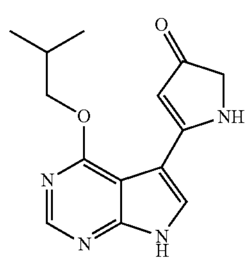 [SMILES: CC(C)COc1ncnc2[nH]cc(C3=CC(=O)CN3)c12] | 5-(4-isobutoxy-7H-pyrrolo[2,3-d]pyrimidin-5-yl)-1H-pyrrol-3(2H)-one |
| 54 | 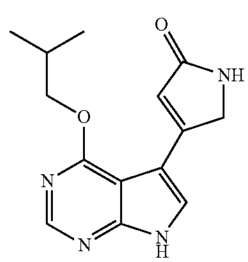 [SMILES: CC(C)COc1ncnc2[nH]cc(C3=CC(=O)NC3)c12] | 4-(4-isobutoxy-7H-pyrrolo[2,3-d]pyrimidin-5-yl)-1H-pyrrol-2(5H)-one |
| 55 | 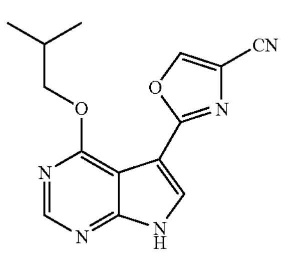 [SMILES: CC(C)COc1ncnc2[nH]cc(-c3nc(C#N)co3)c12] | 2-(4-isobutoxy-7H-pyrrolo[2,3-d]pyrimidin-5-yl)oxazole-4-carbonitrile |

-continued

| Ex. # | Structure | Name |
|---|---|---|
| 56 | 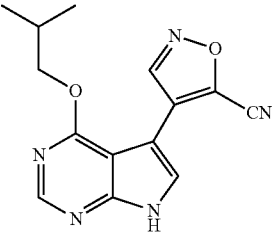 [SMILES: CC(C)COc1ncnc2[nH]cc(-c3cnoc3C#N)c12] | 4-(4-isobutoxy-7H-pyrrolo[2,3-d]pyrimidin-5-yl)isoxazole-5-carbonitrile |
| 57 | 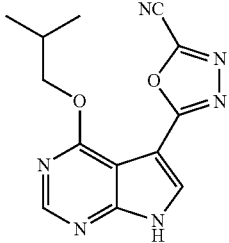 [SMILES: CC(C)COc1ncnc2[nH]cc(-c3nnc(C#N)o3)c12] | 5-(4-isobutoxy-7H-pyrrolo[2,3-d]pyrimidin-5-yl)-1,3,4-oxadiazole-2-carbonitrile |
| 58 | 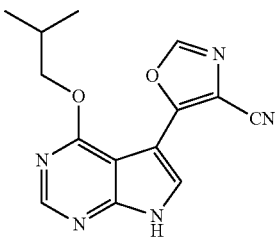 [SMILES: CC(C)COc1ncnc2[nH]cc(-c3ocnc3C#N)c12] | 5-(4-isobutoxy-7H-pyrrolo[2,3-d]pyrimidin-5-yl)oxazole-4-carbonitrile |
| 59 | 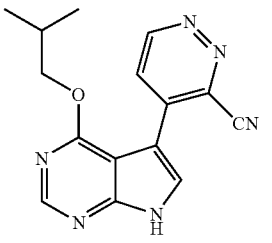 [SMILES: CC(C)COc1ncnc2[nH]cc(-c3ccnnc3C#N)c12] | 4-(4-isobutoxy-7H-pyrrolo[2,3-d]pyrimidin-5-yl)pyridazine-3-carbonitrile |
| 60 | 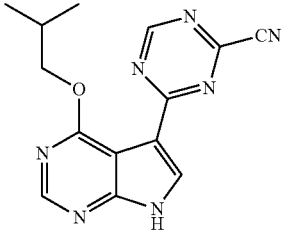 [SMILES: CC(C)COc1ncnc2[nH]cc(-c3ncnc(C#N)n3)c12] | 4-(4-isobutoxy-7H-pyrrolo[2,3-d]pyrimidin-5-yl)-1,3,5-triazine-2-carbonitrile |
| 61 | 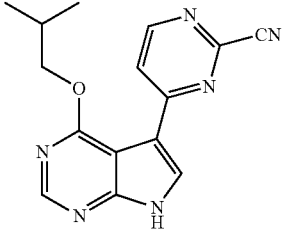 [SMILES: CC(C)COc1ncnc2[nH]cc(-c3ccnc(C#N)n3)c12] | 4-(4-isobutoxy-7H-pyrrolo[2,3-d]pyrimidin-5-yl)pyrimidine-2-carbonitrile |

-continued
| Ex. # | Structure | Name |
|---|---|---|
| 62 | 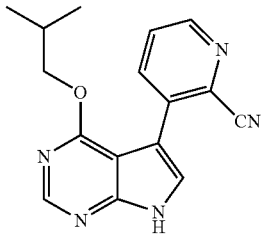 [SMILES: CC(C)COc1ncnc2[nH]cc(-c3cccnc3C#N)c12] | 3-(4-isobutoxy-7H-pyrrolo[2,3-d]pyrimidin-5-yl)picolinonitrile |
| 63 | 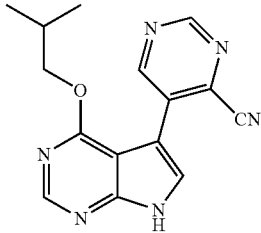 [SMILES: CC(C)COc1ncnc2[nH]cc(-c3cncnc3C#N)c12] | 5-(4-isobutoxy-7H-pyrrolo[2,3-d]pyrimidin-5-yl)pyrimidine-4-carbonitrile |
| 64 | 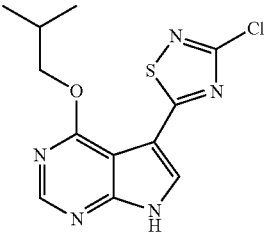 [SMILES: CC(C)COc1ncnc2[nH]cc(-c3nc(Cl)ns3)c12] | 3-chloro-5-(4-isobutoxy-7H-pyrrolo[2,3-d]pyrimidin-5-yl)-1,2,4-thiadiazole |
| 65 | 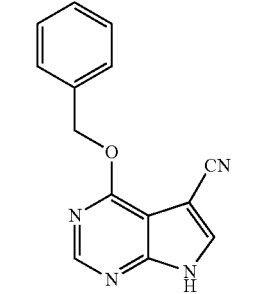 [SMILES: N#Cc1c[nH]c2ncnc(OCc3ccccc3)c12] | 4-(benzyloxy)-7H-pyrrolo[2,3-d]pyrimidine-5-carbonitrile |
| 66 | 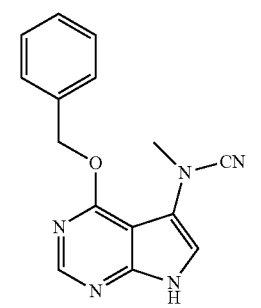 [SMILES: CN(C#N)c1c[nH]c2ncnc(OCc3ccccc3)c12] | N-(4-(benzyloxy)-7H-pyrrolo[2,3-d]pyrimidin-5-yl)-N-methylcyanamide |

-continued
| Ex. # | Structure | Name |
|---|---|---|
| 67 | 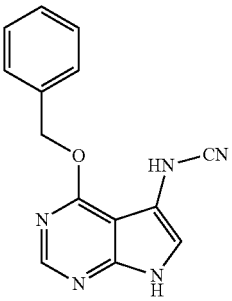 [SMILES: N#CNc1c[nH]c2ncnc(OCc3ccccc3)c12] | N-(4-(benzyloxy)-7H-pyrrolo[2,3-d]pyrimidin-5-yl)cyanamide |
| 68 | 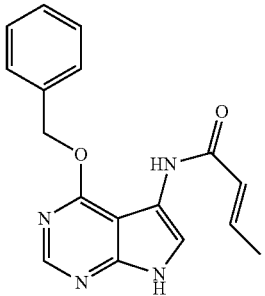 [SMILES: C/C=C/C(=O)Nc1c[nH]c2ncnc(OCc3ccccc3)c12] | (E)-N-(4-(benzyloxy)-7H-pyrrolo[2,3-d]pyrimidin-5-yl)but-2-enamide |
| 69 | 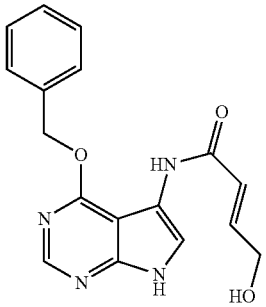 [SMILES: O=C(/C=C/CO)Nc1c[nH]c2ncnc(OCc3ccccc3)c12] | (E)-N-(4-(benzyloxy)-7H-pyrrolo[2,3-d]pyrimidin-5-yl)-4-hydroxybut-2-enamide |
| 70 | 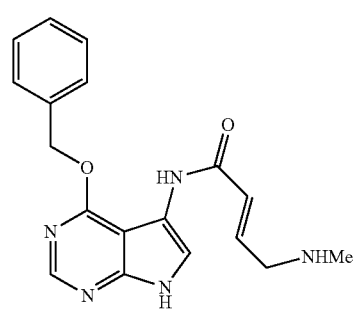 [SMILES: CNC/C=C/C(=O)Nc1c[nH]c2ncnc(OCc3ccccc3)c12] | (E)-N-(4-(benzyloxy)-7H-pyrrolo[2,3-d]pyrimidin-5-yl)-4-(methylamino)but-2-enamide |
| 71 | 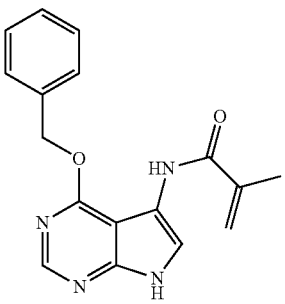 [SMILES: C=C(C)C(=O)Nc1c[nH]c2ncnc(OCc3ccccc3)c12] | N-(4-(benzyloxy)-7H-pyrrolo[2,3-d]pyrimidin-5-yl)methacrylamide |

| Ex. # | Structure | Name |
|---|---|---|
| 72 | 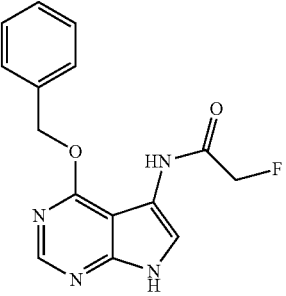 [SMILES: O=C(CF)Nc1c[nH]c2ncnc(OCc3ccccc3)c12] | N-(4-(benzyloxy)-7H-pyrrolo[2,3-d]pyrimidin-5-yl)-2-fluoroacetamide |
| 73 | 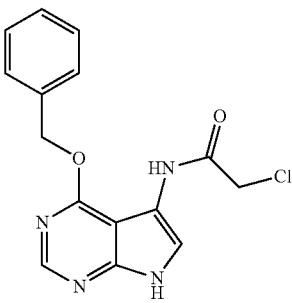 [SMILES: O=C(CCl)Nc1c[nH]c2ncnc(OCc3ccccc3)c12] | N-(4-(benzyloxy)-7H-pyrrolo[2,3-d]pyrimidin-5-yl)-2-chloroacetamide |
| 74 | 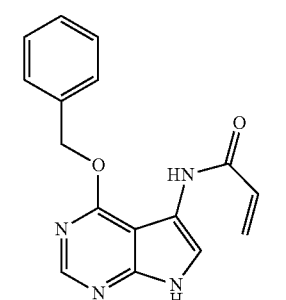 | N-(4-(benzyloxy)-7H-pyrrolo[2,3-d]pyrimidin-5-yl)acrylamide |
| 75 | 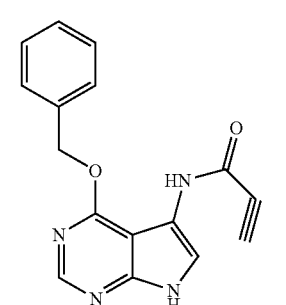 | N-(4-(benzyloxy)-7H-pyrrolo[2,3-d]pyrimidin-5-yl)propiolamide |
| 76 | 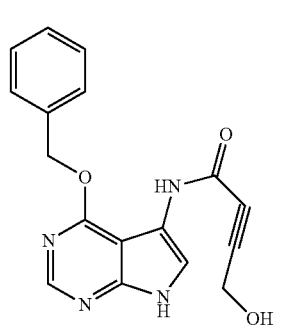 [SMILES: O=C(C#CCO)Nc1c[nH]c2ncnc(OCc3ccccc3)c12] | N-(4-(benzyloxy)-7H-pyrrolo[2,3-d]pyrimidin-5-yl)-4-hydroxybut-2-ynamide |

| Ex. # | Structure | Name |
|---|---|---|
| 77 | 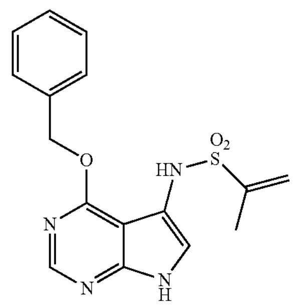 [SMILES: C=C(C)S(=O)(=O)Nc1c[nH]c2ncnc(OCc3ccccc3)c12] | N-(4-(benzyloxy)-7H-pyrrolo[2,3-d]pyrimidin-5-yl)prop-1-ene-2-sulfonamide |
| 78 | 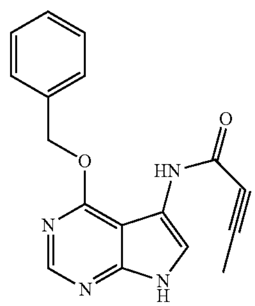 [SMILES: CC#CC(=O)Nc1c[nH]c2ncnc(OCc3ccccc3)c12] | N-(4-(benzyloxy)-7H-pyrrolo[2,3-d]pyrimidin-5-yl)but-2-ynamide |
| 79 | 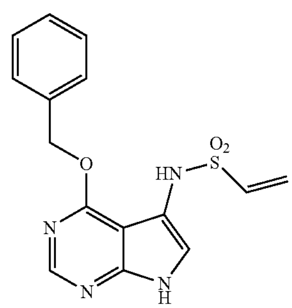 [SMILES: C=CS(=O)(=O)Nc1c[nH]c2ncnc(OCc3ccccc3)c12] | N-(4-(benzyloxy)-7H-pyrrolo[2,3-d]pyrimidin-5-yl)ethenesulfonamide |
| 80 | 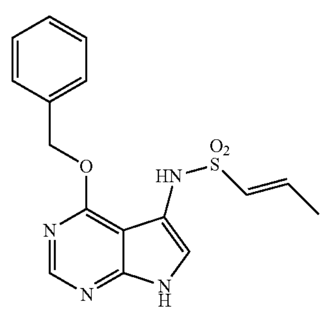 [SMILES: C/C=C/S(=O)(=O)Nc1c[nH]c2ncnc(OCc3ccccc3)c12] | (E)-N-(4-(benzyloxy)-7H-pyrrolo[2,3-d]pyrimidin-5-yl)prop-1-ene-1-sulfonamide |
| 81 | 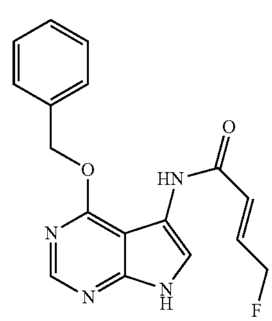 [SMILES: O=C(/C=C/CF)Nc1c[nH]c2ncnc(OCc3ccccc3)c12] | (E)-N-(4-(benzyloxy)-7H-pyrrolo[2,3-d]pyrimidin-5-yl)-4-fluorobut-2-enamide |

-continued

| Ex. # | Structure | Name |
|---|---|---|
| 82 | 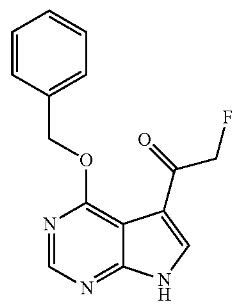 [SMILES: O=C(CF)c1c[nH]c2ncnc(OCc3ccccc3)c12] | 1-(4-(benzyloxy)-7H-pyrrolo[2,3-d]pyrimidin-5-yl)-2-fluoroethanone |
| 83 | 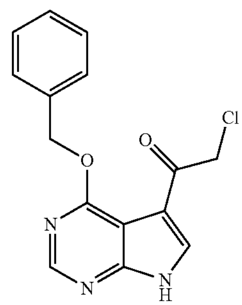 [SMILES: O=C(CCl)c1c[nH]c2ncnc(OCc3ccccc3)c12] | 1-(4-(benzyloxy)-7H-pyrrolo[2,3-d]pyrimidin-5-yl)-2-chloroethanone |
| 84 | 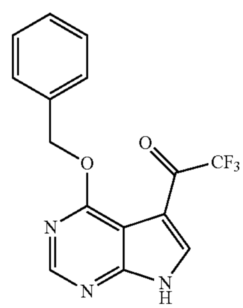 [SMILES: O=C(c1c[nH]c2ncnc(OCc3ccccc3)c12)C(F)(F)F] | 1-(4-(benzyloxy)-7H-pyrrolo[2,3-d]pyrimidin-5-yl)-2,2,2-trifluoroethanone |
| 85 | 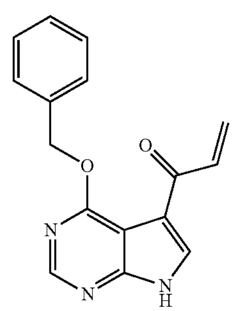 [SMILES: C=CC(=O)c1c[nH]c2ncnc(OCc3ccccc3)c12] | 1-(4-(benzyloxy)-7H-pyrrolo[2,3-d]pyrimidin-5-yl)prop-2-en-1-one |
| 86 | 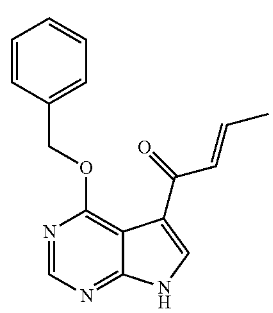 [SMILES: C/C=C/C(=O)c1c[nH]c2ncnc(OCc3ccccc3)c12] | (E)-1-(4-(benzyloxy)-7H-pyrrolo[2,3-d]pyrimidin-5-yl)but-2-en-1-one |

| Ex. # | Structure | Name |
|---|---|---|
| 87 | 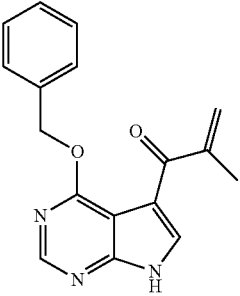 [SMILES: C=C(C)C(=O)c1c[nH]c2ncnc(OCc3ccccc3)c12] | 1-(4-(benzyloxy)-7H-pyrrolo[2,3-d]pyrimidin-5-yl)-2-methylprop-2-en-1-one |
| 88 | 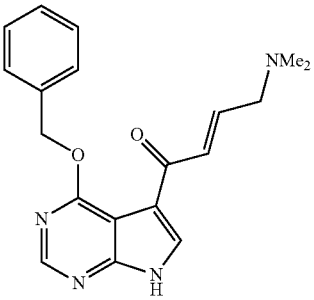 [SMILES: CN(C)C/C=C/C(=O)c1c[nH]c2ncnc(OCc3ccccc3)c12] | (E)-1-(4-(benzyloxy)-7H-pyrrolo[2,3-d]pyrimidin-5-yl)-4-(dimethylamino)but-2-en-1-one |
| 89 | 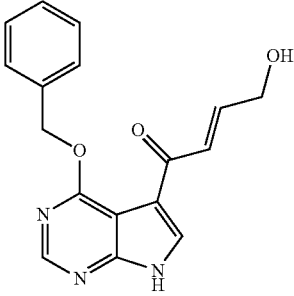 [SMILES: O=C(/C=C/CO)c1c[nH]c2ncnc(OCc3ccccc3)c12] | (E)-1-(4-(benzyloxy)-7H-pyrrolo[2,3-d]pyrimidin-5-yl)-4-hydroxybut-2-en-1-one |
| 90 | 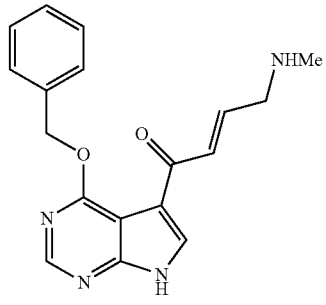 [SMILES: CNC/C=C/C(=O)c1c[nH]c2ncnc(OCc3ccccc3)c12] | (E)-1-(4-(benzyloxy)-7H-pyrrolo[2,3-d]pyrimidin-5-yl)-4-(methylamino)but-2-en-1-one |
| 91 | 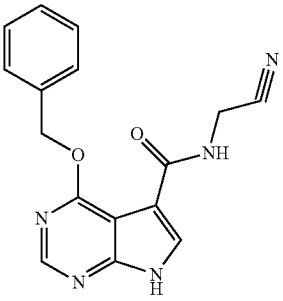 [SMILES: N#CCNC(=O)c1c[nH]c2ncnc(OCc3ccccc3)c12] | 4-(benzyloxy)-N-(cyanomethyl)-7H-pyrrolo[2,3-d]pyrimidine-5-carboxamide |

-continued

| Ex. # | Structure | Name |
|---|---|---|
| 92 | 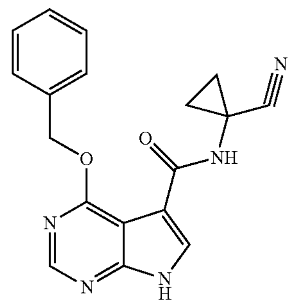 [SMILES: N#CC1(NC(=O)c2c[nH]c3ncnc(OCc4ccccc4)c23)CC1] | 4-(benzyloxy)-N-(1-cyanocyclopropyl)-7H-pyrrolo[2,3-d]pyrimidine-5-carboxamide |
| 93 | 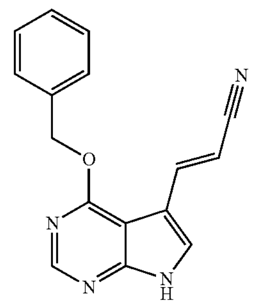 [SMILES: N#C/C=C/c1c[nH]c2ncnc(OCc3ccccc3)c12] | (E)-3-(4-benzyloxy-7H-pyrrolo[2,3-d]pyrimidin-5-yl)-acrylonitrile |
| 94 | 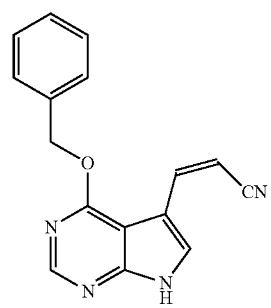 [SMILES: N#C/C=C\c1c[nH]c2ncnc(OCc3ccccc3)c12] | (Z)-3-(4-(benzyloxy)-7H-pyrrolo[2,3-d]pyrimidin-5-yl)acrylonitrile |
| 95 | 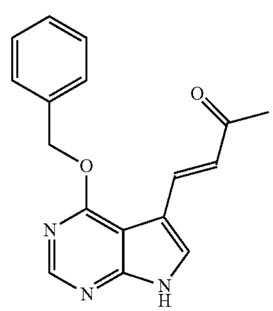 [SMILES: CC(=O)/C=C/c1c[nH]c2ncnc(OCc3ccccc3)c12] | (E)-4-(4-(benzyloxy)-7H-pyrrolo[2,3-d]pyrimidin-5-yl)but-3-en-2-one |
| 96 | 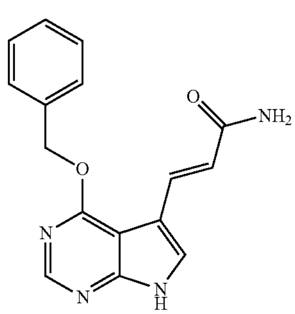 [SMILES: NC(=O)/C=C/c1c[nH]c2ncnc(OCc3ccccc3)c12] | (E)-3-(4-benzyloxy-7H-pyrrolo[2,3-d]pyrimidin-5-yl)-acrylamide |

| Ex. # | Structure | Name |
|---|---|---|
| 97 | 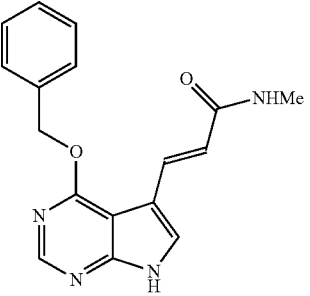 [SMILES: CNC(=O)/C=C/c1c[nH]c2ncnc(OCc3ccccc3)c12] | (E)-3-(4-(benzyloxy)-7H-pyrrolo[2,3-d]pyrimidin-5-yl)-N-methylacrylamide |
| 98 | 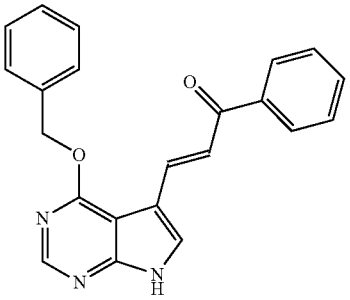 [SMILES: O=C(/C=C/c1c[nH]c2ncnc(OCc3ccccc3)c12)c1ccccc1] | (E)-3-(4-(benzyloxy)-7H-pyrrolo[2,3-d]pyrimidin-5-yl)-1-phenylprop-2-en-1-one |
| 99 | 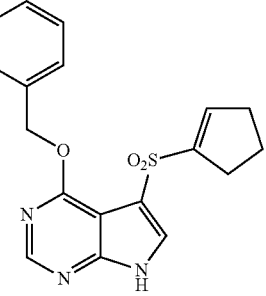 | 4-(benzyloxy)-5-(cyclopent-1-en-1-ylsulfonyl)-7H-pyrrolo[2,3-d]pyrimidine |
| 100 | 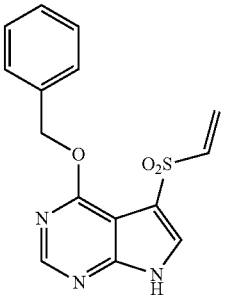 [SMILES: C=CS(=O)(=O)c1c[nH]c2ncnc(OCc3ccccc3)c12] | 4-(benzyloxy)-5-(vinylsulfonyl)-7H-pyrrolo[2,3-d]pyrimidine |
| 101 | 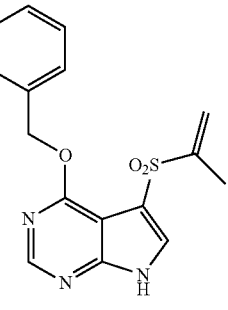 | 4-(benzyloxy)-5-(prop-1-en-2-ylsulfonyl)-7H-pyrrolo[2,3-d]pyrimidine |

| Ex. # | Structure | Name |
|---|---|---|
| 102 | 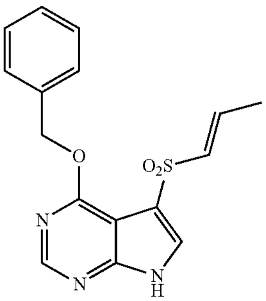 [SMILES: C/C=C/S(=O)(=O)c1c[nH]c2ncnc(OCc3ccccc3)c12] | (E)-4-(benzyloxy)-5-(prop-1-en-1-ylsulfonyl)-7H-pyrrolo[2,3-d]pyrimidine |
| 103 | 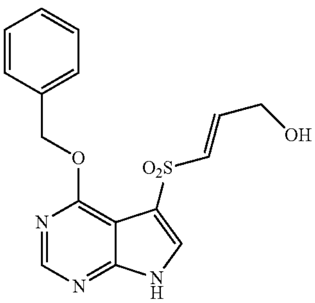 [SMILES: O=S(=O)(/C=C/CO)c1c[nH]c2ncnc(OCc3ccccc3)c12] | (E)-3-((4-(benzyloxy)-7H-pyrrolo[2,3-d]pyrimidin-5-yl)sulfonyl)prop-2-en-1-ol |
| 104 | 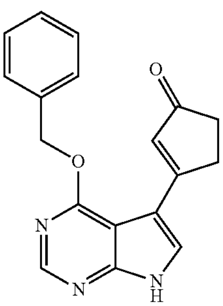 [SMILES: O=C1C=C(c2c[nH]c3ncnc(OCc4ccccc4)c23)CC1] | 3-(4-(benzyloxy)-7H-pyrrolo[2,3-d]pyrimidin-5-yl)cyclopent-2-enone |
| 105 | 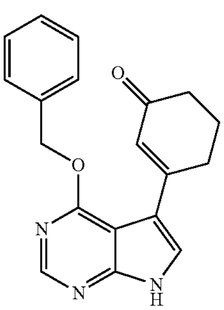 [SMILES: O=C1C=C(c2c[nH]c3ncnc(OCc4ccccc4)c23)CCC1] | 3-(4-(benzyloxy)-7H-pyrrolo[2,3-d]pyrimidin-5-yl)cyclohex-2-enone |
| 106 | 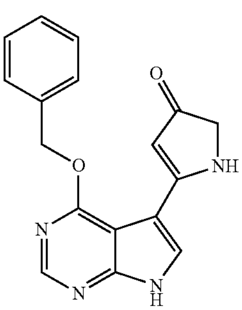 [SMILES: O=C1C=C(c2c[nH]c3ncnc(OCc4ccccc4)c23)NC1] | 5-(4-(benzyloxy)-7H-pyrrolo[2,3-d]pyrimidin-5-yl)-1H-pyrrol-3(2H)-one |

-continued

| Ex. # | Structure | Name |
|---|---|---|
| 107 | 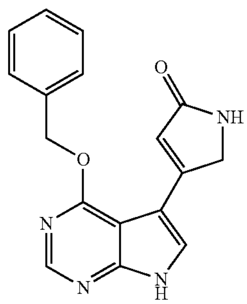 [SMILES: O=C1C=C(c2c[nH]c3ncnc(OCc4ccccc4)c23)CN1] | 4-(4-(benzyloxy)-7H-pyrrolo[2,3-d]pyrimidin-5-yl)-1H-pyrrol-2(5H)-one |
| 108 | 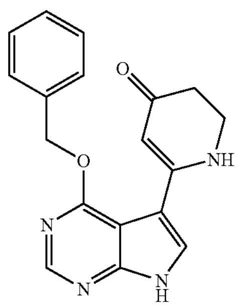 [SMILES: O=C1C=C(c2c[nH]c3ncnc(OCc4ccccc4)c23)NCC1] | 6-(4-(benzyloxy)-7H-pyrrolo[2,3-d]pyrimidin-5-yl)-2,3-dihydropyridin-4(1H)-one |
| 109 | 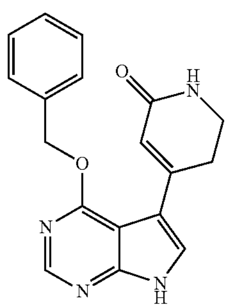 [SMILES: O=C1C=C(c2c[nH]c3ncnc(OCc4ccccc4)c23)CCN1] | 4-(4-(benzyloxy)-7H-pyrrolo[2,3-d]pyrimidin-5-yl)-5,6-dihydropyridin-2(1H)-one |
| 110 | 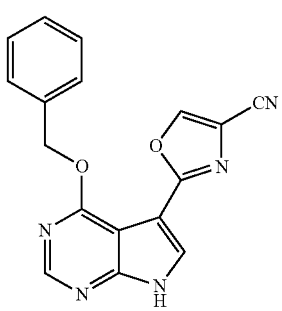 [SMILES: N#Cc1coc(-c2c[nH]c3ncnc(OCc4ccccc4)c23)n1] | 2-(4-(benzyloxy)-7H-pyrrolo[2,3-d]pyrimidin-5-yl)oxazole-4-carbonitrile |
| 111 | 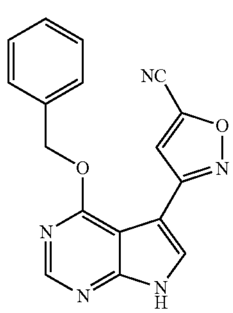 [SMILES: N#Cc1cc(-c2c[nH]c3ncnc(OCc4ccccc4)c23)no1] | 3-(4-(benzyloxy)-7H-pyrrolo[2,3-d]pyrimidin-5-yl)isoxazole-5-carbonitrile |

-continued

| Ex. # | Structure | Name |
|---|---|---|
| 112 | 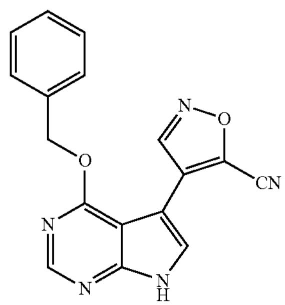 [SMILES: N#Cc1oncc1-c1c[nH]c2ncnc(OCc3ccccc3)c12] | 4-(4-(benzyloxy)-7H-pyrrolo[2,3-d]pyrimidin-5-yl)isoxazole-5-carbonitrile |
| 113 | 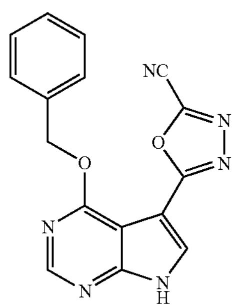 [SMILES: N#Cc1nnc(-c2c[nH]c3ncnc(OCc4ccccc4)c23)o1] | 5-(4-(benzyloxy)-7H-pyrrolo[2,3-d]pyrimidin-5-yl)-1,3,4-oxadiazole-2-carbonitrile |
| 114 | 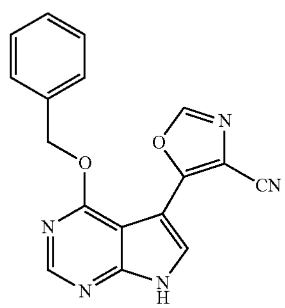 [SMILES: N#Cc1ncoc1-c1c[nH]c2ncnc(OCc3ccccc3)c12] | 5-(4-(benzyloxy)-7H-pyrrolo[2,3-d]pyrimidin-5-yl)oxazole-4-carbonitrile |
| 115 | 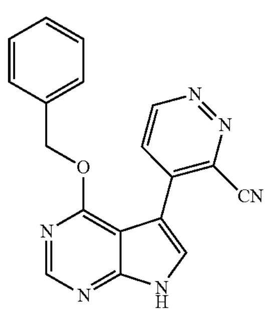 [SMILES: N#Cc1nnccc1-c1c[nH]c2ncnc(OCc3ccccc3)c12] | 4-(4-(benzyloxy)-7H-pyrrolo[2,3-d]pyrimidin-5-yl)pyridazine-3-carbonitrile |
| 116 | 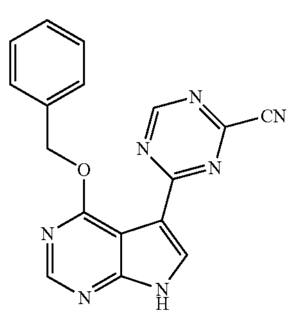 [SMILES: N#Cc1ncnc(-c2c[nH]c3ncnc(OCc4ccccc4)c23)n1] | 4-(4-(benzyloxy)-7H-pyrrolo[2,3-d]pyrimidin-5-yl)-1,3,5-triazine-2-carbonitrile |

| Ex. # | Structure | Name |
|---|---|---|
| 117 | 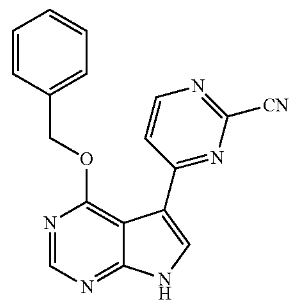 [SMILES: N#Cc1nccc(-c2c[nH]c3ncnc(OCc4ccccc4)c23)n1] | 4-(4-(benzyloxy)-7H-pyrrolo[2,3-d]pyrimidin-5-yl)pyrimidine-2-carbonitrile |
| 118 | 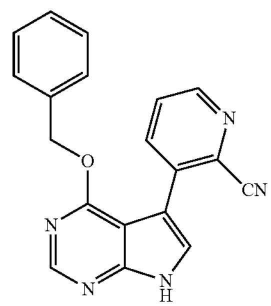 [SMILES: N#Cc1ncccc1-c1c[nH]c2ncnc(OCc3ccccc3)c12] | 3-(4-(benzyloxy)-7H-pyrrolo[2,3-d]pyrimidin-5-yl)picolinonitrile |
| 119 | 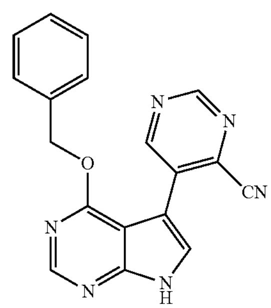 [SMILES: N#Cc1ncncc1-c1c[nH]c2ncnc(OCc3ccccc3)c12] | 5-(4-(benzyloxy)-7H-pyrrolo[2,3-d]pyrimidin-5-yl)pyrimidine-4-carbonitrile |
| 120 | 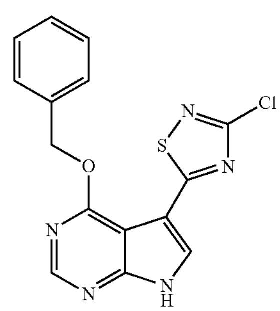 [SMILES: Clc1nsc(-c2c[nH]c3ncnc(OCc4ccccc4)c23)n1] | 5-(4-(benzyloxy)-7H-pyrrolo[2,3-d]pyrimidin-5-yl)-3-chloro-1,2,4-thiadiazole |
| 121 | 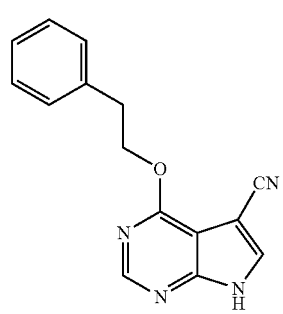 [SMILES: N#Cc1c[nH]c2ncnc(OCCc3ccccc3)c12] | 4-phenethoxy-7H-pyrrolo[2,3-d]pyrimidine-5-carbonitrile |

-continued

| Ex. # | Structure | Name |
|---|---|---|
| 122 | 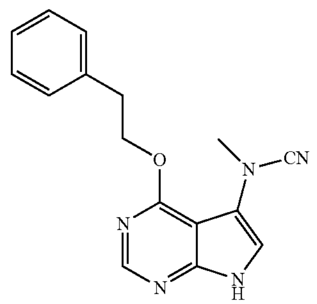 [SMILES: CN(C#N)c1c[nH]c2ncnc(OCCc3ccccc3)c12] | N-methyl-N-(4-phenethoxy-7H-pyrrolo[2,3-d]pyrimidin-5-yl)cyanamide |
| 123 | 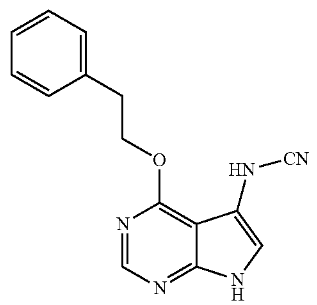 [SMILES: N#CNc1c[nH]c2ncnc(OCCc3ccccc3)c12] | N-(4-phenethoxy-7H-pyrrolo[2,3-d]pyrimidin-5-yl)cyanamide |
| 124 | 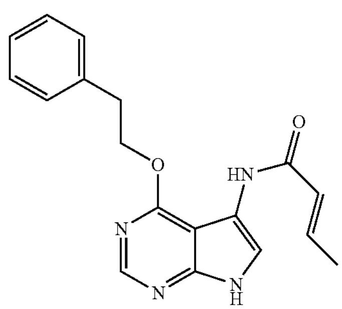 [SMILES: C/C=C/C(=O)Nc1c[nH]c2ncnc(OCCc3ccccc3)c12] | (E)-N-(4-phenethoxy-7H-pyrrolo[2,3-d]pyrimidin-5-yl)but-2-enamide |
| 125 | 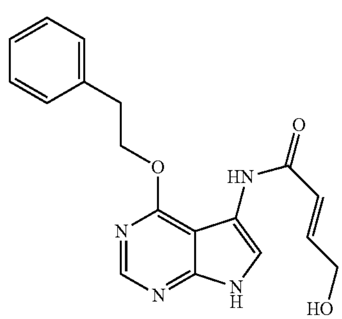 [SMILES: O=C(/C=C/CO)Nc1c[nH]c2ncnc(OCCc3ccccc3)c12] | (E)-4-hydroxy-N-(4-phenethoxy-7H-pyrrolo[2,3-d]pyrimidin-5-yl)but-2-enamide |
| 126 | 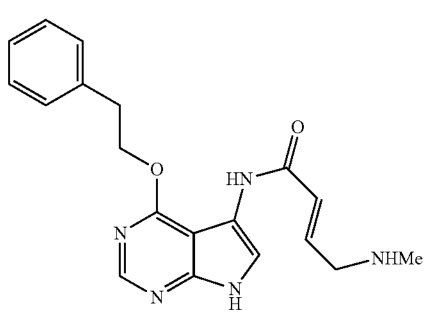 [SMILES: CNC/C=C/C(=O)Nc1c[nH]c2ncnc(OCCc3ccccc3)c12] | (E)-4-(methylamino)-N-(4-phenethoxy-7H-pyrrolo[2,3-d]pyrimidin-5-yl)but-2-enamide |

| Ex. # | Structure | Name |
|---|---|---|
| 127 | 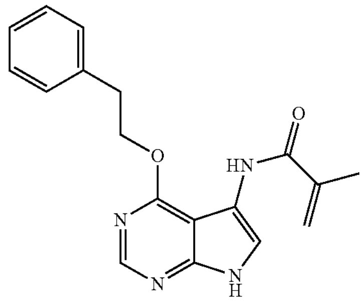 [SMILES: C=C(C)C(=O)Nc1c[nH]c2ncnc(OCCc3ccccc3)c12] | N-(4-phenethoxy-7H-pyrrolo[2,3-d]pyrimidin-5-yl)methacrylamide |
| 128 | 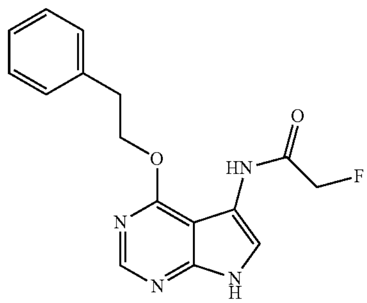 [SMILES: O=C(CF)Nc1c[nH]c2ncnc(OCCc3ccccc3)c12] | 2-fluoro-N-(4-phenethoxy-7H-pyrrolo[2,3-d]pyrimidin-5-yl)acetamide |
| 129 | 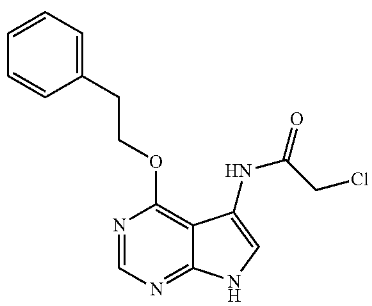 [SMILES: O=C(CCl)Nc1c[nH]c2ncnc(OCCc3ccccc3)c12] | 2-chloro-N-(4-phenethoxy-7H-pyrrolo[2,3-d]pyrimidin-5-yl)acetamide |
| 130 | 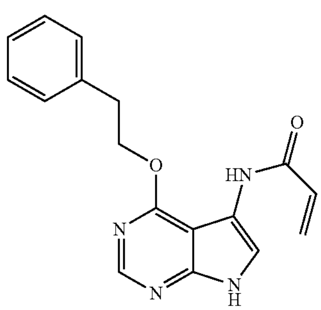 [SMILES: C=CC(=O)Nc1c[nH]c2ncnc(OCCc3ccccc3)c12] | N-(4-phenethoxy-7H-pyrrolo[2,3-d]pyrimidin-5-yl)acrylamide |
| 131 | 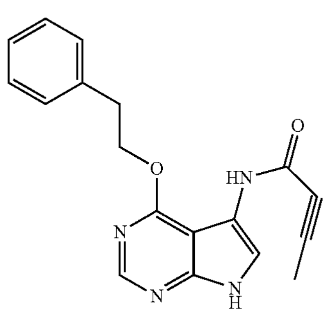 [SMILES: CC#CC(=O)Nc1c[nH]c2ncnc(OCCc3ccccc3)c12] | N-(4-phenethoxy-7H-pyrrolo[2,3-d]pyrimidin-5-yl)but-2-ynamide |

| Ex. # | Structure | Name |
|---|---|---|
| 132 | 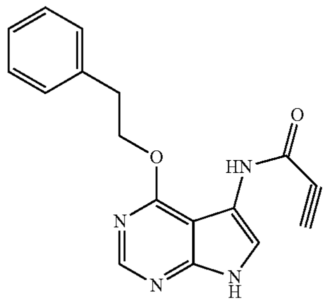 [SMILES: C#CC(=O)Nc1c[nH]c2ncnc(OCCc3ccccc3)c12] | N-(4-phenethoxy-7H-pyrrolo[2,3-d]pyrimidin-5-yl)propiolamide |
| 133 | 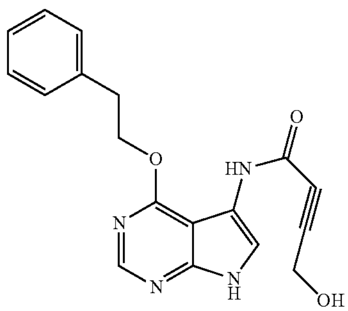 [SMILES: O=C(C#CCO)Nc1c[nH]c2ncnc(OCCc3ccccc3)c12] | 4-hydroxy-N-(4-phenethoxy-7H-pyrrolo[2,3-d]pyrimidin-5-yl)but-2-ynamide |
| 134 | 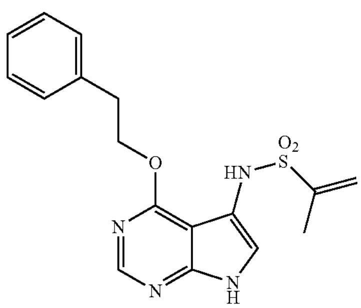 [SMILES: C=C(C)S(=O)(=O)Nc1c[nH]c2ncnc(OCCc3ccccc3)c12] | N-(4-phenethoxy-7H-pyrrolo[2,3-d]pyrimidin-5-yl)prop-1-ene-2-sulfonamide |
| 135 | 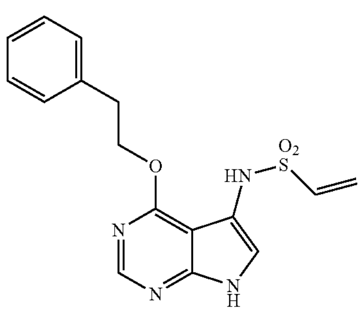 [SMILES: C=CS(=O)(=O)Nc1c[nH]c2ncnc(OCCc3ccccc3)c12] | N-(4-phenethoxy-7H-pyrrolo[2,3-d]pyrimidin-5-yl)ethenesulfonamide |
| 136 | 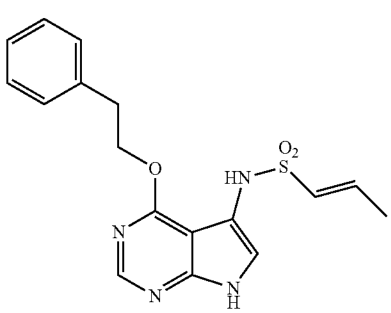 [SMILES: C/C=C/S(=O)(=O)Nc1c[nH]c2ncnc(OCCc3ccccc3)c12] | (E)-N-(4-phenethoxy-7H-pyrrolo[2,3-d]pyrimidin-5-yl)prop-1-ene-1-sulfonamide |

-continued

| Ex. # | Structure | Name |
|---|---|---|
| 137 | 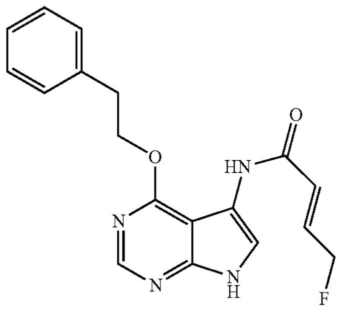 [SMILES: O=C(/C=C/CF)Nc1c[nH]c2ncnc(OCCc3ccccc3)c12] | (E)-4-fluoro-N-(4-phenethoxy-7H-pyrrolo[2,3-d]pyrimidin-5-yl)but-2-enamide |
| 138 | 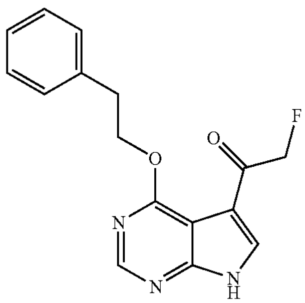 [SMILES: O=C(CF)c1c[nH]c2ncnc(OCCc3ccccc3)c12] | 2-fluoro-1-(4-phenethoxy-7H-pyrrolo[2,3-d]pyrimidin-5-yl)ethanone |
| 139 | 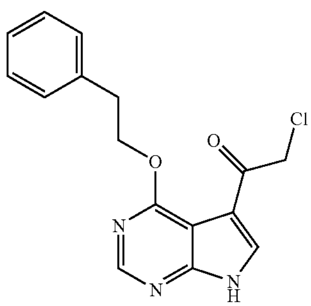 [SMILES: O=C(CCl)c1c[nH]c2ncnc(OCCc3ccccc3)c12] | 2-chloro-1-(4-phenethoxy-7H-pyrrolo[2,3-d]pyrimidin-5-yl)ethanone |
| 140 | 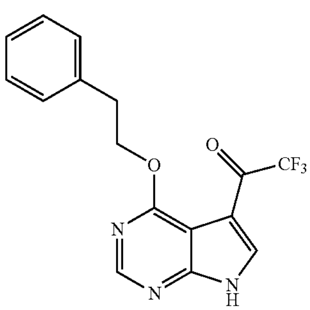 [SMILES: O=C(c1c[nH]c2ncnc(OCCc3ccccc3)c12)C(F)(F)F] | 2,2,2-trifluoro-1-(4-phenethoxy-7H-pyrrolo[2,3-d]pyrimidin-5-yl)ethanone |
| 141 | 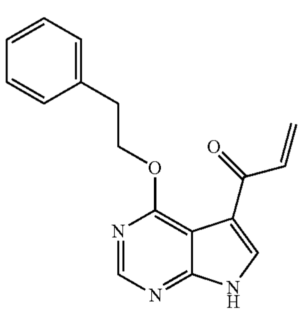 [SMILES: C=CC(=O)c1c[nH]c2ncnc(OCCc3ccccc3)c12] | 1-(4-phenethoxy-7H-pyrrolo[2,3-d]pyrimidin-5-yl)prop-2-en-1-one |

| Ex. # | Structure | Name |
|---|---|---|
| 142 | 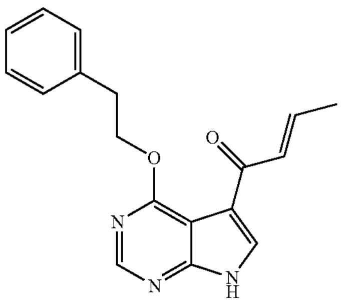 [SMILES: C/C=C/C(=O)c1c[nH]c2ncnc(OCCc3ccccc3)c12] | (E)-1-(4-phenethoxy-7H-pyrrolo[2,3-d]pyrimidin-5-yl)but-2-en-1-one |
| 143 | 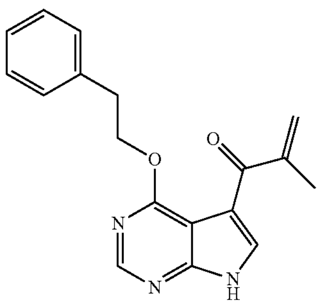 [SMILES: C=C(C)C(=O)c1c[nH]c2ncnc(OCCc3ccccc3)c12] | 2-methyl-1-(4-phenethoxy-7H-pyrrolo[2,3-d]pyrimidin-5-yl)prop-2-en-1-one |
| 144 | 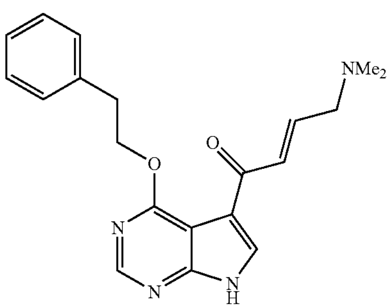 [SMILES: CN(C)C/C=C/C(=O)c1c[nH]c2ncnc(OCCc3ccccc3)c12] | (E)-4-(dimethylamino)-1-(4-phenethoxy-7H-pyrrolo[2,3-d]pyrimidin-5-yl)but-2-en-1-one |
| 145 | 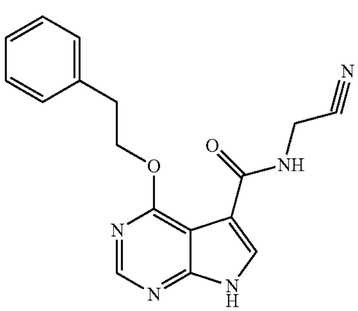 [SMILES: N#CCNC(=O)c1c[nH]c2ncnc(OCCc3ccccc3)c12] | N-(cyanomethyl)-4-phenethoxy-7H-pyrrolo[2,3-d]pyrimidine-5-carboxamide |
| 146 | 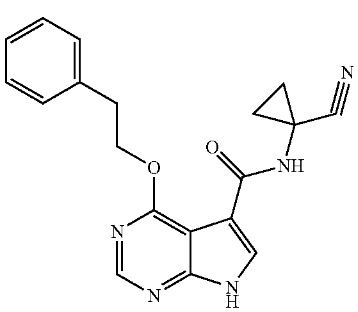 [SMILES: N#CC1(NC(=O)c2c[nH]c3ncnc(OCCc4ccccc4)c23)CC1] | N-(1-cyanocyclopropyl)-4-phenethoxy-7H-pyrrolo[2,3-d]pyrimidine-5-carboxamide |

-continued

| Ex. # | Structure | Name |
|---|---|---|
| 147 | 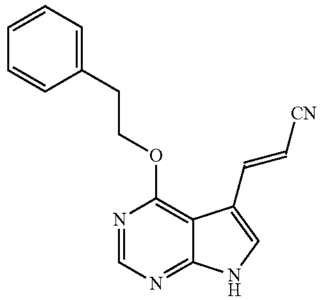 [SMILES: N#C/C=C/c1c[nH]c2ncnc(OCCc3ccccc3)c12] | (E)-3-(4-phenethoxy-7H-pyrrolo[2,3-d]pyrimidin-5-yl)acrylonitrile |
| 148 | 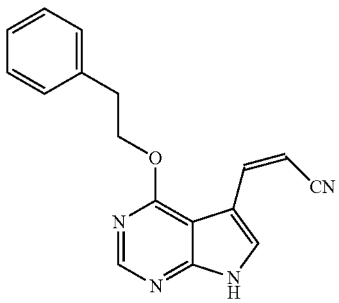 [SMILES: N#C/C=C\c1c[nH]c2ncnc(OCCc3ccccc3)c12] | (Z)-3-(4-phenethoxy-7H-pyrrolo[2,3-d]pyrimidin-5-yl)acrylonitrile |
| 149 | 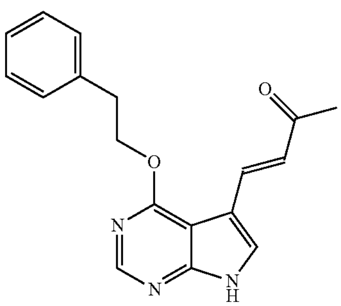 [SMILES: CC(=O)/C=C/c1c[nH]c2ncnc(OCCc3ccccc3)c12] | (E)-4-(4-phenethoxy-7H-pyrrolo[2,3-d]pyrimidin-5-yl)but-3-en-2-one |
| 150 | 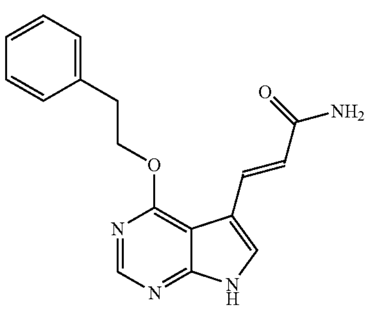 [SMILES: NC(=O)/C=C/c1c[nH]c2ncnc(OCCc3ccccc3)c12] | (E)-3-(4-phenethoxy-7H-pyrrolo[2,3-d]pyrimidin-5-yl)acrylamide |
| 151 | 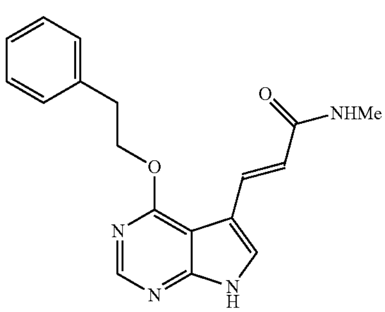 [SMILES: CNC(=O)/C=C/c1c[nH]c2ncnc(OCCc3ccccc3)c12] | (E)-N-methyl-3-(4-phenethoxy-7H-pyrrolo[2,3-d]pyrimidin-5-yl)acrylamide |

| Ex. # | Structure | Name |
|---|---|---|
| 152 | 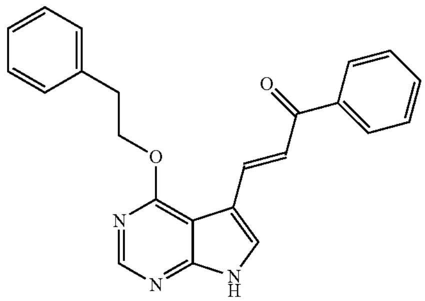 [SMILES: O=C(/C=C/c1c[nH]c2ncnc(OCCc3ccccc3)c12)c1ccccc1] | (E)-3-(4-phenethoxy-7H-pyrrolo[2,3-d]pyrimidin-5-yl)-1-phenylprop-2-en-1-one |
| 153 | 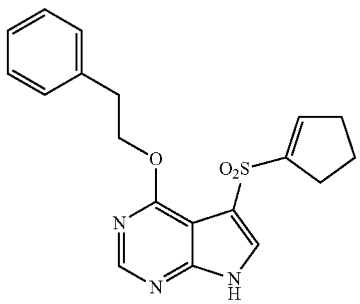 [SMILES: O=S(=O)(C1=CCCC1)c1c[nH]c2ncnc(OCCc3ccccc3)c12] | 5-(cyclopent-1-en-1-ylsulfonyl)-4-phenethoxy-7H-pyrrolo[2,3-d]pyrimidine |
| 154 | 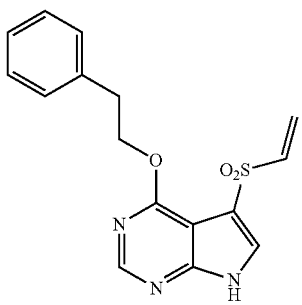 [SMILES: C=CS(=O)(=O)c1c[nH]c2ncnc(OCCc3ccccc3)c12] | 4-phenethoxy-5-(vinylsulfonyl)-7H-pyrrolo[2,3-d]pyrimidine |
| 155 | 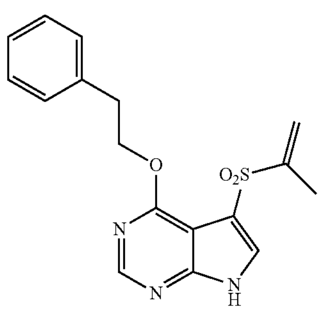 [SMILES: C=C(C)S(=O)(=O)c1c[nH]c2ncnc(OCCc3ccccc3)c12] | 4-phenethoxy-5-(prop-1-en-2-ylsulfonyl)-7H-pyrrolo[2,3-d]pyrimidine |
| 156 | 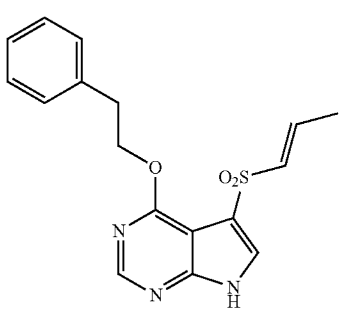 [SMILES: C/C=C/S(=O)(=O)c1c[nH]c2ncnc(OCCc3ccccc3)c12] | (E)-4-phenethoxy-5-(prop-1-en-1-ylsulfonyl)-7H-pyrrolo[2,3-d]pyrimidine |

| Ex. # | Structure | Name |
|---|---|---|
| 157 | 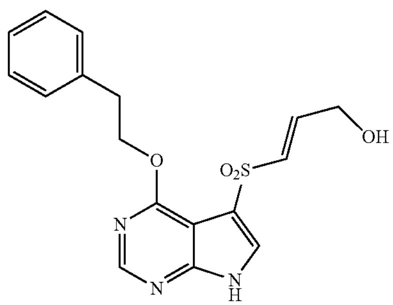 [SMILES: O=S(=O)(/C=C/CO)c1c[nH]c2ncnc(OCCc3ccccc3)c12] | (E)-3-((4-phenethoxy-7H-pyrrolo[2,3-d]pyrimidin-5-yl)sulfonyl)prop-2-en-1-ol |
| 158 | 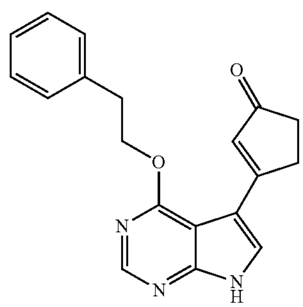 [SMILES: O=C1C=C(c2c[nH]c3ncnc(OCCc4ccccc4)c23)CC1] | 3-(4-phenethoxy-7H-pyrrolo[2,3-d]pyrimidin-5-yl)cyclopent-2-enone |
| 159 | 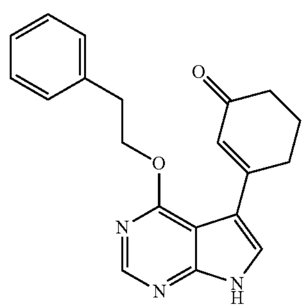 [SMILES: O=C1C=C(c2c[nH]c3ncnc(OCCc4ccccc4)c23)CCC1] | 3-(4-phenethoxy-7H-pyrrolo[2,3-d]pyrimidin-5-yl)cyclohex-2-enone |
| 160 | 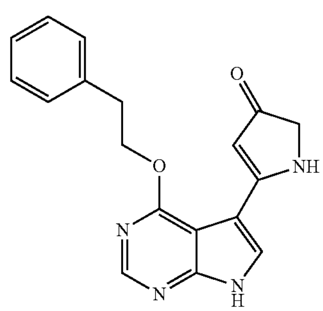 [SMILES: O=C1C=C(c2c[nH]c3ncnc(OCCc4ccccc4)c23)NC1] | 5-(4-phenethoxy-7H-pyrrolo[2,3-d]pyrimidin-5-yl)-1H-pyrrol-3(2H)-one |
| 161 | 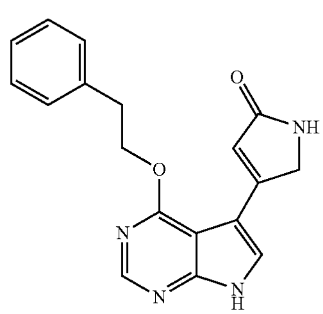 [SMILES: O=C1C=C(c2c[nH]c3ncnc(OCCc4ccccc4)c23)CN1] | 4-(4-phenethoxy-7H-pyrrolo[2,3-d]pyrimidin-5-yl)-1H-pyrrol-2(5H)-one |

-continued

| Ex. # | Structure | Name |
|---|---|---|
| 162 | 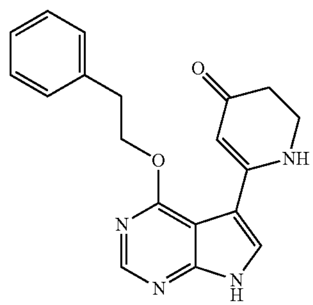 [SMILES: O=C1C=C(c2c[nH]c3ncnc(OCCc4ccccc4)c23)NCC1] | 6-(4-phenethoxy-7H-pyrrolo[2,3-d]pyrimidin-5-yl)-2,3-dihydropyridin-4(1H)-one |
| 163 | 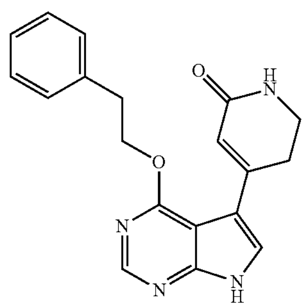 [SMILES: O=C1C=C(c2c[nH]c3ncnc(OCCc4ccccc4)c23)CCN1] | 4-(4-phenethoxy-7H-pyrrolo[2,3-d]pyrimidin-5-yl)-5,6-dihydropyridin-2(1H)-one |
| 164 | 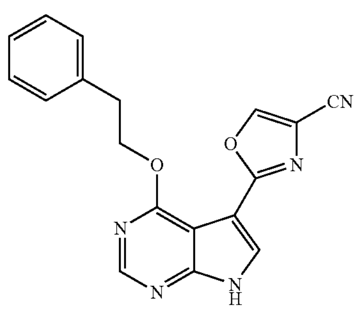 [SMILES: N#Cc1coc(-c2c[nH]c3ncnc(OCCc4ccccc4)c23)n1] | 2-(4-phenethoxy-7H-pyrrolo[2,3-d]pyrimidin-5-yl)oxazole-4-carbonitrile |
| 165 | 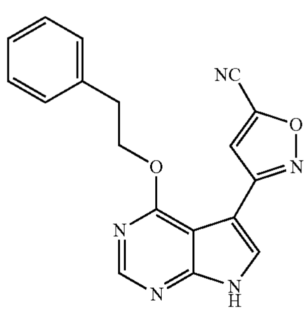 [SMILES: N#Cc1cc(-c2c[nH]c3ncnc(OCCc4ccccc4)c23)no1] | 3-(4-phenethoxy-7H-pyrrolo[2,3-d]pyrimidin-5-yl)isoxazole-5-carbonitrile |
| 166 | 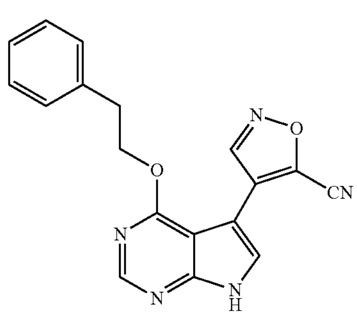 [SMILES: N#Cc1oncc1-c1c[nH]c2ncnc(OCCc3ccccc3)c12] | 4-(4-phenethoxy-7H-pyrrolo[2,3-d]pyrimidin-5-yl)isoxazole-5-carbonitrile |

-continued

| Ex. # | Structure | Name |
|---|---|---|
| 167 | 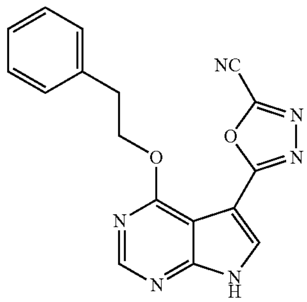 [SMILES: N#Cc1nnc(-c2c[nH]c3ncnc(OCCc4ccccc4)c23)o1] | 5-(4-phenethoxy-7H-pyrrolo[2,3-d]pyrimidin-5-yl)-1,3,4-oxadiazole-2-carbonitrile |
| 168 | 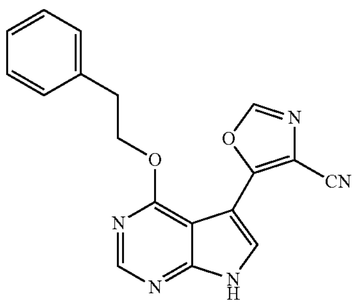 [SMILES: N#Cc1ncoc1-c1c[nH]c2ncnc(OCCc3ccccc3)c12] | 5-(4-phenethoxy-7H-pyrrolo[2,3-d]pyrimidin-5-yl)oxazole-4-carbonitrile |
| 169 | 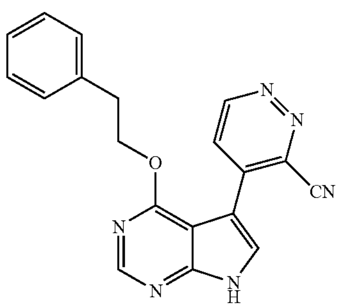 [SMILES: N#Cc1nnccc1-c1c[nH]c2ncnc(OCCc3ccccc3)c12] | 4-(4-phenethoxy-7H-pyrrolo[2,3-d]pyrimidin-5-yl)pyridazine-3-carbonitrile |
| 170 | 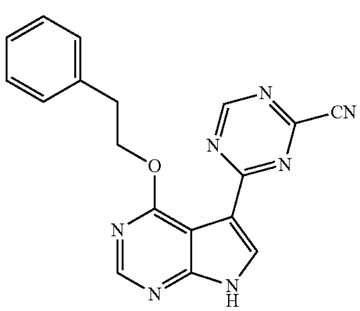 | 4-(4-phenethoxy-7H-pyrrolo[2,3-d]pyrimidin-5-yl)-1,3,5-triazine-2-carbonitrile |
| 171 | 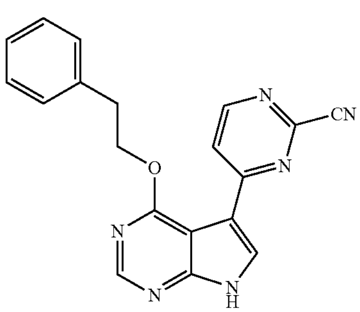 [SMILES: N#Cc1nccc(-c2c[nH]c3ncnc(OCCc4ccccc4)c23)n1] | 4-(4-phenethoxy-7H-pyrrolo[2,3-d]pyrimidin-5-yl)pyrimidine-2-carbonitrile |

-continued

| Ex. # | Structure | Name |
|---|---|---|
| 172 | 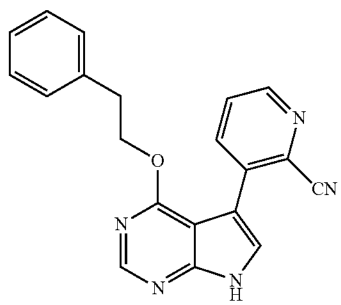 [SMILES: N#Cc1ncccc1-c1c[nH]c2ncnc(OCCc3ccccc3)c12] | 3-(4-phenethoxy-7H-pyrrolo[2,3-d]pyrimidin-5-yl)picolinonitrile |
| 173 | 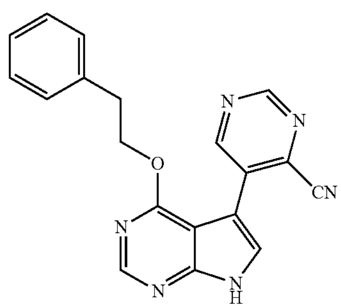 [SMILES: N#Cc1ncncc1-c1c[nH]c2ncnc(OCCc3ccccc3)c12] | 5-(4-phenethoxy-7H-pyrrolo[2,3-d]pyrimidin-5-yl)pyrimidine-4-carbonitrile |
| 174 | 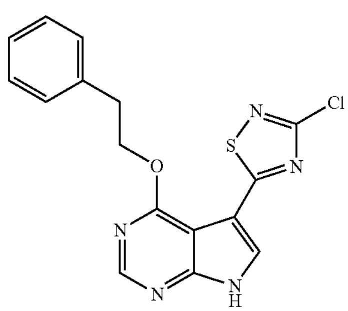 [SMILES: Clc1nsc(-c2c[nH]c3ncnc(OCCc4ccccc4)c23)n1] | 3-chloro-5-(4-phenethoxy-7H-pyrrolo[2,3-d]pyrimidin-5-yl)-1,2,4-thiadiazole |
| 175 | 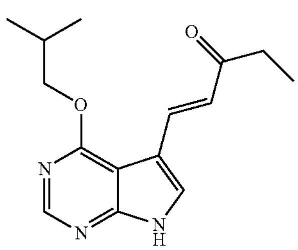 | (E)-1-(4-isobutoxy-7H-pyrrolo[2,3-d]pyrimidin-5-yl)pent-1-en-3-one |
| 176 | 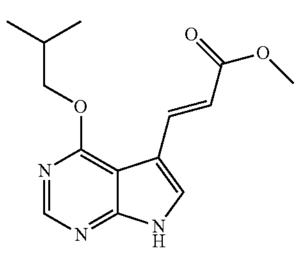 [SMILES: COC(=O)/C=C/c1c[nH]c2ncnc(OCC(C)C)c12] | Synthesis of (E)-methyl 3-(4-isobutoxy-7H-pyrrolo[2,3-d]pyrimidin-5-yl)acrylate |

| Ex. # | Structure | Name |
|---|---|---|
| 177 | 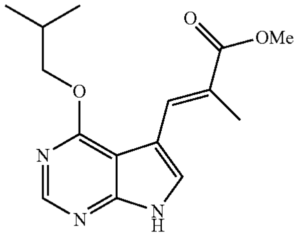 [SMILES: COC(=O)/C(C)=C/c1c[nH]c2ncnc(OCC(C)C)c12] | (E)-methyl 3-(4-isobutoxy-7H-pyrrolo[2,3-d]pyrimidin-5-yl)-2-methylacrylate |
| 178 | 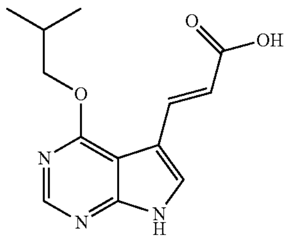 [SMILES: CC(C)COc1ncnc2[nH]cc(/C=C/C(=O)O)c12] | (E)-3-(4-isobutoxy-7H-pyrrolo[2,3-d]pyrimidin-5-yl)acrylic acid |
| 179 | 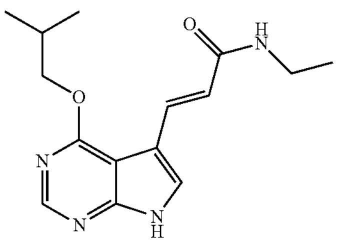 [SMILES: CCNC(=O)/C=C/c1c[nH]c2ncnc(OCC(C)C)c12] | (E)-N-ethyl-3-(4-isobutoxy-7H-pyrrolo[2,3-d]pyrimidin-5-yl)acrylamide |
| 180 | 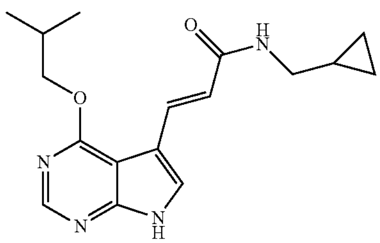 [SMILES: CC(C)COc1ncnc2[nH]cc(/C=C/C(=O)NCC3CC3)c12] | (E)-N-(cyclopropylmethyl)-3-(4-isobutoxy-7H-pyrrolo[2,3-d]pyrimidin-5-yl)acrylamide |
| 181 | 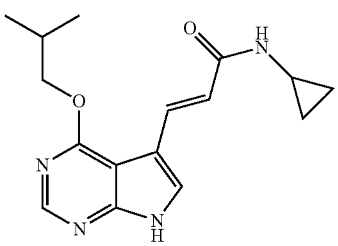 [SMILES: CC(C)COc1ncnc2[nH]cc(/C=C/C(=O)NC3CC3)c12] | (E)-N-cyclopropyl-3-(4-isobutoxy-7H-pyrrolo[2,3-d]pyrimidin-5-yl)acrylamide |
| 182 | 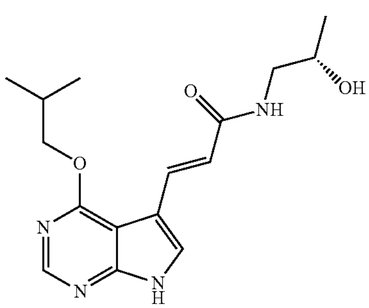 [SMILES: CC(C)COc1ncnc2[nH]cc(/C=C/C(=O)NC[C@H](C)O)c12] | (S,E)-N-(2-hydroxypropyl)-3-(4-isobutoxy-7H-pyrrolo[2,3-d]pyrimidin-5-yl)acrylamide |

-continued

| Ex. # | Structure | Name |
|---|---|---|
| 183 | 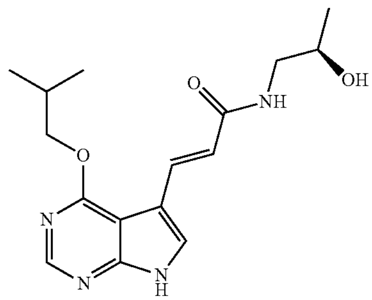 [SMILES: CC(C)COc1ncnc2[nH]cc(/C=C/C(=O)NC[C@@H](C)O)c12] | (R,E)-N-(2-hydroxypropyl)-3-(4-isobutoxy-7H-pyrrolo[2,3-d]pyrimidin-5-yl)acrylamide |
| 184 | 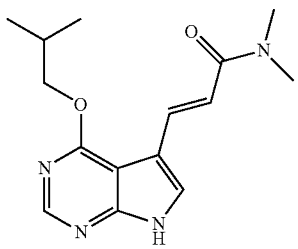 [SMILES: CC(C)COc1ncnc2[nH]cc(/C=C/C(=O)N(C)C)c12] | (E)-3-(4-isobutoxy-7H-pyrrolo[2,3-d]pyrimidin-5-yl)-N,N-dimethylacrylamide |
| 185 | 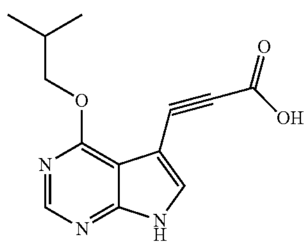 [SMILES: CC(C)COc1ncnc2[nH]cc(C#CC(=O)O)c12] | 3-(4-isobutoxy-7H-pyrrolo[2,3-d]pyrimidin-5-yl)propiolic acid |
| 186 | 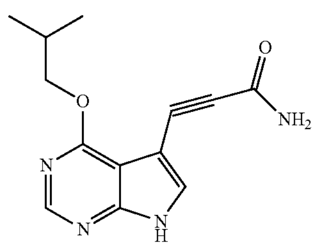 [SMILES: CC(C)COc1ncnc2[nH]cc(C#CC(N)=O)c12] | 3-(4-isobutoxy-7H-pyrrolo[2,3-d]pyrimidin-5-yl)propiolamide |
| 187 | 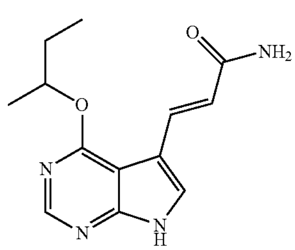 [SMILES: CCC(C)Oc1ncnc2[nH]cc(/C=C/C(N)=O)c12] | (E)-3-(4-(sec-butoxy)-7H-pyrrolo[2,3-d]pyrimidin-5-yl)acrylamide |
| 188 | 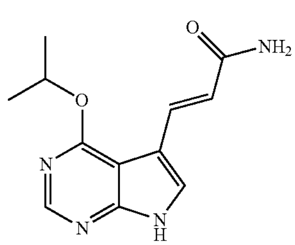 [SMILES: CC(C)Oc1ncnc2[nH]cc(/C=C/C(N)=O)c12] | (E)-3-(4-isopropoxy-7H-pyrrolo[2,3-d]pyrimidin-5-yl)acrylamide |

-continued

| Ex. # | Structure | Name |
|---|---|---|
| 189 | 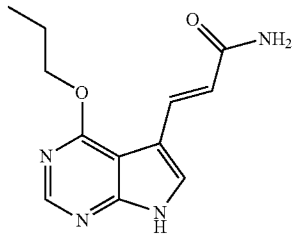 [SMILES: CCCOc1ncnc2[nH]cc(/C=C/C(N)=O)c12] | (E)-3-(4-propoxy-7H-pyrrolo[2,3-d]pyrimidin-5-yl)acrylamide |
| 190 | 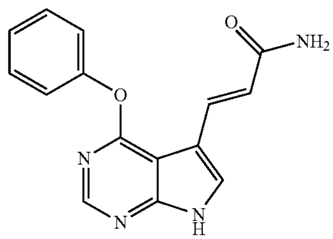 [SMILES: NC(=O)/C=C/c1c[nH]c2ncnc(Oc3ccccc3)c12] | (E)-3-(4-phenoxy-7H-pyrrolo[2,3-d]pyrimidin-5-yl)acrylamide |
| 191 | 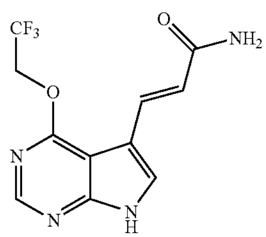 [SMILES: NC(=O)/C=C/c1c[nH]c2ncnc(OCC(F)(F)F)c12] | (E)-3-(4-(2,2,2-trifluoroethoxy)-7H-pyrrolo[2,3-d]pyrimidin-5-yl)acrylamide |
| 192 | 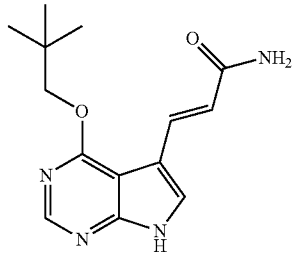 [SMILES: CC(C)(C)COc1ncnc2[nH]cc(/C=C/C(N)=O)c12] | (E)-3-(4-(neopentyloxy)-7H-pyrrolo[2,3-d]pyrimidin-5-yl)acrylamide |
| 193 | 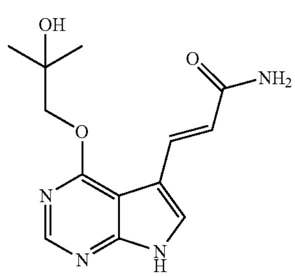 [SMILES: CC(C)(O)COc1ncnc2[nH]cc(/C=C/C(N)=O)c12] | (E)-3-(4-(2-hydroxy-2-methylpropoxy)-7H-pyrrolo[2,3-d]pyrimidin-5-yl)acrylamide |
| 194 | 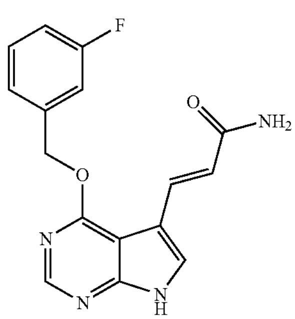 [SMILES: NC(=O)/C=C/c1c[nH]c2ncnc(OCc3cccc(F)c3)c12] | (E)-3-(4-((3-fluorobenzyl)oxy)-7H-pyrrolo[2,3-d]pyrimidin-5-yl)acrylamide |

| Ex. # | Structure | Name |
|---|---|---|
| 195 | 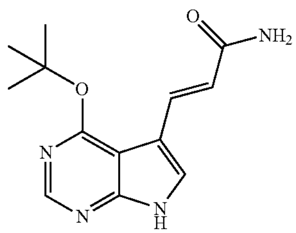 [SMILES: CC(C)(C)Oc1ncnc2[nH]cc(/C=C/C(N)=O)c12] | (E)-3-(4-(tert-butoxy)-7H-pyrrolo[2,3-d]pyrimidin-5-yl)acrylamide |
| 196 | 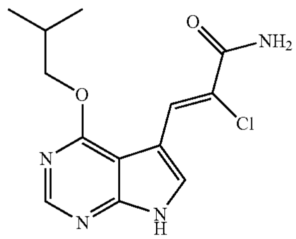 [SMILES: CC(C)COc1ncnc2[nH]cc(/C=C(\Cl)C(N)=O)c12] | (Z)-2-chloro-3-(4-isobutoxy-7H-pyrrolo[2,3-d]pyrimidin-5-yl)acrylamide |
| 197 | 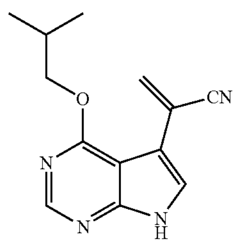 [SMILES: C=C(C#N)c1c[nH]c2ncnc(OCC(C)C)c12] | 2-(4-isobutoxy-7H-pyrrolo[2,3-d]pyrimidin-5-yl)acrylonitrile |
| 198 | 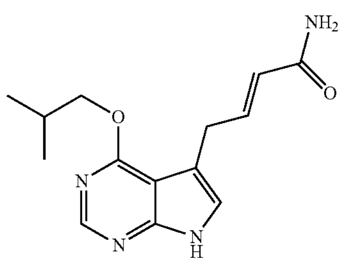 [SMILES: CC(C)COc1ncnc2[nH]cc(C/C=C/C(N)=O)c12] | 4-(4-isobutoxy-7H-pyrrolo[2,3-d]pyrimidin-5-yl)-but-2-enoic acid amide |
| 199 | 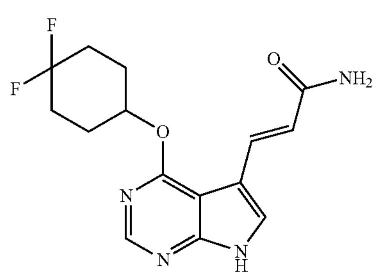 [SMILES: NC(=O)/C=C/c1c[nH]c2ncnc(OC3CCC(F)(F)CC3)c12] | 3-[4-(4,4-difluoro-cyclohexyloxy)-7H-pyrrolo[2,3-c]pyrimidin-5-yl]-acrylamide |
| 200 | 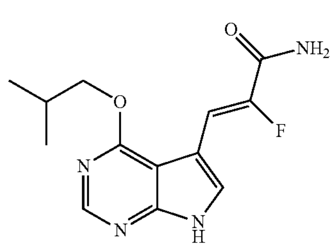 [SMILES: CC(C)COc1ncnc2[nH]cc(/C=C(\F)C(N)=O)c12] | (E) 2-fluoro-3-(4-isobutoxy-7H-pyrrolo[2,3-d]pyrimidin-5-yl)-acrylamide |

-continued

| Ex. # | Structure | Name |
|---|---|---|
| 201 | 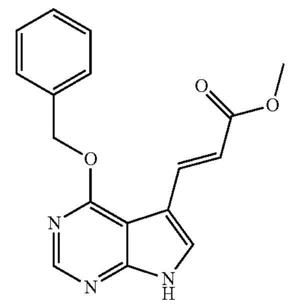 [SMILES: COC(=O)/C=C/c1c[nH]c2ncnc(OCc3ccccc3)c12] | (E)-3-(4-benzyloxy-7H-pyrrolo[2,3-d]pyrimidin-5-yl)-acrylic acid methylester |
| 202 | 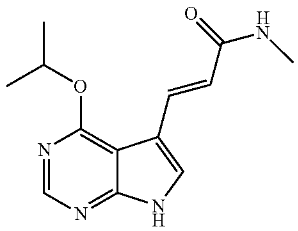 [SMILES: CNC(=O)/C=C/c1c[nH]c2ncnc(OC(C)C)c12] | (E)-3-(4-isopropoxy-7H-pyrrolo[2,3-d]pyrimidin-5-yl)-N-methylacrylamide |
| 203 | 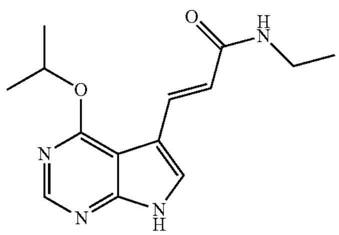 [SMILES: CCNC(=O)/C=C/c1c[nH]c2ncnc(OC(C)C)c12] | (E)-N-ethyl-3-(4-isopropoxy-7H-pyrrolo[2,3-d]pyrimidin-5-yl)acrylamide |
| 204 | 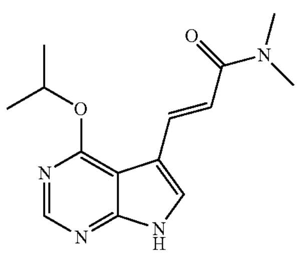 [SMILES: CC(C)Oc1ncnc2[nH]cc(/C=C/C(=O)N(C)C)c12] | (E)-3-(4-isopropoxy-7H-pyrrolo[2,3-d]pyrimidin-5-yl)-N,N-dimethylacrylamide |
| 205 | 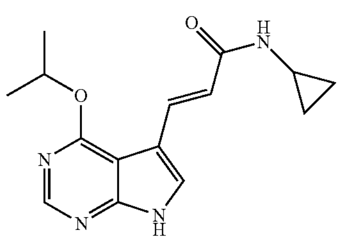 [SMILES: CC(C)Oc1ncnc2[nH]cc(/C=C/C(=O)NC3CC3)c12] | (E)-N-cyclopropyl-3-(4-isopropoxy-7H-pyrrolo[2,3-d]pyrimidin-5-yl)acrylamide |
| 206 | 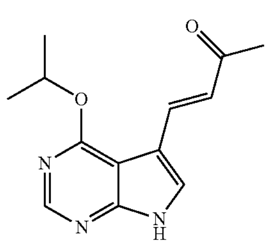 [SMILES: CC(=O)/C=C/c1c[nH]c2ncnc(OC(C)C)c12] | (E)-4-(4-isopropoxy-7H-pyrrolo[2,3-d]pyrimidin-5-yl)but-3-en-2-one |

| Ex. # | Structure | Name |
|---|---|---|
| 207 | 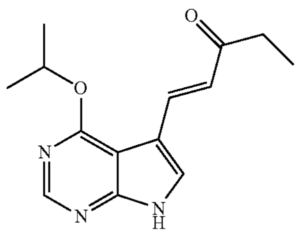 [SMILES: CCC(=O)/C=C/c1c[nH]c2ncnc(OC(C)C)c12] | (E)-1-(4-isopropoxy-7H-pyrrolo[2,3-d]pyrimidin-5-yl)pent-1-en-3-one |
| 208 | 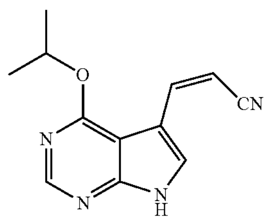 [SMILES: CC(C)Oc1ncnc2[nH]cc(/C=C\C#N)c12] | (Z)-3-(4-isopropoxy-7H-pyrrolo[2,3-d]pyrimidin-5-yl)acrylonitrile |
| 209 | 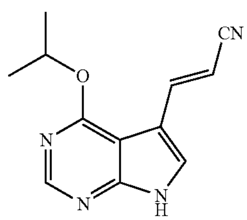 [SMILES: CC(C)Oc1ncnc2[nH]cc(/C=C/C#N)c12] | (E)-3-(4-isopropoxy-7H-pyrrolo[2,3-d]pyrimidin-5-yl)acrylonitrile |
| 210 | 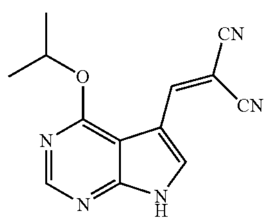 [SMILES: CC(C)Oc1ncnc2[nH]cc(C=C(C#N)C#N)c12] | 2-((4-isopropoxy-7H-pyrrolo[2,3-d]pyrimidin-5-yl)methylene)malononitrile |
| 211 | 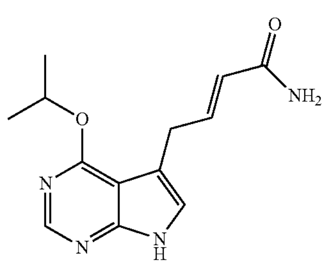 [SMILES: CC(C)Oc1ncnc2[nH]cc(C/C=C/C(N)=O)c12] | (E)-4-(4-isopropoxy-7H-pyrrolo[2,3-d]pyrimidin-5-yl)but-2-enamide |
| 212 | 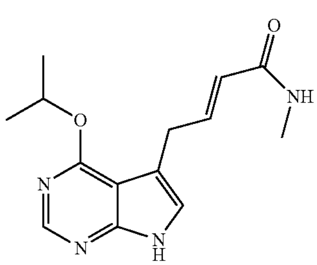 [SMILES: CNC(=O)/C=C/Cc1c[nH]c2ncnc(OC(C)C)c12] | (E)-4-(4-isopropoxy-7H-pyrrolo[2,3-d]pyrimidin-5-yl)-N-methylbut-2-enamide |

| Ex. # | Structure | Name |
|---|---|---|
| 213 | 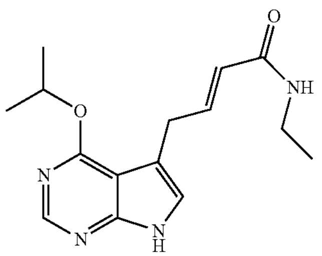 [SMILES: CCNC(=O)/C=C/Cc1c[nH]c2ncnc(OC(C)C)c12] | (E)-N-ethyl-4-(4-isopropoxy-7H-pyrrolo[2,3-d]pyrimidin-5-yl)but-2-enamide |
| 214 | 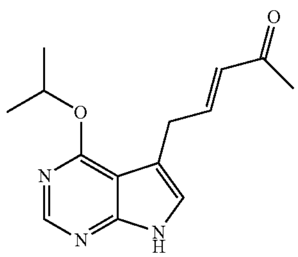 [SMILES: CC(=O)/C=C/Cc1c[nH]c2ncnc(OC(C)C)c12] | (E)-5-(4-isopropoxy-7H-pyrrolo[2,3-d]pyrimidin-5-yl)pent-3-en-2-one |
| 215 | 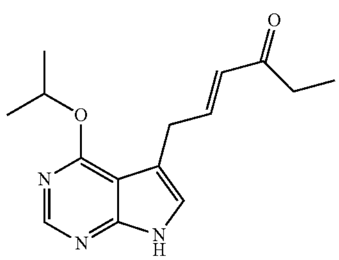 [SMILES: CCC(=O)/C=C/Cc1c[nH]c2ncnc(OC(C)C)c12] | (E)-6-(4-isopropoxy-7H-pyrrolo[2,3-d]pyrimidin-5-yl)hex-4-en-3-one |
| 216 | 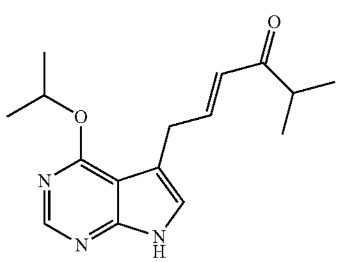 | (E)-6-(4-isopropoxy-7H-pyrrolo[2,3-d]pyrimidin-5-yl)-2-methylhex-4-en-3-one |
| 217 | 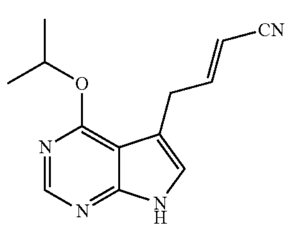 [SMILES: CC(C)Oc1ncnc2[nH]cc(C/C=C/C#N)c12] | (E)-4-(4-isopropoxy-7H-pyrrolo[2,3-d]pyrimidin-5-yl)but-2-enenitrile |
| 218 | 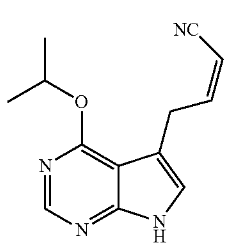 [SMILES: CC(C)Oc1ncnc2[nH]cc(C/C=C\C#N)c12] | (Z)-4-(4-isopropoxy-7H-pyrrolo[2,3-d]pyrimidin-5-yl)but-2-enenitrile |

| Ex. # | Structure | Name |
|---|---|---|
| 219 | 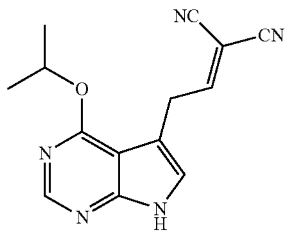 [SMILES: CC(C)Oc1ncnc2[nH]cc(CC=C(C#N)C#N)c12] | 2-(2-(4-isopropoxy-7H-pyrrolo[2,3-d]pyrimidin-5-yl)ethylidene)malononitrile |
| 220 | 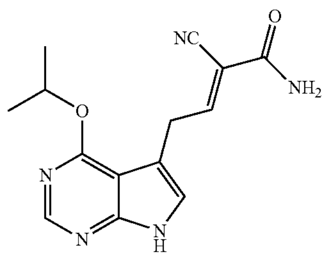 [SMILES: CC(C)Oc1ncnc2[nH]cc(C/C=C(\C#N)C(N)=O)c12] | (E)-2-cyano-4-(4-isopropoxy-7H-pyrrolo[2,3-d]pyrimidin-5-yl)but-2-enamide |
| 221 | 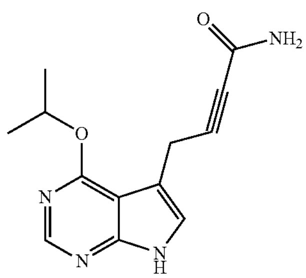 [SMILES: CC(C)Oc1ncnc2[nH]cc(CC#CC(N)=O)c12] | 4-(4-isopropoxy-7H-pyrrolo[2,3-d]pyrimidin-5-yl)but-2-ynamide |
| 222 | 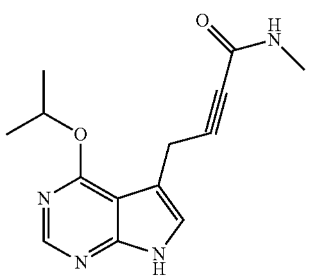 [SMILES: CNC(=O)C#CCc1c[nH]c2ncnc(OC(C)C)c12] | 4-(4-isopropoxy-7H-pyrrolo[2,3-d]pyrimidin-5-yl)-N-methylbut-2-ynamide |
| 223 | 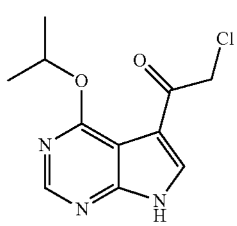 [SMILES: CC(C)Oc1ncnc2[nH]cc(C(=O)CCl)c12] | 2-chloro-1-(4-isopropoxy-7H-pyrrolo[2,3-d]pyrimidin-5-yl)ethanone |
| 224 | 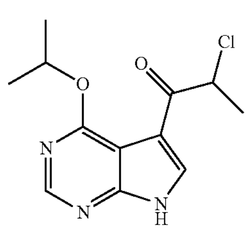 [SMILES: CC(C)Oc1ncnc2[nH]cc(C(=O)C(C)Cl)c12] | 2-chloro-1-(4-isopropoxy-7H-pyrrolo[2,3-d]pyrimidin-5-yl)propan-1-one |

-continued

| Ex. # | Structure | Name |
|---|---|---|
| 225 | 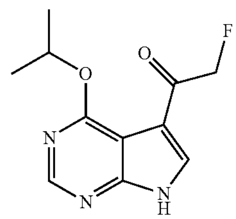 [SMILES: CC(C)Oc1ncnc2[nH]cc(C(=O)CF)c12] | 2-fluoro-1-(4-isopropoxy-7H-pyrrolo[2,3-d]pyrimidin-5-yl)ethanone |
| 226 | 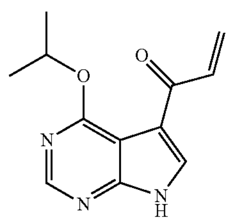 [SMILES: C=CC(=O)c1c[nH]c2ncnc(OC(C)C)c12] | 1-(4-isopropoxy-7H-pyrrolo[2,3-d]pyrimidin-5-yl)prop-2-en-1-one |
| 227 | 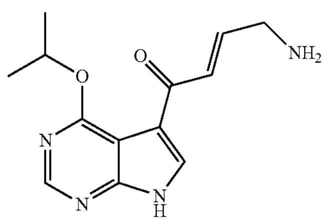 [SMILES: CC(C)Oc1ncnc2[nH]cc(C(=O)/C=C/CN)c12] | (E)-4-amino-1-(4-isopropoxy-7H-pyrrolo[2,3-d]pyrimidin-5-yl)but-2-en-1-one |
| 228 | 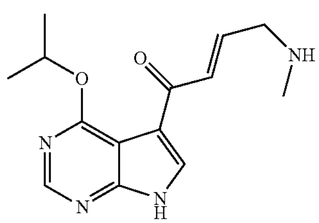 [SMILES: CNC/C=C/C(=O)c1c[nH]c2ncnc(OC(C)C)c12] | (E)-1-(4-isopropoxy-7H-pyrrolo[2,3-d]pyrimidin-5-yl)-4-(methylamino)but-2-en-1-one |
| 229 | 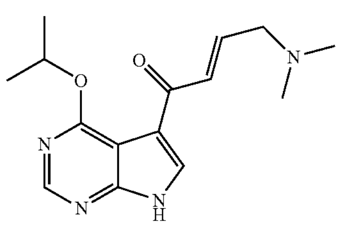 [SMILES: CC(C)Oc1ncnc2[nH]cc(C(=O)/C=C/CN(C)C)c12] | (E)-4-(dimethylamino)-1-(4-isopropoxy-7H-pyrrolo[2,3-d]pyrimidin-5-yl)but-2-en-1-one |
| 230 | 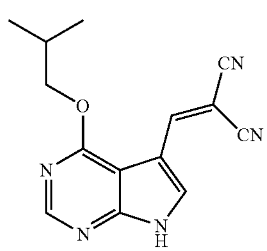 [SMILES: CC(C)COc1ncnc2[nH]cc(C=C(C#N)C#N)c12] | 2-((4-isobutoxy-7H-pyrrolo[2,3-d]pyrimidin-5-yl)methylene)malononitrile |

-continued

| Ex. # | Structure | Name |
|---|---|---|
| 231 | 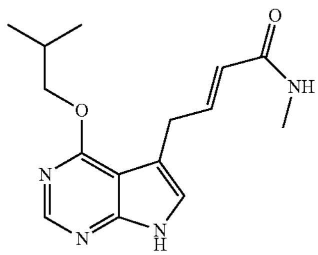 [SMILES: CNC(=O)/C=C/Cc1c[nH]c2ncnc(OCC(C)C)c12] | (E)-4-(4-isobutoxy-7H-pyrrolo[2,3-d]pyrimidin-5-yl)-N-methylbut-2-enamide |
| 232 | 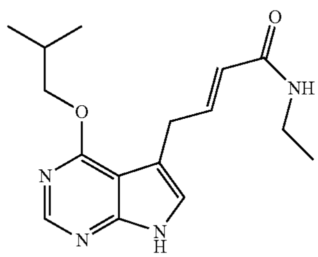 [SMILES: CCNC(=O)/C=C/Cc1c[nH]c2ncnc(OCC(C)C)c12] | (E)-N-ethyl-4-(4-isobutoxy-7H-pyrrolo[2,3-d]pyrimidin-5-yl)but-2-enamide |
| 233 | 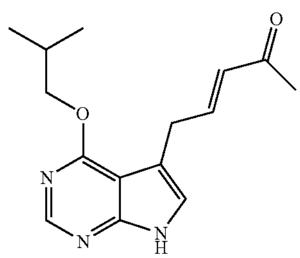 [SMILES: CC(=O)/C=C/Cc1c[nH]c2ncnc(OCC(C)C)c12] | (E)-5-(4-isobutoxy-7H-pyrrolo[2,3-d]pyrimidin-5-yl)pent-3-en-2-one |
| 234 | 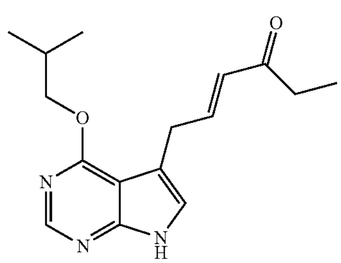 [SMILES: CCC(=O)/C=C/Cc1c[nH]c2ncnc(OCC(C)C)c12] | (E)-6-(4-isobutoxy-7H-pyrrolo[2,3-d]pyrimidin-5-yl)hex-4-en-3-one |
| 235 | 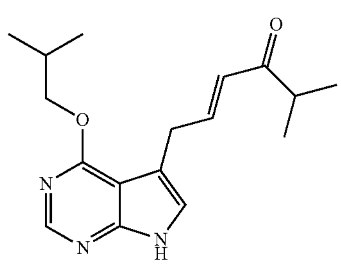 [SMILES: CC(C)COc1ncnc2[nH]cc(C/C=C/C(=O)C(C)C)c12] | (E)-6-(4-isobutoxy-7H-pyrrolo[2,3-d]pyrimidin-5-yl)-2-methylhex-4-en-3-one |
| 236 | 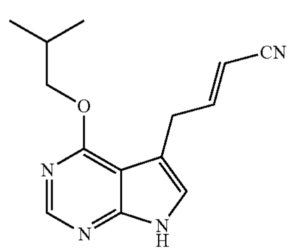 [SMILES: CC(C)COc1ncnc2[nH]cc(C/C=C/C#N)c12] | (E)-4-(4-isobutoxy-7H-pyrrolo[2,3-d]pyrimidin-5-yl)but-2-enenitrile |

| Ex. # | Structure | Name |
|---|---|---|
| 237 | 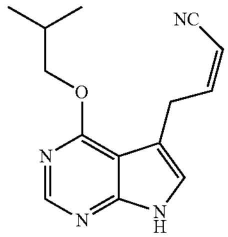 [SMILES: CC(C)COc1ncnc2[nH]cc(C/C=C\C#N)c12] | (Z)-4-(4-isobutoxy-7H-pyrrolo[2,3-d]pyrimidin-5-yl)but-2-enenitrile |
| 238 | 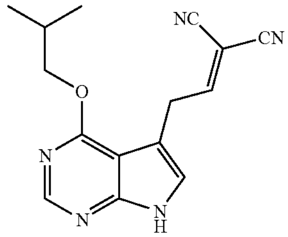 [SMILES: CC(C)COc1ncnc2[nH]cc(CC=C(C#N)C#N)c12] | 2-(2-(4-isobutoxy-7H-pyrrolo[2,3-d]pyrimidin-5-yl)ethylidene)malononitrile |
| 239 | 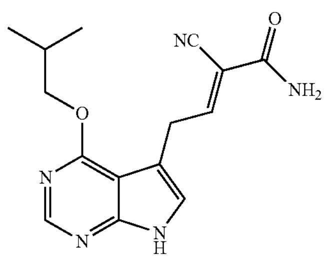 [SMILES: CC(C)COc1ncnc2[nH]cc(C/C=C(\C#N)C(N)=O)c12] | (E)-2-cyano-4-(4-isobutoxy-7H-pyrrolo[2,3-d]pyrimidin-5-yl)but-2-enamide |
| 240 | 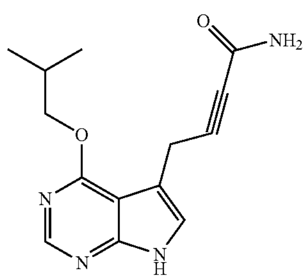 [SMILES: CC(C)COc1ncnc2[nH]cc(CC#CC(N)=O)c12] | 4-(4-isobutoxy-7H-pyrrolo[2,3-d]pyrimidin-5-yl)but-2-ynamide |
| 241 | 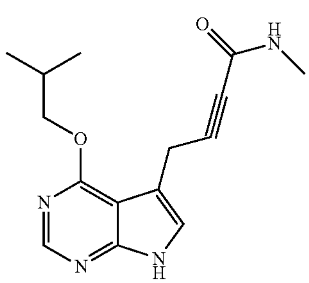 [SMILES: CNC(=O)C#CCc1c[nH]c2ncnc(OCC(C)C)c12] | 4-(4-isobutoxy-7H-pyrrolo[2,3-d]pyrimidin-5-yl)-N-methylbut-2-ynamide |
| 242 | 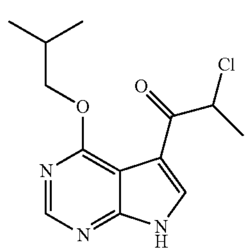 [SMILES: CC(C)COc1ncnc2[nH]cc(C(=O)C(C)Cl)c12] | 2-chloro-1-(4-isobutoxy-7H-pyrrolo[2,3-d]pyrimidin-5-yl)propan-1-one |

| Ex. # | Structure | Name |
|---|---|---|
| 243 | 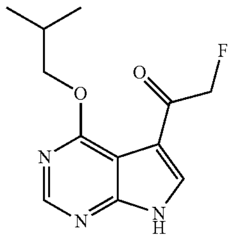 [SMILES: CC(C)COc1ncnc2[nH]cc(C(=O)CF)c12] | 2-fluoro-1-(4-isobutoxy-7H-pyrrolo[2,3-d]pyrimidin-5-yl)ethanone |
| 244 | 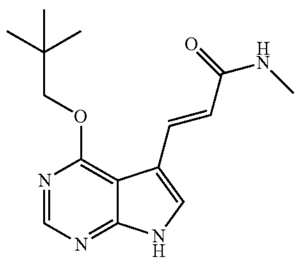 [SMILES: CNC(=O)/C=C/c1c[nH]c2ncnc(OCC(C)(C)C)c12] | (E)-N-methyl-3-(4-(neopentyloxy)-7H-pyrrolo[2,3-d]pyrimidin-5-yl)acrylamide |
| 245 | 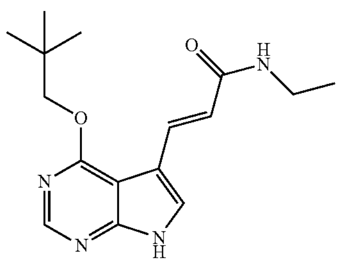 [SMILES: CCNC(=O)/C=C/c1c[nH]c2ncnc(OCC(C)(C)C)c12] | (E)-N-ethyl-3-(4-(neopentyloxy)-7H-pyrrolo[2,3-d]pyrimidin-5-yl)acrylamide |
| 246 | 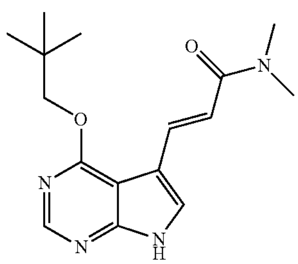 [SMILES: CN(C)C(=O)/C=C/c1c[nH]c2ncnc(OCC(C)(C)C)c12] | (E)-N,N-dimethyl-3-(4-(neopentyloxy)-7H-pyrrolo[2,3-d]pyrimidin-5-yl)acrylamide |
| 247 | 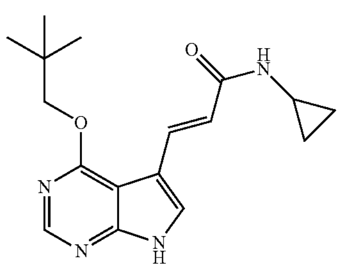 [SMILES: CC(C)(C)COc1ncnc2[nH]cc(/C=C/C(=O)NC3CC3)c12] | (E)-N-cyclopropyl-3-(4-(neopentyloxy)-7H-pyrrolo[2,3-d]pyrimidin-5-yl)acrylamide |
| 248 | 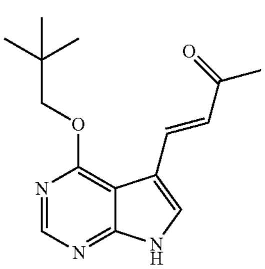 [SMILES: CC(=O)/C=C/c1c[nH]c2ncnc(OCC(C)(C)C)c12] | (E)-4-(4-(neopentyloxy)-7H-pyrrolo[2,3-d]pyrimidin-5-yl)but-3-en-2-one |

-continued

| Ex. # | Structure | Name |
|---|---|---|
| 249 | 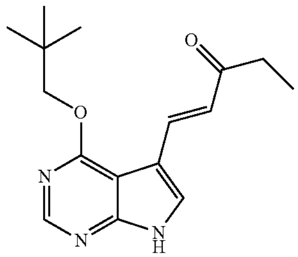 [SMILES: CCC(=O)/C=C/c1c[nH]c2ncnc(OCC(C)(C)C)c12] | (E)-1-(4-(neopentyloxy)-7H-pyrrolo[2,3-d]pyrimidin-5-yl)pent-1-en-3-one |
| 250 | 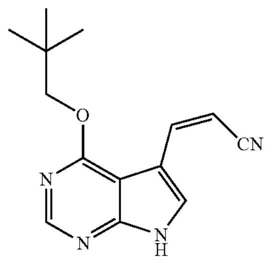 [SMILES: CC(C)(C)COc1ncnc2[nH]cc(/C=C\C#N)c12] | (Z)-3-(4-(neopentyloxy)-7H-pyrrolo[2,3-d]pyrimidin-5-yl)acrylonitrile |
| 251 | 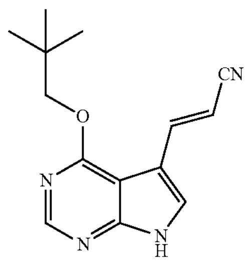 [SMILES: CC(C)(C)COc1ncnc2[nH]cc(/C=C/C#N)c12] | (E)-3-(4-(neopentyloxy)-7H-pyrrolo[2,3-d]pyrimidin-5-yl)acrylonitrile |
| 252 | 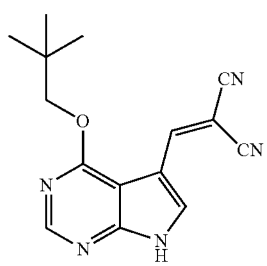 [SMILES: CC(C)(C)COc1ncnc2[nH]cc(C=C(C#N)C#N)c12] | 2-((4-(neopentyloxy)-7H-pyrrolo[2,3-d]pyrimidin-5-yl)methylene)malononitrile |
| 253 | 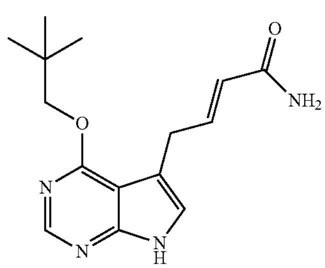 [SMILES: CC(C)(C)COc1ncnc2[nH]cc(C/C=C/C(N)=O)c12] | (E)-4-(4-(neopentyloxy)-7H-pyrrolo[2,3-d]pyrimidin-5-yl)but-2-enamide |
| 254 | 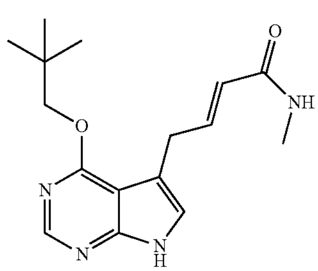 [SMILES: CNC(=O)/C=C/Cc1c[nH]c2ncnc(OCC(C)(C)C)c12] | (E)-N-methyl-4-(4-(neopentyloxy)-7H-pyrrolo[2,3-d]pyrimidin-5-yl)but-2-enamide |

-continued

| Ex. # | Structure | Name |
|---|---|---|
| 255 | 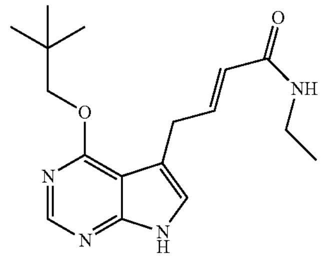 [SMILES: CCNC(=O)/C=C/Cc1c[nH]c2ncnc(OCC(C)(C)C)c12] | (E)-N-ethyl-4-(4-(neopentyloxy)-7H-pyrrolo[2,3-d]pyrimidin-5-yl)but-2-enamide |
| 256 | 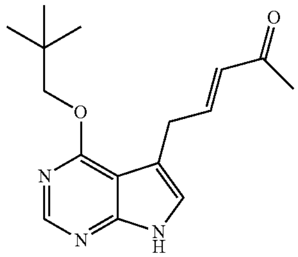 [SMILES: CC(=O)/C=C/Cc1c[nH]c2ncnc(OCC(C)(C)C)c12] | (E)-5-(4-(neopentyloxy)-7H-pyrrolo[2,3-d]pyrimidin-5-yl)pent-3-en-2-one |
| 257 | 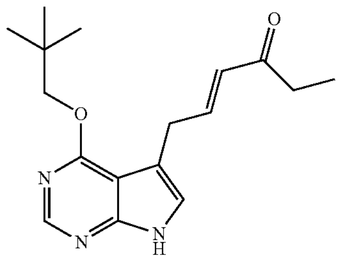 [SMILES: CCC(=O)/C=C/Cc1c[nH]c2ncnc(OCC(C)(C)C)c12] | (E)-6-(4-(neopentyloxy)-7H-pyrrolo[2,3-d]pyrimidin-5-yl)hex-4-en-3-one |
| 258 | 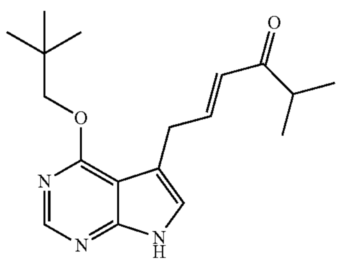 [SMILES: CC(C)C(=O)/C=C/Cc1c[nH]c2ncnc(OCC(C)(C)C)c12] | (E)-2-methyl-6-(4-(neopentyloxy)-7H-pyrrolo[2,3-d]pyrimidin-5-yl)hex-4-en-3-one |
| 259 | 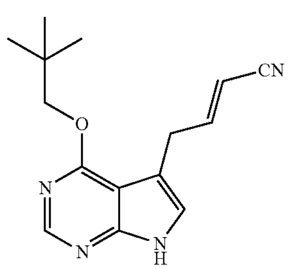 [SMILES: CC(C)(C)COc1ncnc2[nH]cc(C/C=C/C#N)c12] | (E)-4-(4-(neopentyloxy)-7H-pyrrolo[2,3-d]pyrimidin-5-yl)but-2-enenitrile |
| 260 | 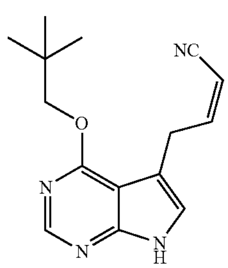 [SMILES: CC(C)(C)COc1ncnc2[nH]cc(C/C=C\C#N)c12] | (Z)-4-(4-(neopentyloxy)-7H-pyrrolo[2,3-d]pyrimidin-5-yl)but-2-enenitrile |

| Ex. # | Structure | Name |
|---|---|---|
| 261 | 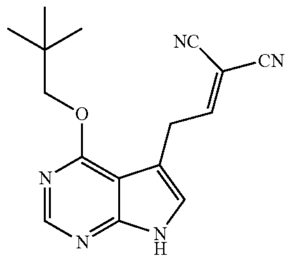 [SMILES: CC(C)(C)COc1ncnc2[nH]cc(CC=C(C#N)C#N)c12] | 2-(2-(4-(neopentyloxy)-7H-pyrrolo[2,3-d]pyrimidin-5-yl)ethylidene)malononitrile |
| 262 | 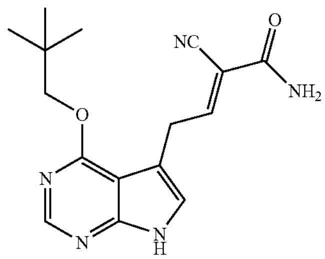 [SMILES: CC(C)(C)COc1ncnc2[nH]cc(C/C=C(\C#N)C(N)=O)c12] | (E)-2-cyano-4-(4-(neopentyloxy)-7H-pyrrolo[2,3-d]pyrimidin-5-yl)but-2-enamide |
| 263 | 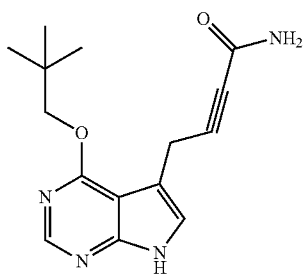 [SMILES: CC(C)(C)COc1ncnc2[nH]cc(CC#CC(N)=O)c12] | 4-(4-(neopentyloxy)-7H-pyrrolo[2,3-d]pyrimidin-5-yl)but-2-ynamide |
| 264 | 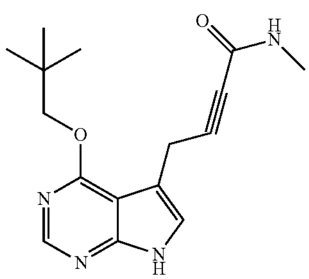 [SMILES: CNC(=O)C#CCc1c[nH]c2ncnc(OCC(C)(C)C)c12] | N-methyl-4-(4-(neopentyloxy)-7H-pyrrolo[2,3-d]pyrimidin-5-yl)but-2-ynamide |
| 265 | 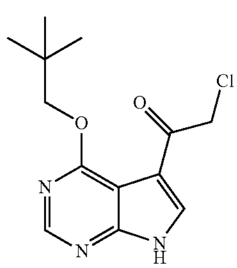 [SMILES: CC(C)(C)COc1ncnc2[nH]cc(C(=O)CCl)c12] | 2-chloro-1-(4-(neopentyloxy)-7H-pyrrolo[2,3-d]pyrimidin-5-yl)ethanone |
| 266 | 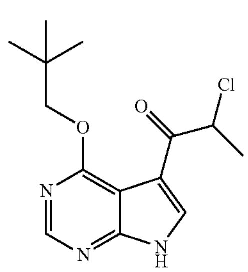 [SMILES: CC(Cl)C(=O)c1c[nH]c2ncnc(OCC(C)(C)C)c12] | 2-chloro-1-(4-(neopentyloxy)-7H-pyrrolo[2,3-d]pyrimidin-5-yl)propan-1-one |

| Ex. # | Structure | Name |
|---|---|---|
| 267 | 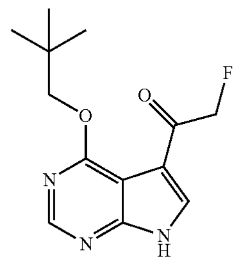 [SMILES: CC(C)(C)COc1ncnc2[nH]cc(C(=O)CF)c12] | 2-fluoro-1-(4-(neopentyloxy)-7H-pyrrolo[2,3-d]pyrimidin-5-yl)ethanone |
| 268 | 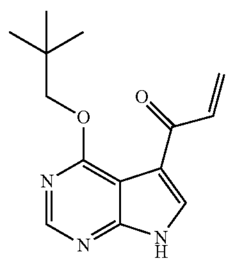 [SMILES: C=CC(=O)c1c[nH]c2ncnc(OCC(C)(C)C)c12] | 1-(4-(neopentyloxy)-7H-pyrrolo[2,3-d]pyrimidin-5-yl)prop-2-en-1-one |
| 269 | 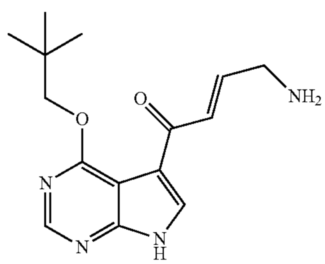 [SMILES: CC(C)(C)COc1ncnc2[nH]cc(C(=O)/C=C/CN)c12] | (E)-4-amino-1-(4-(neopentyloxy)-7H-pyrrolo[2,3-d]pyrimidin-5-yl)but-2-en-1-one |
| 270 | 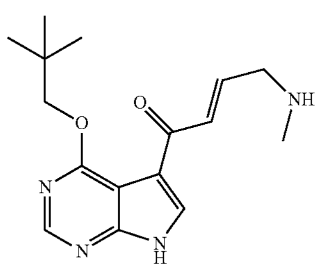 [SMILES: CNC/C=C/C(=O)c1c[nH]c2ncnc(OCC(C)(C)C)c12] | (E)-4-(methylamino)-1-(4-(neopentyloxy)-7H-pyrrolo[2,3-d]pyrimidin-5-yl)but-2-en-1-one |
| 271 | 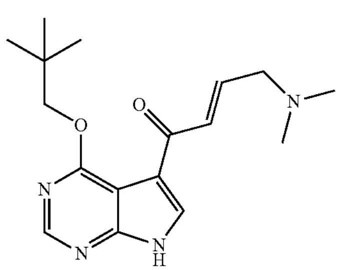 [SMILES: CN(C)C/C=C/C(=O)c1c[nH]c2ncnc(OCC(C)(C)C)c12] | (E)-4-(dimethylamino)-1-(4-(neopentyloxy)-7H-pyrrolo[2,3-d]pyrimidin-5-yl)but-2-en-1-one |

| Ex. # | Structure | Name |
|---|---|---|
| 272 | 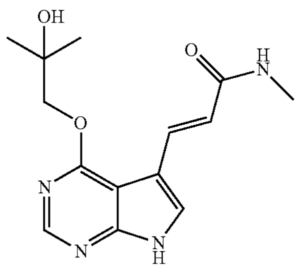 [SMILES: CNC(=O)/C=C/c1c[nH]c2ncnc(OCC(C)(C)O)c12] | (E)-3-(4-(2-hydroxy-2-methylpropoxy)-7H-pyrrolo[2,3-d]pyrimidin-5-yl)-N-methylacrylamide |
| 273 | 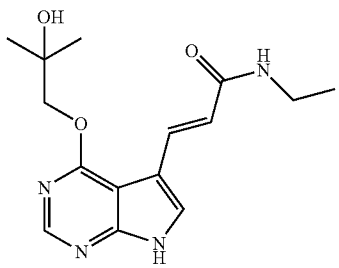 [SMILES: CCNC(=O)/C=C/c1c[nH]c2ncnc(OCC(C)(C)O)c12] | (E)-N-ethyl-3-(4-(2-hydroxy-2-methylpropoxy)-7H-pyrrolo[2,3-d]pyrimidin-5-yl)acrylamide |
| 274 | 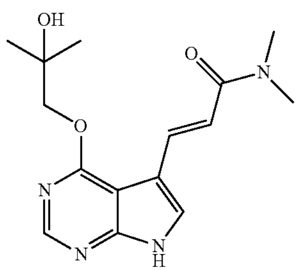 [SMILES: CN(C)C(=O)/C=C/c1c[nH]c2ncnc(OCC(C)(C)O)c12] | (E)-3-(4-(2-hydroxy-2-methylpropoxy)-7H-pyrrolo[2,3-d]pyrimidin-5-yl)-N,N-dimethylacrylamide |
| 275 | 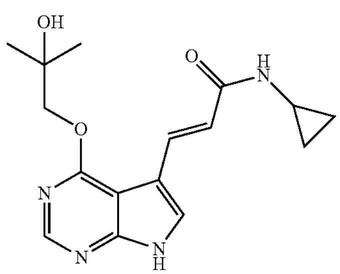 [SMILES: CC(C)(O)COc1ncnc2[nH]cc(/C=C/C(=O)NC3CC3)c12] | (E)-N-cyclopropyl-3-(4-(2-hydroxy-2-methylpropoxy)-7H-pyrrolo[2,3-d]pyrimidin-5-yl)acrylamide |
| 276 | 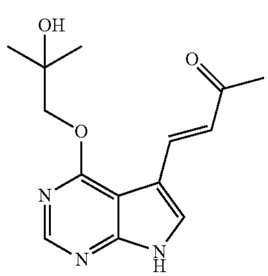 [SMILES: CC(=O)/C=C/c1c[nH]c2ncnc(OCC(C)(C)O)c12] | (E)-4-(4-(2-hydroxy-2-methylpropoxy)-7H-pyrrolo[2,3-d]pyrimidin-5-yl)but-3-en-2-one |

-continued

| Ex. # | Structure | Name |
|---|---|---|
| 277 | 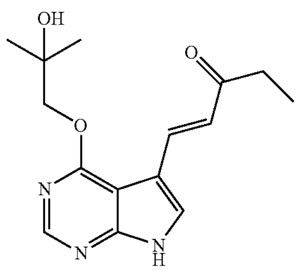 [SMILES: CCC(=O)/C=C/c1c[nH]c2ncnc(OCC(C)(C)O)c12] | (E)-1-(4-(2-hydroxy-2-methylpropoxy)-7H-pyrrolo[2,3-d]pyrimidin-5-yl)pent-1-en-3-one |
| 278 | 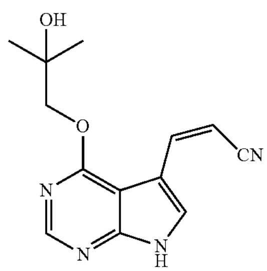 [SMILES: CC(C)(O)COc1ncnc2[nH]cc(/C=C\C#N)c12] | (Z)-3-(4-(2-hydroxy-2-methylpropoxy)-7H-pyrrolo[2,3-d]pyrimidin-5-yl)acrylonitrile |
| 279 | 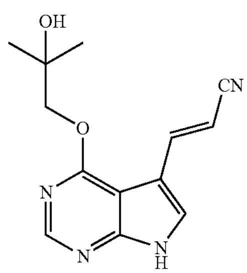 [SMILES: CC(C)(O)COc1ncnc2[nH]cc(/C=C/C#N)c12] | (E)-3-(4-(2-hydroxy-2-methylpropoxy)-7H-pyrrolo[2,3-d]pyrimidin-5-yl)acrylonitrile |
| 280 | 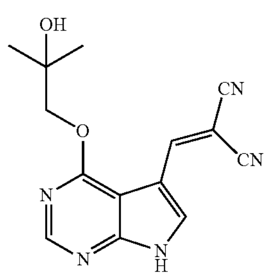 [SMILES: CC(C)(O)COc1ncnc2[nH]cc(C=C(C#N)C#N)c12] | 2-((4-(2-hydroxy-2-methylpropoxy)-7H-pyrrolo[2,3-d]pyrimidin-5-yl)methylene)malononitrile |
| 281 | 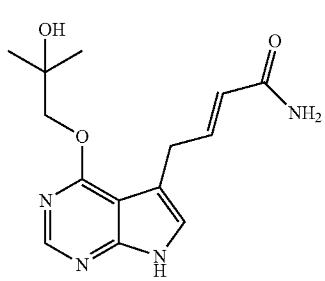 [SMILES: CC(C)(O)COc1ncnc2[nH]cc(C/C=C/C(N)=O)c12] | (E)-4-(4-(2-hydroxy-2-methylpropoxy)-7H-pyrrolo[2,3-d]pyrimidin-5-yl)but-2-enamide |

| Ex. # | Structure | Name |
|---|---|---|
| 282 | 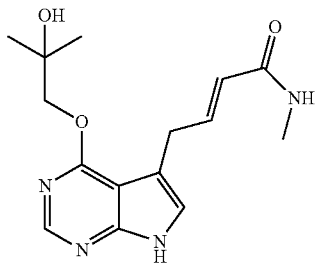 [SMILES: CNC(=O)/C=C/Cc1c[nH]c2ncnc(OCC(C)(C)O)c12] | (E)-4-(4-(2-hydroxy-2-methylpropoxy)-7H-pyrrolo[2,3-d]pyrimidin-5-yl)-N-methylbut-2-enamide |
| 283 | 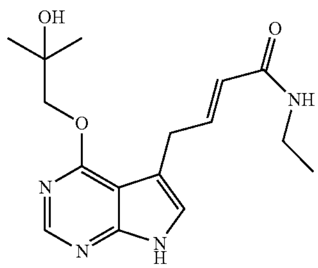 [SMILES: CCNC(=O)/C=C/Cc1c[nH]c2ncnc(OCC(C)(C)O)c12] | (E)-N-ethyl-4-(4-(2-hydroxy-2-methylpropoxy)-7H-pyrrolo[2,3-d]pyrimidin-5-yl)but-2-enamide |
| 284 | 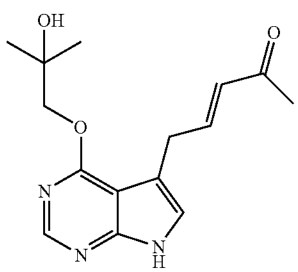 [SMILES: CC(=O)/C=C/Cc1c[nH]c2ncnc(OCC(C)(C)O)c12] | (E)-5-(4-(2-hydroxy-2-methylpropoxy)-7H-pyrrolo[2,3-d]pyrimidin-5-yl)pent-3-en-2-one |
| 285 | 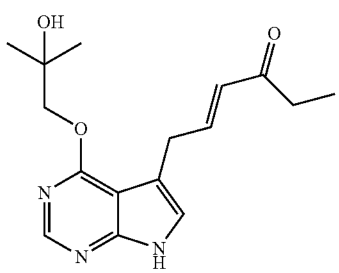 [SMILES: CCC(=O)/C=C/Cc1c[nH]c2ncnc(OCC(C)(C)O)c12] | (E)-6-(4-(2-hydroxy-2-methylpropoxy)-7H-pyrrolo[2,3-d]pyrimidin-5-yl)hex-4-en-3-one |
| 286 | 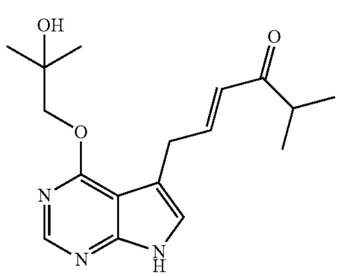 [SMILES: CC(C)C(=O)/C=C/Cc1c[nH]c2ncnc(OCC(C)(C)O)c12] | (E)-6-(4-(2-hydroxy-2-methylpropoxy)-7H-pyrrolo[2,3-d]pyrimidin-5-yl)-2-methylhex-4-en-3-one |

-continued

| Ex. # | Structure | Name |
|---|---|---|
| 287 | 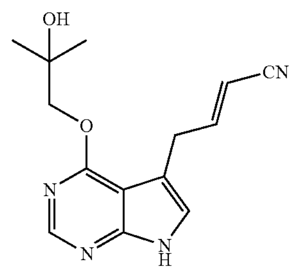 [SMILES: CC(C)(O)COc1ncnc2[nH]cc(C/C=C/C#N)c12] | (E)-4-(4-(2-hydroxy-2-methylpropoxy)-7H-pyrrolo[2,3-d]pyrimidin-5-yl)but-2-enenitrile |
| 288 | 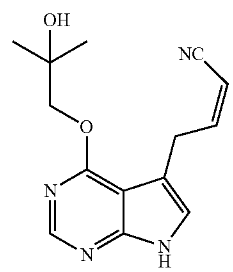 [SMILES: CC(C)(O)COc1ncnc2[nH]cc(C/C=C\C#N)c12] | (Z)-4-(4-(2-hydroxy-2-methylpropoxy)-7H-pyrrolo[2,3-d]pyrimidin-5-yl)but-2-enenitrile |
| 289 | 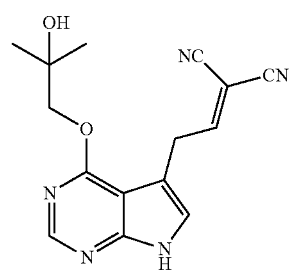 [SMILES: CC(C)(O)COc1ncnc2[nH]cc(CC=C(C#N)C#N)c12] | 2-(2-(4-(2-hydroxy-2-methylpropoxy)-7H-pyrrolo[2,3-d]pyrimidin-5-yl)ethylidene)malononitrile |
| 290 | 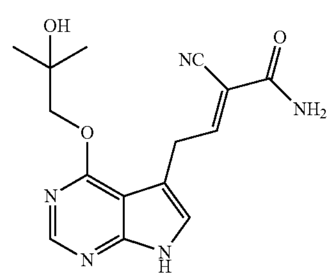 [SMILES: CC(C)(O)COc1ncnc2[nH]cc(C/C=C(\C#N)C(N)=O)c12] | (E)-2-cyano-4-(4-(2-hydroxy-2-methylpropoxy)-7H-pyrrolo[2,3-d]pyrimidin-5-yl)but-2-enamide |
| 291 | 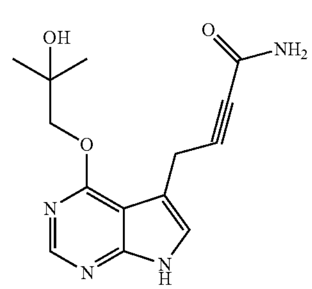 [SMILES: CC(C)(O)COc1ncnc2[nH]cc(CC#CC(N)=O)c12] | 4-(4-(2-hydroxy-2-methylpropoxy)-7H-pyrrolo[2,3-d]pyrimidin-5-yl)but-2-ynamide |

-continued

| Ex. # | Structure | Name |
|---|---|---|
| 292 | 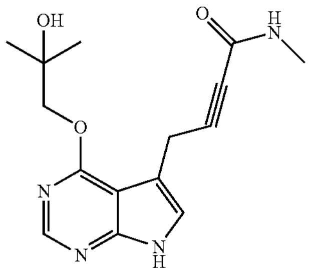 [SMILES: CNC(=O)C#CCc1c[nH]c2ncnc(OCC(C)(C)O)c12] | 4-(4-(2-hydroxy-2-methylpropoxy)-7H-pyrrolo[2,3-d]pyrimidin-5-yl)-N-methylbut-2-ynamide |
| 293 | 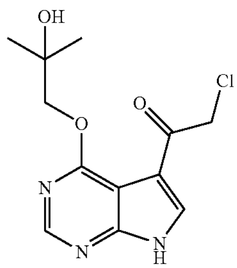 [SMILES: CC(C)(O)COc1ncnc2[nH]cc(C(=O)CCl)c12] | 2-chloro-1-(4-(2-hydroxy-2-methylpropoxy)-7H-pyrrolo[2,3-d]pyrimidin-5-yl)ethanone |
| 294 | 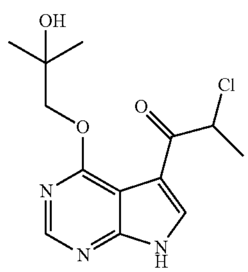 [SMILES: CC(Cl)C(=O)c1c[nH]c2ncnc(OCC(C)(C)O)c12] | 2-chloro-1-(4-(2-hydroxy-2-methylpropoxy)-7H-pyrrolo[2,3-d]pyrimidin-5-yl)propan-1-one |
| 295 | 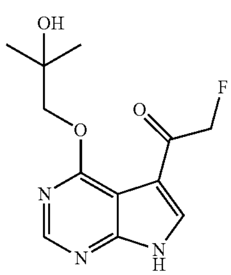 [SMILES: CC(C)(O)COc1ncnc2[nH]cc(C(=O)CF)c12] | 2-fluoro-1-(4-(2-hydroxy-2-methylpropoxy)-7H-pyrrolo[2,3-d]pyrimidin-5-yl)ethanone |
| 296 | 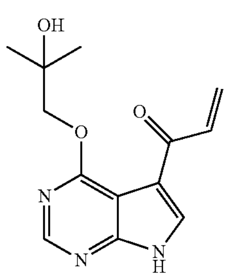 [SMILES: C=CC(=O)c1c[nH]c2ncnc(OCC(C)(C)O)c12] | 1-(4-(2-hydroxy-2-methylpropoxy)-7H-pyrrolo[2,3-d]pyrimidin-5-yl)prop-2-en-1-one |

-continued

| Ex. # | Structure | Name |
|---|---|---|
| 297 | 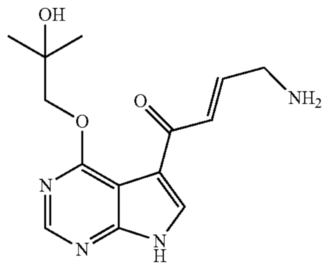 [SMILES: CC(C)(O)COc1ncnc2[nH]cc(C(=O)/C=C/CN)c12] | (E)-4-amino-1-(4-(2-hydroxy-2-methylpropoxy)-7H-pyrrolo[2,3-d]pyrimidin-5-yl)but-2-en-1-one |
| 298 | 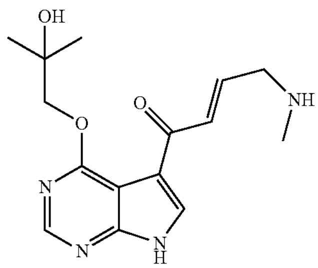 [SMILES: CNC/C=C/C(=O)c1c[nH]c2ncnc(OCC(C)(C)O)c12] | (E)-1-(4-(2-hydroxy-2-methylpropoxy)-7H-pyrrolo[2,3-d]pyrimidin-5-yl)-4-(methylamino)but-2-en-1-one |
| 299 | 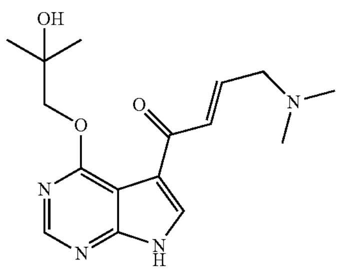 [SMILES: CN(C)C/C=C/C(=O)c1c[nH]c2ncnc(OCC(C)(C)O)c12] | (E)-4-(dimethylamino)-1-(4-(2-hydroxy-2-methylpropoxy)-7H-pyrrolo[2,3-d]pyrimidin-5-yl)but-2-en-1-one |
| 300 | 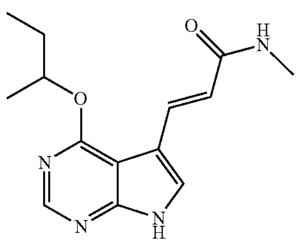 | (E)-3-(4-(sec-butoxy)-7H-pyrrolo[2,3-d]pyrimidin-5-yl)-N-methylacrylamide |
| 301 | 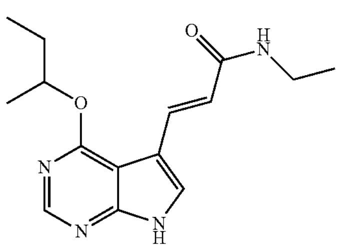 [SMILES: CCNC(=O)/C=C/c1c[nH]c2ncnc(OC(C)CC)c12] | (E)-3-(4-(sec-butoxy)-7H-pyrrolo[2,3-d]pyrimidin-5-yl)-N-ethylacrylamide |
| 302 | 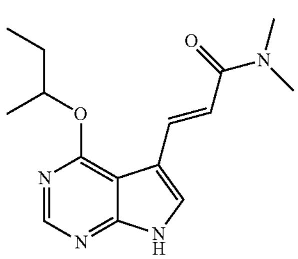 [SMILES: CCC(C)Oc1ncnc2[nH]cc(/C=C/C(=O)N(C)C)c12] | (E)-3-(4-(sec-butoxy)-7H-pyrrolo[2,3-d]pyrimidin-5-yl)-N,N-dimethylacrylamide |

| Ex. # | Structure | Name |
|---|---|---|
| 303 | 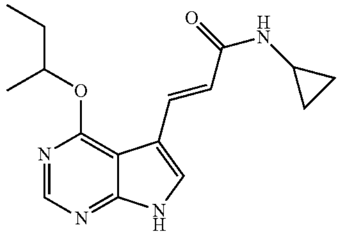 [SMILES: CCC(C)Oc1ncnc2[nH]cc(/C=C/C(=O)NC3CC3)c12] | (E)-3-(4-(sec-butoxy)-7H-pyrrolo[2,3-d]pyrimidin-5-yl)-N-cyclopropylacrylamide |
| 304 | 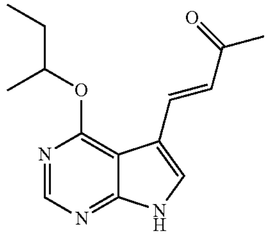 [SMILES: CCC(C)Oc1ncnc2[nH]cc(/C=C/C(C)=O)c12] | (E)-4-(4-(sec-butoxy)-7H-pyrrolo[2,3-d]pyrimidin-5-yl)but-3-en-2-one |
| 305 | 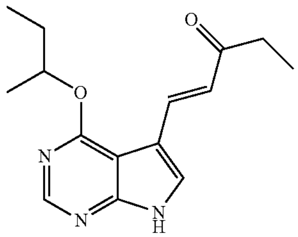 [SMILES: CCC(=O)/C=C/c1c[nH]c2ncnc(OC(C)CC)c12] | (E)-1-(4-(sec-butoxy)-7H-pyrrolo[2,3-d]pyrimidin-5-yl)pent-1-en-3-one |
| 306 | 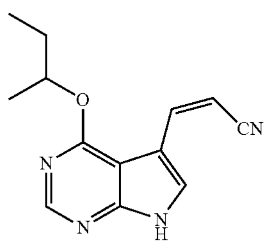 [SMILES: CCC(C)Oc1ncnc2[nH]cc(/C=C\C#N)c12] | (Z)-3-(4-(sec-butoxy)-7H-pyrrolo[2,3-d]pyrimidin-5-yl)acrylonitrile |
| 307 | 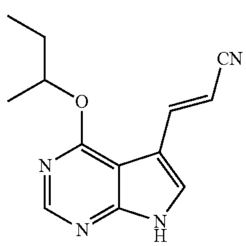 [SMILES: CCC(C)Oc1ncnc2[nH]cc(/C=C/C#N)c12] | (E)-3-(4-(sec-butoxy)-7H-pyrrolo[2,3-d]pyrimidin-5-yl)acrylonitrile |
| 308 | 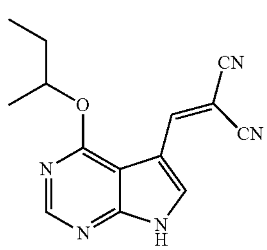 [SMILES: CCC(C)Oc1ncnc2[nH]cc(C=C(C#N)C#N)c12] | 2-((4-(sec-butoxy)-7H-pyrrolo[2,3-d]pyrimidin-5-yl)methylene)malononitrile |

| Ex. # | Structure | Name |
|---|---|---|
| 309 | 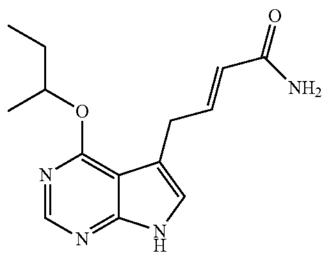 [SMILES: CCC(C)Oc1ncnc2[nH]cc(C/C=C/C(N)=O)c12] | (E)-4-(4-(sec-butoxy)-7H-pyrrolo[2,3-d]pyrimidin-5-yl)but-2-enamide |
| 310 | 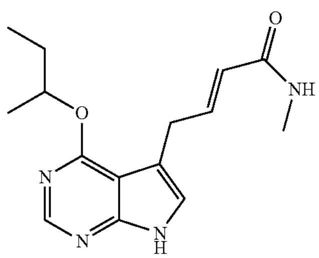 [SMILES: CCC(C)Oc1ncnc2[nH]cc(C/C=C/C(=O)NC)c12] | (E)-4-(4-(sec-butoxy)-7H-pyrrolo[2,3-d]pyrimidin-5-yl)-N-methylbut-2-enamide |
| 311 | 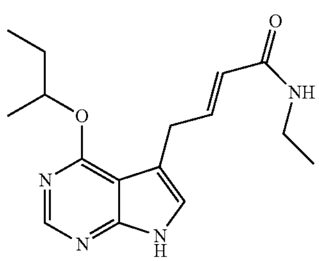 [SMILES: CCNC(=O)/C=C/Cc1c[nH]c2ncnc(OC(C)CC)c12] | (E)-4-(4-(sec-butoxy)-7H-pyrrolo[2,3-d]pyrimidin-5-yl)-N-ethylbut-2-enamide |
| 312 | 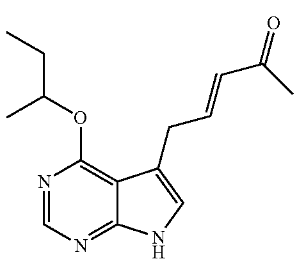 [SMILES: CCC(C)Oc1ncnc2[nH]cc(C/C=C/C(C)=O)c12] | (E)-5-(4-(sec-butoxy)-7H-pyrrolo[2,3-d]pyrimidin-5-yl)pent-3-en-2-one |
| 313 | 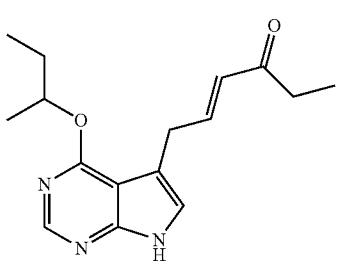 [SMILES: CCC(=O)/C=C/Cc1c[nH]c2ncnc(OC(C)CC)c12] | (E)-6-(4-((3-methylbutan-2-yl)oxy)-7H-pyrrolo[2,3-d]pyrimidin-5-yl)hex-4-en-3-one |
| 314 | 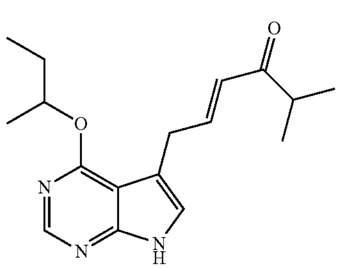 [SMILES: CCC(C)Oc1ncnc2[nH]cc(C/C=C/C(=O)C(C)C)c12] | (E)-6-(4-(sec-butoxy)-7H-pyrrolo[2,3-d]pyrimidin-5-yl)-2-methylhex-4-en-3-one |

| Ex. # | Structure | Name |
|---|---|---|
| 315 | 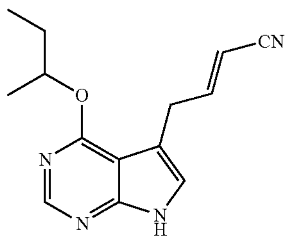 [SMILES: CCC(C)Oc1ncnc2[nH]cc(C/C=C/C#N)c12] | (E)-4-(4-(sec-butoxy)-7H-pyrrolo[2,3-d]pyrimidin-5-yl)but-2-enenitrile |
| 316 | 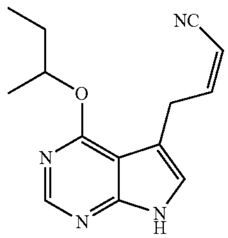 [SMILES: CCC(C)Oc1ncnc2[nH]cc(C/C=C\C#N)c12] | (Z)-4-(4-(sec-butoxy)-7H-pyrrolo[2,3-d]pyrimidin-5-yl)but-2-enenitrile |
| 317 | 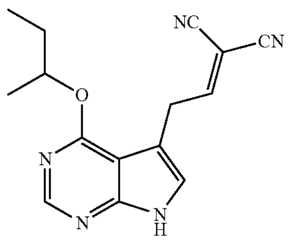 [SMILES: CCC(C)Oc1ncnc2[nH]cc(CC=C(C#N)C#N)c12] | 2-(2-(4-(sec-butoxy)-7H-pyrrolo[2,3-d]pyrimidin-5-yl)ethylidene)malononitrile |
| 318 | 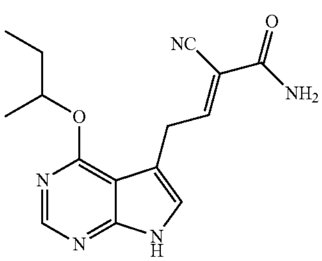 [SMILES: CCC(C)Oc1ncnc2[nH]cc(C/C=C(\C#N)C(N)=O)c12] | (E)-4-(4-(sec-butoxy)-7H-pyrrolo[2,3-d]pyrimidin-5-yl)-2-cyanobut-2-enamide |
| 319 | 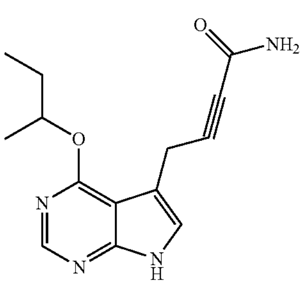 [SMILES: CCC(C)Oc1ncnc2[nH]cc(CC#CC(N)=O)c12] | 4-(4-(sec-butoxy)-7H-pyrrolo[2,3-d]pyrimidin-5-yl)but-2-ynamide |
| 320 | 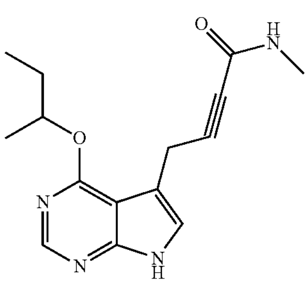 [SMILES: CCC(C)Oc1ncnc2[nH]cc(CC#CC(=O)NC)c12] | 4-(4-(sec-butoxy)-7H-pyrrolo[2,3-d]pyrimidin-5-yl)-N-methylbut-2-ynamide |

-continued

| Ex. # | Structure | Name |
|---|---|---|
| 321 | 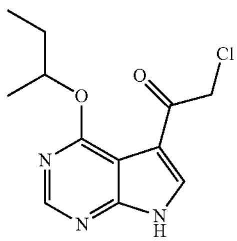 [SMILES: CCC(C)Oc1ncnc2[nH]cc(C(=O)CCl)c12] | 1-(4-(sec-butoxy)-7H-pyrrolo[2,3-d]pyrimidin-5-yl)-2-chloroethanone |
| 322 | 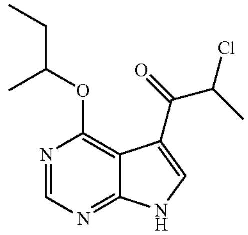 [SMILES: CCC(C)Oc1ncnc2[nH]cc(C(=O)C(C)Cl)c12] | 1-(4-(sec-butoxy)-7H-pyrrolo[2,3-d]pyrimidin-5-yl)-2-chloropropan-1-one |
| 323 | 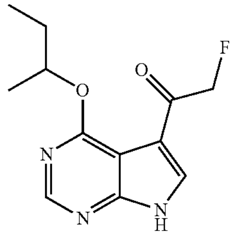 [SMILES: CCC(C)Oc1ncnc2[nH]cc(C(=O)CF)c12] | 1-(4-(sec-butoxy)-7H-pyrrolo[2,3-d]pyrimidin-5-yl)-2-fluoroethanone |
| 324 | 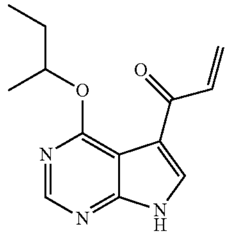 [SMILES: C=CC(=O)c1c[nH]c2ncnc(OC(C)CC)c12] | 1-(4-(sec-butoxy)-7H-pyrrolo[2,3-d]pyrimidin-5-yl)prop-2-en-1-one |
| 325 | 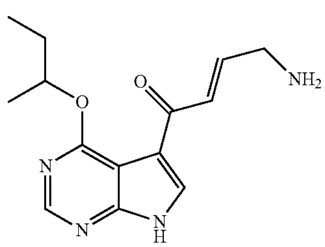 [SMILES: CCC(C)Oc1ncnc2[nH]cc(C(=O)/C=C/CN)c12] | (E)-4-amino-1-(4-(sec-butoxy)-7H-pyrrolo[2,3-d]pyrimidin-5-yl)but-2-en-1-one |
| 326 | 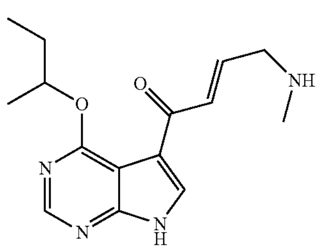 [SMILES: CCC(C)Oc1ncnc2[nH]cc(C(=O)/C=C/CNC)c12] | (E)-1-(4-(sec-butoxy)-7H-pyrrolo[2,3-d]pyrimidin-5-yl)-4-(methylamino)but-2-en-1-one |

-continued

| Ex. # | Structure | Name |
|---|---|---|
| 327 | 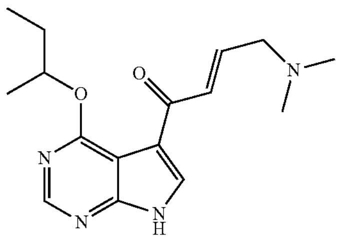 [SMILES: CCC(C)Oc1ncnc2[nH]cc(C(=O)/C=C/CN(C)C)c12] | (E)-1-(4-(sec-butoxy)-7H-pyrrolo[2,3-d]pyrimidin-5-yl)-4-(dimethylamino)but-2-en-1-one |
| 328 | 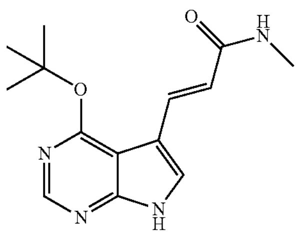 [SMILES: CNC(=O)/C=C/c1c[nH]c2ncnc(OC(C)(C)C)c12] | (E)-3-(4-(tert-butoxy)-7H-pyrrolo[2,3-d]pyrimidin-5-yl)-N-methylacrylamide |
| 329 | 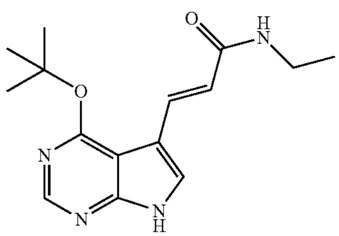 [SMILES: CCNC(=O)/C=C/c1c[nH]c2ncnc(OC(C)(C)C)c12] | (E)-3-(4-(tert-butoxy)-7H-pyrrolo[2,3-d]pyrimidin-5-yl)-N-ethylacrylamide |
| 330 | 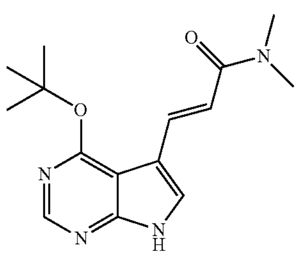 [SMILES: CN(C)C(=O)/C=C/c1c[nH]c2ncnc(OC(C)(C)C)c12] | (E)-3-(4-(tert-butoxy)-7H-pyrrolo[2,3-d]pyrimidin-5-yl)-N,N-dimethylacrylamide |
| 331 | 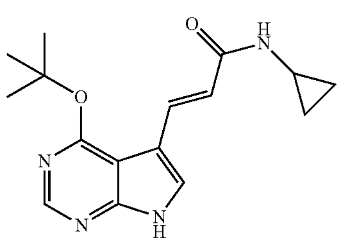 [SMILES: CC(C)(C)Oc1ncnc2[nH]cc(/C=C/C(=O)NC3CC3)c12] | (E)-3-(4-(tert-butoxy)-7H-pyrrolo[2,3-d]pyrimidin-5-yl)-N-cyclopropylacrylamide |
| 332 | 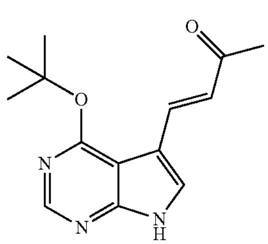 [SMILES: CC(=O)/C=C/c1c[nH]c2ncnc(OC(C)(C)C)c12] | (E)-4-(4-(tert-butoxy)-7H-pyrrolo[2,3-d]pyrimidin-5-yl)but-3-en-2-one |

| Ex. # | Structure | Name |
|---|---|---|
| 333 | 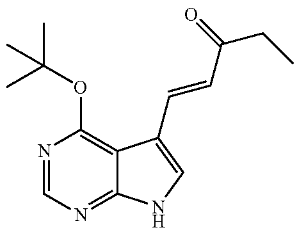 [SMILES: CCC(=O)/C=C/c1c[nH]c2ncnc(OC(C)(C)C)c12] | (E)-1-(4-(tert-butoxy)-7H-pyrrolo[2,3-d]pyrimidin-5-yl)pent-1-en-3-one |
| 334 | 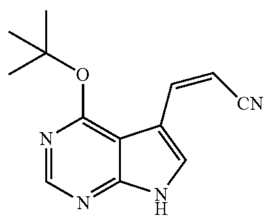 [SMILES: CC(C)(C)Oc1ncnc2[nH]cc(/C=C\C#N)c12] | (Z)-3-(4-(tert-butoxy)-7H-pyrrolo[2,3-d]pyrimidin-5-yl)acrylonitrile |
| 335 | 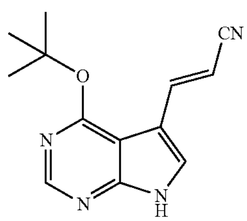 [SMILES: CC(C)(C)Oc1ncnc2[nH]cc(/C=C/C#N)c12] | (E)-3-(4-(tert-butoxy)-7H-pyrrolo[2,3-d]pyrimidin-5-yl)acrylonitrile |
| 336 | 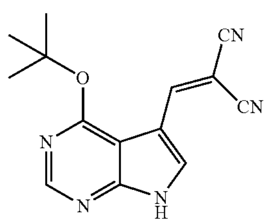 [SMILES: CC(C)(C)Oc1ncnc2[nH]cc(C=C(C#N)C#N)c12] | 2-((4-(tert-butoxy)-7H-pyrrolo[2,3-d]pyrimidin-5-yl)methylene)malononitrile |
| 337 | 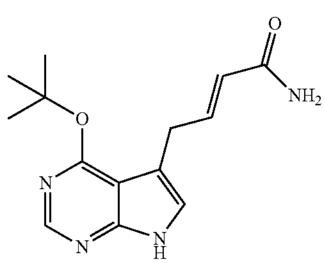 [SMILES: CC(C)(C)Oc1ncnc2[nH]cc(C/C=C/C(N)=O)c12] | (E)-4-(4-(tert-butoxy)-7H-pyrrolo[2,3-d]pyrimidin-5-yl)but-2-enamide |
| 338 | 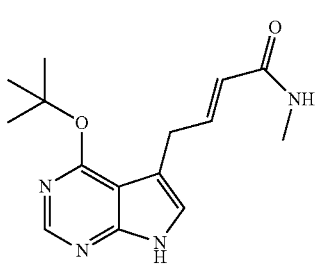 [SMILES: CNC(=O)/C=C/Cc1c[nH]c2ncnc(OC(C)(C)C)c12] | (E)-4-(4-(tert-butoxy)-7H-pyrrolo[2,3-d]pyrimidin-5-yl)-N-methylbut-2-enamide |

-continued

| Ex. # | Structure | Name |
|---|---|---|
| 339 | 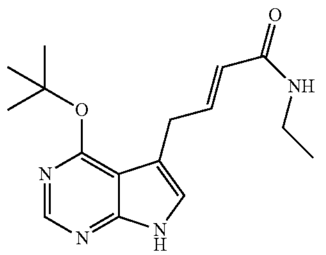 [SMILES: CCNC(=O)/C=C/Cc1c[nH]c2ncnc(OC(C)(C)C)c12] | (E)-4-(4-(tert-butoxy)-7H-pyrrolo[2,3-d]pyrimidin-5-yl)-N-ethylbut-2-enamide |
| 340 | 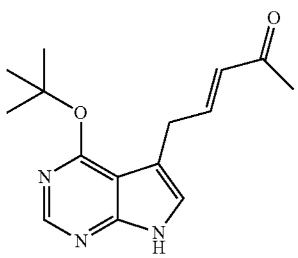 [SMILES: CC(=O)/C=C/Cc1c[nH]c2ncnc(OC(C)(C)C)c12] | (E)-5-(4-(tert-butoxy)-7H-pyrrolo[2,3-d]pyrimidin-5-yl)pent-3-en-2-one |
| 341 | 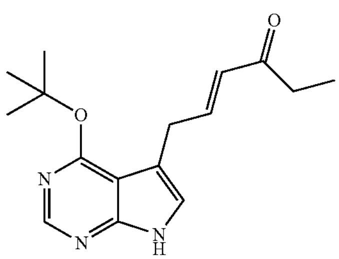 [SMILES: CCC(=O)/C=C/Cc1c[nH]c2ncnc(OC(C)(C)C)c12] | (E)-6-(4-(tert-butoxy)-7H-pyrrolo[2,3-d]pyrimidin-5-yl)hex-4-en-3-one |
| 342 | 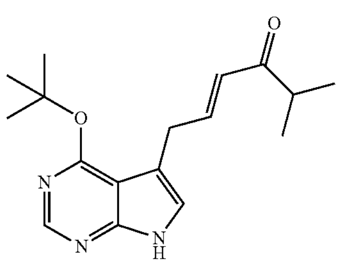 [SMILES: CC(C)C(=O)/C=C/Cc1c[nH]c2ncnc(OC(C)(C)C)c12] | (E)-6-(4-(tert-butoxy)-7H-pyrrolo[2,3-d]pyrimidin-5-yl)-2-methylhex-4-en-3-one |
| 343 | 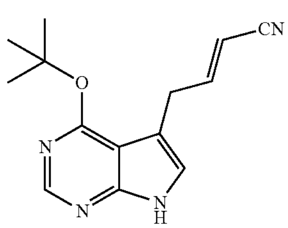 [SMILES: CC(C)(C)Oc1ncnc2[nH]cc(C/C=C/C#N)c12] | (E)-4-(4-(tert-butoxy)-7H-pyrrolo[2,3-d]pyrimidin-5-yl)but-2-enenitrile |
| 344 | 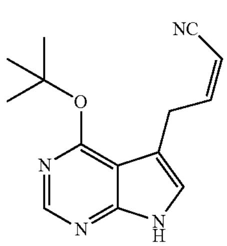 [SMILES: CC(C)(C)Oc1ncnc2[nH]cc(C/C=C\C#N)c12] | (Z)-4-(4-(tert-butoxy)-7H-pyrrolo[2,3-d]pyrimidin-5-yl)but-2-enenitrile |

-continued

| Ex. # | Structure | Name |
|---|---|---|
| 345 | 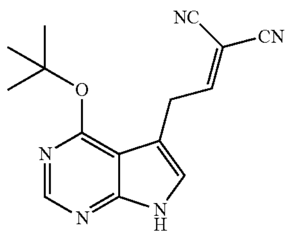 [SMILES: CC(C)(C)Oc1ncnc2[nH]cc(CC=C(C#N)C#N)c12] | 2-(2-(4-(tert-butoxy)-7H-pyrrolo[2,3-d]pyrimidin-5-yl)ethylidene)malononitrile |
| 346 | 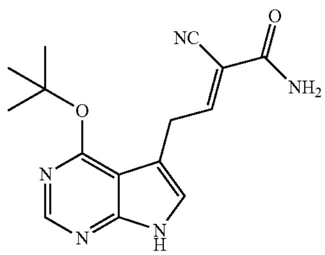 [SMILES: CC(C)(C)Oc1ncnc2[nH]cc(C/C=C(\C#N)C(N)=O)c12] | (E)-4-(4-(tert-butoxy)-7H-pyrrolo[2,3-d]pyrimidin-5-yl)-2-cyanobut-2-enamide |
| 347 | 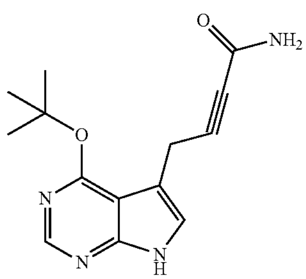 [SMILES: CC(C)(C)Oc1ncnc2[nH]cc(CC#CC(N)=O)c12] | 4-(4-(tert-butoxy)-7H-pyrrolo[2,3-d]pyrimidin-5-yl)but-2-ynamide |
| 348 | 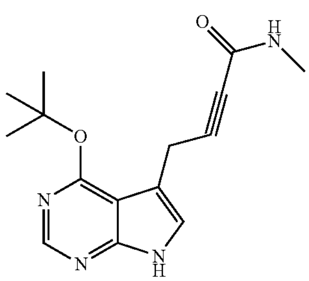 [SMILES: CNC(=O)C#CCc1c[nH]c2ncnc(OC(C)(C)C)c12] | 4-(4-(tert-butoxy)-7H-pyrrolo[2,3-d]pyrimidin-5-yl)-N-methylbut-2-ynamide |
| 349 | 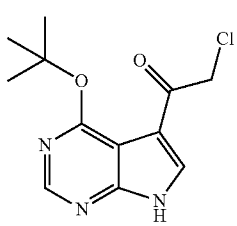 [SMILES: CC(C)(C)Oc1ncnc2[nH]cc(C(=O)CCl)c12] | 1-(4-(tert-butoxy)-7H-pyrrolo[2,3-d]pyrimidin-5-yl)-2-chloroethanone |
| 350 | 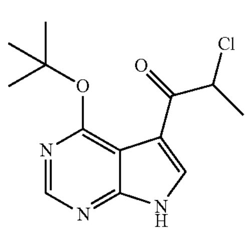 [SMILES: CC(Cl)C(=O)c1c[nH]c2ncnc(OC(C)(C)C)c12] | 1-(4-(tert-butoxy)-7H-pyrrolo[2,3-d]pyrimidin-5-yl)-2-chloropropan-1-one |

-continued

| Ex. # | Structure | Name |
|---|---|---|
| 351 | 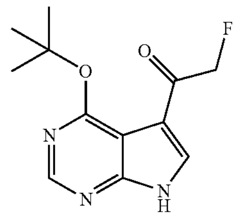 [SMILES: CC(C)(C)Oc1ncnc2[nH]cc(C(=O)CF)c12] | 1-(4-(tert-butoxy)-7H-pyrrolo[2,3-d]pyrimidin-5-yl)-2-fluoroethanone |
| 352 | 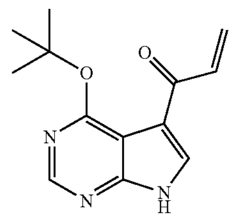 [SMILES: C=CC(=O)c1c[nH]c2ncnc(OC(C)(C)C)c12] | 1-(4-(tert-butoxy)-7H-pyrrolo[2,3-d]pyrimidin-5-yl)prop-2-en-1-one |
| 353 | 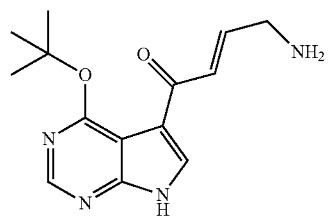 [SMILES: CC(C)(C)Oc1ncnc2[nH]cc(C(=O)/C=C/CN)c12] | (E)-4-amino-1-(4-(tert-butoxy)-7H-pyrrolo[2,3-d]pyrimidin-5-yl)but-2-en-1-one |
| 354 | 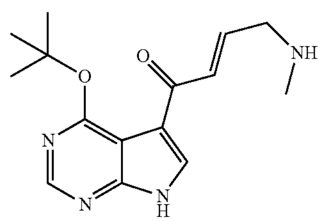 [SMILES: CNC/C=C/C(=O)c1c[nH]c2ncnc(OC(C)(C)C)c12] | (E)-1-(4-(tert-butoxy)-7H-pyrrolo[2,3-d]pyrimidin-5-yl)-4-(methylamino)but-2-en-1-one |
| 355 | 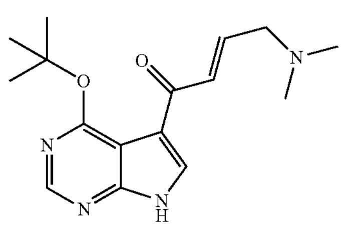 [SMILES: CN(C)C/C=C/C(=O)c1c[nH]c2ncnc(OC(C)(C)C)c12] | (E)-1-(4-(tert-butoxy)-7H-pyrrolo[2,3-d]pyrimidin-5-yl)-4-(dimethylamino)but-2-en-1-one |
| 356 | 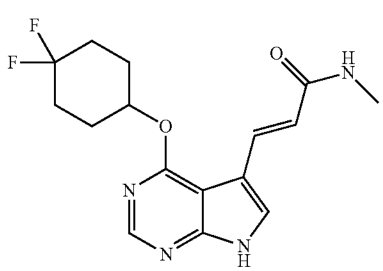 [SMILES: CNC(=O)/C=C/c1c[nH]c2ncnc(OC3CCC(F)(F)CC3)c12] | (E)-3-(4-((4,4-difluorocyclohexyl)oxy)-7H-pyrrolo[2,3-d]pyrimidin-5-yl)-N-methylacrylamide |

| Ex. # | Structure | Name |
|---|---|---|
| 357 | 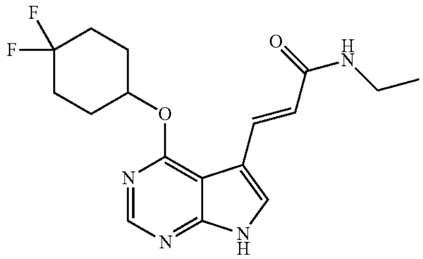 [SMILES: CCNC(=O)/C=C/c1c[nH]c2ncnc(OC3CCC(F)(F)CC3)c12] | (E)-3-(4-((4,4-difluorocyclohexyl)oxy)-7H-pyrrolo[2,3-d]pyrimidin-5-yl)-N-ethylacrylamide |
| 358 | 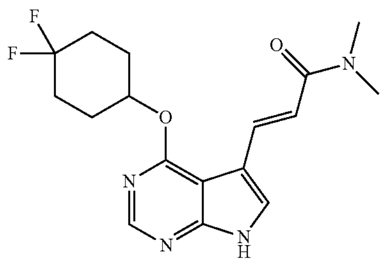 | (E)-3-(4-((4,4-difluorocyclohexyl)oxy)-7H-pyrrolo[2,3-d]pyrimidin-5-yl)-N,N-dimethylacrylamide |
| 359 | 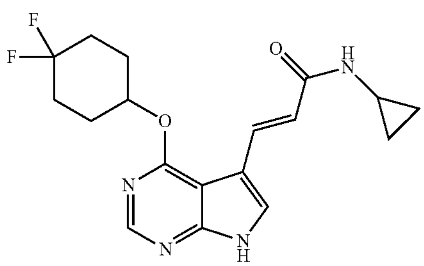 [SMILES: O=C(/C=C/c1c[nH]c2ncnc(OC3CCC(F)(F)CC3)c12)NC1CC1] | (E)-N-cyclopropyl-3-(4-((4,4-difluorocyclohexyl)oxy)-7H-pyrrolo[2,3-d]pyrimidin-5-yl)acrylamide |
| 360 | 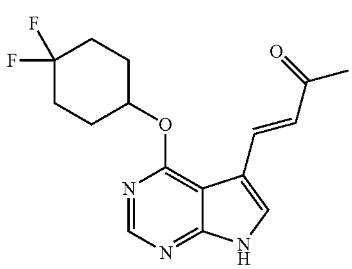 [SMILES: CC(=O)/C=C/c1c[nH]c2ncnc(OC3CCC(F)(F)CC3)c12] | (E)-4-(4-((4,4-difluorocyclohexyl)oxy)-7H-pyrrolo[2,3-d]pyrimidin-5-yl)but-3-en-2-one |
| 361 | 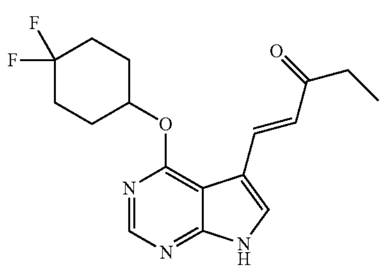 [SMILES: CCC(=O)/C=C/c1c[nH]c2ncnc(OC3CCC(F)(F)CC3)c12] | (E)-1-(4-((4,4-difluorocyclohexyl)oxy)-7H-pyrrolo[2,3-d]pyrimidin-5-yl)pent-1-en-3-one |
| 362 | 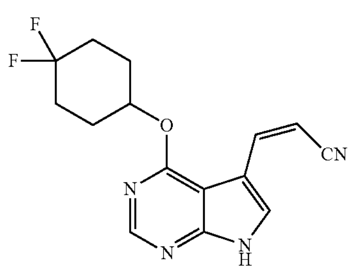 [SMILES: N#C/C=C\c1c[nH]c2ncnc(OC3CCC(F)(F)CC3)c12] | (Z)-3-(4-((4,4-difluorocyclohexyl)oxy)-7H-pyrrolo[2,3-d]pyrimidin-5-yl)acrylonitrile |

-continued

| Ex. # | Structure | Name |
|---|---|---|
| 363 | 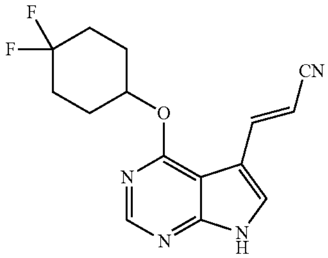 [SMILES: N#C/C=C/c1c[nH]c2ncnc(OC3CCC(F)(F)CC3)c12] | (E)-3-(4-((4,4-difluorocyclohexyl)oxy)-7H-pyrrolo[2,3-d]pyrimidin-5-yl)acrylonitrile |
| 364 | 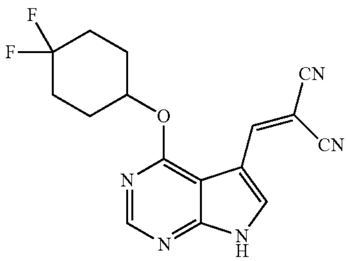 [SMILES: N#CC(C#N)=Cc1c[nH]c2ncnc(OC3CCC(F)(F)CC3)c12] | 2-((4-((4,4-difluorocyclohexyl)oxy)-7H-pyrrolo[2,3-d]pyrimidin-5-yl)methylene)malononitrile |
| 365 | 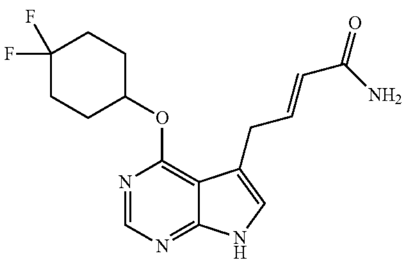 [SMILES: NC(=O)/C=C/Cc1c[nH]c2ncnc(OC3CCC(F)(F)CC3)c12] | (E)-4-(4-((4,4-difluorocyclohexyl)oxy)-7H-pyrrolo[2,3-d]pyrimidin-5-yl)but-2-enamide |
| 366 | 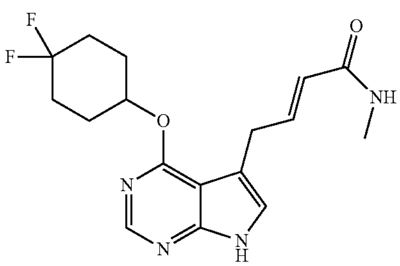 [SMILES: CNC(=O)/C=C/Cc1c[nH]c2ncnc(OC3CCC(F)(F)CC3)c12] | (E)-4-(4-((4,4-difluorocyclohexyl)oxy)-7H-pyrrolo[2,3-d]pyrimidin-5-yl)-N-methylbut-2-enamide |
| 367 | 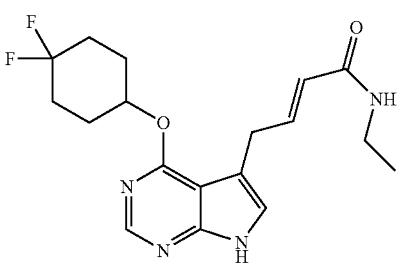 [SMILES: CCNC(=O)/C=C/Cc1c[nH]c2ncnc(OC3CCC(F)(F)CC3)c12] | (E)-4-(4-((4,4-difluorocyclohexyl)oxy)-7H-pyrrolo[2,3-d]pyrimidin-5-yl)-N-ethylbut-2-enamide |
| 368 | 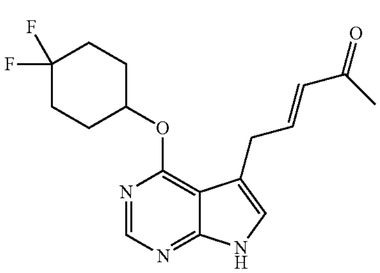 [SMILES: CC(=O)/C=C/Cc1c[nH]c2ncnc(OC3CCC(F)(F)CC3)c12] | (E)-5-(4-((4,4-difluorocyclohexyl)oxy)-7H-pyrrolo[2,3-d]pyrimidin-5-yl)pent-3-en-2-one |

-continued

| Ex. # | Structure | Name |
|---|---|---|
| 369 | 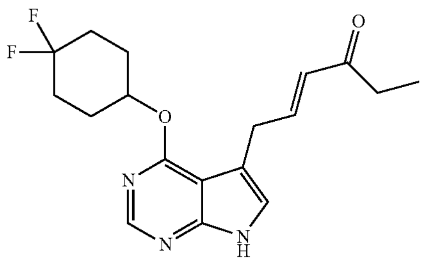 [SMILES: CCC(=O)/C=C/Cc1c[nH]c2ncnc(OC3CCC(F)(F)CC3)c12] | (E)-6-(4-((4,4-difluorocyclohexyl)oxy)-7H-pyrrolo[2,3-d]pyrimidin-5-yl)hex-4-en-3-one |
| 370 | 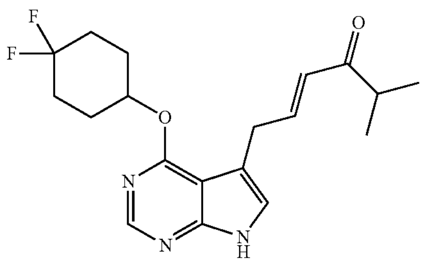 [SMILES: CC(C)C(=O)/C=C/Cc1c[nH]c2ncnc(OC3CCC(F)(F)CC3)c12] | (E)-6-(4-((4,4-difluorocyclohexyl)oxy)-7H-pyrrolo[2,3-d]pyrimidin-5-yl)-2-methylhex-4-en-3-one |
| 371 | 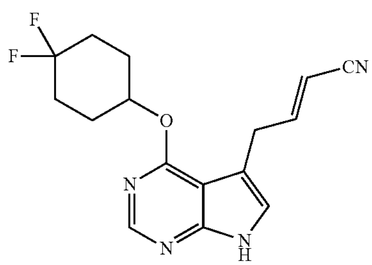 [SMILES: N#C/C=C/Cc1c[nH]c2ncnc(OC3CCC(F)(F)CC3)c12] | (E)-4-(4-((4,4-difluorocyclohexyl)oxy)-7H-pyrrolo[2,3-d]pyrimidin-5-yl)but-2-enenitrile |
| 372 | 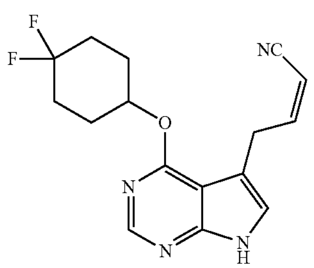 [SMILES: N#C/C=C\Cc1c[nH]c2ncnc(OC3CCC(F)(F)CC3)c12] | (Z)-4-(4-((4,4-difluorocyclohexyl)oxy)-7H-pyrrolo[2,3-d]pyrimidin-5-yl)but-2-enenitrile |
| 373 | 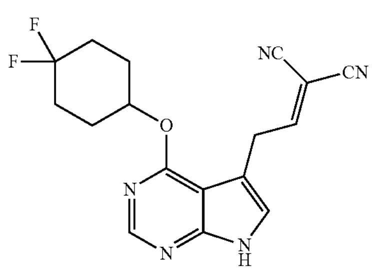 [SMILES: N#CC(C#N)=CCc1c[nH]c2ncnc(OC3CCC(F)(F)CC3)c12] | 2-(2-(4-((4,4-difluorocyclohexyl)oxy)-7H-pyrrolo[2,3-d]pyrimidin-5-yl)ethylidene)malononitrile |
| 374 | 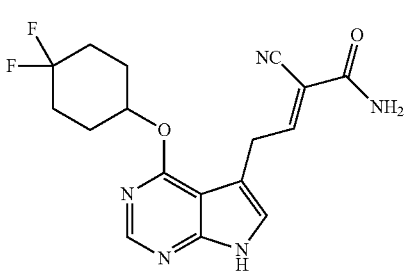 [SMILES: N#C/C(=C\Cc1c[nH]c2ncnc(OC3CCC(F)(F)CC3)c12)C(N)=O] | (E)-2-cyano-4-(4-((4,4-difluorocyclohexyl)oxy)-7H-pyrrolo[2,3-d]pyrimidin-5-yl)but-2-enamide |

| Ex. # | Structure | Name |
|---|---|---|
| 375 | 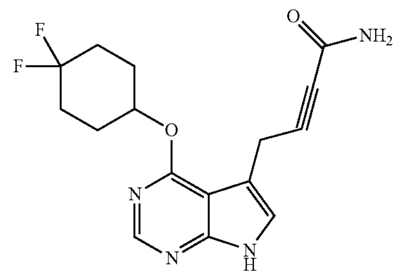 [SMILES: NC(=O)C#CCc1c[nH]c2ncnc(OC3CCC(F)(F)CC3)c12] | 4-(4-((4,4-difluorocyclohexyl)oxy)-7H-pyrrolo[2,3-d]pyrimidin-5-yl)but-2-ynamide |
| 376 | 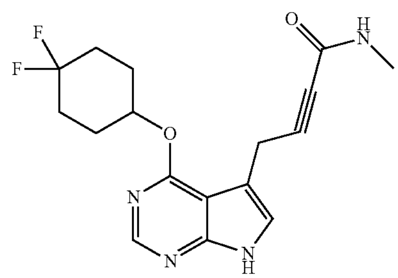 [SMILES: CNC(=O)C#CCc1c[nH]c2ncnc(OC3CCC(F)(F)CC3)c12] | 4-(4-((4,4-difluorocyclohexyl)oxy)-7H-pyrrolo[2,3-d]pyrimidin-5-yl)-N-methylbut-2-ynamide |
| 377 | 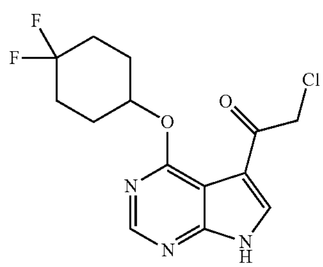 [SMILES: O=C(CCl)c1c[nH]c2ncnc(OC3CCC(F)(F)CC3)c12] | 2-chloro-1-(4-((4,4-difluorocyclohexyl)oxy)-7H-pyrrolo[2,3-d]pyrimidin-5-yl)ethanone |
| 378 | 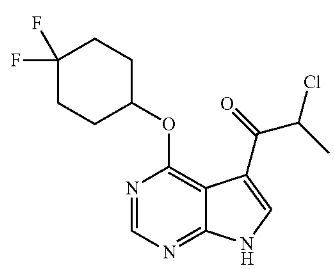 [SMILES: CC(Cl)C(=O)c1c[nH]c2ncnc(OC3CCC(F)(F)CC3)c12] | 2-chloro-1-(4-((4,4-difluorocyclohexyl)oxy)-7H-pyrrolo[2,3-d]pyrimidin-5-yl)propan-1-one |
| 379 | 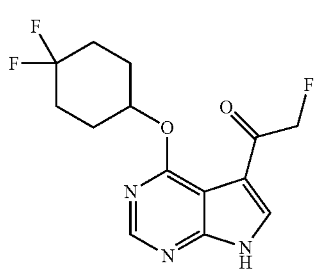 [SMILES: O=C(CF)c1c[nH]c2ncnc(OC3CCC(F)(F)CC3)c12] | 1-(4-((4,4-difluorocyclohexyl)oxy)-7H-pyrrolo[2,3-d]pyrimidin-5-yl)-2-fluoroethanone |

| Ex. # | Structure | Name |
|---|---|---|
| 380 | 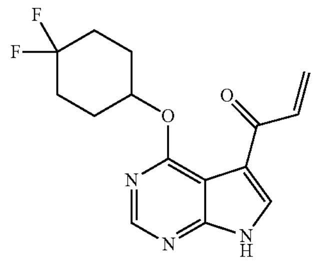 [SMILES: C=CC(=O)c1c[nH]c2ncnc(OC3CCC(F)(F)CC3)c12] | 1-(4-((4,4-difluorocyclohexyl)oxy)-7H-pyrrolo[2,3-d]pyrimidin-5-yl)prop-2-en-1-one |
| 381 | 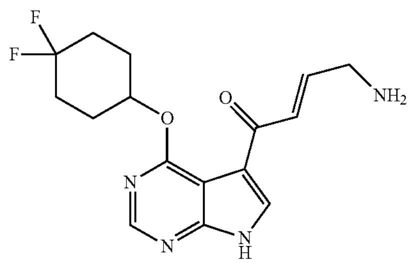 [SMILES: NC/C=C/C(=O)c1c[nH]c2ncnc(OC3CCC(F)(F)CC3)c12] | (E)-4-amino-1-(4-((4,4-difluorocyclohexyl)oxy)-7H-pyrrolo[2,3-d]pyrimidin-5-yl)but-2-en-1-one |
| 382 | 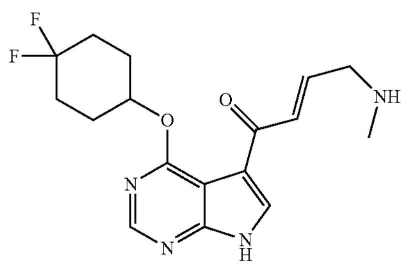 [SMILES: CNC/C=C/C(=O)c1c[nH]c2ncnc(OC3CCC(F)(F)CC3)c12] | (E)-1-(4-((4,4-difluorocyclohexyl)oxy)-7H-pyrrolo[2,3-d]pyrimidin-5-yl)-4-(methylamino)but-2-en-1-one |
| 383 | 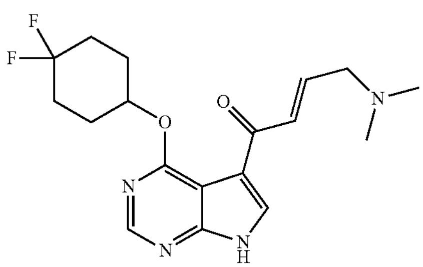 [SMILES: CN(C)C/C=C/C(=O)c1c[nH]c2ncnc(OC3CCC(F)(F)CC3)c12] | (E)-1-(4-((4,4-difluorocyclohexyl)oxy)-7H-pyrrolo[2,3-d]pyrimidin-5-yl)-4-(dimethylamino)but-2-en-1-one |
| 384 | 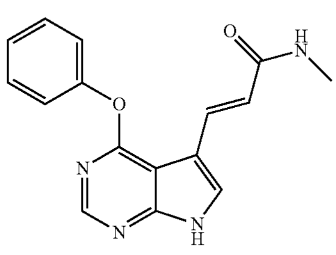 [SMILES: CNC(=O)/C=C/c1c[nH]c2ncnc(Oc3ccccc3)c12] | (E)-N-methyl-3-(4-phenoxy-7H-pyrrolo[2,3-d]pyrimidin-5-yl)acrylamide |
| 385 | 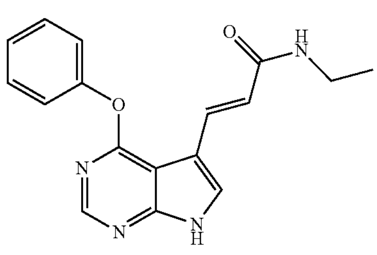 [SMILES: CCNC(=O)/C=C/c1c[nH]c2ncnc(Oc3ccccc3)c12] | (E)-N-ethyl-3-(4-phenoxy-7H-pyrrolo[2,3-d]pyrimidin-5-yl)acrylamide |

| Ex. # | Structure | Name |
|---|---|---|
| 386 | 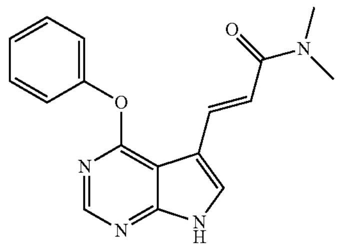 [SMILES: CN(C)C(=O)/C=C/c1c[nH]c2ncnc(Oc3ccccc3)c12] | (E)-N,N-dimethyl-3-(4-phenoxy-7H-pyrrolo[2,3-d]pyrimidin-5-yl)acrylamide |
| 387 | 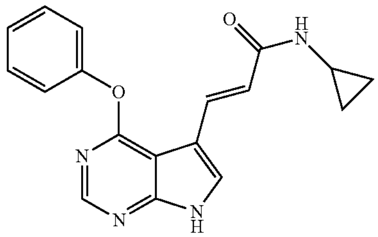 [SMILES: O=C(/C=C/c1c[nH]c2ncnc(Oc3ccccc3)c12)NC1CC1] | (E)-N-cyclopropyl-3-(4-phenoxy-7H-pyrrolo[2,3-d]pyrimidin-5-yl)acrylamide |
| 388 | 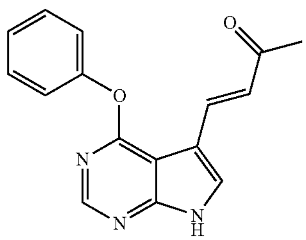 [SMILES: CC(=O)/C=C/c1c[nH]c2ncnc(Oc3ccccc3)c12] | (E)-4-(4-phenoxy-7H-pyrrolo[2,3-d]pyrimidin-5-yl)but-3-en-2-one |
| 389 | 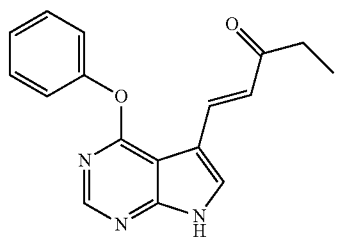 [SMILES: CCC(=O)/C=C/c1c[nH]c2ncnc(Oc3ccccc3)c12] | (E)-1-(4-phenoxy-7H-pyrrolo[2,3-d]pyrimidin-5-yl)pent-1-en-3-one |
| 390 | 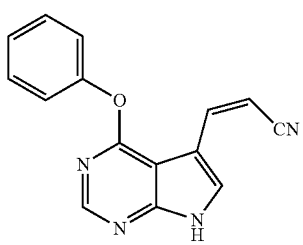 [SMILES: N#C/C=C\c1c[nH]c2ncnc(Oc3ccccc3)c12] | (Z)-3-(4-phenoxy-7H-pyrrolo[2,3-d]pyrimidin-5-yl)acrylonitrile |
| 391 | 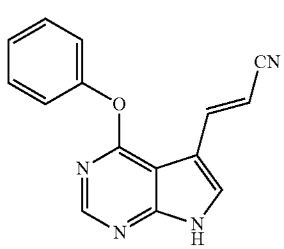 [SMILES: N#C/C=C/c1c[nH]c2ncnc(Oc3ccccc3)c12] | (E)-3-(4-phenoxy-7H-pyrrolo[2,3-d]pyrimidin-5-yl)acrylonitrile |

| Ex. # | Structure | Name |
|---|---|---|
| 392 | 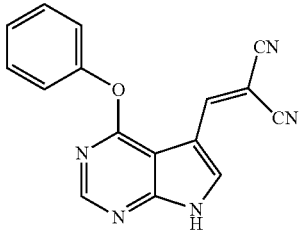 [SMILES: N#CC(C#N)=Cc1c[nH]c2ncnc(Oc3ccccc3)c12] | 2-((4-((4-7H-pyrrolo[2,3-d]pyrimidin-5-yl)methylene)malononitrile |
| 393 | 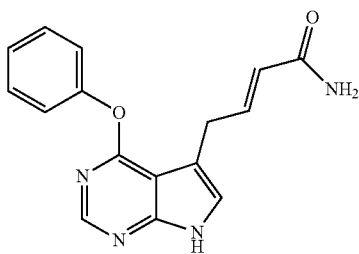 [SMILES: NC(=O)/C=C/Cc1c[nH]c2ncnc(Oc3ccccc3)c12] | (E)-4-(4-phenoxy-7H-pyrrolo[2,3-d]pyrimidin-5-yl)but-2-enamide |
| 394 | 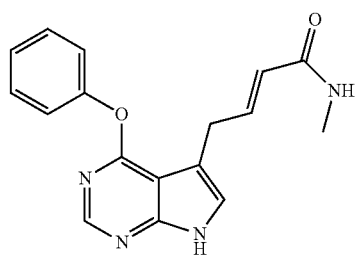 [SMILES: CNC(=O)/C=C/Cc1c[nH]c2ncnc(Oc3ccccc3)c12] | (E)-N-methyl-4-(4-phenoxy-7H-pyrrolo[2,3-d]pyrimidin-5-yl)but-2-enamide |
| 395 | 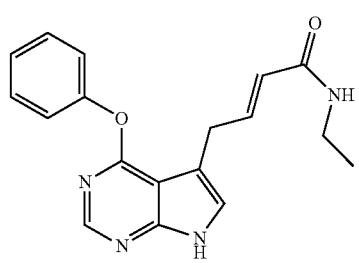 [SMILES: CCNC(=O)/C=C/Cc1c[nH]c2ncnc(Oc3ccccc3)c12] | (E)-N-ethyl-4-(4-phenoxy-7H-pyrrolo[2,3-d]pyrimidin-5-yl)but-2-enamide |
| 396 | 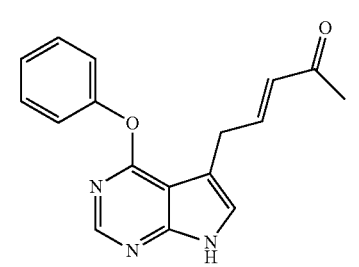 [SMILES: CC(=O)/C=C/Cc1c[nH]c2ncnc(Oc3ccccc3)c12] | (E)-5-(4-phenoxy-7H-pyrrolo[2,3-d]pyrimidin-5-yl)pent-3-en-2-one |
| 397 | 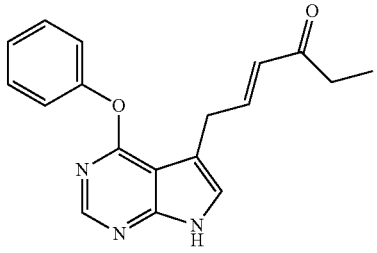 [SMILES: CCC(=O)/C=C/Cc1c[nH]c2ncnc(Oc3ccccc3)c12] | (E)-6-(4-phenoxy-7H-pyrrolo[2,3-d]pyrimidin-5-yl)hex-4-en-3-one |

-continued

| Ex. # | Structure | Name |
|---|---|---|
| 398 | 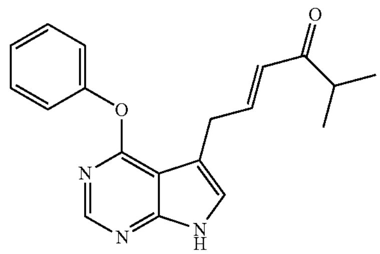 [SMILES: CC(C)C(=O)/C=C/Cc1c[nH]c2ncnc(Oc3ccccc3)c12] | (E)-2-methyl-6-(4-phenoxy-7H-pyrrolo[2,3-d]pyrimidin-5-yl)hex-4-en-3-one |
| 399 | 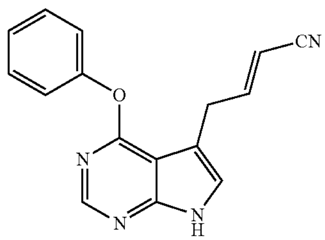 [SMILES: N#C/C=C/Cc1c[nH]c2ncnc(Oc3ccccc3)c12] | (E)-4-(4-phenoxy-7H-pyrrolo[2,3-d]pyrimidin-5-yl)but-2-enenitrile |
| 400 | 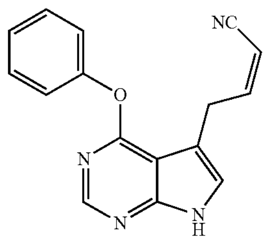 [SMILES: N#C/C=C\Cc1c[nH]c2ncnc(Oc3ccccc3)c12] | (Z)-4-(4-phenoxy-7H-pyrrolo[2,3-d]pyrimidin-5-yl)but-2-enenitrile |
| 401 | 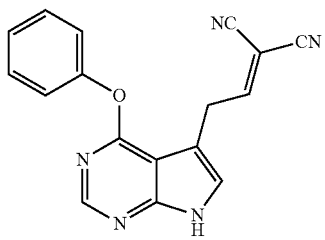 [SMILES: N#CC(C#N)=CCc1c[nH]c2ncnc(Oc3ccccc3)c12] | 2-(2-(4-phenoxy-7H-pyrrolo[2,3-d]pyrimidin-5-yl)ethylidene)malononitrile |
| 402 | 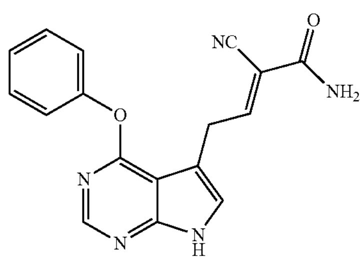 [SMILES: N#C/C(=C\Cc1c[nH]c2ncnc(Oc3ccccc3)c12)C(N)=O] | (E)-2-cyano-4-(4-phenoxy-7H-pyrrolo[2,3-d]pyrimidin-5-yl)but-2-enamide |
| 403 | 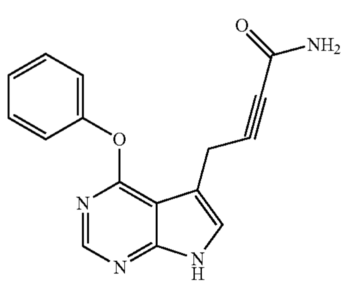 [SMILES: NC(=O)C#CCc1c[nH]c2ncnc(Oc3ccccc3)c12] | 4-(4-phenoxy-7H-pyrrolo[2,3-d]pyrimidin-5-yl)but-2-ynamide |

-continued

| Ex. # | Structure | Name |
|---|---|---|
| 404 | 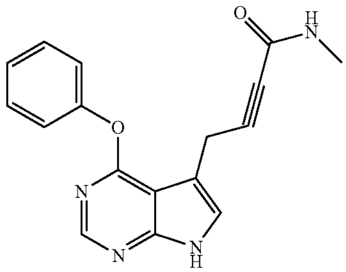 [SMILES: CNC(=O)C#CCc1c[nH]c2ncnc(Oc3ccccc3)c12] | N-methyl-4-(4-phenoxy-7H-pyrrolo[2,3-d]pyrimidin-5-yl)but-2-ynamide |
| 405 | 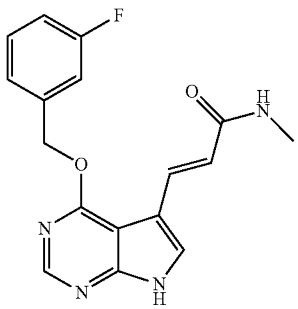 [SMILES: CNC(=O)/C=C/c1c[nH]c2ncnc(OCc3cccc(F)c3)c12] | (E)-3-(4-((3-fluorobenzyl)oxy)-7H-pyrrolo[2,3-d]pyrimidin-5-yl)-N-methylacrylamide |
| 406 | 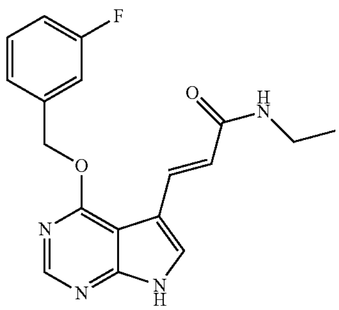 [SMILES: CCNC(=O)/C=C/c1c[nH]c2ncnc(OCc3cccc(F)c3)c12] | (E)-N-ethyl-3-(4-((3-fluorobenzyl)oxy)-7H-pyrrolo[2,3-d]pyrimidin-5-yl)acrylamide |
| 407 | 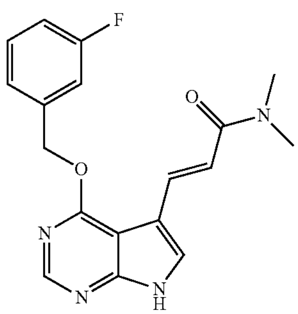 [SMILES: CN(C)C(=O)/C=C/c1c[nH]c2ncnc(OCc3cccc(F)c3)c12] | (E)-3-(4-((3-fluorobenzyl)oxy)-7H-pyrrolo[2,3-d]pyrimidin-5-yl)-N,N-dimethylacrylamide |
| 408 | 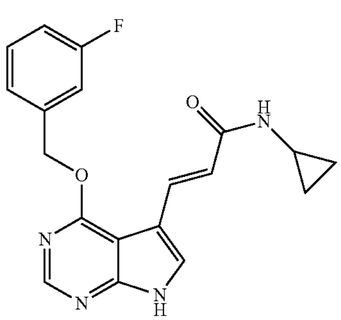 [SMILES: O=C(/C=C/c1c[nH]c2ncnc(OCc3cccc(F)c3)c12)NC1CC1] | (E)-N-cyclopropyl-3-(4-((3-fluorobenzyl)oxy)-7H-pyrrolo[2,3-d]pyrimidin-5-yl)acrylamide |

-continued

| Ex. # | Structure | Name |
|---|---|---|
| 409 | 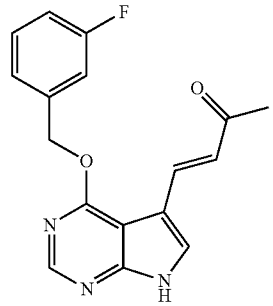 [SMILES: CC(=O)/C=C/c1c[nH]c2ncnc(OCc3cccc(F)c3)c12] | (E)-4-(4-((3-fluorobenzyl)oxy)-7H-pyrrolo[2,3-d]pyrimidin-5-yl)but-3-en-2-one |
| 410 | 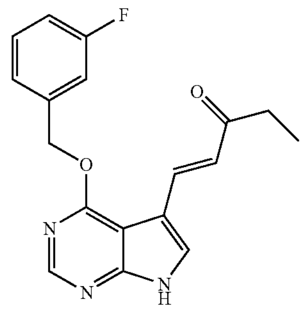 [SMILES: CCC(=O)/C=C/c1c[nH]c2ncnc(OCc3cccc(F)c3)c12] | (E)-1-(4-((3-fluorobenzyl)oxy)-7H-pyrrolo[2,3-d]pyrimidin-5-yl)pent-1-en-3-one |
| 411 | 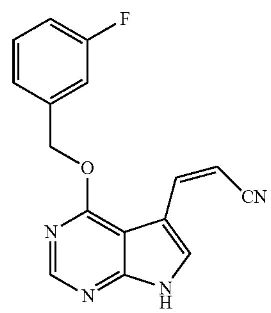 [SMILES: N#C/C=C\c1c[nH]c2ncnc(OCc3cccc(F)c3)c12] | (Z)-3-(4-((3-fluorobenzyl)oxy)-7H-pyrrolo[2,3-d]pyrimidin-5-yl)acrylonitrile |
| 412 | 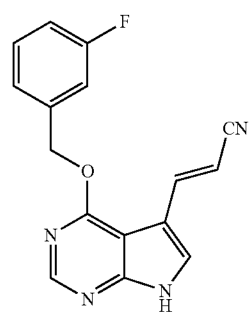 [SMILES: N#C/C=C/c1c[nH]c2ncnc(OCc3cccc(F)c3)c12] | (E)-3-(4-((3-fluorobenzyl)oxy)-7H-pyrrolo[2,3-d]pyrimidin-5-yl)acrylonitrile |
| 413 | 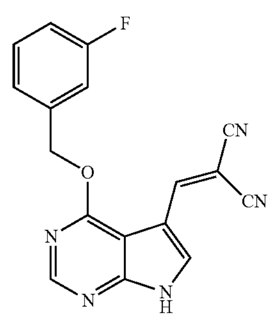 [SMILES: N#CC(C#N)=Cc1c[nH]c2ncnc(OCc3cccc(F)c3)c12] | 2-((4-((3-fluorobenzyl)oxy)-7H-pyrrolo[2,3-d]pyrimidin-5-yl)methylene)malononitrile |

| Ex. # | Structure | Name |
|---|---|---|
| 414 | 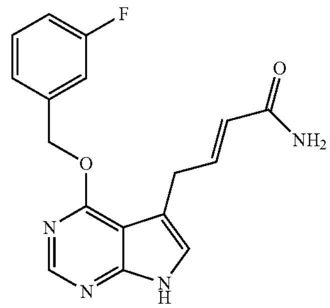 [SMILES: NC(=O)/C=C/Cc1c[nH]c2ncnc(OCc3cccc(F)c3)c12] | (E)-4-(4-((3-fluorobenzyl)oxy)-7H-pyrrolo[2,3-d]pyrimidin-5-yl)but-2-enamide |
| 415 | 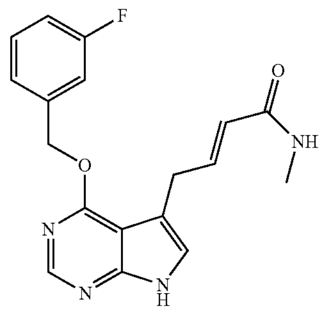 [SMILES: CNC(=O)/C=C/Cc1c[nH]c2ncnc(OCc3cccc(F)c3)c12] | (E)-4-(4-((3-fluorobenzyl)oxy)-7H-pyrrolo[2,3-d]pyrimidin-5-yl)-N-methylbut-2-enamide |
| 416 | 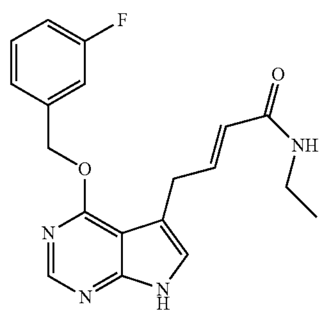 [SMILES: CCNC(=O)/C=C/Cc1c[nH]c2ncnc(OCc3cccc(F)c3)c12] | (E)-N-ethyl-4-(4-((3-fluorobenzyl)oxy)-7H-pyrrolo[2,3-d]pyrinindin-5-yl)but-2-enamide |
| 417 | 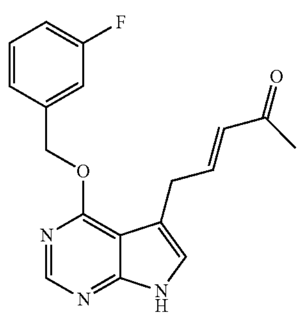 [SMILES: CC(=O)/C=C/Cc1c[nH]c2ncnc(OCc3cccc(F)c3)c12] | (E)-5-(4-((3-fluorobenzyl)oxy)-7H-pyrrolo[2,3-d]pyrimidin-5-yl)pent-3-en-2-one |
| 418 | 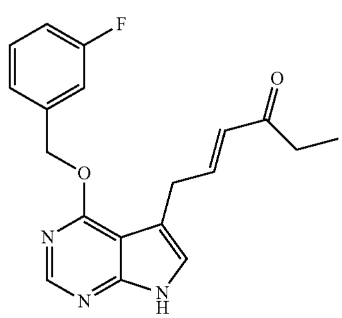 [SMILES: CCC(=O)/C=C/Cc1c[nH]c2ncnc(OCc3cccc(F)c3)c12] | (E)-6-(4-((3-fluorobenzyl)oxy)-7H-pyrrolo[2,3-d]pyrinindin-5-yl)hex-4-en-3-one |

-continued

| Ex. # | Structure | Name |
|---|---|---|
| 419 | 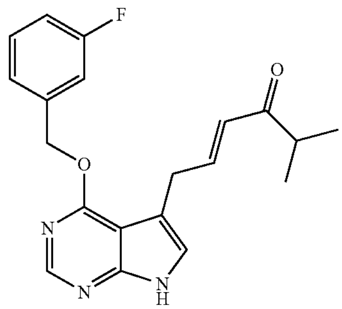 [SMILES: CC(C)C(=O)/C=C/Cc1c[nH]c2ncnc(OCc3cccc(F)c3)c12] | (E)-6-(4-((3-fluorobenzyl)oxy)-7H-pyrrolo[2,3-d]pyrimidin-5-yl)-2-methylhex-4-en-3-one |
| 420 | 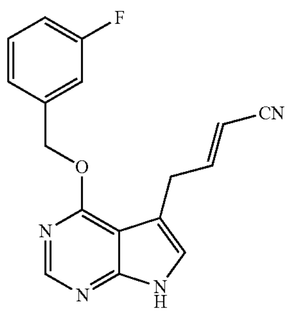 [SMILES: N#C/C=C/Cc1c[nH]c2ncnc(OCc3cccc(F)c3)c12] | (E)-4-(4-((3-fluorobenzyl)oxy)-7H-pyrrolo[2,3-d]pyrimidin-5-yl)but-2-enenitrile |
| 421 | 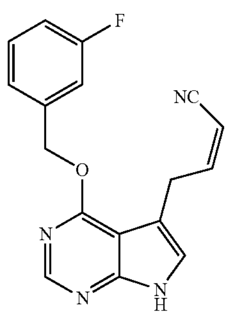 [SMILES: N#C/C=C\Cc1c[nH]c2ncnc(OCc3cccc(F)c3)c12] | (Z)-4-(4-((3-fluorobenzyl)oxy)-7H-pyrrolo[2,3-d]pyrimidin-5-yl)but-2-enenitrile |
| 422 | 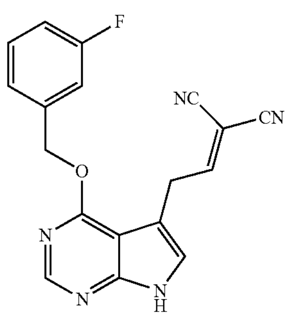 [SMILES: N#CC(C#N)=CCc1c[nH]c2ncnc(OCc3cccc(F)c3)c12] | 2-(2-(4-((3-fluorobenzyl)oxy)-7H-pyrrolo[2,3-d]pyrimidin-5-yl)ethylidene)malononitrile |
| 423 | 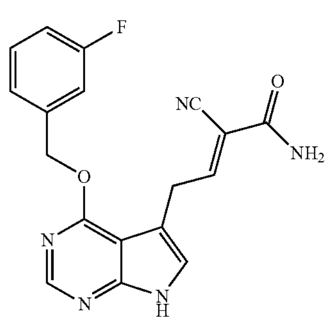 [SMILES: N#C/C(=C\Cc1c[nH]c2ncnc(OCc3cccc(F)c3)c12)C(N)=O] | (E)-2-cyano-4-(4-((3-fluorobenzyl)oxy)-7H-pyrrolo[2,3-d]pyrimidin-5-yl)but-2-enamide |

-continued

| Ex. # | Structure | Name |
|---|---|---|
| 424 | 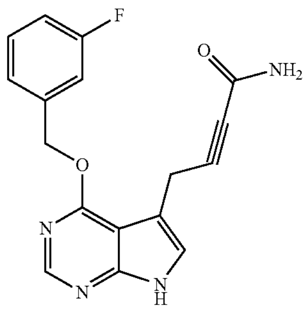 [SMILES: NC(=O)C#CCc1c[nH]c2ncnc(OCc3cccc(F)c3)c12] | 4-(4-((3-fluorobenzyl)oxy)-7H-pyrrolo[2,3-d]pyrimidin-5-yl)but-2-ynamide |
| 425 | 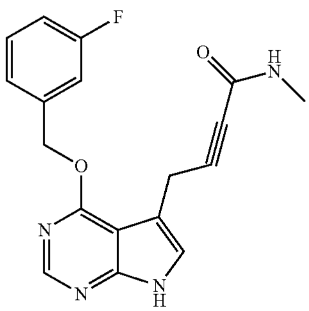 [SMILES: CNC(=O)C#CCc1c[nH]c2ncnc(OCc3cccc(F)c3)c12] | 4-(4-((3-fluorobenzyl)oxy)-7H-pyrrolo[2,3-d]pyrimidin-5-yl)-N-methylbut-2-ynamide |
| 426 | 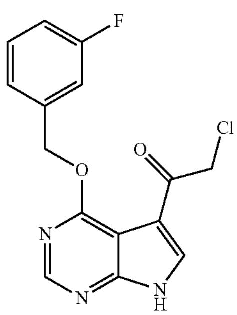 [SMILES: O=C(CCl)c1c[nH]c2ncnc(OCc3cccc(F)c3)c12] | 2-chloro-1-(4-((3-fluorobenzyl)oxy)-7H-pyrrolo[2,3-d]pyrimidin-5-yl)ethanone |
| 427 | 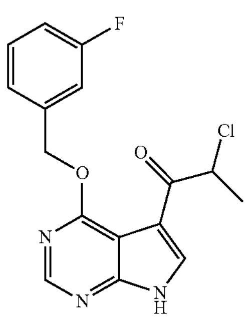 [SMILES: CC(Cl)C(=O)c1c[nH]c2ncnc(OCc3cccc(F)c3)c12] | 2-chloro-1-(4-((3-fluorobenzyl)oxy)-7H-pyrrolo[2,3-d]pyrimidin-5-yl)propan-1-one |
| 428 | 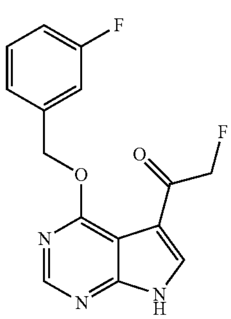 [SMILES: O=C(CF)c1c[nH]c2ncnc(OCc3cccc(F)c3)c12] | 2-fluoro-1-(4-((3-fluorobenzyl)oxy)-7H-pyrrolo[2,3-d]pyrimidin-5-yl)ethanone |

-continued

| Ex. # | Structure | Name |
|---|---|---|
| 429 | 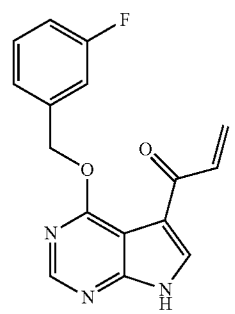 [SMILES: C=CC(=O)c1c[nH]c2ncnc(OCc3cccc(F)c3)c12] | 1-(4-((3-fluorobenzyl)oxy)-7H-pyrrolo[2,3-d]pyrimidin-5-yl)prop-2-en-1-one |
| 430 | 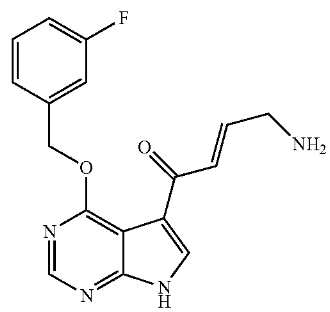 [SMILES: NC/C=C/C(=O)c1c[nH]c2ncnc(OCc3cccc(F)c3)c12] | (E)-4-amino-1-(4-((3-fluorobenzyl)oxy)-7H-pyrrolo[2,3-d]pyrimidin-5-yl)but-2-en-1-one |
| 431 | 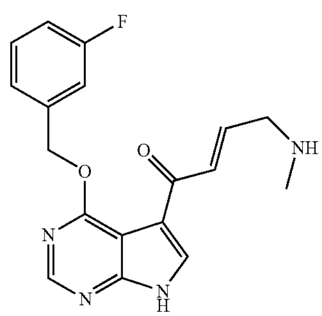 [SMILES: CNC/C=C/C(=O)c1c[nH]c2ncnc(OCc3cccc(F)c3)c12] | (E)-1-(4-((3-fluorobenzyl)oxy)-7H-pyrrolo[2,3-d]pyrimidin-5-yl)-4-(methylamino)but-2-en-1-one |
| 432 | 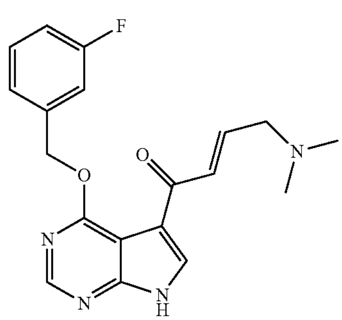 [SMILES: CN(C)C/C=C/C(=O)c1c[nH]c2ncnc(OCc3cccc(F)c3)c12] | (E)-4-(dimethylamino)-1-(4-((3-fluorobenzyl)oxy)-7H-pyrrolo[2,3-d]pyrimidin-5-yl)but-2-en-1-one |
| 433 | 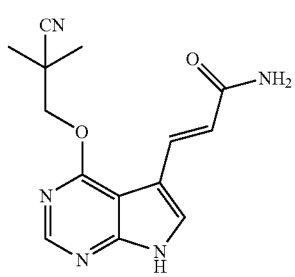 [SMILES: CC(C)(C#N)COc1ncnc2[nH]cc(/C=C/C(N)=O)c12] | (E)-3-(4-(2-cyano-2-methylpropoxy)-7H-pyrrolo[2,3-d]pyrimidin-5-yl)acrylamide |

| Ex. # | Structure | Name |
|---|---|---|
| 434 | 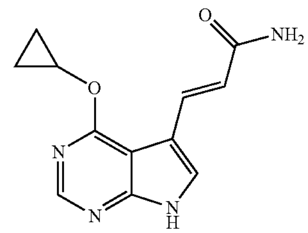 [SMILES: NC(=O)/C=C/c1c[nH]c2ncnc(OC3CC3)c12] | (E)-3-(4-cyclopropoxy-7H-pyrrolo[2,3-d]pyrimidin-5-yl)acrylamide |
| 435 | 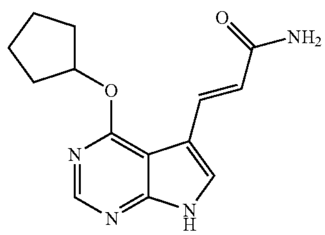 [SMILES: NC(=O)/C=C/c1c[nH]c2ncnc(OC3CCCC3)c12] | (E)-3-(4-(cyclopentyloxy)-7H-pyrrolo[2,3-d]pyrimidin-5-yl)acrylamide |
| 436 | 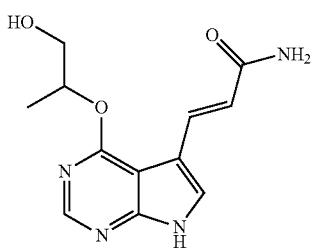 [SMILES: CC(CO)Oc1ncnc2[nH]cc(/C=C/C(N)=O)c12] | (E)-3-(4-((1-hydroxypropan-2-yl)oxy)-7H-pyrrolo[2,3-d]pyrimidin-5-yl)acrylamide |
| 437 | 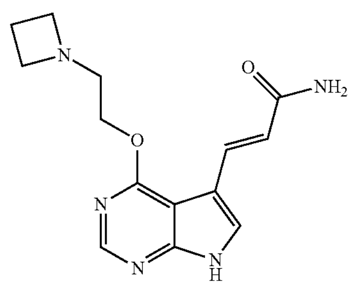 [SMILES: NC(=O)/C=C/c1c[nH]c2ncnc(OCCN3CCC3)c12] | (E)-3-(4-(2-(azetidin-1-yl)ethoxy)-7H-pyrrolo[2,3-d]pyrimidin-5-yl)acrylamide |
| 438 | 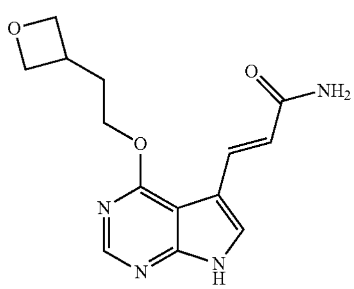 [SMILES: NC(=O)/C=C/c1c[nH]c2ncnc(OCCC3COC3)c12] | (E)-3-(4-(2-(oxetan-3-yl)ethoxy)-7H-pyrrolo[2,3-d]pyrimidin-5-yl)acrylamide |
| 439 | 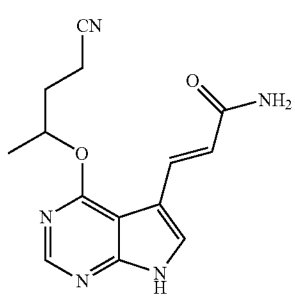 [SMILES: CC(CCC#N)Oc1ncnc2[nH]cc(/C=C/C(N)=O)c12] | (E)-3-(4-((4-cyanobutan-2-yl)oxy)-7H-pyrrolo[2,3-d]pyrimidin-5-yl)acrylamide |

| Ex. # | Structure | Name |
|---|---|---|
| 440 | 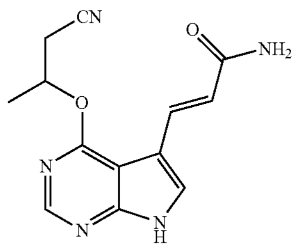 [SMILES: CC(CC#N)Oc1ncnc2[nH]cc(/C=C/C(N)=O)c12] | (E)-3-(4-((1-cyanopropan-2-yl)oxy)-7H-pyrrolo[2,3-d]pyrimidin-5-yl)acrylamide |
| 441 | 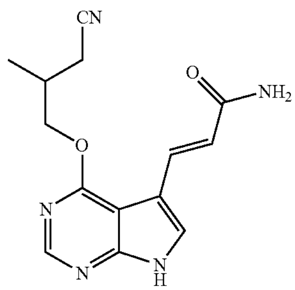 [SMILES: CC(CC#N)COc1ncnc2[nH]cc(/C=C/C(N)=O)c12] | (E)-3-(4-(3-cyano-2-methylpropoxy)-7H-pyrrolo[2,3-d]pyrimidin-5-yl)acrylamide |
| 442 | 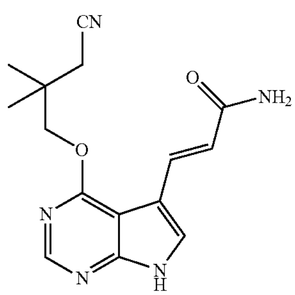 [SMILES: CC(C)(CC#N)COc1ncnc2[nH]cc(/C=C/C(N)=O)c12] | (E)-3-(4-(3-cyano-2,2-dimethylpropoxy)-7H-pyrrolo[2,3-d]pyrimidin-5-yl)acrylamide |
| 443 | 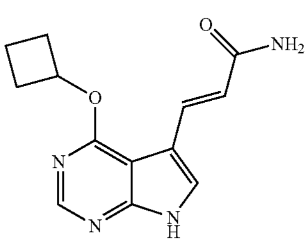 [SMILES: NC(=O)/C=C/c1c[nH]c2ncnc(OC3CCC3)c12] | (E)-3-(4-cyclobutoxy-7H-pyrrolo[2,3-d]pyrimidin-5-yl)acrylamide |
| 444 | 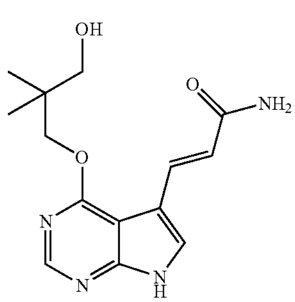 | (E)-3-(4-(3-hydroxy-2,2-dimethylpropoxy)-7H-pyrrolo[2,3-d]pyrimidin-5-yl)acrylamide |

| Ex. # | Structure | Name |
|---|---|---|
| 445 | 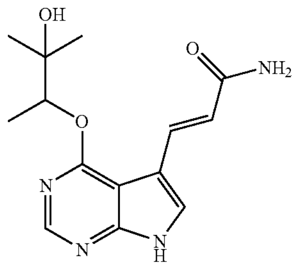 [SMILES: CC(Oc1ncnc2[nH]cc(/C=C/C(N)=O)c12)C(C)(C)O] | (E)-3-(4-((3-hydroxy-3-methylbutan-2-yl)oxy)-7H-pyrrolo[2,3-d]pyrimidin-5-yl)acrylamide |
| 446 | 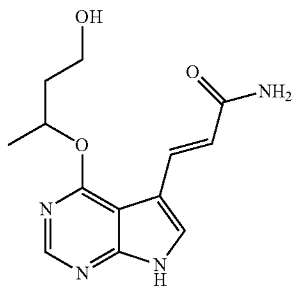 | (E)-3-(4-((4-hydroxybutan-2-yl)oxy)-7H-pyrrolo[2,3-d]pyrimidin-5-yl)acrylamide |
| 447 | 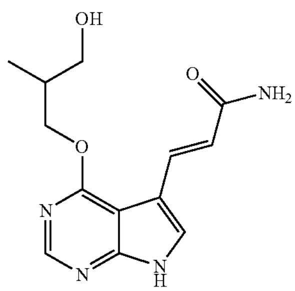 [SMILES: CC(CO)COc1ncnc2[nH]cc(/C=C/C(N)=O)c12] | (E)-3-(4-(3-hydroxy-2-methylpropoxy)-7H-pyrrolo[2,3-d]pyrimidin-5-yl)acrylamide |
| 448 | 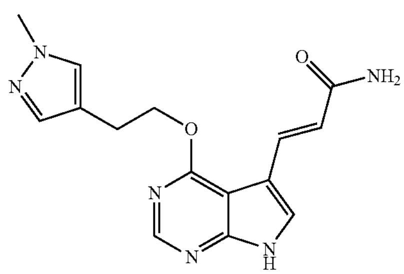 [SMILES: Cn1cc(CCOc2ncnc3[nH]cc(/C=C/C(N)=O)c23)cn1] | (E)-3-(4-(2-(1-methyl-1H-pyrazol-4-yl)ethoxy)-7H-pyrrolo[2,3-d]pyrimidin-5-yl)acrylamide |
| 449 | 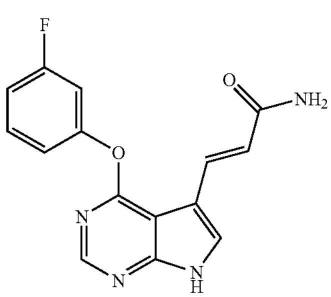 [SMILES: NC(=O)/C=C/c1c[nH]c2ncnc(Oc3cccc(F)c3)c12] | (E)-3-(4-(3-fluorophenoxy)-7H-pyrrolo[2,3-d]pyrimidin-5-yl)acrylamide |

C. General Synthetic Schemes

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1-6 below. Solvents and reagents, whose synthetic preparations are not described below, can be purchased at Sigma-Aldrich or Fisher Scientific.

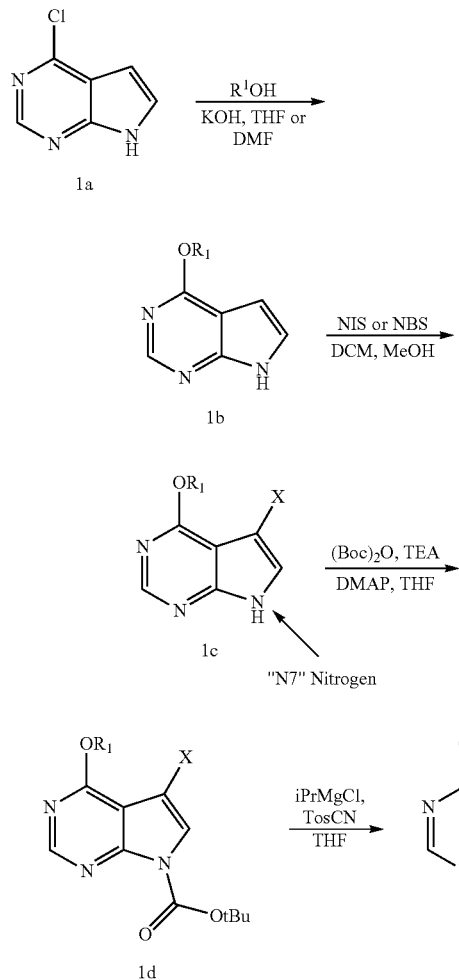

X = Br or I
R[1] = isobutyl, benzyl or phenylethyl (1b) Ether Formation: Reaction of an alcohol (R[1]OH) (See Table 1), with chloropyrimidine (1a) (See Table 1) and potassium hydroxide (KOH) in tetrahydrofuran (THF) or N,N-dimethylformamide (DMF) provides ether (1b).

(1c) Halogenation: Halogenation of (1b) using either NBS or NIS in dichloromethane (DCM) and methanol (MeOH) furnishes halide (1c) where X is Br or I.

Protecting Group Addition (1d): Protection of N7 nitrogen with Boc is accomplished with Boc anhydride, triethylamine (TEA), dimethylaminopyridine (DMAP) and THF yielding (1d).

(1e) Cyano Pyrrolopyrimidine: Treatment of (1d) with isopropyl magnesium chloride (iPrMgCl) in THF followed by addition of tosyl cyanide (TosCN) furnishes nitrile pyrrolopyrimidine (1e) (See Table 2).

TABLE 1

Commercially Available Reagents.

| Structure | Name | CAS# |
|---|---|---|
| (1a) | 4-Chloropyrrolo[2,3-d]pyrimidine | 3680-69-1 (Oakwood Products) |
| R[1] = isobutyl | Isobutanol | 78-83-1 |
| R[1] = benzyl | Benzyl alcohol | 100-51-6 |
| R[1] = phenylethyl | Phenylethyl alcohol | 60-12-8 |

TABLE 2

Starting Materials and Corresponding Nitrile Pyrrolopyrimidines (1e).

| Ex. # | R[1]OH | Species-Compounds (1e) |
|---|---|---|
| 1 | Isobutanol | (isobutyl ether pyrrolopyrimidine-CN) |
| 65 | Benzyl alcohol | (benzyl ether pyrrolopyrimidine-CN) |
| 121 | Phenylethyl alcohol | (phenylethyl ether pyrrolopyrimidine-CN) |

Scheme 2. Preparation of Pyrrolopyrimidines with Amino-Linked Electrophiles.

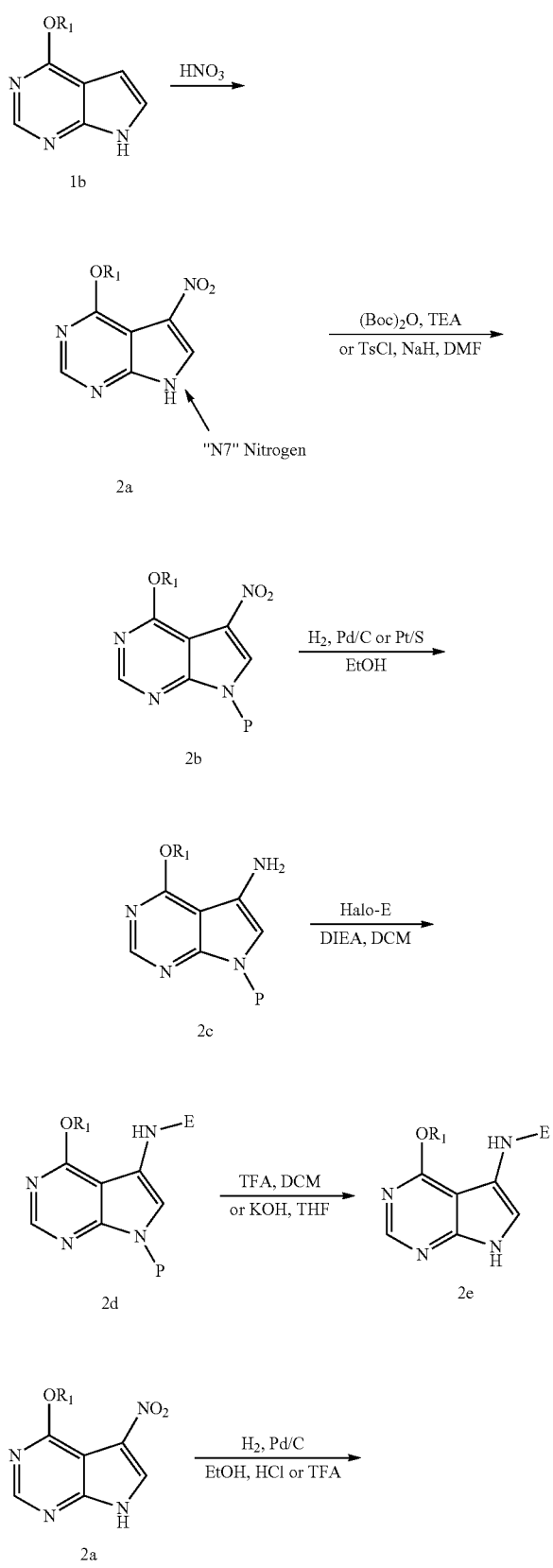

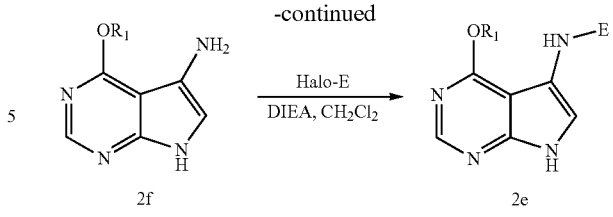

R¹ = isobutyl, benzyl or phenylethyl
P = Protecting Group
Halo-E = Halo Electrophile (1b) is synthesized according to Scheme 1 above.

(2a) Nitration: Nitration of appropriate 1b (i.e., R¹=isobutyl, benzyl or phenylethyl, see Table 3) using nitric acid yields 2a.

(2b) Protecting Group Addition: N7 nitrogen is protected by reacting 2a with either Boc anhydride in TEA, or tosyl chloride in DMF using NaH, yielding 2b.

(2c) Hydrogenation: 2b is dissolved in EtOH and hydrogen gas is added in the presence of a Pd or Pt supported catalyst. In some cases a small amount of TFA or HCl may be added to the hydrogenation mixture.

(2d) Acylation of Electrophile: Reaction of a halo-electrophile (E-Cl) (see Table 3) with 2c in DCM or DMF in the presence of diisopropylethylamine (DIEA) furnishes 2d. Deprotection of 2d can occur in-situ yielding 2e.

(2e) Deprotection: 2d is dissolved in THF and treated with TFA in DCM, KOH in THF, or tetrabutylammonium fluoride in DCM, yielding 2e (See Table 3).

(2f) Un-Protected Addition of Electrophile: 2a is dissolved in EtOH and hydrogenated with hydrogen gas in the presence of a Pd or Pt supported catalyst. In some cases a small amount of TFA or HCl may be added to the hydrogenation mixture. Reaction of a halo-electrophile with 2f in DCM with DIEA furnishes 2e (See Table 3).

In some cases the halo electrophile has a protecting group on a side chain (amine Examples include 7 and 8 (and homologs) and hydroxy Examples 6, 10, and 16 (and homologs)). Suitable side chain protecting groups include Boc, TIPS, acetyl or other common protecting groups (e.g., protecting groups listed in Table 9). After the coupled product is prepared, the protecting group is removed by conventional methods (e.g., deprotection with either TFA, KOH, or tetrabutylammonium fluoride in THF).

Alternative synthetic routes: Amines 2f and 2e may also be synthesized via Buchwald-Hartwig amination reaction of a protected 1c (From Scheme 1) (e.g., G. D. Vo, J. F. Hartwig, J. Am. Chem. Soc., 131(31), 11049-11061 (2009)). Alternatively, the synthetic routes of Scheme 2 may be similarly carried out on a substituted pyrrole followed by acylation and deprotection to provide pyrrolopyrimidines 2d and 2e.

Examples 3, 66 and 122 may be prepared by treatment of Example 2 (or the corresponding analog) with methyl iodide in the presence of potassium carbonate or sodium hydride in DMF.

Table 3 shows each R¹ radical and corresponding example number (at left) of species-compounds of Scheme 2.

TABLE 3
Pyrrolopyrimidines with Amino-Linked Electrophiles (2e)
(2f) Amino-Pyrrolopyrimidine
| When R¹ = | When R¹ = | When R¹ = | Halo-Electrophile | Pyrrolopyrimidines with Amino-Linked Electrophiles (2e) |
|---|---|---|---|---|
| isobutyl | benzyl | phenethyl | | |
| Ex. # is: | Ex. # is: | Ex. # is: | | |
| 2 | 67 | 123 | BrCN | 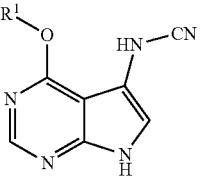 |
| 3 | 66 | 122 | MeI and Ex.# 2, 63 or 120, respectively | 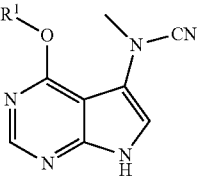 |
| 4 | 74 | 130 | 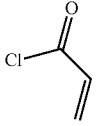 | 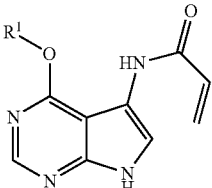 |
| 5 | 68 | 124 | 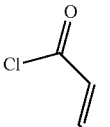 | 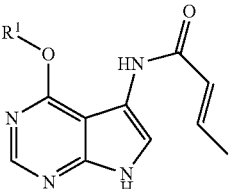 |
| 6 | 69 | 125 | 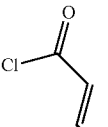 | 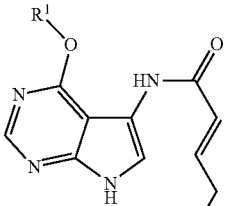 |

TABLE 3-continued

| # | | | Acid chloride | Product |
|---|---|---|---|---|
| 7 | — | — | (acryloyl chloride with CH2NH2) | pyrrolopyrimidine amide with CH2NH2 |
| 8 | 70 | 126 | (acryloyl chloride with CH2NHMe) | pyrrolopyrimidine amide with CH2NHMe |
| 9 | 71 | 127 | methacryloyl chloride | methacrylamide pyrrolopyrimidine |
| 10 | — | — | (acryloyl chloride with CH2OH) | pyrrolopyrimidine amide with CH2OH |
| 11 | 72 | 128 | fluoroacetyl chloride | fluoroacetamide pyrrolopyrimidine |
| 12 | 73 | 129 | chloroacetyl chloride | chloroacetamide pyrrolopyrimidine |
| 13 | — | — | trifluoroacetyl chloride | trifluoroacetamide pyrrolopyrimidine |

TABLE 3-continued
| | | | | |
|---|---|---|---|---|
| 14 | 75 | 132 | 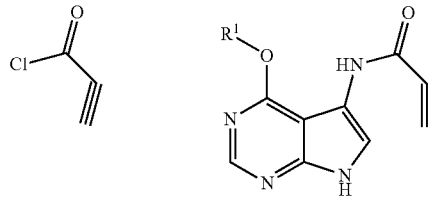 | 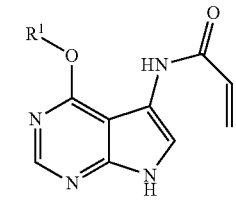 |
| 15 | 78 | 131 | 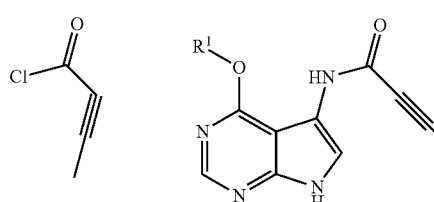 | 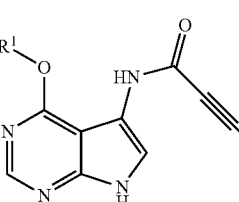 |
| 16 | 76 | 133 | 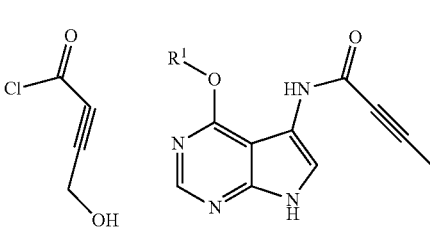 | 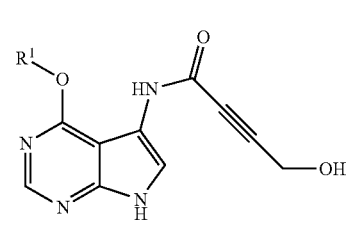 |
| 17 | 77 | 134 | 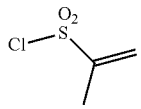 | 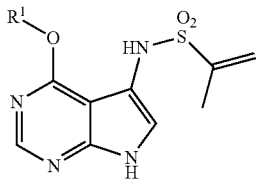 |
| 18 | 79 | 135 | 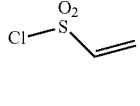 | 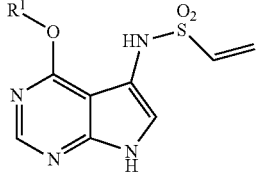 |
| 19 | 80 | 136 | 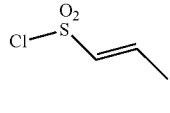 | 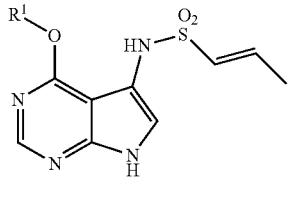 |
| 20 | 81 | 137 | 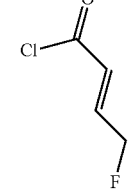 | 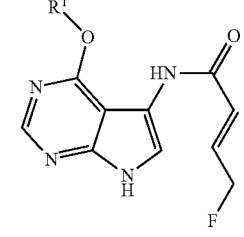 |

Scheme 3. Preparation of Pyrrolopyrimidines with Direct-Bound Electrophile.

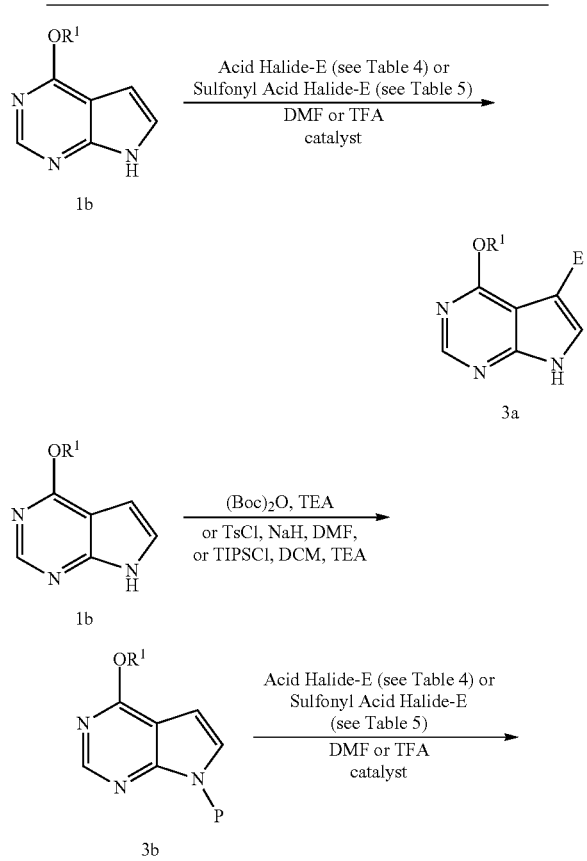

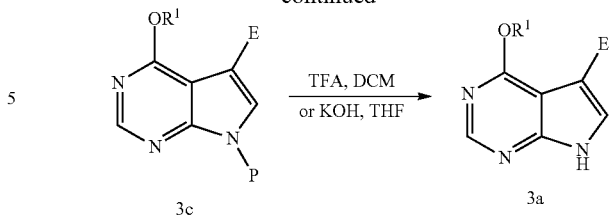

R[1] = isobutyl, benzyl or phenylethyl
E = Electrophile
P = Protecting Group (3a) Unprotected Addition of Electrophile: Reaction of 1b (see Scheme 1) with an acid halide-electrophile (see Table 4) or sulfonyl acid halide-electrophile (See Table 5), in the presence of a catalyst provides 3a. The catalyst used is a Brønsted acid (e.g., TFA or HCl) or Lewis acid (e.g., AlCl$_3$ or ZnCl$_2$).

(3c) Protected Addition of Electrophile: Reaction of 1b with Boc anhydride (Boc)$_2$O in TEA, tosyl chloride (TsCl) with NaH in DMF, or TIPS chloride in DCM, provides 3b. 3b is reacted with an acid halide-electrophile (Table 4) or sulfonyl acid halide electrophile (Table 5), yielding 3c. In-situ deprotection of 3c can occur, providing 3a directly, if the protecting group is unstable at elevated temperatures or unstable under acidic conditions. If the protecting group is not removed in-situ, 3c is deprotected using TFA in DCM, potassium hydroxide (KOH) in THF or tetrabutyl ammonium fluoride in DCM, furnishing 3a.

In some cases the chloro electrophile has a protecting group on a side chain (amine Examples include 30 and 31 (and homologs) and hydroxy Examples 29 and 47 (and homologs)). Suitable protecting groups include Boc, TIPS, acetyl or other common protecting groups (e.g., protecting groups listed in Table 9). After the final product is prepared, the protecting group is removed by conventional methods (e.g., deprotection with either TFA, KOH, or tetrabutylammonium fluoride in THF).

Table 4 shows each R[1] radical and corresponding example number (at left) of species-compounds of Scheme 3.

TABLE 4

Pyrrolopyrimidines with Direct-Bound Electrophile Synthesized with Acid Halide Electrophile (3a)

(1b) Ether-Pyrrolopyrimidine

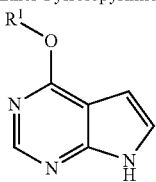

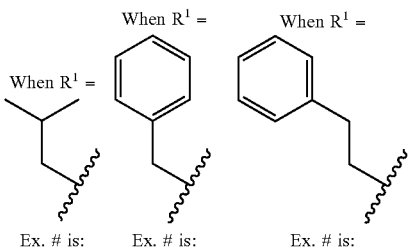

| When R[1] = isobutyl | When R[1] = benzyl | When R[1] = phenylethyl | Acid Halide Electrophile | Pyrrolopyrimidines with Direct-Bound Acyl Electrophile (3a) |
|---|---|---|---|---|
| Ex. # is: 21 | Ex. # is: — | Ex. # is: — |  | 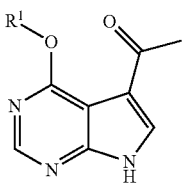 |

TABLE 4-continued
Pyrrolopyrimidines with Direct-Bound Electrophile Synthesized with Acid Halide Electrophile (3a)
(1b) Ether-Pyrrolopyrimidine
| When R¹ = | When R¹ = | When R¹ = | Acid Halide Electrophile | Pyrrolopyrimidines with Direct-Bound Acyl Electrophile (3a) |
|---|---|---|---|---|
| Ex. # is: | Ex. # is: | Ex. # is: | | |
| 22 | 82 | 138 | 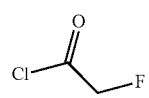 | 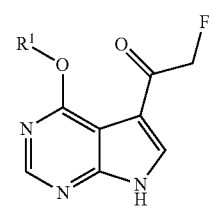 |
| 23 | 83 | 139 | 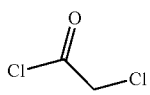 | 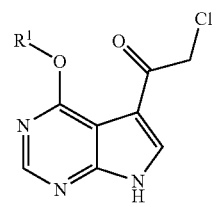 |
| 24 | 84 | 140 | 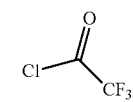 | 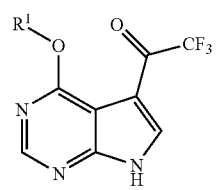 |
| 25 | 85 | 141 | 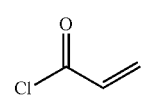 | 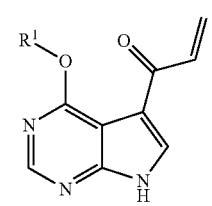 |

TABLE 4-continued
Pyrrolopyrimidines with Direct-Bound Electrophile Synthesized with Acid Halide Electrophile (3a)
(1b) Ether-Pyrrolopyrimidine
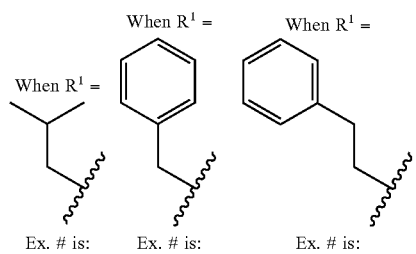
| Ex. # is: | Ex. # is: | Ex. # is: | Acid Halide Electrophile | Pyrrolopyrimidines with Direct-Bound Acyl Electrophile (3a) |
|---|---|---|---|---|
| 26 | — | — | 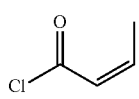 | 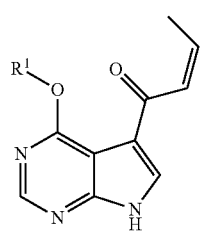 |
| 27 | 86 | 142 | 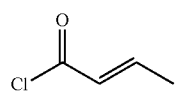 | 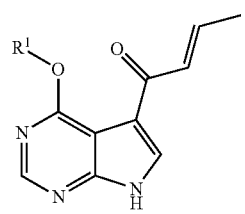 |
| 28 | 87 | 143 | 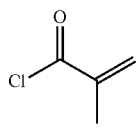 |  |
| 29 | 89 | — | 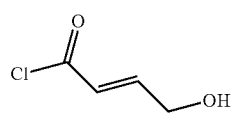 | 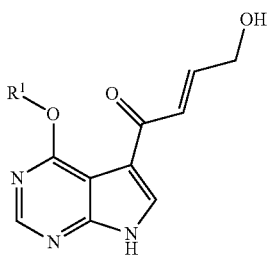 |

TABLE 4-continued
Pyrrolopyrimidines with Direct-Bound Electrophile Synthesized with Acid Halide Electrophile (3a)
(1b) Ether-Pyrrolopyrimidine
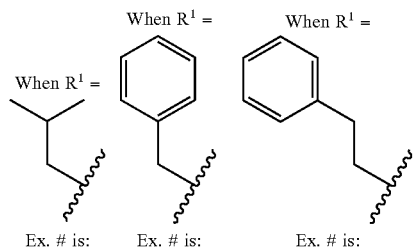
| Ex. # is: | Ex. # is: | Ex. # is: | Acid Halide Electrophile | Pyrrolopyrimidines with Direct-Bound Acyl Electrophile (3a) |
|---|---|---|---|---|
| 30 | — | — | 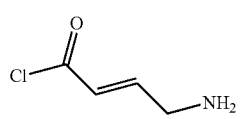 | 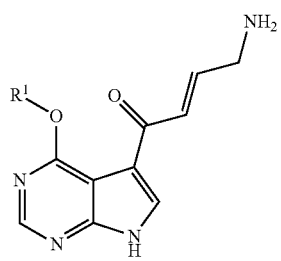 |
| 31 | 90 | — | 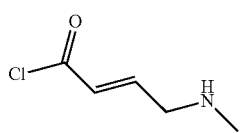 | 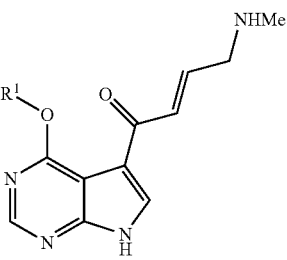 |
| 32 | 88 | 144 | 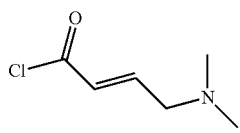 | 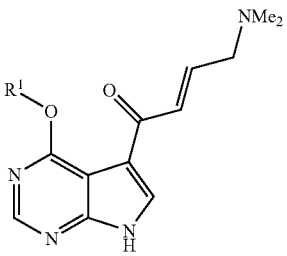 |

TABLE 5
Pyrrolopyrimidines with Direct-Bound Electrophile Synthesized with Sulfonyl Acid Halide Electrophile (3a)

Scheme 4. Preparation of Pyrrolopyrimidines with Vinyl-Linked Electrophiles (Boc Anhydride Protecting Group).

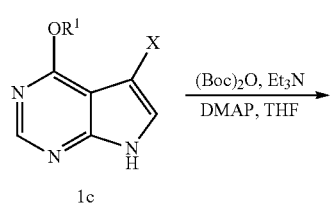

1c

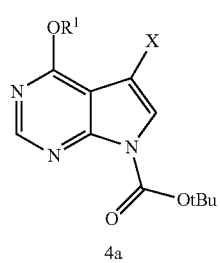

4a

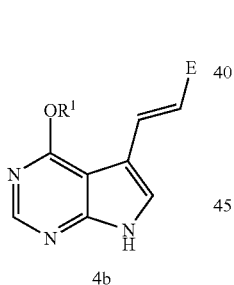

4b

Scheme 5. Preparation of Pyrrolopyrimidines with Vinyl-Linked Electrophiles (TosCl Protecting Group).

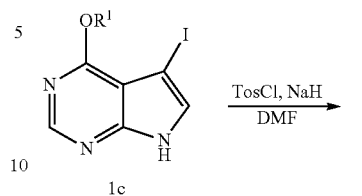

1c

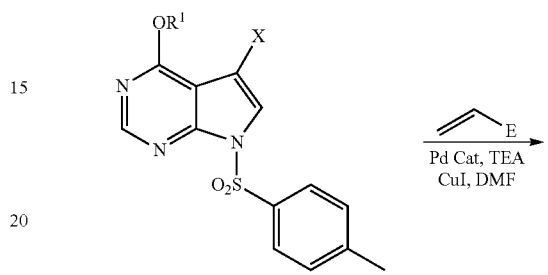

5a

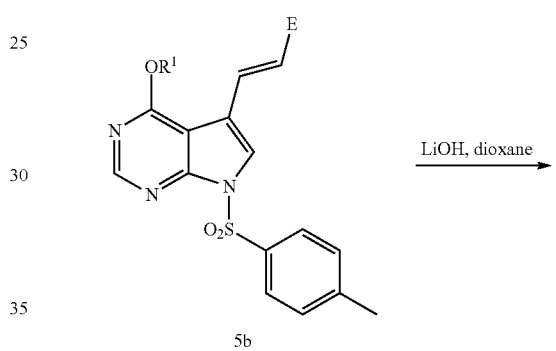

5b

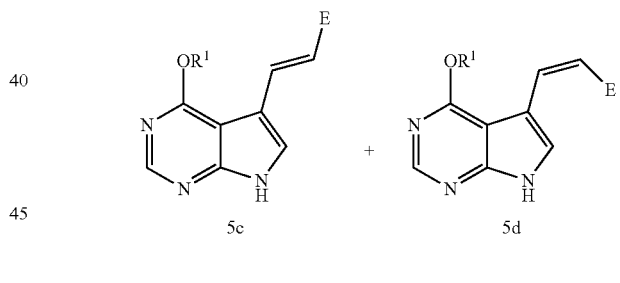

5c    5d (4a) Addition of Protecting Group: Reaction of Boc anhydride in TEA, DMAP and THF provides 4a. Alternatively, additional protecting groups from Table 9 may be used.

(4b) Addition of Electrophile: Treatment of 4a with desired electrophile (see Table 6), Pd Cat (e.g., (PhCN)$_2$PdCl$_2$) and CuI in TEA and DMF furnishs 4b. In-situ deprotection of 4a can occur, providing 4b directly, if the protecting group is unstable at elevated temperatures or unstable under acidic conditions. If the protecting group is not removed in-situ, 4a is deprotected using TFA in DCM, furnishing 4b.

(5a) Addition of Protecting Group: Treatment of 1c with sodium hydride (NaH) in DMF followed by tosyl chloride (TosCl) furnishes 5a.

(5b) Addition of Electrophile: Treatment of 5a with an electrophile (see Table 6), Pd Cat (e.g., (PhCN)$_2$PdCl$_2$) and CuI in TEA and DMF furnishes 5b. E and Z isomers can be separated using HPLC or carried on as a mixture of isomers.

(5c) & (5d) Deprotection: Deprotection of the individual isomers using lithium hydroxide (LiOH) in dioxane furnishes 5c or 5d. Alternatively, the mixture of isomers may be deprotected with LiOH in dioxane yielding 5c and 5d. Individual isomers are then isolated by HPLC.

Table 6 shows each R$^1$ radical and corresponding example number (at left) of species-compounds of Scheme 4 and 5.

TABLE 6
Pyrrolopyrimidines with Vinyl-Linked Electrophiles
(1c) Ether-Halo-Pyrrolopyrimidine
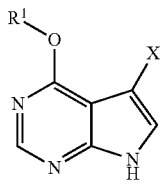
| When R¹ = 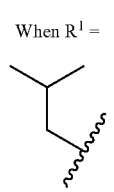 | When R¹ = 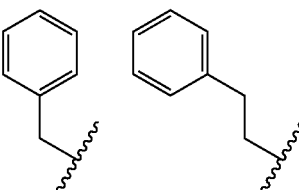 | When R¹ = | | |
|---|---|---|---|---|
| Ex. # is: | Ex. # is: | Ex. # is: | Vinyl-Containing Electrophile | Pyrrolopyrimidines with Vinyl-Linked Electrophiles |
| 35 | 93 | 147 |  | 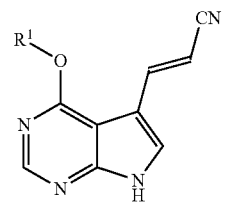 |
| 36 | 94 | 148 |  | 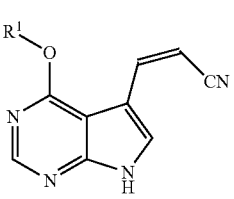 |
| 37 | 95 | 149 |  | 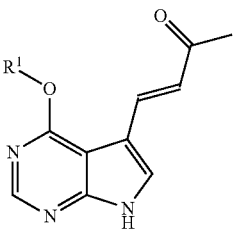 |
| 38 | 96 | 150 | 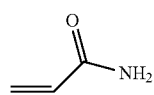 | 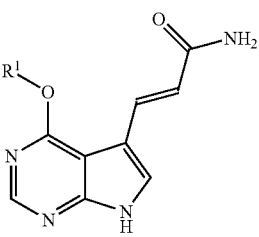 |
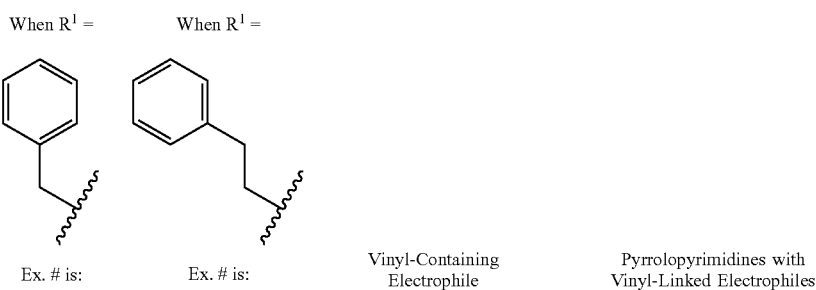

TABLE 6-continued

Pyrrolopyrimidines with Vinyl-Linked Electrophiles (1c) Ether-Halo-Pyrrolopyrimidine

| When R¹ = (isobutyl) | When R¹ = (benzyl) | When R¹ = (phenethyl) | Vinyl-Containing Electrophile | Pyrrolopyrimidines with Vinyl-Linked Electrophiles |
|---|---|---|---|---|
| Ex. # is: | Ex. # is: | Ex. # is: | | |
| 39 | 97 | 151 | acrylamide, N-methyl | |
| 40 | 98 | 152 | phenyl vinyl ketone | |
| 41 | — | — | 1-(pyridin-2-yl)prop-2-en-1-one | |
| 42 | — | — | 1-(pyridin-3-yl)prop-2-en-1-one | |

TABLE 6-continued
Pyrrolopyrimidines with Vinyl-Linked Electrophiles
(1c) Ether-Halo-Pyrrolopyrimidine
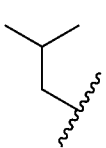
| When R¹ = | When R¹ = | When R¹ = | | |
|---|---|---|---|---|
| 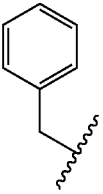 | 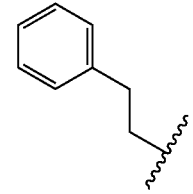 | 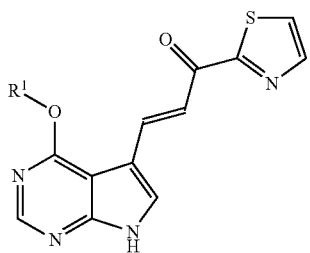 | | |
| Ex. # is: | Ex. # is: | Ex. # is: | Vinyl-Containing Electrophile | Pyrrolopyrimidines with Vinyl-Linked Electrophiles |
| 43 | — | — | 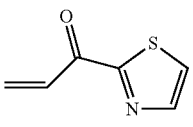 |  |
| 49 | 105 | 160 | 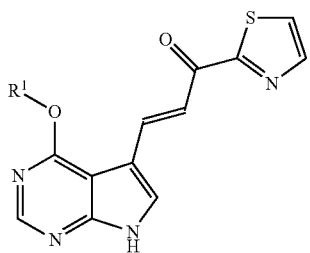 | 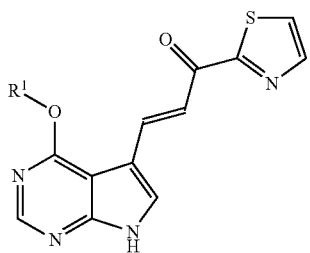 |
| 50 | 104 | 158 | 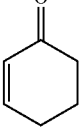 | 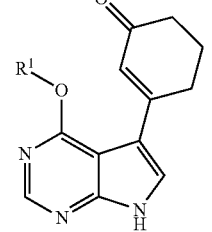 |
| 51 | 108 | 162 | 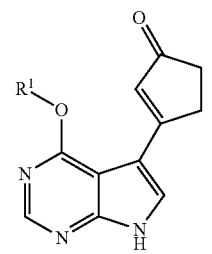 | 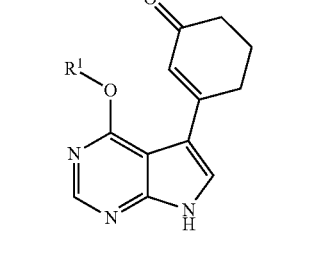 |

TABLE 6-continued
Pyrrolopyrimidines with Vinyl-Linked Electrophiles
(1c) Ether-Halo-Pyrrolopyrimidine
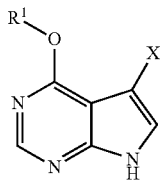
| When R¹ = 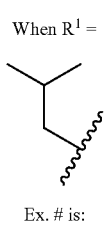 | When R¹ = 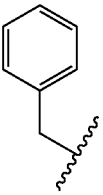 | When R¹ = 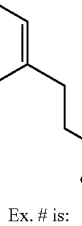 | Vinyl-Containing Electrophile | Pyrrolopyrimidines with Vinyl-Linked Electrophiles |
|---|---|---|---|---|
| Ex. # is: | Ex. # is: | Ex. # is: | | |
| 52 | 109 | 163 | 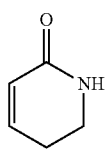 | 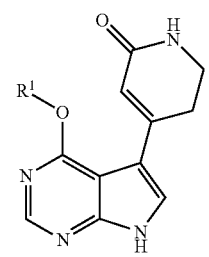 |
| 53 | 106 | 160 | 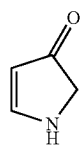 | 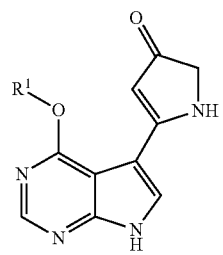 |
| 54 | 107 | 161 | 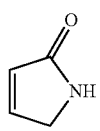 | 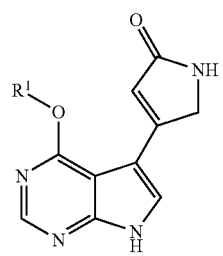 |

Scheme 6. Preparation of Heteroaryl-Containing Pyrrolopyrimidines.

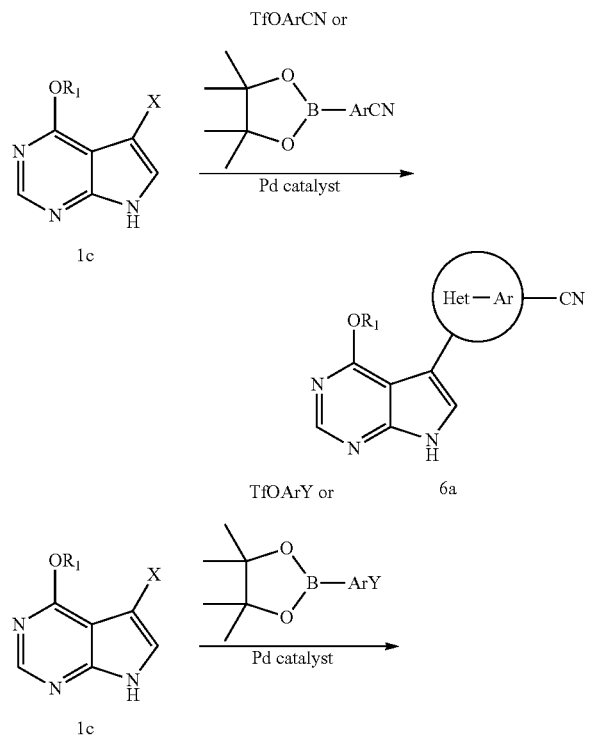

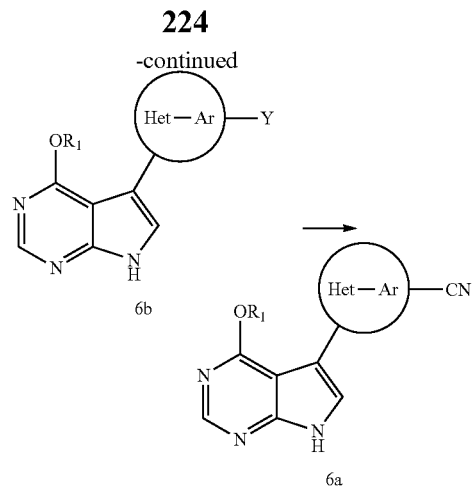

TfO = Triflate
X = Br or I
Y = amide or Cl (6a) Heteroaryl Coupling to Pyrrolopyrimidine (Suzuki Coupling): Reaction of 1c (from Scheme 1) with desired triflate or boronate (see Table 7), in the presence of a palladium catalyst (e.g., tetrakis(triphenylphosphine)palladium) and an amine base (e.g., DIEA) furnishes 6a (see Table 7a). In some examples, heteroaryl (Het-Ar) contains moiety Y (6b). Examples of (6b) species-compounds are listed in Table 7b. Alternatively, (6b) can be converted to nitrile 6a using methods known to those skilled in the art (e.g., dehydration of an amide, direct displacement or reaction with tosyl cyanide).

Table 7a & 7b shows each $R^1$ radical and corresponding example number (at left) of species-compounds of Scheme 6.

TABLE 7a

Heteroaryl-Containing Pyrrolopyrimidines (6a)

(1c) Ether-Halo-Pyrrolopyrimidine

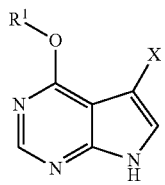

| When $R^1$ = 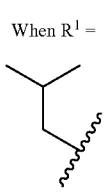 | When $R^1$ = 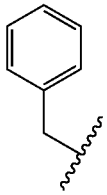 | When $R^1$ =  | | |
|---|---|---|---|---|
| Ex. # is: | Ex. # is: | Ex. # is: | Het-Ar-Triflate | Heteroaryl-Containing Pyrrolopyrimidines (6a) |
| 55 | 110 | 164 | 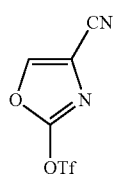 | 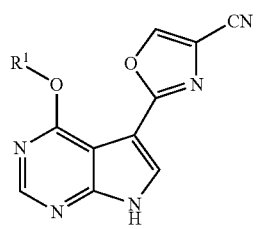 |

TABLE 7a-continued
Heteroaryl-Containing Pyrrolopyrimidines (6a)
(1c) Ether-Halo-Pyrrolopyrimidine
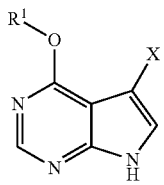
| When R¹ = 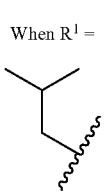 | When R¹ = 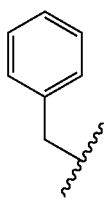 | When R¹ = 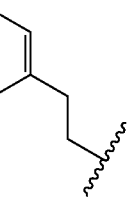 | Het-Ar-Triflate | Heteroaryl-Containing Pyrrolopyrimidines (6a) |
|---|---|---|---|---|
| Ex. # is: | Ex. # is: | Ex. # is: | | |
| — | 111 | 165 | 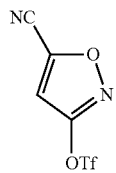 | 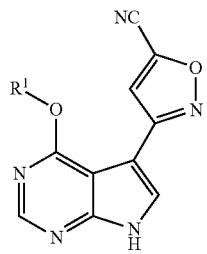 |
| 56 | 112 | 166 | 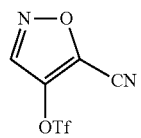 | 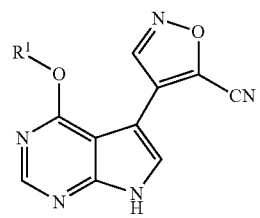 |
| 57 | 113 | 167 | 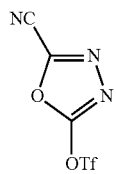 | 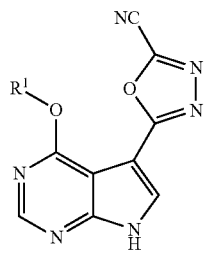 |
| 58 | 114 | 168 | 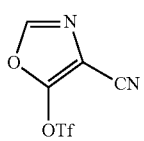 | 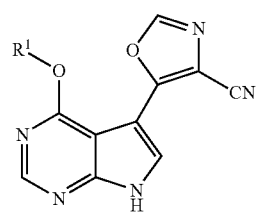 |

TABLE 7a-continued
Heteroaryl-Containing Pyrrolopyrimidines (6a)
(1c) Ether-Halo-Pyrrolopyrimidine
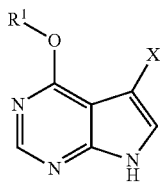
| When R¹ = | When R¹ = | When R¹ = | Het-Ar-Triflate | Heteroaryl-Containing Pyrrolopyrimidines (6a) |
|---|---|---|---|---|
| 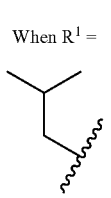 | 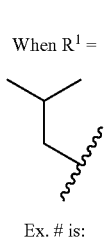 | 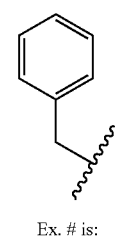 | | |
| Ex. # is: | Ex. # is: | Ex. # is: | | |
| 59 | 115 | 169 | 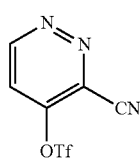 [SMILES: N#Cc1nnccc1OS(=O)(=O)C(F)(F)F] | 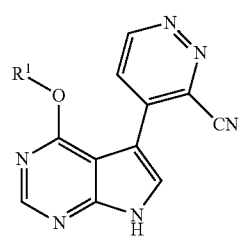 |
| 60 | 116 | 170 | 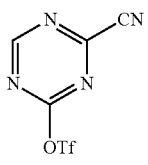 | 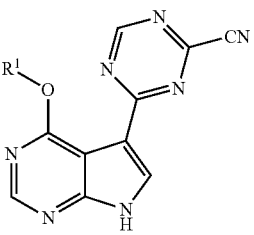 |
| 61 | 117 | 171 | 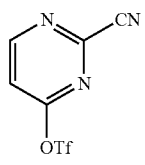 [SMILES: N#Cc1nccc(OS(=O)(=O)C(F)(F)F)n1] | 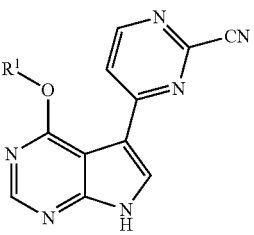 |
| 62 | 118 | 172 | 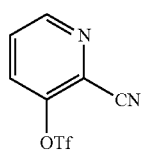 [SMILES: N#Cc1ncccc1OS(=O)(=O)C(F)(F)F] | 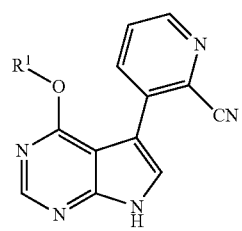 |

TABLE 7a-continued

Heteroaryl-Containing Pyrrolopyrimidines (6a)

(1c) Ether-Halo-Pyrrolopyrimidine

| When $R^1$ = isobutyl | When $R^1$ = benzyl | When $R^1$ = phenethyl | Het-Ar-Triflate | Heteroaryl-Containing Pyrrolopyrimidines (6a) |
|---|---|---|---|---|
| Ex. # is: 63 | Ex. # is: 119 | Ex. # is: 173 | pyrimidine with CN and OTf | pyrrolopyrimidine-pyrimidine-CN product |

TABLE 7b

Heteroaryl-Containing Pyrrolopyrimidines (6b)

| 64 | 120 | 174 | Chloro-thiadiazole-OTf | $R^1$-O-pyrrolopyrimidine-thiadiazole-Cl |

Scheme 7. Preparation of Pyrrolopyrimidines with Amide Alkyl Nitrile Electrophiles.

6a X = I → (CO, DMF, Pd(dppf)Cl$_2$, H$_2$O) → carboxylic acid intermediate → (NH$_2$R$^6$, HBTU, DIEA, DMF) → 7a (amide) → 7b → (LiOH, dioxane) → 7c -continued

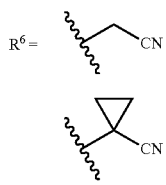

(7a) Carbonylation: Treatment of 6a with a Pd Cat. (e.g., (Pd(dppf))Cl₂) and carbon monoxide followed by water yields 7a.

(7b) Amide Bond Formation: Treatment of acid 7a with O-(Benzotriazol-1-yl)-N,N,N',N'-tetramethyluronium hexafluorophosphate (HBTU) or hydroxybenzotriazole (HOBT) in DMF, followed by addition of desired amine provides amide 7b.

Deprotection: Hydrolysis of the tosylate using lithium hydroxide (LiOH) in dioxane furnishes 7c.

Table 8 shows each R¹ radical and corresponding example number (at left) of species-compounds of Scheme 7.

TABLE 8

Pyrrolopyrimidines with Amide alkyl nitriles Electrophiles (7c)

(1b) Ether-Pyrrolopyrimidine

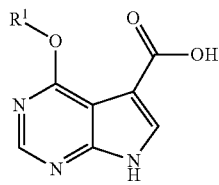

| When R¹ = 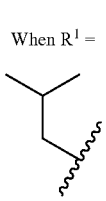 | When R¹ = 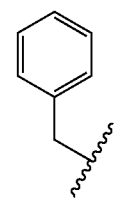 | When R¹ =  | Amine | Pyrrolopyrimidines with Amidealkyl nitriles Electrophiles (7c) |
|---|---|---|---|---|
| Ex. # is: | Ex. # is: | Ex. # is: | | |
| 33 | 91 | 145 | H₂N―CN | 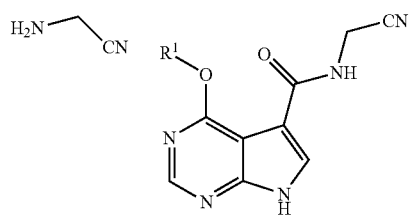 |
| 34 | 92 | 146 |  | 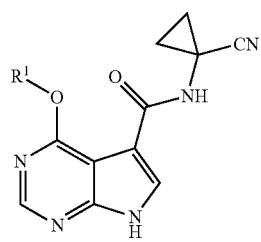 |

Scheme 8.
Preparation of Pyrrolopyrimidines with Allyl-Linked Electrophiles

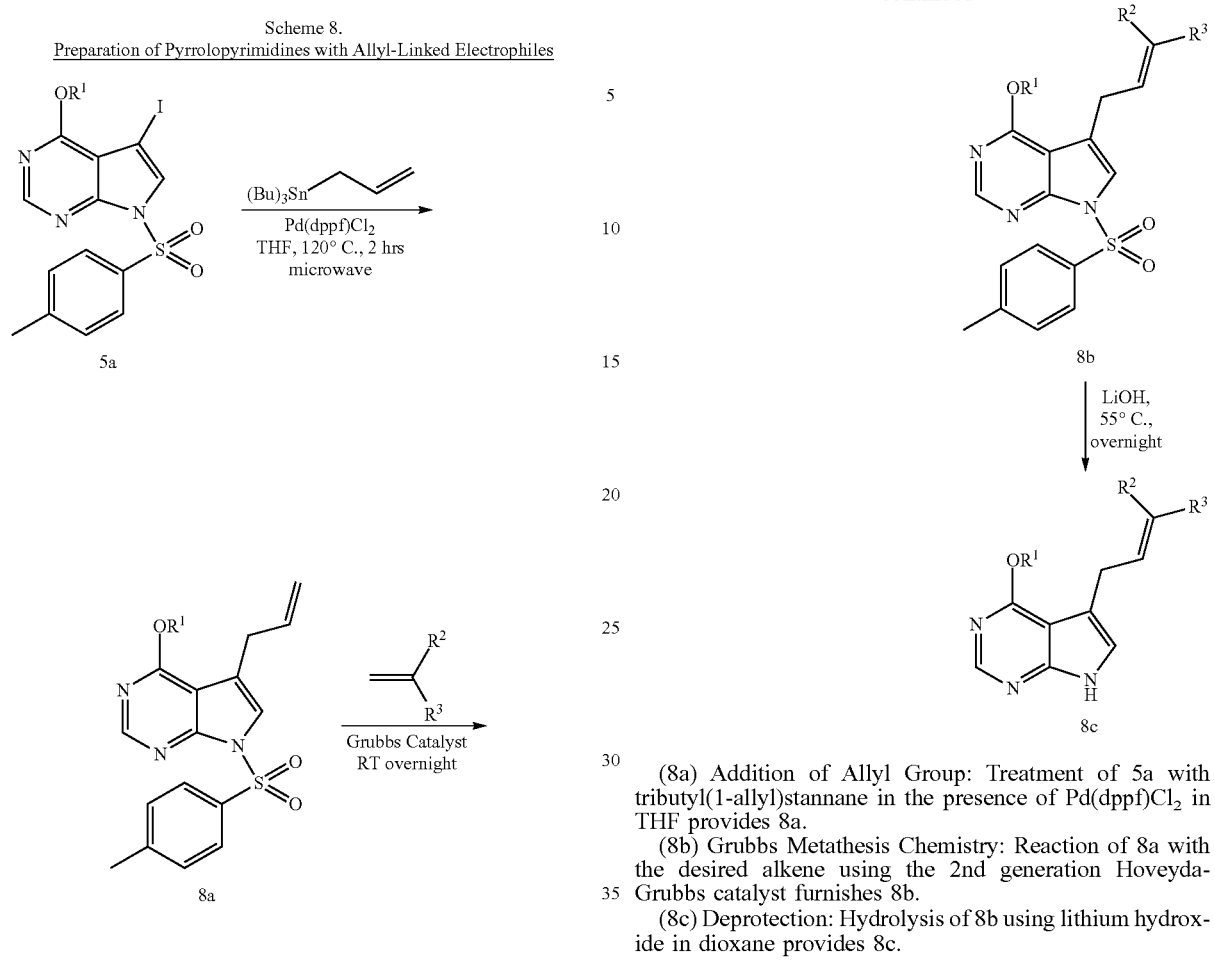

(8a) Addition of Allyl Group: Treatment of 5a with tributyl(1-allyl)stannane in the presence of Pd(dppf)Cl₂ in THF provides 8a.

(8b) Grubbs Metathesis Chemistry: Reaction of 8a with the desired alkene using the 2nd generation Hoveyda-Grubbs catalyst furnishes 8b.

(8c) Deprotection: Hydrolysis of 8b using lithium hydroxide in dioxane provides 8c.

Scheme 9. Preparation of Pyrrolopyrimidines with Vinyl-Linked Electrophiles (Wittig Route)

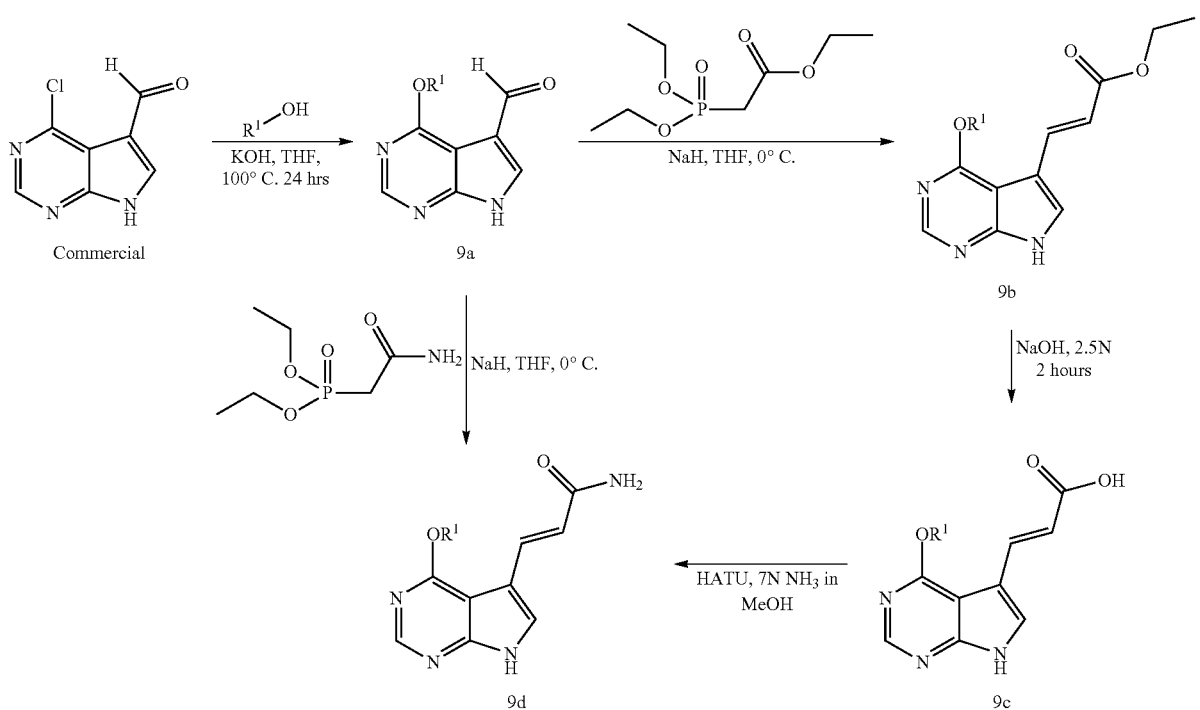

(9a) Ether Formation: Reaction of an alcohol (R$^1$OH) with 4-chloro-7H-pyrrolo[2,3-d]pyrimidine-5-carbaldehyde and potassium hydroxide in THF or dioxane provides ether 9a.

(9b) Horner-Emmons: Olefination of 9a using (diethoxy-phosphoryl)-acetic acid ethyl ester in the presence of sodium hydride in THF furnishes 9b.

(9c) Ester Hydrolysis: Hydrolysis of 9b using aqueous sodium hydroxide provides carboxylic acid 9c.

(9d) Amide Formation from Acid 9c: Standard amide formation was done by exposure of acid 9c to HATU in the presence diisopropylethylamine in DMF followed by methanolic ammonia, which provides 9d.

(9d) Horner-Emmons: Olefination of 9a using 2-amino-2-oxoethylphosphonate in the presence of sodium hydride in THF furnishes 9d.

INTERMEDIATES

Intermediate 1

Synthesis of
5-chloro-4-isobutoxy-7H-pyrrolo[2,3-d]pyrimidine

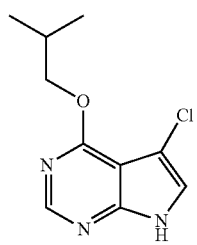

Step A: Synthesis of
4-isobutoxy-7H-pyrrolo[2,3-d]pyrimidine

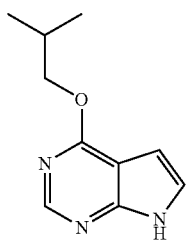

A mixture of 4-chloropyrrolopyrimidine (8.0 g, 52 mmol), 2-methyl-1-propanol (70 mL), potassium hydroxide (6.8 g, 121 mmol) and 18-crown-6 (0.25 g, 0.95 mmol) was heated at 90° C. for 4 days. After cooling to room temperature, the residue was diluted with ice water (150 mL), extracted with ethyl acetate, the organic layers washed, dried over MgSO$_4$, and concentrated. The residue was triturated with EtOH, cooled and filtered to give 6.4 g of 4-isobutoxy-7H-pyrrolo[2,3-d]pyrimidine: $^1$H-NMR (400 MHz, DMSO-d$_6$): δ 12.00 (br s, 1H), 8.33 (s, 1 H), 7.34 (d, J=3.6 Hz, 1 H), 6.47 (d, J=3.2 Hz, 1 H), 4.25 (d, J=6.4 Hz, 2 H), 2.05-2.20 (m, 1 H), 1.00 (d, J=7.2 Hz, 6 H); LC/MS m/z 192 (M+H).

Step B: Synthesis of
5-chloro-4-isobutoxy-7H-pyrrolo[2,3-d]pyrimidine

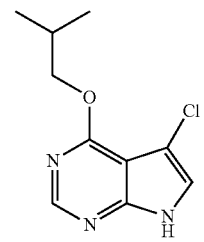

A mixture of 4-isobutoxy-7H-pyrrolo[2,3-d]pyrimidine (0.10 g, 0.52 mmol), N-chlorosuccinimide (0.076 g, 0.57 mmol) in THF (3.0 mL) containing 0.05 mL of dichloroacetic acid was heated at 60° C. for 3 h. The reaction mixture was concentrated under reduced pressure and the resulting residue was purified by flash chromatography, eluting with 40% ethyl acetate in heptane to give the title compound (0.09 g) as a white solid: $^1$H-NMR (400 MHz, DMSO-d$_6$) δ 8.38 (s, 1 H), 7.52 (s, 1 H), 4.24 (d, J=6 Hz, 2 H), 2.0-2.15 (m, 1 H), 1.03 (d, J=6 Hz, 6 H); LC Rt=4.31 min; LC/MS m/z 226 (M+H).

Intermediate 2

5-iodo-4-isobutoxy-7H-pyrrolo[2,3-d]pyrimidine

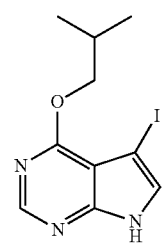

To a solution of 4-isobutoxy-7H-pyrrolo[2,3-d]pyrimidine (prepared as described in Intermediate 1, 1.4 g, 7.3 mmol) in dichloromethane (15 mL) and methanol (2.0 mL), was added N-iodosuccinimide (1.8 g, 8.0 mmol). The mixture was stirred at room temperature for 1 h. The reaction mixture was concentrated under reduced pressure. The residue was partitioned between ethyl acetate and water, the combined organic layers washed, dried over MgSO$_4$, filtered and concentrated. The residue was crystalized from ethyl acetate to give 1.57 g of product. The filtrate was concentrated and diluted with ethyl acetate. Isolation of the precipitate provided an additional 410 mg (total=1.97 g): $^1$H-NMR (400 MHz, DMSO-d$_6$) δ 12.34 (s, 1 H), 8.34 (s, 1H), 7.54 (s, 1 H), 4.25 (d, J=6.4 Hz, 2 H), 2.05-2.20 (m, 1 H), 1.08 (d, J=6.4 Hz, 6 H); LC Rt=4.47 min; LC/MS m/z 318 (M+H).

Intermediate 3

4-(sec-butoxy)-5-iodo-7H-pyrrolo[2,3-d]pyrimidine

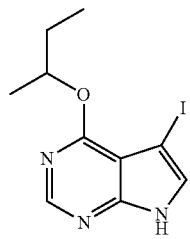

Step A: Synthesis of 4-(sec-butoxy)-7H-pyrrolo[2,3-d]pyrimidine

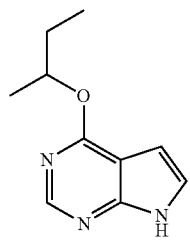

A mixture of 4-chloropyrrolopyrimidine (2.0 g, 13 mmol), 2-butanol (12 mL) and potassium hydroxide (1.7 g, 30 mmol) was heated at 100° C. for 3 days. An additional amount of potassium hydroxide (0.34 g, 6.1 mmol) was added and the heating continued for 24 h. After cooling to room temperature, the residue was diluted with water, extracted with ethyl acetate, the organic layers dried over MgSO₄, filtered, and concentrated to give 1.55 g of a mixture of 4-(sec-butoxy)-7H-pyrrolo[2,3-d]pyrimidine and starting material.

The crude residue was diluted with 2-butanol (3.0 mL) and cooled to 0° C. Sodium hydride (60% mineral oil dispersion, 0.19 g, 4.8 mmol) and 18-crown-6 (50 mg) were added. The solution was allowed to warm to room temperature, stirred for 4 h and then heated at reflux for 10 h. After cooling to room temperature, aqueous workup as described above provided 1.46 g of a mixture of 4-(sec-butoxy)-7H-pyrrolo[2,3-d]pyrimidine and starting material which was carried on crude.

Step B: Synthesis of 4-(sec-butoxy)-5-iodo-7H-pyrrolo[2,3-d]pyrimidine

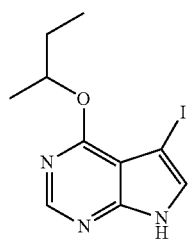

The crude mixture of 4-(sec-butoxy)-7H-pyrrolo[2,3-d] pyrimidine (1.46 g, 7.63 mmol), N-iodosuccinimide (1.7 g, 7.6 mmol) in dichloromethane (8.0 mL) and MeOH (2.0 mL) was stirred at room temperature for 4 h. The reaction mixture was diluted with CH₂Cl₂ (15 mL), washed with 5% aqueous sodium sulfite and water, dried (MgSO₄), filtered and concentrated. The resulting residue was purified by flash chromatography, eluting with 20% ethyl acetate in heptane. The appropriate fractions were combined and concentrated. The residue was suspended in ethyl acetate, diluted with heptane, cooled and a solid filtered off to provide 1.41 g of the title compound: LC/MS: m/z 318 (M+H)

EXAMPLES

Example 1

Synthesis of 4-isobutoxy-7H-pyrrolo[2,3-d]pyrimidine-5-carbonitrile

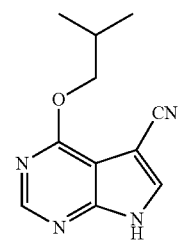 [SMILES: CC(C)COc1ncnc2[nH]cc(C#N)c12]

Step A: Synthesis of tert-butyl 5-iodo-4-isobutoxy-7H-pyrrolo[2,3-d]pyrimidine-7-carboxylate

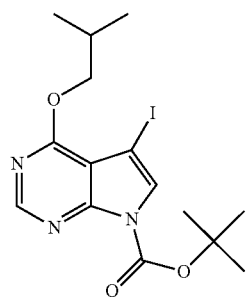 [SMILES: CC(C)COc1ncnc2c1c(I)cn2C(=O)OC(C)(C)C]

A mixture of 5-iodo-4-isobutoxy-7H-pyrrolo[2,3-d]pyrimidine (0.38 g, 1.3 mmol), di-tert-butyl dicarbonate (300 mg, 1.37 mmol) and DMAP (0.014 g, 0.11 mmol) in CH₂Cl₂ (10.0 mL) was stirred at room temperature under nitrogen for 14 h. The reaction mixture was concentrated and the residue purified by flash chromatography on silica gel eluting with 15% ethyl acetate in heptane to give the title compound (0.52 g) as a colorless syrup: LC Rt=5.32 min; LC/MS m/z 420 (M+Na).

Step B: Synthesis of 4-isobutoxy-7H-pyrrolo[2,3-d]pyrimidine-5-carbonitrile

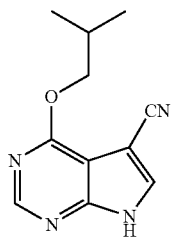 [SMILES: CC(C)COc1ncnc2[nH]cc(C#N)c12]

To a solution of tert-butyl 5-iodo-4-isobutoxy-7H-pyrrolo[2,3-d]pyrimidine-7-carboxylate (0.32 g, 0.77 mmol) in anhydrous DCM (5.0 mL), was added dropwise a solution of 2 M isopropylmagnesium chloride in THF (0.50 mL, 1.0 mmol) and the mixture stirred at 0° C. for 45 min. The reaction mixture was cooled to −70° C., added dropwise a solution of p-toluenesulfonyl cyanide (200 mg, 1.1 mmol) in DCM (1 mL) and the solution allowed to warm to room temperature and was stirred for 2 h. The reaction was quenched with saturated NH$_4$Cl and extracted with DCM (2×15 mL). The combined organic extracts were washed with brine and concentrated. The resulting residue was triturated with ethyl acetate, cooled and filtered. The filtrate was concentrated and the residue was purified by reverse-phase HPLC using 5-95% acetonitrile in water (20 min. gradient). Appropriate fractions were combined and freeze-dried to give 8.2 mg of the title compound as a white solid: $^1$H-NMR (400 MHz, DMSO-d$_6$) δ 8.52 (s, 1 H), 8.35 (s, 1 H), 4.32 (d, J=6 Hz, 2 H), 2.05-2.20 (m, 1 H), 1.04 (d, J=6 Hz, 6 H); LC Rt=3.72 min; LC/MS m/z 217 (M+H).

Examples 35 & 36

Synthesis of (E)-3-(4-isobutoxy-7H-pyrrolo[2,3-d]pyrimidin-5-yl)acrylonitrile and (Z)-3-(4-isobutoxy-7H-pyrrolo[2,3-d]pyrimidin-5-yl)acrylonitrile

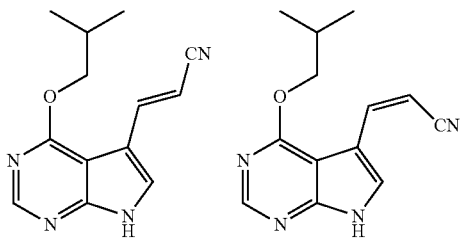 [SMILES: CC(C)COc1ncnc2[nH]cc(/C=C/C#N)c12 ; CC(C)COc1ncnc2[nH]cc(/C=C\C#N)c12]

Step A: Synthesis of 5-iodo-4-isobutoxy-7-tosyl-7H-pyrrolo[2,3-d]pyrimidine

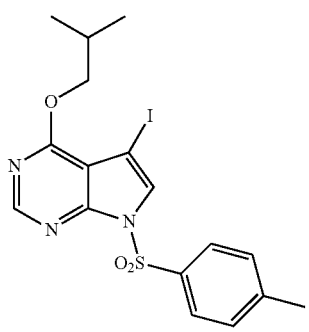 [SMILES: Cc1ccc(S(=O)(=O)n2cc(I)c3c(OCC(C)C)ncnc32)cc1]

To a cold (5° C.) solution of 5-iodo-4-isobutoxy-7H-pyrrolo[2,3-d]pyrimidine (Intermediate 2, 0.20 g, 0.63 mmol) in DMF (2.5 mL), was added NaH (60% mineral oil dispersion, 0.030 g, 0.75 mmol) and the mixture stirred at 5° C. under nitrogen. After 15 min, a solution of p-toluenesulfonylchloride (0.14 g, 0.73 mmol) in DMF (1 mL) was added dropwise. After stirring at room temperature for 12 h, the reaction was quenched by the addition of 5% citric acid (5 mL) and extracted with ethyl acetate (2×10 mL). The combined extracts were washed with brine, dried over MgSO$_4$, filtered and concentrated under reduced pressure. The resulting residue was purified by flash chromatography using 25% ethyl acetate in heptane to afford the title compound as a white solid (0.26 g): MS (ES) m/z 472 (M+H).

Step B: Synthesis of (E)-3-(4-isobutoxy-7-tosyl-7H-pyrrolo[2,3-d]pyrimidin-5-yl)acrylonitrile and (Z)-3-(4-isobutoxy-7-tosyl-7H-pyrrolo[2,3-d]pyrimidin-5-yl)acrylonitrile

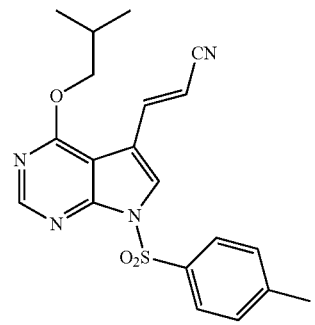

To a solution of 5-iodo-4-isobutoxy-7-tosyl-7H-pyrrolo[2,3-d]pyrimidine (0.25 g, 0.53 mmol) in DMF (5.0 mL), were added CuI (0.02 g, 0.1 mmol), triethylamine (0.15 ml, 1.1 mmol) and acrylonitrile (0.56 g, 11 mmol) under a nitrogen atmosphere. The resulting mixture was degassed for 10 min, (PhCN)$_2$PdCl$_2$ (40 mg, 0.10 mmol) was added and the mixture heated at 65° C. under nitrogen (20 psi) for 16 h. The reaction mixture was allowed to cool and was partitioned between water (25 mL) and ethyl acetate (15 mL). The organic phase was filtered through a bed of celite, washed with water, dried over MgSO$_4$, filtered and concentrated. The residue was purified by silica gel flash chromatography using 25% ethyl acetate in heptane to afford a mixture of the title compounds as a 3:2 mixture favoring the E-isomer as a white solid (0.13 g): MS (ES) m/z 397 (M+H).

Step C: Synthesis of (E)-3-(4-isobutoxy-7H-pyrrolo[2,3-d]pyrimidin-5-yl)acrylonitrile and (Z)-3-(4-isobutoxy-7H-pyrrolo[2,3-d]pyrimidin-5-yl)acrylonitrile

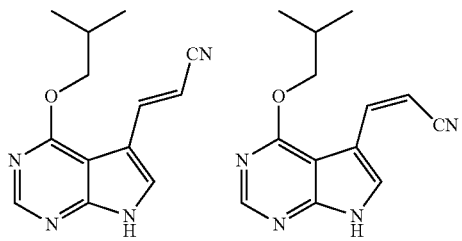 [SMILES: CC(C)COc1ncnc2[nH]cc(/C=C/C#N)c12 ; CC(C)COc1ncnc2[nH]cc(/C=C\C#N)c12]

The product from step B (0.12 g, 0.30 mmol), 1.5 N LiOH (0.25 mL, 0.38 mmol) and dioxane (0.25 mL) was stirred at room temperature. After 1 h, more dioxane (0.25 mL) was added. After an additional 1 h more of 1.5 N LiOH (0.3 mL, 0.45 mmol) was added and stirring was continued for another 2 h. The reaction mixture was diluted with water (10 mL) and extracted with ethyl acetate (2×15 mL). The combined organic extracts were washed with water (10 mL), dried over $MgSO_4$, filtered and concentrated under reduced pressure. The residue was purified by flash chromatography using 1:1 ethyl acetate/heptane to give two products:

(E)-3-(4-isobutoxy-7H-pyrrolo[2,3-d]pyrimidin-5-yl)acrylonitrile (0.019 g) as a white solid: $^1$H-NMR (400 MHz, DMSO-$d_6$): δ 12.76 (br s, 1 H), 8.49 (s, 1 H), 8.03 (s, 1 H), 7.73 (d, J=17.0 Hz, 1 H), 6.46 (d, J=17.0 Hz, 1 H), 4.39 (d, J=6.65 Hz, 2 H), 2.15-2.25 (m, 1 H), 1.08 (d, J=6.7 Hz, 6 H); MS (ES) m/z 243 (M+H); and (Z)-3-(4-isobutoxy-7H-pyrrolo[2,3-d]pyrimidin-5-yl)acrylonitrile (0.02 g): $^1$H-NMR (400 MHz, DMSO-$d_6$): δ 12.76 (br s, 1 H), 8.44 (s, 1 H), 8.14 (s, 1 H), 7.67 (d, J=12.0 Hz, 1 H), 5.72 (d, J=12.0 Hz, 1 H), 4.31 (d, J=6.2 Hz, 2 H), 2.05-2.20 (m, 1 H), 1.03 (d, J=6.2 Hz, 6 H); MS (ES) m/z 243 (M+H).

Examples 35 and 36 were also isolated as trifluoro acetate salts as a result of $C_{18}$ reverse phase chromatography. These salts can be converted into their corresponding free base form by standard extractive acid-base chemistry.

Example 38

Synthesis of (E)-3-(4-isobutoxy-7H-pyrrolo[2,3-d]pyrimidin-5-yl)acrylamide

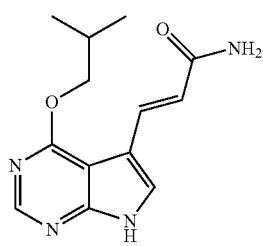 [SMILES: CC(C)COc1ncnc2[nH]cc(/C=C/C(N)=O)c12]

Step A: Synthesis of (E)-3-(4-isobutoxy-7-tosyl-7H-pyrrolo[2,3-d]pyrimidin-5-yl)acrylamide

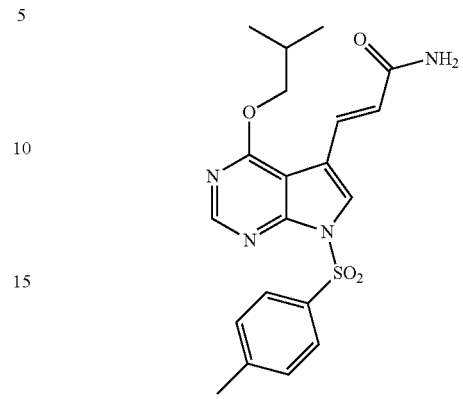

To a solution of 5-iodo-4-isobutoxy-7-tosyl-7H-pyrrolo[2,3-d]pyrimidine (Example 35 Step A, 0.25 g, 0.53 mmol) in DMF (5.0 mL), were added CuI (0.02 g, 0.1 mmol), triethylamine (0.15 ml, 1.1 mmol) and acrylamide (0.60 g, 8.45 mmol) under a nitrogen atmosphere. The resulting mixture was degassed for 10 min, $(PhCN)_2PdCl_2$ (40 mg, 0.10 mmol) was added and the mixture heated at 65° C. under nitrogen (20 psi) for 16 h. The reaction mixture was allowed to cool and was partitioned between cold water (25 mL) and ethyl acetate (15 mL). A precipitate was formed which was filtered, washed with water, ethyl acetate, and dried to give 0.16 g of the title compound. The organic phase was washed with water, dried over $MgSO_4$, filtered and concentrated. The residue was purified by silica gel flash chromatography using 60% ethyl acetate in heptane to afford an additional 0.035 g of the desired product: MS (ES) m/z 415 (M+H).

Step B: Synthesis of (E)-3-(4-isobutoxy-7H-pyrrolo[2,3-d]pyrimidin-5-yl)acrylamide

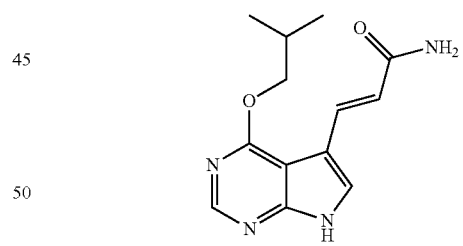

The product from above (0.16 g, 0.39 mmol), 1.5 N LiOH (0.40 mL, 0.6 mmol), THF (0.5 mL) and dioxane (0.6 mL) was stirred at room temperature for 2 h. The reaction mixture was diluted with water (10 mL) and extracted with ethyl acetate several times. The combined organic extracts were washed with water (10 mL), dried over $MgSO_4$, filtered and concentrated under reduced pressure. The residue was purified by flash chromatography using 5% MeOH in dichloromethane to give the title compound: (0.044 g): $^1$H-NMR (400 MHz, DMSO-$d_6$): δ 12.44 (br s, 1 H), 8.43 (s, 1 H), 7.83 (s, 1 H), 7.74 (d, J=16.0 Hz, 1 H), 7.35 (br s, 1 H), 6.94 (br s, 1 H), 6.68 (d, J=16.0 Hz, 1 H), 4.38 (d, J=6.0 Hz, 2 H), 2.15-2.25 (m, 1 H), 1.08 (d, J=6.4 Hz, 6 H); MS (ES) m/z 261 (M+H).

Example 37

Synthesis of (E)-4-(4-isobutoxy-7H-pyrrolo[2,3-d]pyrimidin-5-yl)but-3-en-2-one

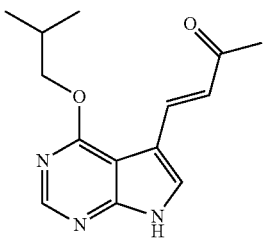 [SMILES: CC(=O)/C=C/c1c[nH]c2ncnc(OCC(C)C)c12]

The title compound was prepared in a similar manner to Example 38 for (E)-3-(4-isobutoxy-7H-pyrrolo[2,3-d]pyrimidin-5-yl)acrylamide, wherein acrylamide was substituted with but-3-en-2-one in step A. The title compound was isolated by flash chromatography using 40% ethyl acetate/heptane and crystallization from ethyl acetate (0.015 g): $^1$H-NMR (400 MHz, DMSO-$d_6$) δ 12.60 (br s, 1 H), 8.41 (s, 1 H), 8.05 (s, 1 H), 7.82 (d, J=16.0 Hz, 1 H), 6.98 (d, J=16.0 Hz, 1 H), 4.32 (d, J=6.4 Hz, 2 H), 2.33 (s, 3 H), 2.10-2.20 (m, 1 H), 1.07 (d, J=6.8 Hz, 6 H); MS (ES) m/z 260 (M+H).

Example 175

Synthesis of (E)-1-(4-isobutoxy-7H-pyrrolo[2,3-d]pyrimidin-5-yl)pent-1-en-3-one

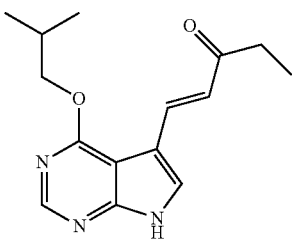 [SMILES: CCC(=O)/C=C/c1c[nH]c2ncnc(OCC(C)C)c12]

The title compound was prepared in a similar manner to Example 38 for (E)-3-(4-isobutoxy-7H-pyrrolo[2,3-d]pyrimidin-5-yl)acrylamide, wherein acrylamide was substituted with pent-1-en-3-one in step A. The title compound was isolated by trituration from ethyl acetate (0.022 g): $^1$H-NMR (400 MHz, DMSO-$d_6$) δ 12.57 (br s, 1 H), 8.41 (s, 1 H), 8.04 (s, 1 H), 7.83 (d, J=16.4 Hz, 1 H), 7.04 (d, J=16.4 Hz, 1 H), 4.32 (d, J=6.4 Hz, 2 H), 2.55-2.70 (m, 2 H), 2.10-2.20 (m, 1 H), 0.95-1.15 (m, 9 H); MS (ES) m/z 274 (M+H).

Example 176

Synthesis of (E)-methyl 3-(4-isobutoxy-7H-pyrrolo[2,3-d]pyrimidin-5-yl)acrylate

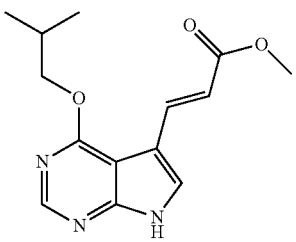

The title compound was prepared in a similar manner to Example 38 for (E)-3-(4-isobutoxy-7H-pyrrolo[2,3-d]pyrimidin-5-yl)acrylamide, wherein acrylamide was substituted with methyl acrylate. The title compound was isolated by flash chromatography using 30% ethyl acetate/heptane and crystallization from ethyl acetate (0.040 g): $^1$H-NMR (400 MHz, DMSO-$d_6$) δ 12.64 (br s, 1 H), 8.47 (s, 1 H), 8.11 (s, 1 H), 7.98 (d, J=15.6 Hz, 1 H), 6.82 (d, J=16.0 Hz, 1 H), 4.39 (d, J=6.4 Hz, 2 H), 3.38 (s, 3 H), 2.15-2.25 (m, 1 H), 1.12 (d, J=6.4 Hz, 6 H).

Example 177

Synthesis of (E)-methyl 3-(4-isobutoxy-7H-pyrrolo[2,3-d]pyrimidin-5-yl)-2-methylacrylate

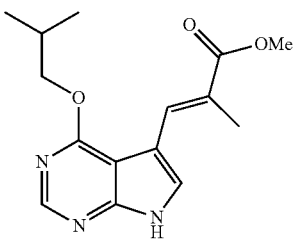 [SMILES: COC(=O)/C(C)=C/c1c[nH]c2ncnc(OCC(C)C)c12]

The title compound was prepared in a similar manner to Example 38 for (E)-3-(4-isobutoxy-7H-pyrrolo[2,3-d]pyrimidin-5-yl)acrylamide, wherein acrylamide was substituted with methyl methacrylate. The title compound was isolated by trituration using ethyl acetate (0.0055 g): $^1$H-NMR (400 MHz, DMSO-$d_6$) δ 12.60 (br s, 1 H), 8.40 (s, 1 H), 8.27 (s, 1 H), 7.73 (s, 1 H), 4.31 (br s, 2 H), 3.71 (s, 3 H), 2.09 (s, 3 H), 1.09 (d, J=4.4 Hz, 6 H); MS (ES) m/z 444 (M+H).

Example 178

Synthesis of (E)-3-(4-isobutoxy-7H-pyrrolo[2,3-d]pyrimidin-5-yl)acrylic acid

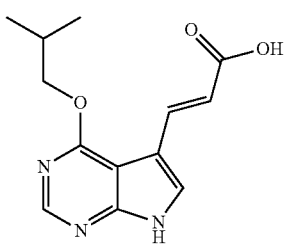 [SMILES: CC(C)COc1ncnc2[nH]cc(/C=C/C(=O)O)c12]

A solution of (E)-methyl 3-(4-isobutoxy-7H-pyrrolo[2,3-d]pyrimidin-5-yl)acrylate (200 mg, 0.73 mmol), 1.5 N LiOH (0.6 mL, 0.90 mmol) and dioxane (0.9 mL) was stirred at 55° C. for 4 h. The solution was allowed to cool to room temperature and then acetic acid and water were added. The resultant solid was collected, washed with water and dried to provide 155 mg of the title compound: $^1$H-NMR (400 MHz, DMSO-$d_6$) δ 12.52 (s, 1 H), 11.97 (s, 1 H), 8.40 (s, 1 H), 8.00 (narrow m, 1 H, 7.83 (d, J=16.0 Hz, 1 H), 6.66 (d, J=16.0 Hz, 1 H), 4.32 (d, J=6.4 Hz, 2 H), 2.05-2.20 (m, 1 H), 1.05 (d, J=6.8 Hz, 6 H).

Example 39

Synthesis of (E)-3-(4-isobutoxy-7H-pyrrolo[2,3-d]pyrimidin-5-yl)-N-methylacrylamide

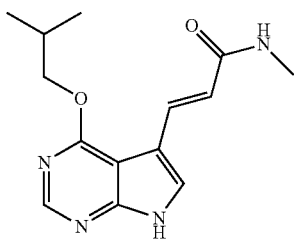 [SMILES: CNC(=O)/C=C/c1c[nH]c2ncnc(OCC(C)C)c12]

A solution of (E)-3-(4-isobutoxy-7H-pyrrolo[2,3-d]pyrimidin-5-yl)acrylic acid (150 mg, 0.57 mmol) and DMF (2.0 mL) was cooled to 0° C. Diisopropylethylamine (0.2 mL, 2.1 mmol) and HATU (0.26 g, 0.68 mmol) were added and the mixture stirred at 5° C. for 30 min. A solution of methylamine in THF (2 M, 1.5 mL, 3.0 mmol) was added. The mixture was stirred for 1 h at 5° C. and 1 h at room temperature. The reaction was quenched with water and extracted several times with ethyl acetate. The combined organic layers were washed with water, dried (MgSO$_4$), filtered and concentrated. The residue was purified by flash chromatography (3% MeOH in ethyl acetate) to give 41 mg of the title compound: $^1$H-NMR (400 MHz, DMSO-d$_6$) δ 12.43 (br s, 1 H), 8.43 (s, 1 H), 7.83 (s, 1 H), 7.77 (d, J=15.6 Hz, 1 H), 6.62 (d, J=15.6 Hz, 1 H), 4.39 (d, J=6.8 Hz, 2 H), 2.76 (s, 3 H), 2.20-2.30 (m, 1 H), 1.08 (d, J=6.8 Hz, 6 H); MS (ES) m/z 275 (MH+).

The following compounds were prepared following Example 39 starting with (E)-3-(4-isobutoxy-7H-pyrrolo[2,3-d]pyrimidin-5-yl)acrylic acid and using the desired amine to form the appropriate amide

| Ex. # | Structure | Name | Experimental Data |
|---|---|---|---|
| 179 | 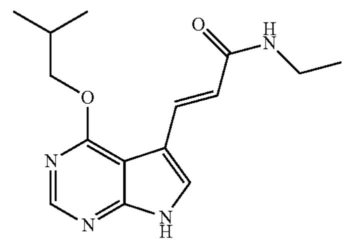 [SMILES: CCNC(=O)/C=C/c1c[nH]c2ncnc(OCC(C)C)c12] | (E)-N-ethyl-3-(4-isobutoxy-7H-pyrrolo[2,3-d]pyrimidin-5-yl)acrylamide | $^1$H-NMR (400 MHz, DMSO-d$_6$) δ 12.36 (br s, 1 H), 8.37 (s, 1 H), 7.65-7.90 (m, 3 H), 6.58 (d, J = 15.6 Hz, 1 H), 4.32 (d, J = 6.8 Hz, 2 H), 3.10-3.25 (m, 2 H), 2.10-2.25 (m, 1 H), 0.95-1.10 (m, 9 H); MS (ES) 289 m/z (M + H). |
| 180 | 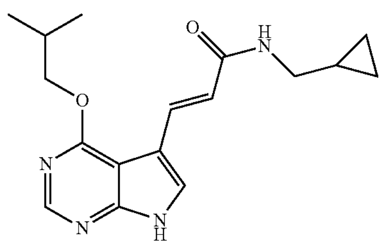 [SMILES: CC(C)COc1ncnc2[nH]cc(/C=C/C(=O)NCC3CC3)c12] | (E)-N-(cyclopropylmethyl)-3-(4-isobutoxy-7H-pyrrolo[2,3-d]pyrimidin-5-yl)acrylamide | $^1$H-NMR (400 MHz, DMSO-d$_6$) δ 12.36 (br s, 1 H), 8.37 (s, 1 H), 7.93 (s, 1 H), 7.65-7.80 (m, 2 H), 6.61 (d, J = 14.4 Hz, 1 H), 4.33 (d, J = 3.9 Hz, 2 H), 3.00-3.10 (narrow m, 2 H), 2.10-2.25 (m, 1 H), 1.03 (d, J = 3.9 Hz, 6 H), 0.95 (s, 1 H), 0.43 (br s, 2 H), 0.19 (br s, 2 H); MS (ES) 315 m/z (M + H). |
| 181 | 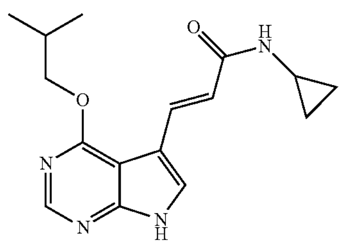 [SMILES: CC(C)COc1ncnc2[nH]cc(/C=C/C(=O)NC3CC3)c12] | (E)-N-cyclopropyl-3-(4-isobutoxy-7H-pyrrolo[2,3-d]pyrimidin-5-yl)acrylamide | $^1$H-NMR (400 MHz, DMSO-d$_6$) δ 12.36 (br s, 1 H), 8.37 (s, 1 H), 7.95 (narrow m, 1 H), 7.65-7.80 (m, 2 H), 6.51 (d, J = 15.6 Hz, 1 H), 4.32, (d, J = 6.8 Hz, 2 H), 2.70-2.80 (m, 1 H), 2.05-2.20 (m, 1 H), 1.02 (d, J = 6.8 Hz, 6 H), 0.60-0.70 (m, 2 H), 0.40-0.50 (m, 2 H); MS (ES) 301 m/z (M + H). |
| 182 | 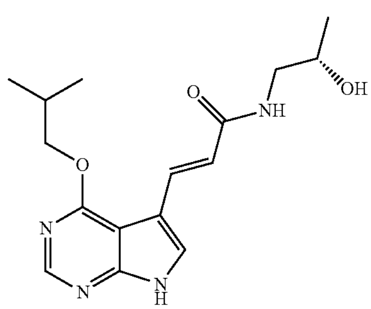 [SMILES: CC(C)COc1ncnc2[nH]cc(/C=C/C(=O)NC[C@H](C)O)c12] | (S,E)-N-(2-hydroxypropyl)-3-(4-isobutoxy-7H-pyrrolo[2,3-d]pyrimidin-5-yl)acrylamide | $^1$H-NMR (400 MHz. DMSO-d$_6$) δ 12.35 (br s, 1 H), 8.43 (s, 1 H), 7.89 (t, J = 5.4 Hz, 1 H), 7.74 (d, J = 5.4 Hz, 1 H), 7.70 (s, 1 H), 6.64 (d, J = 16.0 Hz, 1 H), 4.72 (d, J = 5.0 Hz, 1 H), 4.32 (d, J = 6.5 Hz, 2 H), 3.70 (m, 1H), 3.12 (m, 2 H), 2.19 (m, 1 H), 1.08 (m, 9 H); MS (ES) 319 m/z (M + H). |

| Ex. # | Structure | Name | Experimental Data |
|---|---|---|---|
| 183 | 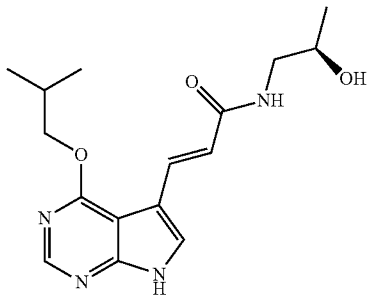 [SMILES: CC(C)COc1ncnc2[nH]cc(/C=C/C(=O)NC[C@@H](C)O)c12] | (R,E)-N-(2-hydroxypropyl)-3-(4-isobutoxy-7H-pyrrolo[2,3-d]pyrimidin-5-yl)acrylamide | $^1$H-NMR (400 MHz. DMSO-$d_6$) δ 12.35 (br s, 1 H), 8.43 (s, 1H), 7.89 (t, J = 5.4 Hz, 1 H), 7.74 (d, J = 5.4 Hz, 1 H), 7.70 (s, 1 H), 6.64 (d, J = 16.0 Hz, 1 H), 4.72 (d, J = 5.0 Hz, 1 H), 4.32 (d, J = 6.5 Hz 2H), 3.70 (m, 1H), 3.12 (m, 2 H), 2.19 (m, 1 H), 1.08 (m, 9H); LCMS (ES) m/z 319 (M + H); MS (ES) 319 m/z (M + H). |
| 184 | 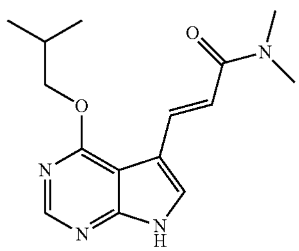 [SMILES: CC(C)COc1ncnc2[nH]cc(/C=C/C(=O)N(C)C)c12] | (E)-3-(4-isobutoxy-7H-pyrrolo[2,3-d]pyrimidin-5-yl)-N,N-dimethylacrylamide | $^1$H-NMR (400 MHz, DMSO-$d_6$) δ 12.47 (br s, 1 H), 8.44 (s, 1 H), 8.04 (s, 1 H), 7.84 (d, J = 15.2 Hz, 1 H), 7.28 (d, J = 15.6 Hz, 1 H), 4.39 (d, J = 6.8 Hz, 2 H), 3.20 (s, 3 H), 2.99 (s, 3 H), 2.15-2.30 (m, 1 H), 1.09 (d, J = 6.8 Hz, 6 H); MS (ES) 289 m/z (M + H). |

Example 185

Synthesis of 3-(4-isobutoxy-7H-pyrrolo[2,3-d]pyrimidin-5-yl)propiolic acid

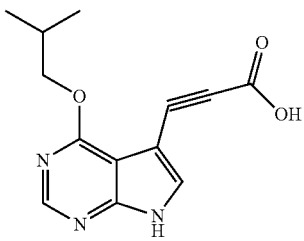 [SMILES: CC(C)COc1ncnc2[nH]cc(C#CC(=O)O)c12]

Step A: Synthesis of methyl 3-(4-isobutoxy-7-tosyl-7H-pyrrolo[2,3-d]pyrimidin-5-yl)propiolate

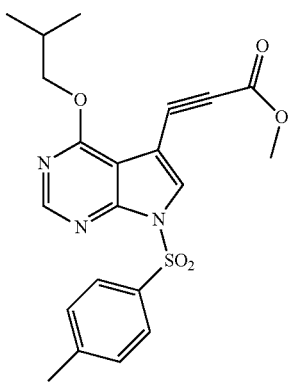 [SMILES: COC(=O)C#Cc1cn(S(=O)(=O)c2ccc(C)cc2)c2ncnc(OCC(C)C)c12]

To a solution of 5-iodo-4-isobutoxy-7-tosyl-7H-pyrrolo[2,3-d]pyrimidine (0.40 g, 0.85 mmol) in DMF (3.0 mL), were added CuI (0.03 g, 0.16 mmol), N-methylmorpholine (0.14 ml, 1.3 mmol) and methyl propiolate (0.28 g, 3.33 mmol) under a nitrogen atmosphere. The resulting mixture was degassed for 10 min, (Ph$_3$P)$_4$Pd (95 mg, 0.08 mmol) was added and the mixture heated at 80° C. under nitrogen (20 psi) for 12 h. The reaction mixture was allowed to cool and 5% acetic acid (10 mL) was added. The mixture was extracted with ethyl acetate, the combined organic layers were washed, dried (MgSO$_4$), filtered, and concentrated. The residue was purified by silica gel flash chromatography using 5% ethyl acetate in heptane to afford 120 mg of the intermediate product: $^1$H-NMR (400 MHz, DMSO-$d_6$) δ 8.60 (s, 1 H), 8.55 (s, 1 H), 8.05 (d, J=8.8 Hz, 2 H), 7.48 (d, J=7.6 Hz, 2 H), 4.25 (d, J=6.0 Hz, 2 H), 3.78 (s, 3 H), 2.38 (s, 3 H), 2.00-2.10 (m, 1 H), 1.01 (d, J=6.8 Hz, 6 H); MS (ES) m/z 428 (M+H).

Step B: Synthesis of 3-(4-isobutoxy-7H-pyrrolo[2,3-d]pyrimidin-5-yl)propiolic acid

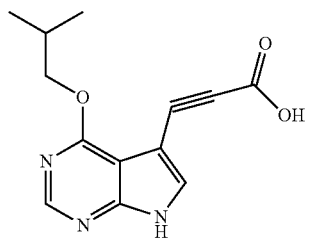 [SMILES: CC(C)COc1ncnc2[nH]cc(C#CC(=O)O)c12]

A solution of methyl 3-(4-isobutoxy-7-tosyl-7H-pyrrolo[2,3-d]pyrimidin-5-yl)propiolate (0.10 g, 0.23 mmol), 1.5 N LiOH (0.27 mL, 041 mmol), and dioxane (0.6 mL) was stirred at 40° C. for 2 h. An additional 0.1 mL of 1.5 N lithium hydroxide (0.15 mmol) was added and the mixture stirred for another 3 h at room temperature. The reaction mixture was diluted with 5% citric acid (5 mL) and extracted with ethyl acetate several times. The combined organic extracts were washed with water (10 mL), dried over MgSO$_4$, filtered and concentrated under reduced pressure. The residue was triturated with ethyl acetate to give 38 mg of the title compound: MS (ES) m/z 260 (M+H).

Example 186

Synthesis of 3-(4-isobutoxy-7H-pyrrolo[2,3-d]pyrimidin-5-yl)propiolamide

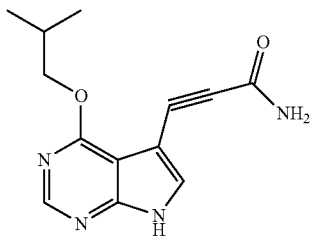 [SMILES: CC(C)COc1ncnc2[nH]cc(C#CC(N)=O)c12]

A solution of 3-(4-isobutoxy-7H-pyrrolo[2,3-d]pyrimidin-5-yl)propiolic acid (38 mg, 0.15 mmol) and DMF (1.5 mL) was cooled to −5° C. Diisopropylethylamine (40 mg, 0.31 mmol) and HATU (0.07 g, 0.18 mmol) were added and the mixture stirred at −5° C. for 30 min. Methanolic ammonia (7 M, 0.06 mL, 0.42 mmol) was added. The mixture was stirred at −5° C. for 30 min and 1 h at room temperature. The reaction mixture was quenched with ice water and extracted several times with ethyl acetate. The combined organic layers were washed with water, dried (MgSO$_4$), filtered, and concentrated. The residue was purified by flash chromatography (2% EtOH in ethyl acetate) and the residue triturated with cold ethyl acetate, filtered, and dried to give 24 mg of the title compound: $^1$H-NMR (400 MHz, DMSO-d$_6$) δ 12.58 (br s, 1 H), 8.40 (s, 1 H), 7.80-7.85 (m, 2 H), 7.49 (s, 1 H), 4.20-4.30 (m, 2 H), 2.05-2.15 (m, 1 H), 1.03 (d, J=6.4 Hz, 6 H); MS (ES) m/z 203 (M-C$_4$H$_8$).

Example 187

Synthesis of (E)-3-(4-(sec-butoxy)-7H-pyrrolo[2,3-d]pyrimidin-5-yl)acrylamide

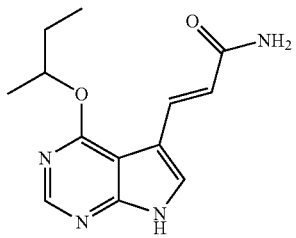 [SMILES: CCC(C)Oc1ncnc2[nH]cc(/C=C/C(N)=O)c12]

The title compound was prepared in a similar manner to Example 38 for (E)-3-(4-isobutoxy-7H-pyrrolo[2,3-d]pyrimidin-5-yl)acrylamide, wherein 5-chloro-4-isobutoxy-7H-pyrrolo[2,3-d]pyrimidine (intermediate 1) was substituted with 4-(sec-butoxy)-5-iodo-7H-pyrrolo[2,3-d]pyrimidine (intermediate 3). The title compound was isolated by flash chromatography using 5% methanol in dichloromethane: $^1$H-NMR (400 MHz, DMSO-d$_6$) δ 12.36 (s, 1 H), 8.36 (s, 1 H), 7.76 (s, 1 H), 7.64 (d, J=15.6 Hz, 1 H), 7.30 (s, 1 H), 6.90 (s, 1 H), 6.62 (d, J=15.6 Hz, 1 H), 5.30-5.45 (m, 1 H), 1.65-1.85 (m, 2 H), 1.39 (d, J=6.4 Hz, 3 H), 0.95 (t, J=7.4 Hz, 3 H).

The following compounds were prepared following the procedures described for intermediates 2 or 3 but by changing the ether substituent in combination with the procedure in Example 38 using acrylamide, which after base hydrolysis provides the compounds indicated below.

| Ex. # | Structure | Name | Experimental Data |
|---|---|---|---|
| 188 | ![structure] | (E)-3-(4-isopropoxy-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.83 (s, 1 H), 7.74 (d, J = 16.0 Hz, 1 H), 7.35 (br s, 1 H), 6.94 (br s, 1 H), 6.68 (d, J = 16.0 Hz, 1 H) 5.63 (m, 1 H), 1.65 (q, J = 5.8 Hz, 6 H); LCMS (ES) 247 m/z (M + H). |
| 189 | ![structure] | (E)-3-(4-propoxy-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.83 (s, 1 H), 7.74 (d, J = 16.0 Hz, 1 H), 7.35 (br s, 1 H), 6.94 (br s, 1 H), 6.68 (d, J = 16.0 Hz, 1 H), 4.05 (t, J = 6.5 Hz 2 H), 1.77 (m, 2 H), 1.00 (t, J = 6.6 Hz, 3 H); LCMS (ES) 247 m/z (M + H). |

-continued

| Ex. # | Structure | Name | Experimental Data |
|---|---|---|---|
| 190 | 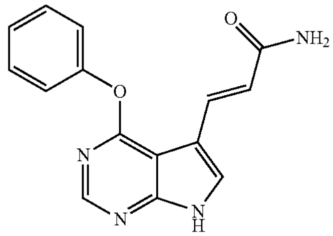 [SMILES: NC(=O)/C=C/c1c[nH]c2ncnc(Oc3ccccc3)c12] | (E)-3-(4-phenoxy-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.95 (s, 1 H), 7.74 (d, J = 16.0 Hz, 1 H), 7.41 (br, 3 H), 7.32 (br, 2 H), 6.94 (br, 2 H), 6.68 (d, J = 16.0 Hz, 1 H); LCMS (ES) 281 m/z (M + H)). |
| 191 | 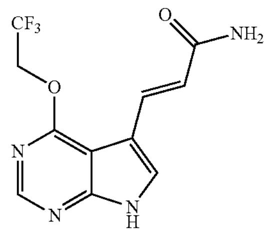 [SMILES: NC(=O)/C=C/c1c[nH]c2ncnc(OCC(F)(F)F)c12] | (E)-3-(4-(2,2,2-trifluoroethoxy)-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.83 (s, 1 H), 7.74 (d, J = 16.0 Hz, 1 H), 7.35 (br s, 1 H), 6.94 (br s, 1 H), 6.68 (d, J = 16.0 Hz, 1 H), 4.46 (q, J = 4.12 Hz, 2 H); LCMS (ES) 287 m/z (M + H). |
| 192 | 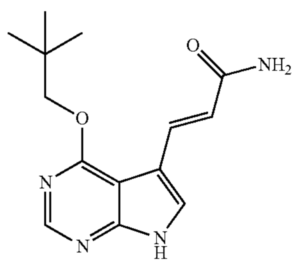 [SMILES: CC(C)(C)COc1ncnc2[nH]cc(/C=C/C(N)=O)c12] | (E)-3-(4-(neopentyloxy)-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.83 (s, 1 H), 7.74 (d, J = 16.0 Hz, 1 H), 7.35 (br s, 1 H), 6.94 (br s, 1 H), 6.68 (d, J = 16.0 Hz, 1 H), 3.87 (s, 2 H), 0.92 (s, 9 H); LCMS (ES) 275 m/z (M + H). |
| 193 | 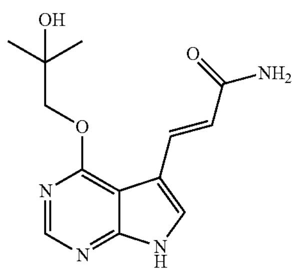 [SMILES: CC(C)(O)COc1ncnc2[nH]cc(/C=C/C(N)=O)c12] | (E)-3-(4-(2-hydroxy-2-methylpropoxy)-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.83 (s, 1 H), 7.74 (d, J = 16.0 Hz, 1 H), 7.35 (br s, 1 H), 6.94 (br s, 1 H), 6.68 (d, J = 16.0 Hz, 1 H), 4.00 (s, 2 H), 3.12 (s, 1 H), 1.27 (s, 6 H); LCMS (ES) 277 m/z (M + H). |
| 194 | 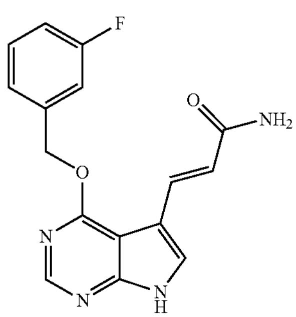 [SMILES: NC(=O)/C=C/c1c[nH]c2ncnc(OCc3cccc(F)c3)c12] | (E)-3-(4-((3-fluorobenzyl)oxy)-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.83 (s, 1 H), 7.74 (d, J = 16.0 Hz, 1 H), 7.15-7.45 (m, 4 H), 6.94 (br s, 2 H), 6.68 (d, J = 16.0 Hz, 1 H), 5.60 (s, 2 H); LCMS (ES) 314 m/z (M + H). |
| 195 | 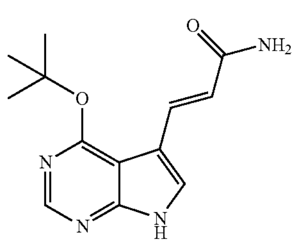 [SMILES: CC(C)(C)Oc1ncnc2[nH]cc(/C=C/C(N)=O)c12] | (E)-3-(4-(tert-butoxy)-7H-pyrrolo[2,3-d]pyrimidin-5-yl)acrylamide | $^1$H-NMR (400 MHz. DMSO-d$_6$) δ 12.44 (br s, 1 H), 8.43 (s, 1 H), 7.83 (s, 1 H), 7.74 (d, J = 16.0 Hz, 1 H), 7.35 (br s, 1 H), 6.94 (br s, 1 H), 6.68 (d, J = 16.0 Hz, 1 H), 1.34 (s, 9 H); LCMS (ES) 261 m/z (M + H). |

Example 21

Synthesis of 1-(4-isobutoxy-7H-pyrrolo[2,3-d]pyrimidin-5-yl)ethanone

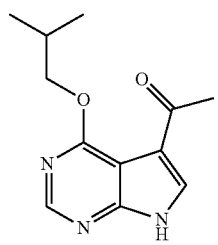

Step A. Synthesis of 1-(4-isobutoxy-7-tosyl-7H-pyrrolo[2,3-d]pyrimidin-5-yl)ethanone

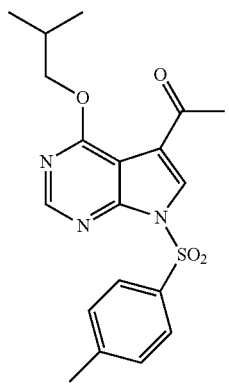 [SMILES: CC(=O)c1cn(S(=O)(=O)c2ccc(C)cc2)c2ncnc(OCC(C)C)c12]

To a solution of 5-iodo-4-isobutoxy-7-tosyl-7H-pyrrolo[2,3-d]pyrimidine (Example 35 Step A, 0.40 g, 0.85 mmol) in DMF (5.0 mL) was added the tributyl(1-ethoxyvinyl)stannane (0.368 g, 1.02 mmol) under a nitrogen atmosphere. The resulting mixture was degassed for 10 min, (PhCN)$_2$PdCl$_2$ (64 mg, 0.17 mmol) was added and the mixture heated at 90° C. under nitrogen (20 psi) for 16 h. The reaction mixture was allowed to cool and 5% HCl (7 mL) was added. The mixture was stirred for 30 min and then diluted with ethyl acetate and water. The mixture was filtered through celite, the organic phase collected and washed with water, dried over MgSO$_4$, filtered and concentrated. The residue was purified by flash chromatography using 25% ethyl acetate in heptane to afford 220 mg of the intermediate: MS (ES) m/z 388 (M+H).

Step B: Synthesis of 1-(4-isobutoxy-7H-pyrrolo[2,3-d]pyrimidin-5-yl)ethanone

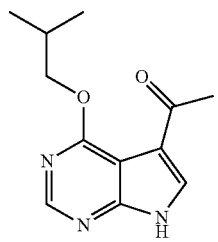 [SMILES: CC(=O)c1c[nH]c2ncnc(OCC(C)C)c12]

A mixture of 1-(4-isobutoxy-7-tosyl-7H-pyrrolo[2,3-d]pyrimidin-5-yl)ethanone (0.11 g, 0.28 mmol), 1.5 N LiOH (0.28 mL, 0.42 mmol), and dioxane (0.5 mL) was stirred at room temperature for 1.5 h. The reaction mixture was diluted with 5% citric acid and extracted with ethyl acetate several times. The combined organic extracts were washed with water, dried over MgSO$_4$, filtered and concentrated under reduced pressure. The residue was purified by flash chromatography using 50% ethyl acetate in heptane to give 55 mg of the title compound: $^1$H-NMR (400 MHz, DMSO-d$_6$) δ 12.36 (br s, 1 H), 8.36 (s, 1 H), 7.76 (s, 1 H), 7.64 (d, J=15.6 Hz, 1 H), 7.30 (s, 1 H), 6.90 (s, 1 H), 6.62 (d, J=15.6 Hz, 1 H), 5.30-5.50 (m, 1 H), 1.65-1.85 (m, 2 H), 1.39 (d, J=6.4 Hz, 3 H), 0.95 (t, J=7.4 Hz, 3 H).

Example 23

Synthesis of 2-chloro-1-(4-isobutoxy-7H-pyrrolo[2,3-d]pyrimidin-5-yl)ethanone

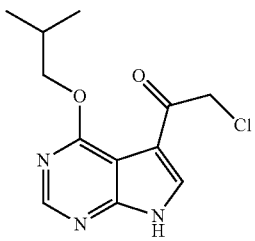 [SMILES: CC(C)COc1ncnc2[nH]cc(C(=O)CCl)c12]

A mixture of 1-(4-isobutoxy-7H-pyrrolo[2,3-d]pyrimidin-5-yl)ethanone (Example 21, 50 mg, 0.22 mmol), benzyltrimethylammonium dichloroiodate (89 mg, 0.26 mmol), p-toluene sulfonic acid (5 mg), dichloroethane (2.0 mL) and methanol (1.0 mL) was stirred for 16 h at ambient temperature. An additional 5 mg of p-toluene sulfonic acid was added after 4 h. The mixture was concentrated and the residue partitioned between 5% citric acid and ethyl acetate. The organic phase was washed with aqueous sodium sulfite, water, dried (MgSO$_4$), filtered and concentrated. Purification by flash chromatography using 1:1 ethyl acetate:heptane provided 23 mg of the title compound: $^1$H-NMR (400 MHz, DMSO-d$_6$) δ 12.92 (s, 1 H), 8.45 (s, 1 H), 8.36 (s, 1 H), 5.03 (s, 2 H), 4.28 (d, J=6.8 Hz, 2 H), 2.05-2.20 (m, 1 H), 1.06 (d, J=6.8 Hz, 6 H); MS (ES) m/z 268 (M+H).

Example 196

Synthesis of (Z)-2-chloro-3-(4-isobutoxy-7H-pyrrolo[2,3-d]pyrimidin-5-yl)acrylamide

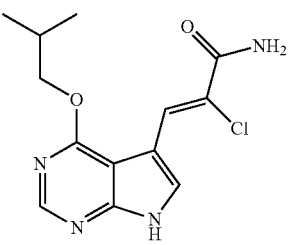 [SMILES: CC(C)COc1ncnc2[nH]cc(/C=C(\Cl)C(N)=O)c12]

N-chlorosuccinimide (30 mg, 0.22 mmol) was added to a solution of (E)-3-(4-isobutoxy-7H-pyrrolo[2,3-d]pyrimidin-5-yl)acrylamide (Example 38, 50 mg, 0.19 mmol), THF (3.0 mL) and dichloroacetic acid (0.05 mL). The mixture was stirred for 12 h at room temperature and for 3 h at 70° C. After cooling to room temperature the mixture was concentrated and purified by flash chromatography using 4% ethanol in ethyl acetate to give 19 mg of the title compound: $^1$H-NMR (400 MHz, DMSO-d$_6$) δ 12.69 (br s, 1 H), 8.42 (s, 1 H), 8.41 (s, 1 H), 8.18 (s, 1 H), 7.69 (s, 1 H), 7.53 (br s, 1 H), 4.31 (d, J=6.0 Hz, 2 H), 2.05-2.20 (m, 1 H), 1.06 (d, J=6.8 Hz, 6 H); MS 295 (M+H)

Example 197

Synthesis of 2-(4-isobutoxy-7H-pyrrolo[2,3-d]pyrimidin-5-yl)acrylonitrile

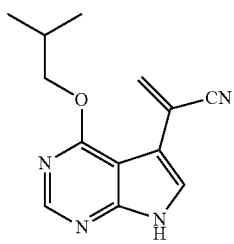 [SMILES: C=C(C#N)c1c[nH]c2ncnc(OCC(C)C)c12]

Step A: Synthesis of 1-cyano-1-(4-isobutoxy-7-tosyl-7H-pyrrolo[2,3-d]pyrimidin-5-yl)ethyl diethyl phosphate

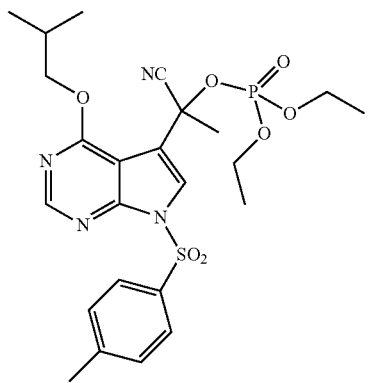 [SMILES: CCOP(=O)(OCC)OC(C)(C#N)c1cn(S(=O)(=O)c2ccc(C)cc2)c2ncnc(OCC(C)C)c12]

A solution of 1-(4-isobutoxy-7-tosyl-7H-pyrrolo[2,3-d]pyrimidin-5-yl)ethanone (Example 21, 250 mg, 0.65 mmol) in THF (4.0 mL) was added dropwise over 15 min to a solution of LDA (2 M, 0.16 mL, 0.36 mmol) in THF (2.0 mL) at −20° C. After 15 min diethylphosphonate nitrile (0.13 g, 0.80 mmol) was added directly. The solution was stirred for 2.5 h at 0° C. and was quenched by pouring onto sat ammonium chloride (10 mL). The mixture was extracted with ethyl acetate several times, the combined organics washed with water, dried (MgSO₄), filtered and concentrated. The residue was dried and used without further purification: MS (ES) m/z 551 (M+H).

Step B. Synthesis of 2-(4-isobutoxy-7-tosyl-7H-pyrrolo[2,3-d]pyrimidin-5-yl)acrylonitrile

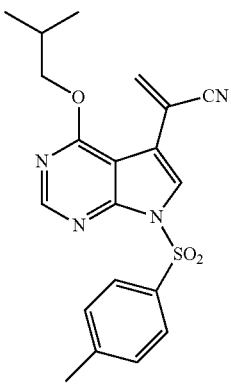 [SMILES: C=C(C#N)c1cn(S(=O)(=O)c2ccc(C)cc2)c2ncnc(OCC(C)C)c12]

Boron trifluoride etherate (0.3 mL, 2.4 mmol) was added to a solution of crude 1-cyano-1-(4-isobutoxy-7-tosyl-7H-pyrrolo[2,3-d]pyrimidin-5-yl)ethyl diethyl phosphate (0.65 mmol) in dichloromethane (4.0 mL) at 0° C. The mixture was stirred for 1 h at 0° C. and was then quenched by pouring onto 5% sodium bicarbonate. The mixture was extracted several times with dichloromethane, the combined organics washed, dried (MgSO₄), filtered and concentrated. Purification by flash chromatography using 35% ethyl acetate in heptane provided 120 mg of the desired compound: MS (ES) m/z 397 (M+H).

Step C: Synthesis of 2-(4-isobutoxy-7H-pyrrolo[2,3-d]pyrimidin-5-yl)acrylonitrile

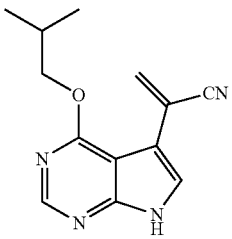

A mixture of 2-(4-isobutoxy-7-tosyl-7H-pyrrolo[2,3-d]pyrimidin-5-yl)acrylonitrile (90 mg, 23 mmol), 1.5 N lithium hydroxide (0.25 mL, 0.38 mmol) in dioxane (0.5 mL) was stirred at room temperature for 45 min. The mixture was cooled, acidified with 5% citric acid (3 mL) and extracted with several times with ethyl acetate. The organic layers were washed with water, dried (MgSO₄), filtered and concentrated. Purification by flash chromatography using 35% ethyl acetate in heptane provided 13 mg of the title compound: $^1$H-NMR (400 MHz, DMSO-d₆) δ 12.64 (br s, 1 H), 8.49 (s, 1 H), 7.73 (s, 1 H), 6.81 (s, 1 H), 6.29 (s, 1 H), 4.36 (d, J=6.4 Hz, 2 H), 2.10-2.30 (m, 1 H), 1.07 (d, J=6.8 Hz, 6 H); MS (ES) m/z 243 (M+H).

Example 198

Synthesis of 4-(4-isobutoxy-7H-pyrrolo[2,3-d]pyrimidin-5-yl)-but-2-enoic acid amide

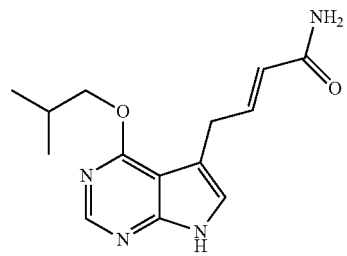 [SMILES: CC(C)COc1ncnc2[nH]cc(C/C=C/C(N)=O)c12]

Step A: Synthesis of 5-allyl-4-isobutoxy-7-(toluene-4-sulfonyl)-7H-pyrrolo[2,3-d]pyrimidine

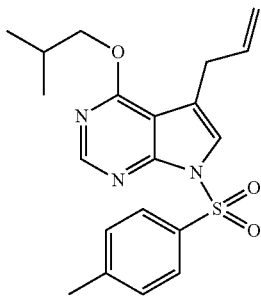 [SMILES: C=CCc1cn(S(=O)(=O)c2ccc(C)cc2)c2ncnc(OCC(C)C)c12]

To a solution of 5-iodo-4-isobutoxy-7-(toluene-4-sulfonyl)-7H-pyrrolo[2,3-d]pyrimidine (Example 35 Step A, 0.120 g, 0.25 mmol) in DMF (5.0 mL) was added the tributyl(1-allyl)stannane (0.884 g, 0.31 mmol) under a nitrogen atmosphere. The resulting mixture was degassed for 10 min, (PhCN)$_2$PdCl$_2$ (19 mg, 0.05 mmol) was added and the mixture heated at 90° C. under nitrogen (20 psi) for 16 h. The reaction mixture was allowed to cool and 5% HCl (7 mL) was added. The mixture was stirred for 30 min and then diluted with ethyl acetate and water. The mixture was filtered through celite, the organic phase collected and washed with water, dried over MgSO$_4$, filtered and concentrated. The residue was purified by flash chromatography (0-95% gradient ethyl acetate in heptane) to afford 0.028 g of the intermediate 5-allyl-4-isobutoxy-7-(toluene-4-sulfonyl)-7H-pyrrolo[2,3-d]pyrimidine: LCMS (ES) m/z 386 (M+H).

Step B: Synthesis of 4-[4-isobutoxy-7-(toluene-4-sulfonyl)-7H-pyrrolo[2,3-d]pyrimidin-5-yl]-but-2-enoic acid amide

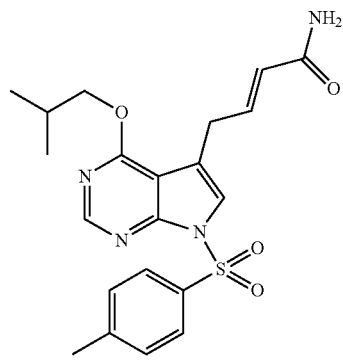 [SMILES: Cc1ccc(S(=O)(=O)n2cc(C/C=C/C(N)=O)c3c(OCC(C)C)ncnc32)cc1]

A mixture of 5-allyl-4-isobutoxy-7-(toluene-4-sulfonyl)-7H-pyrrolo[2,3-d]pyrimidine (0.040 g, 0.10 mmol), acrylamide (0.011 g, 0.156 mmol), Hoveyda-Grubbs catalyst 2$^{nd}$ generation [(1,3-Bis-(2,4,6-trimethylphenyl)-2-imidazolidinylidene)dichloro(o-isopropoxyphenylmethylene)ruthenium] (0.054 g, 0.10 mmol) in DCM (2.0 mL) was allowed to stir at room temperature for 3 h. The reaction mixture was concentrated under reduced pressure and the resulting residue was purified by flash chromatography (0-95% gradient ethyl acetate in heptane) to give 0.026 g of the intermediate 4-[4-isobutoxy-7-(toluene-4-sulfonyl)-7H-pyrrolo[2,3-d]pyrimidin-5-yl]-but-2-enoic acid amide: LC/MS (ES) m/z 429 (M+H).

Step C: Synthesis of 4-(4-isobutoxy-7H-pyrrolo[2,3-d]pyrimidin-5-yl)-but-2-enoic acid amide

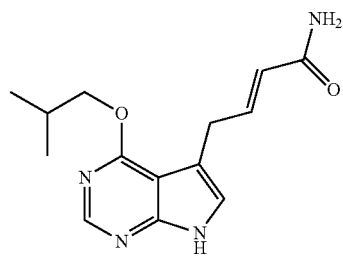 [SMILES: CC(C)COc1ncnc2[nH]cc(C/C=C/C(N)=O)c12]

A mixture of 4-[4-isobutoxy-7-(toluene-4-sulfonyl)-7H-pyrrolo[2,3-d]pyrimidin-5-yl]-but-2-enoic acid amide (0.020 mg, 0.047 mmol), 1.5 N lithium hydroxide (0.03 mL, 0.045 mmol) in dioxane (2 mL) was stirred at 55° C. for 12 h. The mixture was cooled, acidified with 5% citric acid (3 mL) and extracted with several times with ethyl acetate. The organic layers were washed with water, dried (MgSO$_4$), filtered and concentrated. Purification by reverse phase chromatography (5-95% acetonitrile in water, 0.01% TFA) to give 9 mg of 4-(4-isobutoxy-7H-pyrrolo[2,3-d]pyrimidin-5-yl)-but-2-enoic acid amide: $^1$H-NMR (400 MHz, DMSO-d$_6$) δ 12.44 (br s, 1 H), 8.43 (s, 1 H), 8.15 (s, 1 H), 7.74 (d, J=16.0 Hz, 1 H), 6.94 (m, 2 H), 6.68 (d, J=16.0 Hz, 1 H), 5.8 (m, 1 H), 5.4 (m, 1 H), 3.2 (d, J=6.0 Hz, 2 H), 1.93 (m, J=6.5 Hz, 1 H), 1.08 (d, J=6.4 Hz, 6 H); LCMS (ES) m/z 275 (M+H).

Example 198 was also isolated as a trifluoro acetate salt as a result of C$_{18}$ reverse phase chromatography. This salt can be converted into the corresponding free base form by standard extractive acid-base chemistry.

Example 199

3-[4-(4,4-difluoro-cyclohexyloxy)-7H-pyrrolo[2,3-d]pyrimidin-5-yl]-acrylamide

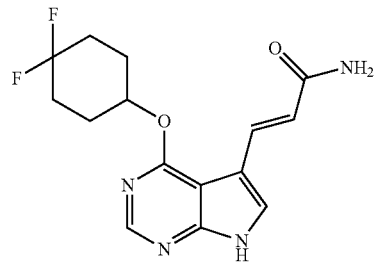 [SMILES: NC(=O)/C=C/c1c[nH]c2ncnc(OC3CCC(F)(F)CC3)c12]

Step A: Synthesis of 4-(4,4-difluoro-cyclohexyloxy)-7H-pyrrolo[2,3-d]pyrimidine-5-carbaldehyde

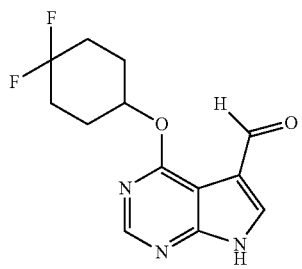 [SMILES: O=Cc1c[nH]c2ncnc(OC3CCC(F)(F)CC3)c12]

A mixture of commercially available 4-chloro-7H-pyrrolo[2,3-d]pyrimidine-5-carbaldehyde in THF (0.20 g, 1.1 mmol), 4,4-Difluoro-cyclohexanol (1 mL), potassium hydroxide (0.155 g, 2.75 mmol) and 18-crown-6 (0.005 g, 0.022 mmol) was heated at 100° C. for 4 days. After cooling to room temperature, the residue was diluted with ice water (25 mL), extracted with ethyl acetate, the organic layers washed, dried over MgSO$_4$, and concentrated. The residue was triturated with EtOH, cooled and filtered to give 0.247 g of 4-(4,4-difluoro-cyclohexyloxy)-7H-pyrrolo[2,3-d]pyrimidine-5-carbaldehyde: LCMS (ES) m/z 282 (M+H).

Step B: Synthesis of 3-[4-(4,4-difluoro-cyclohexyloxy)-7H-pyrrolo[2,3-d]pyrimidin-5-yl]-acrylamide

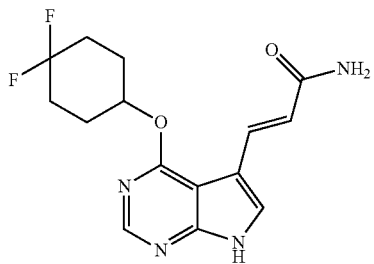 [SMILES: NC(=O)/C=C/c1c[nH]c2ncnc(OC3CCC(F)(F)CC3)c12]

A mixture of diethyl 2-amino-2-oxoethylphosphonate (0.083 g, 0.43 mmol) in DMF (2.5 mL), was added NaH (60% mineral oil dispersion, 0.015 g, 0.57 mmol) and the mixture stirred at 5° C. under nitrogen. After 15 min, a solution 4-(4,4-difluoro-cyclohexyloxy)-7H-pyrrolo[2,3-d]pyrimidine-5-carbaldehyde (Step A, 0.100 g, 0.35 mmol), in DMF (1 mL) was added dropwise. After stifling at room temperature for 12 h, the reaction was quenched by the addition of 5% citric acid (5 mL) and extracted with ethyl acetate (2×10 mL). The combined extracts were washed with brine, dried over MgSO$_4$, filtered and concentrated under reduced pressure. The resulting residue was purified by flash chromatography (0-95% gradient ethyl acetate in heptane) to afford 0.016 g of 3-[4-(4,4-difluoro-cyclohexyloxy)-7H-pyrrolo[2,3-d]pyrimidin-5-yl]-acrylamide:
$^1$H-NMR (400 MHz, DMSO-d$_6$) δ 12.44 (br s, 1 H), 8.43 (s, 1 H), 8.15 (s, 1 H), 7.92 (s, 2 H), 7.81 (d, J=16.0 Hz, 1 H), 6.34 (d, J=16.0 Hz, 1 H), 4.37 (m, 1 H), 2.61 (m, 2 H), 2.18 (m, 2 H), 1.93 (m, 2 H), 1.7 (m, 2 H); LCMS (ES) m/z 323 (M+H).

Example 199 was also isolated as a trifluoro acetate salt as a result of C$_{18}$ reverse phase chromatography. This salt can be converted into the corresponding free base form by standard extractive acid-base chemistry.

Example 200

Synthesis of (E) 2-fluoro-3-(4-isobutoxy-7H-pyrrolo[2,3-d]pyrimidin-5-yl)-acrylamide

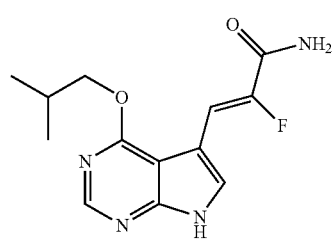 [SMILES: CC(C)COc1ncnc2[nH]cc(/C=C(\F)C(N)=O)c12]

Step A: Synthesis of 4-isobutoxy-7H-pyrrolo[2,3-d]pyrimidine-5-carbaldehyde

A mixture of commercially available 4-chloro-7H-pyrrolo[2,3-d]pyrimidine-5-carbaldehyde (0.100 g, 0.55 mmol), 2-methyl-propan-1-ol (1 mL), potassium hydroxide (0.101 g, 1.38 mmol) and 18-crown-6 (0.003 g, 0.011 mmol) was heated at 100° C. for 4 days. After cooling to room temperature, the residue was diluted with ice water (25 mL), extracted with ethyl acetate, the organic layers washed, dried over MgSO$_4$, and concentrated. The residue was triturated with EtOH, cooled and filtered to give 0.084 g of 4-isobutoxy-7H-pyrrolo[2,3-d]pyrimidine-5-carbaldehyde:
$^1$H-NMR (400 MHz, DMSO-d$_6$): δ 12.29 (s, 1 H), 10.52 (s, 1 H), 8.10 (s, 1 H), 7.73 (s, 1 H), 4.02 (d, J=6 Hz, 2 H), 2.00 (m, 1 H), 1.00 (q, J=6 Hz, 6 H); LCMS (ES) m/z 220 (M+H).

Step B: Synthesis of (E) 2-fluoro-3-(4-isobutoxy-7H-pyrrolo[2,3-d]pyrimidin-5-yl)-acrylic acid ethyl ester and (Z) 2-fluoro-3-(4-isobutoxy-7H-pyrrolo[2,3-d]pyrimidin-5-yl)-acrylic acid ethyl ester

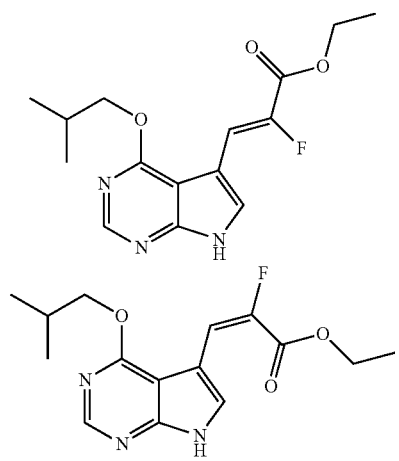

A mixture of (diethoxy-phosphoryl)-fluoro-acetic acid ethyl ester (0.050 mL, 0.25 mmol) in DMF (2.5 mL), was added NaH (60% mineral oil dispersion, 0.009 g, 0.37 mmol) and the mixture stirred at 5° C. under nitrogen. After 15 min, a solution 4-isobutoxy-7H-pyrrolo[2,3-d]pyrimidine-5-carbaldehyde (Step A, 0.050 g, 0.23 mmol), in DMF (1 mL) was added dropwise. After stifling at room temperature for 12 h, the reaction was quenched by the addition of 5% citric acid (5 mL) and extracted with ethyl acetate (2×10 mL). The combined extracts were washed with brine, dried over MgSO$_4$, filtered and concentrated under reduced pressure. The resulting residue was purified by flash chromatography (0-95% gradient ethyl acetate in heptane) to afford 0.042 g of (E) 2-fluoro-3-(4-isobutoxy-7H-pyrrolo[2,3-d]

pyrimidin-5-yl)-acrylic acid ethyl ester (0.26 g): ¹H-NMR (400 MHz, DMSO-d₆) δ 12.45 (s, 1 H), 8.38 (s, 1 H), 8.03 (s, 1 H), 7.73 (d, J=13.0 Hz, 1 H), 4.24 (q, J=6 Hz, 2 H), 4.00 (d, J=8 Hz, 2 H), 2.00 (m, 1 H), 1.29 (t, J=6.0 Hz, 3 H), 1.03 (q, J=6 Hz, 6 H); LCMS (ES) m/z 308 (M+H).

A small amount of the isomer (Z) 2-fluoro-3-(4-isobutoxy-7H-pyrrolo[2,3-d]pyrimidin-5-yl)-acrylic acid ethyl ester was also isolated (0.012 g): ¹H-NMR (400 MHz. DMSO-d₆) δ 12.45 (s, 1 H), 8.38 (s, 1 H), 8.03 (s, 1 H), 7.75 (d, J=30 Hz, 1 H), 4.24 (q, J=6 Hz, 2 H), 4.00 (d, J=8 Hz, 2 H), 2.00 (m, 1 H), 1.29 (t, J=6.0 Hz, 3 H), 1.03 (q, J=6 Hz, 6 H); LCMS (ES) m/z 308 (M+H).

Step C: Synthesis of (E) 2-fluoro-3-(4-isobutoxy-7H-pyrrolo[2,3-d]pyrimidin-5-yl)-acrylic acid

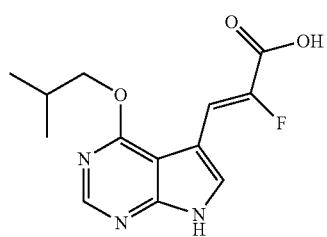 [SMILES: CC(C)COc1ncnc2[nH]cc(/C=C(\F)C(=O)O)c12]

A solution of (E) 2-fluoro-3-(4-isobutoxy-7H-pyrrolo[2,3-d]pyrimidin-5-yl)-acrylic acid ethyl ester (0.030 g, 0.098 mmol), 1.5 N LiOH (0.37 mL, 0.24 mmol) and dioxane (2 mL) was stirred at 55° C. for 4 h. The solution was allowed to cool to room temperature and then acetic acid and water were added. The resultant solid was collected, washed with water and dried to provide 0.025 g of (E) 2-fluoro-3-(4-isobutoxy-7H-pyrrolo[2,3-d]pyrimidin-5-yl)-acrylic acid: LCMS (ES) m/z 280 (M+H).

Step D: Synthesis of (E) 3-[4-(4,4-difluoro-cyclohexyloxy)-7H-pyrrolo[2,3-d]pyrimidin-5-yl]-acrylamide

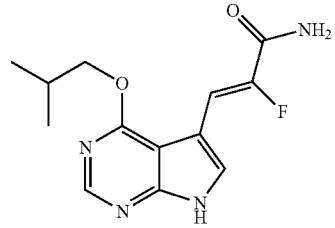 [SMILES: CC(C)COc1ncnc2[nH]cc(/C=C(\F)C(N)=O)c12]

A solution of (E) 2-fluoro-3-(4-isobutoxy-7H-pyrrolo[2,3-d]pyrimidin-5-yl)-acrylic acid and DMF (2.0 mL) was cooled to −5° C. Diisopropylethylamine (0.020 g, 0.07 mmol) and HATU (0.028 g, 0.030 mmol) were added and the mixture stirred at −5° C. for 30 min. Methanolic ammonia (7 M, 0.015 mL, 0.11 mmol) was added. The mixture was stirred at −5° C. for 30 min and 1 h at room temperature. The reaction mixture was quenched with ice water and extracted several times with ethyl acetate. The combined organic layers were washed with water, dried (MgSO₄), filtered, and concentrated. The residue was purified by reverse phase chromatography (5-95% acetonitrile in water, 0.01% TFA) and the solvent removed in vacuo to give 0.007 g of separated (E) 3-[4-(4,4-difluoro-cyclohexyloxy)-7H-pyrrolo[2,3-d]pyrimidin-5-yl]-acrylamide: ¹H-NMR (400 MHz, DMSO-d₆) δ 12.45 (s, 1 H), 8.38 (s, 1 H), 8.10 (s, 1 H), 7.73 (d, J=13.0 Hz, 1 H), 6.52 (s, 2 H), 4.00 (d, J=8 Hz, 2 H), 2.00 (m, 1 H), 1.03 (q, J=6 Hz, 6 H); LCMS (ES) m/z 279 (M+H).

The following compounds were prepared following the procedures described for Example 200 but by changing the ether substituent in combination with the procedure in Example 200 Step A and the appropriate Horner-Emmons Wittig reagent in Example 200 Step B, providing the compounds indicated below.

| Ex. # | Structure | Name | Experimental Data |
|---|---|---|---|
| 201 | 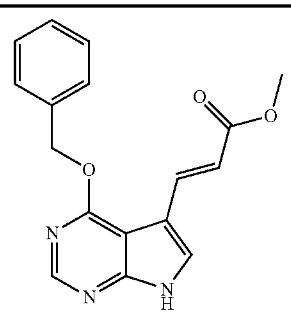 | (E)-3-(4-benzyloxy-7H-pyrrolo[2,3-d]pyrimidin-5-yl)-acrylic acid methyl ester | ¹H-NMR (400 MHz, DMSO-d₆) δ 12.51 (br s, 1 H), 8.43 (s, 1 H), 7.83 (s, 1 H), 7.74 (d, J = 16.0 Hz, 1 H), 7.45 (q, J = 13.0 Hz, 2 H), 7.35 (m, 3 H), 6.37 (d, J = 16.0 Hz, 1 H) 5.53 (s, 2 H), 3.71 (s, 3 H); LCMS (ES) 310 m/z (M + H). |
| 93 | 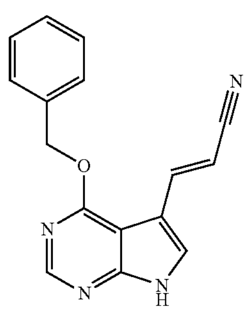 [SMILES: N#C/C=C/c1c[nH]c2ncnc(OCc3ccccc3)c12] | (E)-3-(4-benzyloxy-7H-pyrrolo[2,3-d]pyrimidin-5-yl)-acrylonitrile | ¹H-NMR (400 MHz, DMSO-d₆) δ 12.51 (br s, 1 H), 8.43 (s, 1 H), 7.83 (s, 1 H), 7.74 (d, J = 16.0 Hz, 1 H), 7.45 (q, J = 13.0 Hz, 2 H), 7.35 (m, 3 H), 6.37 (d, J = 16.0 Hz, 1 H) 5.53 (s, 2 H); LCMS (ES) 278 m/z (M + H). |

| Ex. # | Structure | Name | Experimental Data |
|---|---|---|---|
| 96 | 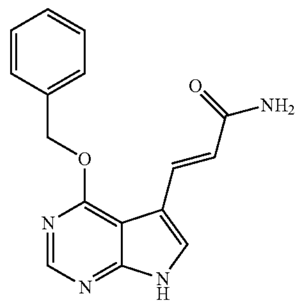 [SMILES: NC(=O)/C=C/c1c[nH]c2ncnc(OCc3ccccc3)c12] | (E)-3-(4-benzyloxy-7H-pyrrolo[2,3-d]pyrimidin-5-yl)-acrylamide | $^1$H-NMR (400 MHz, DMSO-d$_6$) δ 12.51 (br s, 1 H), 8.43 (s, 1 H), 7.83 (s, 1 H), 7.74 (d, J = 16.0 Hz, 1 H), 7.45 (q, J = 13.0 Hz, 2 H), 7.35 (m, 3 H), 6.83 (br, 2 H), 6.37 (d, J = 16.0 Hz, 1 H), 5.53 (s, 2 H); LCMS (ES) 295 m/z (M + H). |

TABLE 9

Additional Suitable Protecting Groups

Acetyl (Ac)
Acylals
Benzoyl (Bz)
Benzyl (Bn, Bnl)
Benzyloxy carbonyl
Carbamate
Carbobenzyloxy (Cbz)
Dimethoxytrityl, [bis-(4-methoxyphenyl)phenylmethyl] (DMT)
Dithianes
Ethoxyethyl (EE)
Methoxymethyl (MOM)
Methoxytrityl [(4-methoxyphenyl)diphenylmethyl], (MMT)
Methoxy
Methyl (Me)
Methyloxy carbonyl
Methylthiomethoxy
trialkoxymethyl
Oxazoline
Pivaloyl (Piv)
Phthalimido
p-Methoxybenzyl carbonyl (Moz or MeOZ)
p-methoxyphenyl (PMP)
Silyl groups (e.g., trimethylsilyl (TMS), tert-butyldimethylsilyl (TBDMS), tri-iso-propylsilyloxymethyl (TOM) and triisopropylsilyl (TIPS))
Silyloxy carbonyl
tert-butoxy carbonyl
tert-Butyloxycarbonyl (BOC or tBOC)
Tetrahydropyranyl (THP)
Tosyl (Ts or Tos)
Trimethylsilylethoxymethyl (SEM)
Trityl (triphenylmethyl, Tr)
β-Methoxyethoxymethyl (MEM)
(4-nitrophenyl)sulfonyl or (4-nitrophenyl)(dioxido)-lambda(6)-sulfanyl) (Nosyl)
2-cyanoethyl
2-nitrophenylsulfenyl (Nps)
3,4-Dimethoxybenzyl (DMPM)
9-Fluorenylmethyloxycarbonyl (FMOC)

D. Method of Treatment

A compound of Formula (I), as used herein, is meant to include a pharmaceutically acceptable salt, or solvate of a compound or salt, of Formula (I).

The present disclosure further provides methods for treating a condition in a subject having or susceptible to having such a condition, by administering to the subject a therapeutically-effective amount of one or more compounds as described above. In one embodiment, the treatment is preventative treatment. In another embodiment, the treatment is palliative treatment. In another embodiment, the treatment is restorative treatment.

1. Conditions

The conditions that can be treated in accordance with the present invention include, but are not limited to, autoimmune disorders, chronic inflammatory disorders, acute inflammatory disorders, auto-inflammatory disorders, pain, cancer, neoplasia, pancreatic cancer, breast cancer, lung cancer, colorectal cancer, inflammatory disorders, allergic disorders, autoimmune disorders and the like.

In some embodiments, methods described herein are used to treat a disease condition comprising administering to a subject in need thereof a therapeutically effective amount of a compound of Formula (I) or pharmaceutically acceptable salt thereof, wherein the condition is independently selected from pancreatic cancer, non-Hodgkin's lymphoma, chronic lymphocytic leukemia, multiple myeloma, T-cell leukemia and tumors of the head and neck, breast, colon, prostate, lung, skin, liver and ovary.

In some embodiments, methods described herein are used to treat a disease condition comprising administering to a subject in need thereof a therapeutically effective amount of a compound of Formula (I) or pharmaceutically acceptable salt thereof, wherein the condition is pancreatic cancer.

In some embodiments, methods described herein are used to treat a disease condition comprising administering to a subject in need thereof a therapeutically effective amount of a compound of Formula (I) or pharmaceutically acceptable salt thereof, wherein the condition is cancer which has developed resistance to chemotherapeutic drugs and/or ionizing radiation.

In some embodiments the methods described herein are used to treat patients with disorders arising from a dysregulated TAK1 molecule or dysregulated activation of TAK1 or related signaling transduction molecules. Examples of TAK1 signaling molecules include TAB1, TAB2, IRAK1, IRAK4, TRAF-6 and IL-6.

In some embodiments the methods described herein are used to treat patients with disorders arising from activation of p38, JNK or NF-κB signaling pathways.

In some embodiments, the methods described herein are used to treat a patient in need thereof suffering from inflammatory disorders, allergic disorders, autoinflammatory disorders and autoimmune disorders. Examples of disorders include, but are not limited to rheumatoid arthritis, juvenile idiopathic arthritis, psoriatic arthritis, psoriasis, type 2 diabetes, Behcet's disease, chronic gout, cryopyrin associated periodic syndromes, familial Mediterranean fever, neonatal onset multisystem inflammatory disease, ankylosing spondylitis, contact hypersensitivity, chronic obstructive pulmonary disorder, multiple sclerosis and inflammatory bowel disease.

In some embodiments, the methods described herein can be used to treat a patient in need thereof and suffering from neoplasia. Examples of these conditions include but are not limited to the following:

acral lentiginous melanoma
actinic keratoses
adenocarcinoma
adenoid cyestic carcinoma
adenomas
adenosarcoma
adenosquamous carcinoma
astrocytic tumors
bartholin gland carcinoma
basal cell carcinoma
bronchial gland carcinomas
capillary
carcinoids
carcinoma
carcinosarcoma
cavernous
cholangiocarcinoma
chondosarcoma
choroid plexus papilloma/carcinoma
clear cell carcinoma
cystadenoma
endodermal sinus tumor
endometrial hyperplasia
endometrial stromal sarcoma
endometrioid adenocarcinoma
ependymal
epitheloid
Ewing's sarcoma
familial adenomatous polyposis (FAP)
fibrolamellar carcinoma
focal nodular hyperplasia
gastrinoma
germ cell tumors
glioblastoma
glucagonoma
hemangiblastomas
hemangioendothelioma
hemangiomas
hepatic adenoma
hepatic adenomatosis
hepatocellular carcinoma
insulinoma
intaepithelial neoplasia
interepithelial squamous cell neoplasia
invasive squamous cell carcinoma
large cell carcinoma
leiomyosarcoma
lentigo maligna melanomas
malignant melanoma
malignant mesothelial tumors
medulloblastoma
medulloepithelioma
melanoma
meningeal
mesothelial
metastatic carcinoma
mucoepidermoid carcinoma
neuroblastoma
neuroepithelial
adenocarcinoma
nodular melanoma
oat cell carcinoma
oligodendroglial
osteosarcoma
pancreatic cancer
papillary serous adenocarcinoma
pineal cell
pituitary tumors
plasmacytoma
pseudosarcoma
pulmonary blastoma -continued renal cell carcinoma
retinoblastoma
rhabdomyosarcoma
sarcoma
serous carcinoma
small cell carcinoma
soft tissue carcinomas
somatostatin-secreting tumor
squamous carcinoma
squamous cell carcinoma
submesothelial
superficial spreading melanoma
undifferentiatied carcinoma
uveal melanoma
verrucous carcinoma
vipoma
well differentiated carcinoma
Wilm's tumor The term patient refers to both humans and nonhuman animals with the abovementioned conditions. Nonhuman animals could be companion animals such as, but not limited to, canine and feline species.

2. Subjects

Suitable subjects to be treated according to the present invention include mammalian subjects. Mammals according to the present invention include, but are not limited to, human, canine, feline, bovine, caprine, equine, ovine, porcine, rodents, lagomorphs, primates, and the like, and encompass mammals in utero. Subjects may be of either gender and at any stage of development.

3. Administration and Dosing

The compounds of the present invention are generally administered in a therapeutically effective amount.

The compounds of the present invention can be administered by any suitable route in the form of a pharmaceutical composition adapted to such a route, and in a dose effective for the treatment intended. Therapeutically effective doses of the compounds of the present invention required to prevent or arrest the progress of, or to treat the medical condition, are readily ascertained by one of ordinary skill in the art using preclinical and clinical approaches familiar to the medicinal arts.

For convenience the compounds of the present invention can be administered in a unit dosage form. If desired, multiple doses per day of the unit dosage form can be used to increase the total daily dose. The unit dosage form, for example, may be a tablet or capsule containing about 0.01, 0.05, 0.1, 0.5, 1, 5, 10, 15, 20, 25, 30, 35, 40, 45, 50, 55, 60, 65, 70, 75, 80, 85, 90, 95, 100, 125, 150, 175, 200, 250 or 500 mg of the compound of the present invention. In one embodiment, the unit dosage form contains from about 0.01 mg to about 500 mg of the compound of the present invention. In another embodiment, the unit dosage form contains from about 0.02 to about 400 mg of the compound of the present invention. In another embodiment, the unit dosage form contains from about 0.05 mg to about 250 mg of the compound of the present invention. In another embodiment, the unit dosage form contains from about 0.1 mg to about 200 mg of the compound of the present invention. In another embodiment, the unit dosage form contains from about 0.5 mg to about 150 mg of the compound of the present invention. In another embodiment, the unit dosage form contains from about 1.0 mg to about 100 mg of the compound of the present invention.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary based on the specific situation. Dosage levels from about 0.001 mg to about 100 mg of the compound of the present invention per kilogram of body weight per day are useful in the treatment of the above-indicated conditions. In one embodiment, the total daily dose of the compound of the present invention (administered in single or divided doses) is typically from about 0.001 mg/kg to about 20 mg/kg (i.e., mg compound/kg body weight). In another embodiment, the total daily dose of the compound of the present invention is from about 0.005 mg/kg to about 10 mg/kg. In another embodiment, the total daily dose is from about 0.005 mg/kg to about 5 mg/kg. In another embodiment, the total daily dose is from about 0.01 mg/kg to about 1 mg/kg. In another embodiment, the total daily dose is from about 0.8 mg/kg to about 15 mg/kg. In another embodiment, the total daily dose is from about 0.2 mg/kg to about 4 mg/kg. These dosages are based on an average human subject having a weight of about 65 kg to about 75 kg. A physician will readily be able to determine doses for subjects whose weight falls outside of this range, such as infants. The administration of the compound of the present invention can be repeated a plurality of times in a day (typically no greater than 4 times) to achieve the desired daily dose.

The present invention further comprises use of a compound of the present invention as a medicament (such as a unit dosage tablet or unit dosage capsule).

In another embodiment, the present invention comprises the use of a compound of the present invention for the manufacture of a medicament (such as a unit dosage tablet or unit dosage capsule) to treat one or more of the conditions previously identified in the above sections discussing methods of treatment. In one embodiment, the condition is cancer. In another embodiment the condition is an inflammatory condition.

E. Pharmaceutical Compositions

For treatment of the conditions referred to above, the compounds described herein can be administered as follows:

1. Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, or powders.

In a tablet dosage form the amount of drug present may be from about 0.05% to about 95% by weight, more typically from about 2% to about 50% by weight of the dosage form.

In addition, tablets may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet, may be present in amounts from about 0.1% to about 3% by weight, and include polysorbate 80, sodium dodecyl sulfate, talc and silicon dioxide.

Suitable lubricants, for use in a tablet, may be present in amounts from about 0.1% to about 5% by weight, and include calcium, zinc or magnesium stearate, sodium stearyl fumarate and the like.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

2. Parenteral Administration

Compounds of the present invention may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release.

3. Topical Administration

Compounds of the present invention may be administered topically to the skin or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Compositions for topical administration may be formulated as immediate or modified release, including delayed or sustained release.

4. Rectal Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

F. Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-cancer drugs, anti-proliferative drugs, and anti-inflammatory drugs.

TAK1 inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a TAK1 inhibitor compound, as described herein, in combination with another therapeutic agent. By way of example only, the therapeutic effectiveness of a TAK1 inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a TAK1 inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a TAK1 inhibitor is optionally used in combination with procedures that provide additional benefit to the patient. A TAK1 inhibitor and any additional therapies are optionally administered before, during or after the occurrence of a disease or condition, and the timing of administering the composition containing a TAK1 inhibitor varies in some embodiments. Thus, for example, a TAK1 inhibitor is used as a prophylactic and is administered continuously to subjects with a propensity to develop conditions or diseases in order to prevent the occurrence of the disease or condition. A TAK1 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A TAK1 inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a TAK1 inhibitor may be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) antimetabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

Where a subject is suffering from or at risk of suffering from an inflammatory condition, a TAK1 inhibitor compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) non-steroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

G. Kits

The present invention further comprises kits that are suitable for use in performing the methods of treatment or prevention described above. In one embodiment, the kit contains a first dosage form comprising one or more of the compounds of the present invention and a container for the dosage, in quantities sufficient to carry out the methods of the present invention. In another embodiment, the kit contains a TAK1 inhibitor compound in lyophilized form and a suitable diluent, provided as separated components for combination prior to use. In another embodiment, the kit contains a TAK1 inhibitor compound and one or more additional therapeutic agent(s) for co-administration, either simultaneously or sequentially. The TAK1 inhibitor and additional therapeutic agent(s) may be provided as a single mixed dosage or individually in separate containers, which containers may be associated in a single packaged presentation. The materials in the containers may be prepared as suitable for the type of administration. For example, capsules or tablets for oral administration, vials or pre-filled syringes for parenteral administration, and creams or patches for topical administration.

H. Biological Assays

TAK1, a key downstream effector of TGF-β, has been implicated in transformation and metastasis of cancer cells as well as in the development of resistance to chemotherapeutic drugs and ionizing radiation. Mitogen-activated protein kinase kinase kinase 7-interacting protein 1 (TAB1) is a TAK1 signaling molecule.

TAK1-TAB1 Binding Inhibitory Potency: The ability of candidate compounds to interact with TAK1-TAB1 is quantitated by a competitive binding assay using the LanthaScreen technology developed by Life Technologies. This assay is based on the binding of a proprietary, Alexa Fluor® 647-labeled, ATP-competitive kinase inhibitor (kinase tracer-236) to the TAK1-TAB1 construct in presence of a europium-conjugated antibody, resulting in a FRET (fluorescence resonance energy transfer) signal. Displacement of the kinase tracer by compound results in a lower emission ratio upon excitation of the europium chelate. Candidate compounds are designed as potential irreversible inhibitors of TAK1-TAB1, capable of ligating to an active site cysteine residue. The time dependent nature of irreversible inhibition is investigated by performing the binding assay with and without a pre-incubation of compound and TAK1-TAB1. An increase in potency in the pre-incubated assay suggests the candidate compound could be irreversibly modifying TAK-TAB or having a slowly reversible mechanism.

The inhibitory potency of candidate compounds is measured in 20 mM HEPES pH 7.5, 10 mM $MgCl_2$, 0.01% BSA, 0.0005% Tween-20, and 2% DMSO in the presence of 10 nM TAK1-TAB1, 2 nM Eu-anti-his antibody, and 100 nM kinase tracer-236 using a 384-well plate format. Background signal is defined in the absence of TAK1-TAB1 and uninhibited signal is defined in the presence of vehicle (2% DMSO) alone. Compounds were evaluated in an 11 point dose-response ranging from 20 μM to 0.34 nM. The binding assays are performed under two conditions to evaluate time dependence of inhibition. For the pre-incubation assay, TAK1-TAB1 and Eu-anti-his antibody are preincubated with compound or vehicle for two hours prior to the addition of kinase tracer. The non-preincubated assay is run in which TAK1-TAB1 and Eu-anti-his antibody are added to a mixture of compound and kinase tracer. $IC_{50}$ values of compounds are determined using a 4 parameter logistical fit of emission ratio as a function of the concentration of compound.

Compounds were tested in accordance with the above described assay, without pre-incubation, yielding the values described below:

| Ex. # | Structure | TAK1-TAB1 Inhibition IC$_{50}$ (µM) |
|---|---|---|
| 1 | 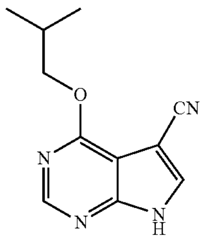 [SMILES: CC(C)COc1ncnc2[nH]cc(C#N)c12] | 0.56 |
| 21 | 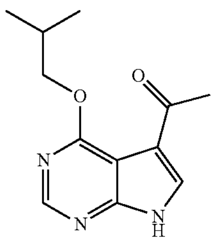 [SMILES: CC(=O)c1c[nH]c2ncnc(OCC(C)C)c12] | 1.7 |
| 23 | 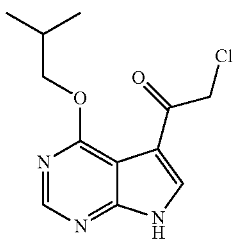 [SMILES: CC(C)COc1ncnc2[nH]cc(C(=O)CCl)c12] | 0.28 |
| 35 | 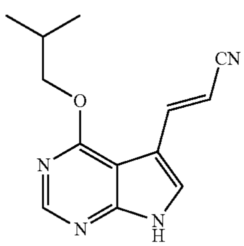 [SMILES: CC(C)COc1ncnc2[nH]cc(/C=C/C#N)c12] | 0.21 |
| 36 | 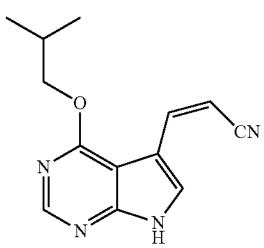 [SMILES: CC(C)COc1ncnc2[nH]cc(/C=C\C#N)c12] | 0.17 |
| 37 | 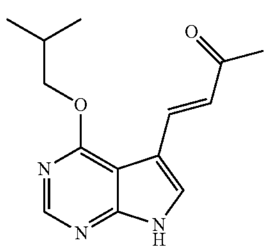 [SMILES: CC(=O)/C=C/c1c[nH]c2ncnc(OCC(C)C)c12] | 0.10 |
| 38 | | 0.0031 |
| 39 | | 0.041 |
| 93 | | 0.33 |
| 96 | | 0.73 |
| 175 | | 0.20 |

275
-continued

| Ex. # | Structure | TAK1-TAB1 Inhibition IC$_{50}$ (μM) |
|---|---|---|
| 176 | 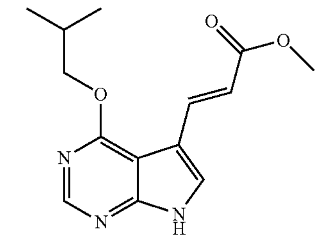 [SMILES: COC(=O)/C=C/c1c[nH]c2ncnc(OCC(C)C)c12] | 0.20 |
| 177 | 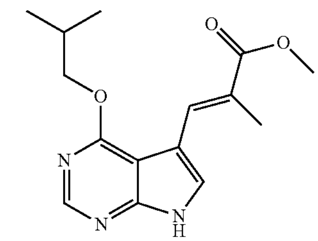 [SMILES: COC(=O)/C(C)=C/c1c[nH]c2ncnc(OCC(C)C)c12] | 0.43 |
| 178 | 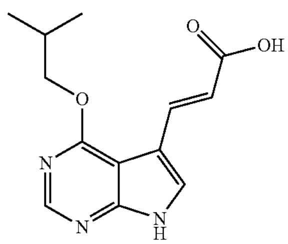 [SMILES: CC(C)COc1ncnc2[nH]cc(/C=C/C(=O)O)c12] | 0.34 |
| 179 | 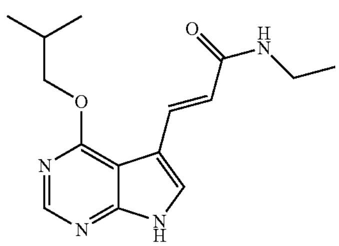 [SMILES: CCNC(=O)/C=C/c1c[nH]c2ncnc(OCC(C)C)c12] | 0.34 |
| 180 | 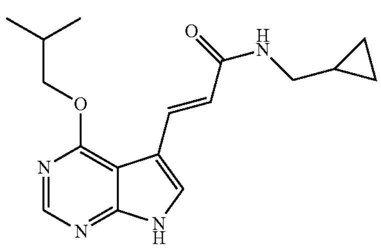 [SMILES: CC(C)COc1ncnc2[nH]cc(/C=C/C(=O)NCC3CC3)c12] | 0.38 |
| 181 | 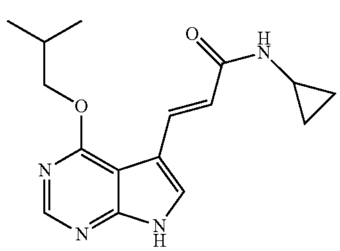 [SMILES: CC(C)COc1ncnc2[nH]cc(/C=C/C(=O)NC3CC3)c12] | 0.18 |

276
-continued

| Ex. # | Structure | TAK1-TAB1 Inhibition IC$_{50}$ (μM) |
|---|---|---|
| 182 | 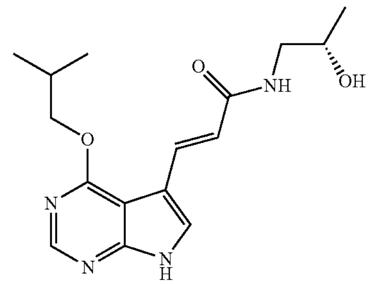 [SMILES: CC(C)COc1ncnc2[nH]cc(/C=C/C(=O)NC[C@H](C)O)c12] | 1.6 |
| 183 | 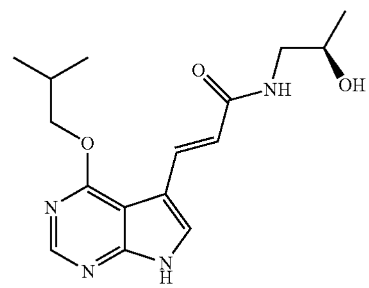 [SMILES: CC(C)COc1ncnc2[nH]cc(/C=C/C(=O)NC[C@@H](C)O)c12] | 2.5 |
| 184 | 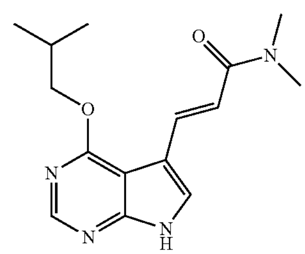 [SMILES: CC(C)COc1ncnc2[nH]cc(/C=C/C(=O)N(C)C)c12] | 0.097 |
| 185 | 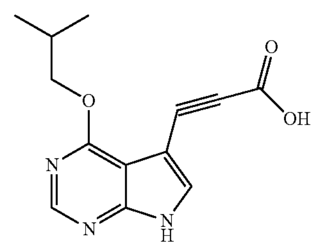 [SMILES: CC(C)COc1ncnc2[nH]cc(C#CC(=O)O)c12] | |
| 186 | 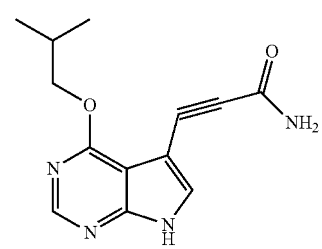 [SMILES: CC(C)COc1ncnc2[nH]cc(C#CC(N)=O)c12] | 0.007 |
| 187 | 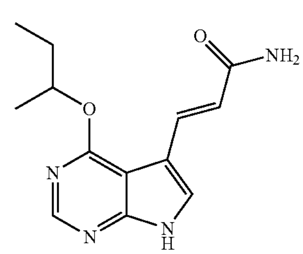 [SMILES: CCC(C)Oc1ncnc2[nH]cc(/C=C/C(N)=O)c12] | 0.0043 |

-continued

| Ex. # | Structure | TAK1-TAB1 Inhibition IC$_{50}$ (μM) |
|---|---|---|
| 188 | (isopropoxy pyrrolopyrimidine acrylamide) | 0.0044 |
| 189 | (n-propoxy pyrrolopyrimidine acrylamide) | 0.019 |
| 190 | (phenoxy pyrrolopyrimidine acrylamide) | 0.17 |
| 191 | (2,2,2-trifluoroethoxy pyrrolopyrimidine acrylamide) | 0.033 |
| 192 | (neopentyloxy pyrrolopyrimidine acrylamide) | 0.0052 |
| 193 | (2-hydroxy-2-methylpropoxy pyrrolopyrimidine acrylamide) | 0.075 |

-continued

| Ex. # | Structure | TAK1-TAB1 Inhibition IC$_{50}$ (μM) |
|---|---|---|
| 194 | (3-fluorobenzyloxy pyrrolopyrimidine acrylamide) | 0.051 |
| 195 | (tert-butoxy pyrrolopyrimidine acrylamide) | 0.013 |
| 196 | (isobutoxy pyrrolopyrimidine α-chloroacrylamide) | 0.36 |
| 197 | (isobutoxy pyrrolopyrimidine acrylonitrile) | 0.75 |
| 198 | (isobutoxy pyrrolopyrimidine butenamide) | 0.42 |
| 199 | (4,4-difluorocyclohexyloxy pyrrolopyrimidine acrylamide) | 0.016 |

-continued

| Ex. # | Structure | TAK1-TAB1 Inhibition IC$_{50}$ (μM) |
|---|---|---|
| 200 | 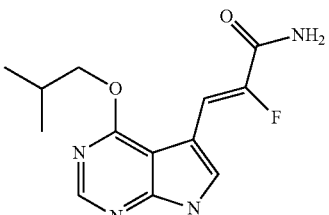 | 0.86 |
| 201 | 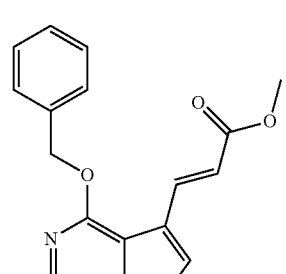 | 0.35 |

TAK1 is also a key mediator of pro-inflammatory and stress signals. Cellular activation of TAK1 activity is promoted by pro-inflammatory cytokines such as tumor necrosis factor-α (TNF-α) and interleukin-1β (IL-1β) as well as by the engagement of T cell, B cell and toll-like receptors.

IL-1β stimulated IL-6 Production in A549 cells: The cellular efficacy of compound candidates is determined using the human lung epithelial cell line A549 (ATCC #CCL-185), based upon the methods of Wheeler et al. (2004) J. Nutrition 134, 1039-1044, and Eda et al. (2011) Cell Biol. Int. 35, 355-358. A549 cells produce a number of cytokines (IL6, IL8 and TNFα) in response to stimulation with IL1β. To induce the production of inflammatory mediators, A549 cells are plated at a final concentration of $3\times10^5$ cells/well of a 96 well flat bottom plate in F12-K medium supplemented with 10% fetal bovine serum, 100 units/ml penicillin and 100 μg/ml streptomycin (Gibco BRL Life Technologies). Cells are treated with or without inhibitors for 3 hrs then stimulated with 1 ng/ml rhIL1β (R & D Systems) for an additional 18 hrs at 37° C. with 5% CO$_2$. The supernatants are removed and stored at −20° C. until they are to be assayed. The levels of inflammatory mediators are determined using commercial MSD cytokine kits (Meso Scale Discovery) as per the manufacturer's instructions. Standard curves are based on 7 steps of 4× serial dilutions, with a wide dynamic range of 10000 pg/ml to 2.4 pg/ml, and the blank in triplicate. Lower limit of detection (LLOD) is calculated at the commonly used 3× the standard deviation of the blank.

Compounds were tested in accordance with the above described assay, yielding the values described below:

| Ex. # | Structure | IL-6 Production % Control 50 μM | IL-6 Production % Control 5 μM | IL-6 Production IC (μM) |
|---|---|---|---|---|
| 1 | 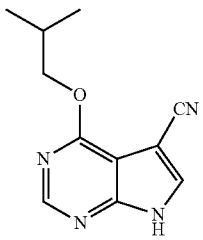 [SMILES: CC(C)COc1ncnc2[nH]cc(C#N)c12] | 6 | 83 | |
| 21 | 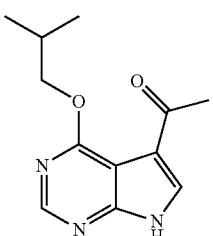 | | | |
| 23 | 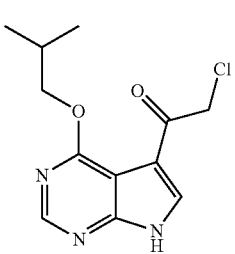 [SMILES: CC(C)COc1ncnc2[nH]cc(C(=O)CCl)c12] | 0 | 117 | 12 |

-continued

| Ex. # | Structure | IL-6 Production % Control 50 μM | IL-6 Production % Control 5 μM | IL-6 Production IC (μM) |
|---|---|---|---|---|
| 35 | 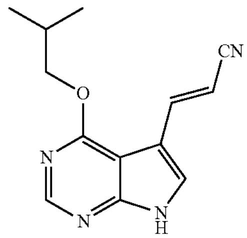 [SMILES: CC(C)COc1ncnc2[nH]cc(/C=C/C#N)c12] | | | |
| 36 | 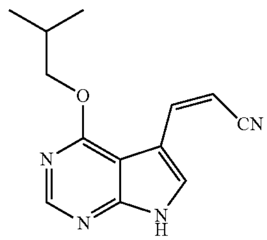 [SMILES: CC(C)COc1ncnc2[nH]cc(/C=C\C#N)c12] | | | |
| 37 | 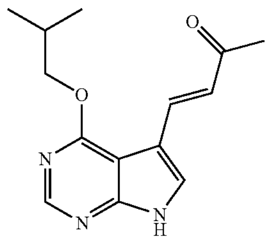 [SMILES: CC(=O)/C=C/c1c[nH]c2ncnc(OCC(C)C)c12] | | | |
| 38 | 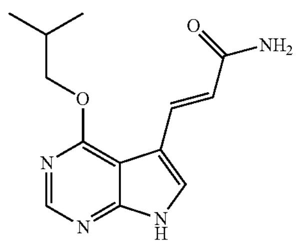 [SMILES: CC(C)COc1ncnc2[nH]cc(/C=C/C(N)=O)c12] | 0 | 0 | 0.085 |
| 39 | 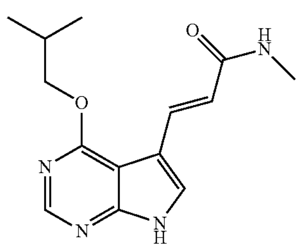 [SMILES: CNC(=O)/C=C/c1c[nH]c2ncnc(OCC(C)C)c12] | 0 | 0 | 0.043 |
| 93 | 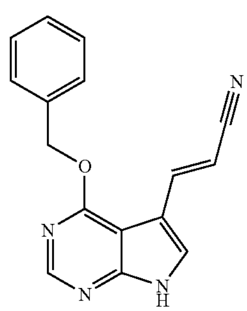 [SMILES: N#C/C=C/c1c[nH]c2ncnc(OCc3ccccc3)c12] | 15 | 21 | 2.2 |

-continued

| Ex. # | Structure | IL-6 Production % Control 50 μM | IL-6 Production % Control 5 μM | IL-6 Production IC (μM) |
|---|---|---|---|---|
| 96 | 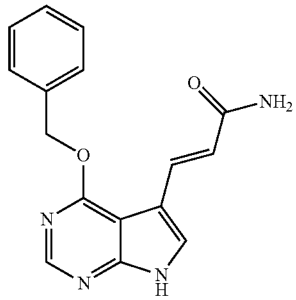 [SMILES: NC(=O)/C=C/c1c[nH]c2ncnc(OCc3ccccc3)c12] | 0 | 78 | |
| 175 | 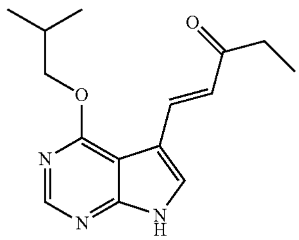 [SMILES: CCC(=O)/C=C/c1c[nH]c2ncnc(OCC(C)C)c12] | 0 | 3 | 0.99 |
| 176 | 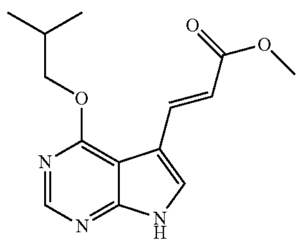 [SMILES: COC(=O)/C=C/c1c[nH]c2ncnc(OCC(C)C)c12] | 0 | 1 | |
| 177 | 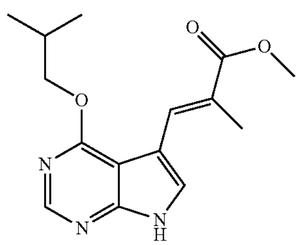 [SMILES: COC(=O)/C(C)=C/c1c[nH]c2ncnc(OCC(C)C)c12] | 0 | 0 | 0.62 |
| 178 | 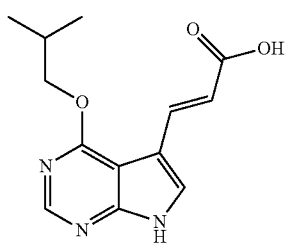 [SMILES: CC(C)COc1ncnc2[nH]cc(/C=C/C(=O)O)c12] | 1 | 68 | |
| 179 | 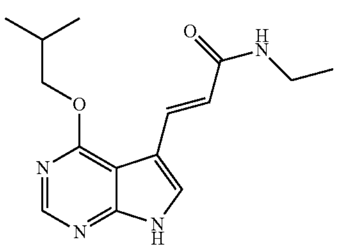 [SMILES: CCNC(=O)/C=C/c1c[nH]c2ncnc(OCC(C)C)c12] | 0 | 0 | 0.087 |

-continued

| Ex. # | Structure | IL-6 Production % Control 50 μM | IL-6 Production % Control 5 μM | IL-6 Production IC (μM) |
| --- | --- | --- | --- | --- |
| 180 | 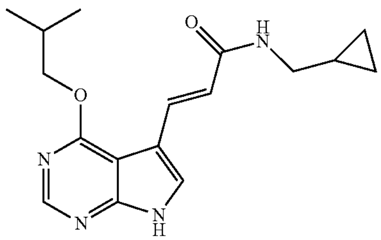 [SMILES: CC(C)COc1ncnc2[nH]cc(/C=C/C(=O)NCC3CC3)c12] | 0 | 2 | 0.63 |
| 181 | 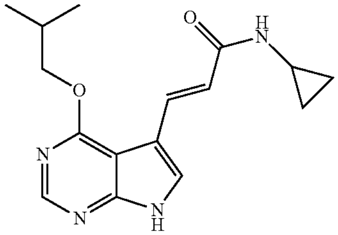 [SMILES: CC(C)COc1ncnc2[nH]cc(/C=C/C(=O)NC3CC3)c12] | 0 | 1 | 0.18 |
| 182 | 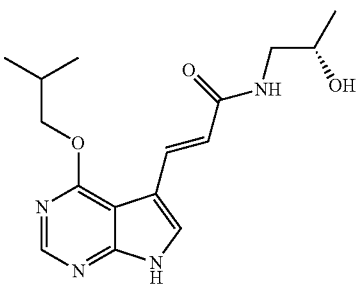 [SMILES: CC(C)COc1ncnc2[nH]cc(/C=C/C(=O)NC[C@H](C)O)c12] | 1 | 36 | 3.4 |
| 183 | 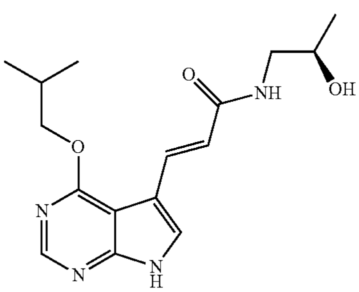 [SMILES: CC(C)COc1ncnc2[nH]cc(/C=C/C(=O)NC[C@@H](C)O)c12] | 1 | 78 | 12 |
| 184 | 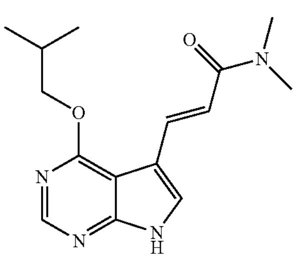 [SMILES: CC(C)COc1ncnc2[nH]cc(/C=C/C(=O)N(C)C)c12] | 0 | 1 | 0.19 |
| 185 | 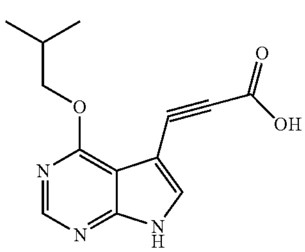 [SMILES: CC(C)COc1ncnc2[nH]cc(C#CC(=O)O)c12] | | | |

-continued

| Ex. # | Structure | IL-6 Production % Control 50 μM | IL-6 Production % Control 5 μM | IL-6 Production IC (μM) |
|---|---|---|---|---|
| 186 | 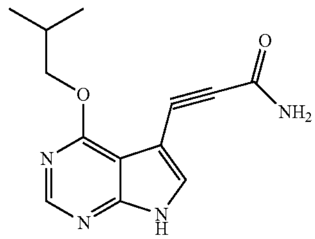 [SMILES: CC(C)COc1ncnc2[nH]cc(C#CC(N)=O)c12] | 0 | 1 | 0.85 |
| 187 | 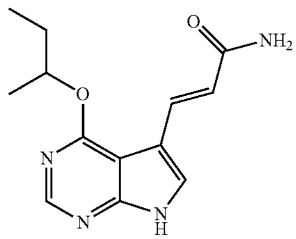 [SMILES: CCC(C)Oc1ncnc2[nH]cc(/C=C/C(N)=O)c12] | 0 | 0 | 0.19 |
| 188 | 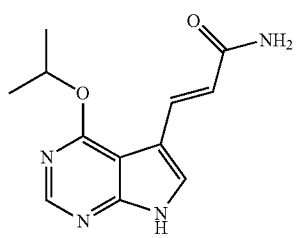 [SMILES: CC(C)Oc1ncnc2[nH]cc(/C=C/C(N)=O)c12] | 0 | 0 | 0.17 |
| 189 | 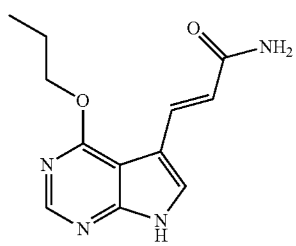 [SMILES: CCCOc1ncnc2[nH]cc(/C=C/C(N)=O)c12] | 0 | 0 | 0.18 |
| 190 | 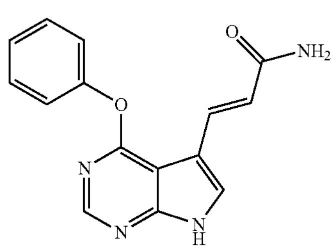 [SMILES: NC(=O)/C=C/c1c[nH]c2ncnc(Oc3ccccc3)c12] | 0 | 15 | 1.0 |
| 191 | 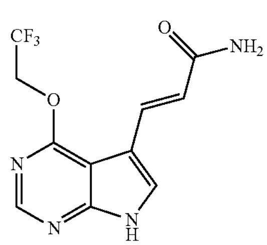 [SMILES: NC(=O)/C=C/c1c[nH]c2ncnc(OCC(F)(F)F)c12] | 0 | 0 | 0.15 |

-continued

| Ex. # | Structure | IL-6 Production % Control 50 μM | IL-6 Production % Control 5 μM | IL-6 Production IC (μM) |
|---|---|---|---|---|
| 192 | 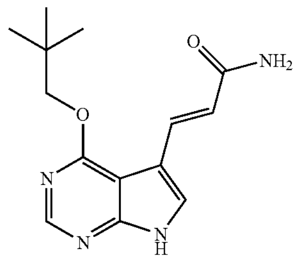 [SMILES: CC(C)(C)COc1ncnc2[nH]cc(/C=C/C(N)=O)c12] | 0 | 0 | 0.078 |
| 193 | 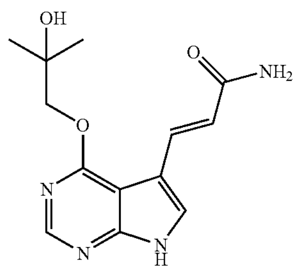 [SMILES: CC(C)(O)COc1ncnc2[nH]cc(/C=C/C(N)=O)c12] | 0 | 22 | 1.2 |
| 194 | 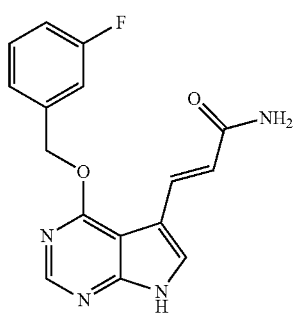 [SMILES: NC(=O)/C=C/c1c[nH]c2ncnc(OCc3cccc(F)c3)c12] | 1 | 1 | 0.043 |
| 195 | 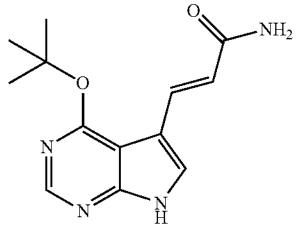 [SMILES: CC(C)(C)Oc1ncnc2[nH]cc(/C=C/C(N)=O)c12] | 1 | 19 | 0.92 |
| 196 | 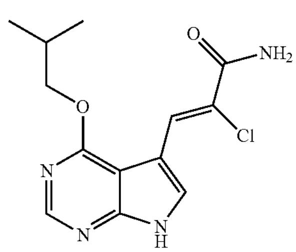 [SMILES: CC(C)COc1ncnc2[nH]cc(/C=C(\Cl)C(N)=O)c12] | 0 | 0 | 0.75 |

| Ex. # | Structure | IL-6 Production % Control 50 µM | IL-6 Production % Control 5 µM | IL-6 Production IC (µM) |
|---|---|---|---|---|
| 197 | 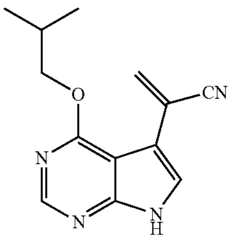 [SMILES: C=C(C#N)c1c[nH]c2ncnc(OCC(C)C)c12] | 75 | 128 | |
| 198 | 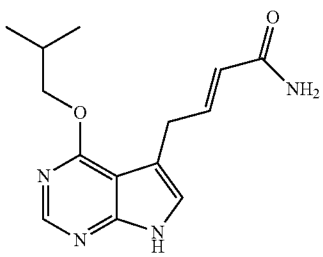 [SMILES: CC(C)COc1ncnc2[nH]cc(C/C=C/C(N)=O)c12] | 0 | 4 | 8.4 |
| 199 | 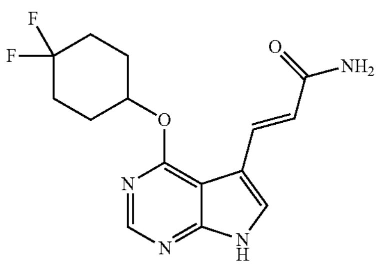 [SMILES: NC(=O)/C=C/c1c[nH]c2ncnc(OC3CCC(F)(F)CC3)c12] | 0 | 0 | 0.18 |
| 200 | 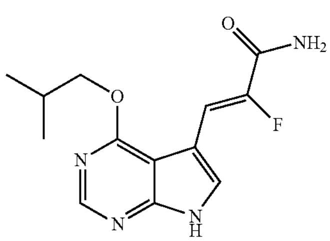 [SMILES: CC(C)COc1ncnc2[nH]cc(/C=C(\F)C(N)=O)c12] | 14 | 61 | |
| 201 | 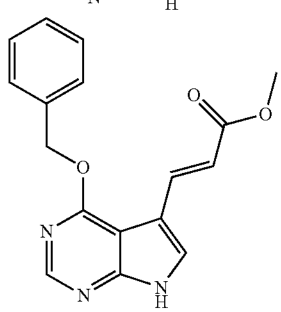 | 1 | 26 | 0.80 |

The following are additional assays used to evaluate the biological efficacy of compounds of Formula (I).

IL-1β stimulated TAK phosphorylation in A549 cells: To induce the phosphorylation of TAK, A549 cells are plated at a final concentration of $1.5 \times 10^6$ cells/well in a 24 well plate in F12-K medium supplemented with 10% fetal bovine serum, 100 units/ml penicillin and 100 ug/ml streptomycin (Gibco BRL Life Technologies). Cells are treated with or without inhibitors for 3 hrs then stimulated with 10 ng/ml rhIL1β (R & D Systems) for an additional 5 minutes at 37° C. with 5% $CO_2$. The media are removed by aspiration then the cells are washed with 1 ml of ice cold phosphate buffered saline without calcium and magnesium. The cells will then be lysed with 2× NUPAGE LDS Sample Buffer and stored at −20° C. until they are assayed. Phosphorylated TAK is assayed by Western Blot analysis with anti-phospho-TAK antibody (Cell Signaling) using NUPAGE Tris-Bis gels (Invitrogen). Gels are imaged using the BioRad ChemiDoc Imager.

IL-1β stimulated IRAK1 Degradation in A549 cells: To induce the degradation of IRAK1, A549 cells are plated at a final concentration of $1.5 \times 10^6$ cells/well in a 24 well plate in F12-K medium supplemented with 10% fetal bovine serum, 100 units/ml penicillin and 100 ug/ml streptomycin (Gibco BRL Life Technologies). Cells are treated with or without inhibitors for 3 hrs then stimulated with 10 ng/ml rhIL1β (R & D Systems) for an additional 30 minutes at 37° C. with 5% $CO_2$. The media are removed by aspiration then the cells are washed with 1 ml of ice cold phosphate buffered saline without calcium or magnesium. The cells will then be lysed with 2× NUPAGE LDS Sample Buffer and stored at −20° C. until they are assayed. IRAK1 is assayed by Western Blot analysis with anti-IRAK1 antibody (Cell Signaling) using NUPAGE Tris-Bis gels (Invitrogen). Gels are imaged using the BioRad ChemiDoc Imager.

IL-1β stimulated p65 phosphorylation in A549 cells: To induce the phosphorylation of p65 (NFκB), A549 cells are plated at a final concentration of $3 \times 10^5$ cells/well in a 96 well flat bottom plate in F12-K medium supplemented with 10% fetal bovine serum, 100 units/ml penicillin and 100 ug/ml streptomycin (Gibco BRL Life Technologies). Cells are treated with or without inhibitors for 3 hrs then stimulated with 10 ng/ml rhIL1β (R & D Systems) for an additional 10 minutes at 37° C. with 5% $CO_2$. The media are removed by aspiration then the cells are washed with 1 ml of ice cold phosphate buffered saline without calcium or magnesium. The cells will then be lysed according to the MESO Scale Discovery Phospho-p65 kit and stored at −20° C. until they are assayed. Phosphorylated p65 is assayed using the MESO Scale Discovery Phospho-p65 (NFκB) kit.

IL-1β stimulated IL6 Production in Human Whole Blood: Whole blood contains cytokine producing cells such as macrophages and monocytes. Cytokines produced in human whole blood in response to IL1b include IL6, IL8 and TNFα. To induce the production of inflammatory mediators, 200 μl of fresh human whole blood are plated per well of a 96 well round bottom plate. The blood is treated with or without inhibitors (final DMSO concentration in all cases 0.1%) for 3 hrs then stimulated with 10 ng/ml rhIL1β (R & D Systems) for an additional 18 hrs at 37° C. with 5% $CO_2$. Plasma samples are generated by pelleting the red blood cells at 1200×g and removing the plasma. Plasma samples are stored at −20° C. until they are to be assayed. The levels of inflammatory mediators are determined using commercial MSD cytokine kits (Meso Scale Discovery) as described above.

Reduction of Chemo-Resistance: The potential ability of candidate compounds to decrease pancreatic cancer resistance to cytotoxicity induced by standard chemotherapeutics is evaluated with an in vitro cell-based assay. Cell proliferation $IC_{50}$ values for each candidate compound are determined in the gemcitabine resistant human pancreatic cell line PANC-1. Two dose response curves will then be generated, one for gemcitabine alone, and the other for gemcitabine in the constant presence of the candidate compound at its $IC_{50}$. For a candidate to be considered successful at decreasing gemcitabine resistance, the decrease in cell survival must be more than simply an additive effect of the two compounds. Successful candidates are further evaluated against other chemotherapeutics such as cisplatin, and also to determine if the increase in sensitivity is due to general toxicity or increased induction of apoptosis.

Nude Mouse Xenograft Model: Evidence of in vivo efficacy of TAK1 inhibitors is evaluated using a mouse xenograft model of human pancreatic tumor growth. Female athymic nude mice (6- to 8-weeks old) are maintained in specific pathogen-free conditions. To produce pancreatic tumors, pancreatic cancer cells are harvested from sub-confluent cultures by brief exposure to 0.05% trypsin and 0.02% EDTA. Trypsin activity is stopped with medium containing 10% fetal bovine serum, and the cells washed once in serum-free medium and resuspended in serum-free Hanks balanced salt solution. To administer cells, mice are anesthetized and the tumor cell suspension injected in the left abdominal flank. Compound is orally administered at various dose levels (6 mice/dose group) daily over a 4 week period. Mice are weighed weekly and tumor growth observed. When the tumor reaches a volume greater than 2000 $mm^3$ mice are euthanized and tumor volume quantitated via imaging analysis.

Assessment of Anti-Cancer Activity of Test Compounds by MTT Based Cell Proliferation Assay: Anti-tumor growth potential of test compounds are evaluated in vitro using various human tumor cells, available from the American Type Culture Collection ATCC), such as A549 lung tumor cells, DU145 prostate tumor cells, HT29 colon cancer cells, MIA PaCa-2 pancreatic cancer cells, MCF-7 ($ER^+$) breast tumor cells and BEAS-2B cells (immortalized normal lung epithelial cells) as control [Hida, et al., Clin. Cancer Res. 6, 2006-2011 (2000)]. Test compound effect on cell proliferation is determined using the MTT based cell proliferation assay. MTT based cell proliferation assays are described in U.S. Pat. No. 8,143,237.

MTT [3-(4,5-dimethylthiazol-2-yl)-2,5-diphenyltetrazolium bromide] incorporation based cell proliferation assay is performed using the MTT cell proliferation assay kit (Roche Applied Sciences, Germany). The assay is carried out according to the instruction provided by the vendor. Briefly, equal numbers of cells are plated in 96-well flat-bottomed plates and are incubated with test compounds at various concentrations for a period of three days. Vehicle control culture wells receive an equal volume of vehicle solution. Thereafter, 0.5 mg/ml of MTT reagent is added to each well and the microplate is incubated further for 4 hours at 37° C. in presence of 5% $CO_2$. Cells are then solubilized by adding solubilizing solution and allowed to incubate at 37° C. overnight. After complete solubilization of the formazan crystals, the absorbance is read at 540 nm in a microplate reader (BioRad, USA). The results (mean optical density (OD)±standard deviation (SD)) obtained from quadruplicate wells are used to calculate the inhibition of cell proliferation (50% of inhibitory concentration, $IC_{50}$) of the test compounds.

Suppression of Lung Cancer Cell Migration: Efficacy testing is done to evaluate test compound suppression of lung cancer cell migration, a model of metastasis. Methods to evaluate lung cancer cell migration are described in Park, et al. Mol. Med. Reports 3, 1007-1013 (2010).

Cell Culture: Human lung cancer cells A549 are obtained from American Type Culture Collection (ATCC, Manassas, Va.). Cells are incubated in RPMI-1640 medium supplemented with 10% fetal bovine serum (FBS) and penicillin/streptomycin (GibcoBRL, Grand Island, N.Y., USA).

Monolayer Wound Healing Assay: Cell proliferation in confluent A549 monolayers is blocked by a 30 minute pre-incubation in the presence of mitomycin C (3 μg/ml). Test compounds, in cell culture buffer, are added to confluent monolayers 30 minutes before wound induction. A549 monolayers are subsequently scratched with a pipette tip. Wound areas are evaluated with phase contrast microscopy on an inverted microscope. Images of the same areas are obtained at intervals from zero to 96 hours. Cell migration rate via wound healing is evaluated from the images using Paint.Net v.3.10 software. Cell migration is expressed as the fold change in the migration area, relative to untreated control cells at the same time period.

Compound Formulations for Intravenous (IV), Oral Gavage (PO) or Intraperitoneal (IP) Administration: Compounds are formulated for administration using 25% hydroxypropyl-beta-cyclodextrin-PBS buffer (HBCD-PBS) at 1 mg/ml. HBCD-PBS is the preferred formulation media for compound administration. Additional formulation vehicles may also be used, including 2% Tween 80 in saline, and 20% polyethylene glycol (PEG-300) in 0.9% sodium chloride in water.

Determination of Maximum Tolerated Dose (MTD) of Test Compounds in Rats: In order to estimate the doses of test compounds for use in efficacy testing in animal models of cancer, it is determined at what doses adverse events occur. Methods to determine MTD in rats are described in Rao, et al., Mol. Cancer Ther. 5, 1530-1538 (2006).

In order to determine doses for efficacy studies, the maximum tolerated dose (MTD) is determined. Male F344 rats are fed various concentrations of test compounds for six weeks. MTD is determined based on the highest dose that causes a 10% loss in body weight without mortality or signs of toxicity. Body weights are recorded twice weekly. Animals are examined daily for signs of toxicity. At termination, animals are euthanized and organs dissected and examined.

Anti-inflammatory Efficacy—Rat Carrageenan Foot Pad Edema: The compounds of the present invention are evaluated for efficacy in vivo in a model of inflammation. Methods to determine efficacy in rat carrageenan foot pad edema are described in U.S. Pat. No. 5,760,068.

Male Sprague Dawley rats are selected for equal average body weight per group. After fasting, with free access to water sixteen hours prior to test, animals are dosed orally (1 mL) with test compounds in a vehicle containing 0.5% methylcellulose and 0.025% surfactant. The control group is dosed with vehicle alone.

One hour after dosing, a subplantar injection of 0.1 mL of 1% solution of carrageenan/sterile 0.9% saline is administered in one foot, to all animals. The volume of the injected foot is measured using a displacement plethysmometer. Foot volume is measured again three hours after carrageenan injection. The three hour foot volume measurement is compared between treated and control groups; the percent inhibition of edema is calculated.

Anti-inflammatory Efficacy—Rat Carrageenan-Induced Analgesia Test: The compounds of the present invention are evaluated for efficacy in vivo in a model of inflammatory analgesia. Methods to determine efficacy in rat carrageenan-induced analgesia test are described in U.S. Pat. No. 5,760,068.

Male Sprague Dawley rats are selected for equal average body weight per group. After fasting, with free access to water sixteen hours prior to test, animals are dosed orally (1 mL) with test compounds in vehicle containing 0.5% methylcellulose and 0.025% surfactant. Control groups are dosed with vehicle alone.

One hour after dosing, a subplantar injection of 0.1 mL of 1% solution of carrageenan/sterile 0.9% saline is administered in one foot, to all animals. Three hours after carrageenan injection, rats are placed in a plexiglass container with a high intensity lamp under the floor. After twenty minutes, thermal stimulation is begun on either the injected or the uninjected foot. Foot withdrawal is determined by a photoelectric cell. The time until foot withdrawal is measured and compared between treated and control groups. The percent inhibition of the hyperalgesic foot withdrawal is calculated.

Efficacy in Collagen-Induced Arthritis: The compounds of the present invention are evaluated in a mouse autoimmune model of rheumatoid arthritis. Methods to determine efficacy in collagen-induced arthritis in the mouse are described by Grimstein, et al. (2011) J. Tranlational Med. 9, 1-13.

Six week-old male DBA/1J mice are obtained from The Jackson Laboratory. At eight weeks of age, mice are orally administered test compounds daily. Mice are immunized by intradermal injection, at twelve weeks of age, with 0.1 ml of emulsion containing 100 µg of bovine type II collagen (bCII). At 21 days following immunization, mice are boosted with 0.1 ml of bCII (100 µg) emulsified in equal volume of incomplete Freund's Adjuvant (IFA) (Difco, Detroit, Mich.). All mice are monitored three times for the incidence of arthritis and evaluation of a clinical score, ranging from 0-4 was used (0: no swelling or redness; 1: detectable arthritis with erythema; 2: significant swelling and redness; 3: severe swelling and redness from joint to digit; 4: joint stiffness or deformity with ankylosis). The score is calculated from the average cumulative value of all four paws. Severe arthritis is defined as a score>3.

For terminal evaluation of arthritis, mice are euthanized 28 days after initial immunization. The two hind limbs are removed, fixed in formalin, decalcified in RDO solution (Apex Engineering, Aurora, Ill.) for 10-20 min depending on tissue size and examined for pliability. Sections are cut (4 µm thick) and stained with hematoxylin and eosin. Histological evaluation is performed by examining for infiltration of immune cells, hyperplasia, pannus formation and bone deformation for each paw, using a scale ranging from 0-3, according to severity of pathological changes (0: normal, 1: mild, 2: moderate, 3: severe).

Tumor Growth Inhibition in Xenograft Mouse Model of Non-Small Cell Lung Cancer (NSCLC): Efficacy testing is done in animal models of cancer tumors. Methods to determine tumor growth inhibition in xenograft mouse models of NSCLC are described in Williams, et al., Clin. Cancer Res. 7, 724-733 (2001)

Female HRLN nu/nu mice are injected subcutaneously with $1\times10^7$ MV-522 cells in 0.1 ml of phosphate-buffered saline. Treatment is initiated when tumors measure 5×5 mm. Mice are weighed and tumors measured by calipers twice weekly. Animals are euthanized and tumors harvested and measured after 67 days or when animal dies. Drug efficacy is measured based on animal survival and tumor growth.

Tumor Growth Inhibition in Xenograft Mouse Model of Colon Cancer: Efficacy testing is done in animal models of cancer tumors. Methods to determine tumor growth inhibition in xenograft mouse models of colon cancer are described in Carle, et al., J. Drug Delivery 2011, 1-9 (Article ID 869027).

Female HRLN nu/nu mice are injected subcutaneously with $5\times10^7$ HT-29 cells in 0.1 ml of phosphate-buffered saline. Treatment is initiated when tumors measure 5×5 mm. Mice are weighed and tumors measured by calipers twice weekly. Animals are euthanized and tumors harvested and measured after 67 days or when animal dies. Drug efficacy is measured based on animal survival and tumor growth.

Growth Inhibition of Gallbladder Adenocarcinoma in Transgenic Mice: Efficacy testing is done in animal models of cancer tumors. Gallbladder adenocarcinoma in transgenic mice is described in Kiguchi, et al., Mol. Cancer Ther. 6, 1709-1717 (2007).

Homozygous BK5.ErbB-2 transgenic mice, that overexpress rat ErbB-2, and nontransgenic littermates receive a control AIN76A diet or an experimental diet containing the test compound for one month. The transgenic mice develop adenocarcinoma of the gallbladder with a 90% incidence. Ultrasound image analysis and histologic evaluation are used to determine compound effects on gall bladder tumor reversion to a milder phenotype and inhibition of tumor progression.

Inhibition of Colon Cancer in Azomethane-Treated Rats: Efficacy testing is done in animal models of cancer tumors. Colon cancer in azomethane-treated rats is described in Rao, et al., Mol. Cancer Ther. 5, 1530-1538 (2006).

Male F344 rats (Charles River Breeding Laboratories) are given test compounds blended into the diet. Efficacy of test compounds are determined following initiation of azoxymethane-induced colon cancer. Rats are randomly distributed by weight into various groups and housed in cages. Azomethane treated animals are injected subcutaneous (s.c.), twice weekly, at 15 mg/kg body weight. Vehicle-treated groups are injected with normal saline. Rats are placed on control diet or diets containing test compounds, two weeks after the second injection of azomethane or saline. Body weights are measured every two weeks until termination, 52 weeks after the last azoxymethane treatment. Organs are dissected and examined using a dissecting microscope.

Colon tumors with a diameter of >0.4 cm are fixed in 10% neutral buffered formalin for histopathologic evaluation. Test compounds are evaluated for effect on colonocyte proliferation. Proliferating cell nuclear antigen (PCNA) expression is determined by immunohistochemistry. Paraffin-embedded colons are sectioned and mounted on slides. PCNA antibody (PharMingen, San Diego, Calif.), at a 1:200 dilution, is added for 1 hour. Sections are washed, then incubated with secondary anti-rabbit IgG (30 minutes). Following washing, avidin biotin-complex reagent (Vector Laboratories, Burlingame, Calif.) is added. Sections are washed and 3,3"-diaminobenzidine is added and sections are counterstained with hematoxylin. Proliferation index is calculated based on the number of positive cells (brown nucleus) per crypt.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A compound, or a pharmaceutically acceptable salt, or solvate of a compound or salt, of Formula (I):

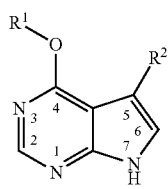

(I)

wherein:
$R^1$ is selected from the group consisting of alkyl, cycloalkyl, aryl, aralkyl, fully or partially saturated heterocyclylalkyl, heteroaryl and heteroaralkyl, wherein alkyl, cycloalkyl, aryl, aralkyl, fully or partially saturated heterocyclylalkyl, heteroaryl and heteroaralkyl are optionally substituted, on any substitutable carbon, with one or more $R^3$ radicals;

$R^2$ is selected from the group consisting of alkenyl, alkynyl,

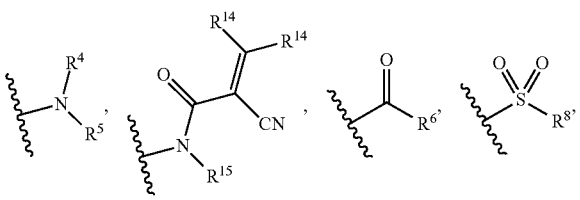

cycloalkenyl, heterocycloalkenyl and heteroaryl, wherein each alkenyl moiety is optionally substituted on any substitutable carbon with one or more $R^7$ or $R^{17}$ radicals, wherein alkynyl is optionally substituted on any substitutable carbon with one or more $R^{117}$ radicals, wherein cycloalkenyl is optionally substituted on any substitutable carbon with one or more $R^9$ radicals, wherein heterocycloalkenyl is optionally substituted on any substitutable carbon with one or more $R^{119}$ radicals, and wherein heteroaryl is optionally substituted on any substitutable carbon with one or more $R^{19}$ radicals;

$R^3$ is selected from the group consisting of alkyl, hydroxy, alkoxy, aryloxy, oxo, acyl, carboxy, hydroxyalkyl, halo, haloalkyl, cyano, amino, monoalkylamino, dialkylamino, acylamino, aminoalkyl, monoalkylaminoalkylene, dialkylaminoalkylene, cycloalkyl, alkylsulfonyl, alkylsulfonylamino, aminosulfonyl, aminocarbonyl, cyanoalkylcarbonyl, alkoxycarbonyl, alkoxycarbonyloxy, alkoxycarbonylamino, alkoxycarbonylaminoalkylene, alkylureido, alkylureidoalkylene, dialkylaminosulfonyl and monoalkylaminosulfonyl;

$R^4$ is selected from the group consisting of cyano, haloacyl, alkenylcarbonyl, hydroxyalkenylcarbonyl, aminoalkenylcarbonyl, monoalkylaminoalkenylcarbonyl, dialkylaminoalkenylcarbonyl, haloalkenylcarbonyl, cyanoalkenylcarbonyl, alkoxycarbonylalkenylcarbonyl, alkynylcarbonyl, hydroxyalkynylcarbonyl, alkylcarbonylalkenylcarbonyl, arylcarbonylalkenylcarbonyl, cycloalkylcarbonylalkenylcarbonyl, aminocarbonylalkenylcarbonyl, monoalkylaminocarbonylalkenylcarbonyl, dialkylaminocarbonylalkenylcarbonyl and alkenylsulfonyl;

$R^{14}$ is selected from the group consisting of H, alkyl, cycloalkyl and aryl;

$R^5$ is selected from the group consisting of H, alkyl and cycloalkyl;

$R^{15}$ is selected from the group consisting of H, alkyl and cycloalkyl;

$R^6$ is selected from the group consisting of alkyl, haloalkyl, alkenyl, hydroxyalkenyl, cyanoalkenyl, haloalkenyl, aminoalkenyl, monoalkylaminoalkenyl, dialkylaminoalkenyl, cyanoalkylamino, aminocarbonylalkenyl, monoalkylaminocarbonylalkenyl, dialkylaminocarbonylalkenyl, alkoxycarbonylalkenyl, alkylcarbonylalkenyl, arylcarbonylalkenyl, heteroarylcarbonylalkenyl, cycloalkylcarbonylalkenyl and cyanocycloalkylamino;

each of $R^7$, $R^{17}$ and $R^{117}$ is independently selected from the group consisting of alkyl, acyl, cyano, halo, aminocarbonyl, monoalkylaminocarbonyl, dialkylaminocarbonyl, mono(hydroxyalkyl)aminocarbonyl, aroyl and heterocyclocarbonyl;

$R^8$ is selected from the group consisting of alkenyl, hydroxyalkenyl and cycloalkenyl;

each of $R^9$ and $R^{119}$ is independently selected from the group consisting of alkyl, oxo, cyano and halo; and $R^{19}$ is selected from the group consisting of alkyl, cyano and halo.

2. Compound of claim 1, wherein:

$R^1$ is selected from the group consisting of iso-butyl, benzyl,

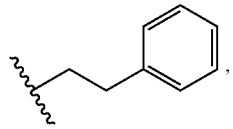 [SMILES: *CCc1ccccc1]

sec-butyl, iso-propyl, propyl, phenyl, 2,2,2-trifluoroethyl, neopentyl, 2-hydroxy-2-methylpropyl, 3-fluorobenzyl, tert-butyl, 4,4-difluorocyclohexyl, 2-cyano-2-methylpropyl, cyclopropyl, cyclopentyl, 1-hydroxypropan-2-yl, 2-(azetidin-1 yl)ethyl, 2-(oxetan-3-yl)ethyl, 4-cyanobutan-2-yl, 1-cyanopropan-2-yl, 3-cyano-2-methylpropyl, 3-cyano-2,2-dimethylpropyl, cyclobutyl, 3-hydroxy-2,2-dimethylpropyl, 3-hydroxy-3-methylbutan -2-yl, 4-hydroxybutan-2-yl, 3-hydroxy-2-methylpropyl, 2-(1-methyl-1H-pyrazol-4-yl)ethyl, and 3-fluorophenyl;

$R^2$ is selected from the group consisting of alkynyl, alkenyl,

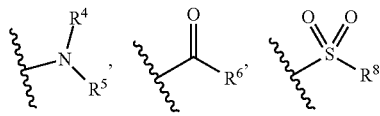

and heteroaryl, wherein each alkenyl moiety is optionally substituted on any substitutable carbon with one or more $R^7$ or $R^{17}$ radicals, wherein alkynyl is optionally substituted on any substitutable carbon with one or more $R^{117}$ radicals, and wherein heteroaryl is optionally substituted on any substitutable carbon with one or more $R^{19}$ radicals;

$R^4$ is selected from the group consisting of cyano, haloacyl, alkenylcarbonyl, hydroxyalkenylcarbonyl, aminoalkenylcarbonyl, monoalkylaminoalkenylcarbonyl, dialkylaminoalkenylcarbonyl, haloalkenylcarbonyl, cyanoalkenylcarbonyl, alkoxycarbonylalkenylcarbonyl, alkynylcarbonyl, hydroxyalkynylcarbonyl, alkylcarbonylalkenylcarbonyl, arylcarbonylalkenylcarbonyl, cycloalkylcarbonylalkenylcarbonyl, aminocarbonylalkenylcarbonyl, monoalkylaminocarbonylalkenylcarbonyl, dialkylaminocarbonylalkenylcarbonyl and alkenylsulfonyl;

$R^5$ is selected from the group consisting of H, alkyl and cycloalkyl;

$R^6$ is selected from the group consisting of alkyl, haloalkyl, alkenyl, hydroxyalkenyl, cyanoalkenyl, haloalkenyl, aminoalkenyl, monoalkylaminoalkenyl, dialkylaminoalkenyl, cyanoalkylamino, aminocarbonylalkenyl, monoalkylaminocarbonylalkenyl, dialkylaminocarbonylalkenyl, alkoxycarbonylalkenyl, alkylcarbonylalkenyl, arylcarbonylalkenyl, heteroarylcarbonylalkenyl, cycloalkylcarbonylalkenyl and cyanocycloalkylamino;

each of $R^7$, $R^{17}$ and $R^{117}$ is independently selected from the group consisting of alkyl, acyl, cyano, halo, aminocarbonyl, monoalkylaminocarbonyl, dialkylaminocarbonyl,

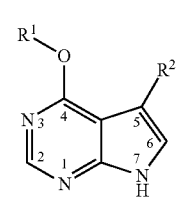

aroyl and heterocyclocarbonyl;

$R^8$ is selected from the group consisting of alkenyl, hydroxyalkenyl and cycloalkenyl; and $R^{19}$ is selected from the group consisting of alkyl, cyano and halo.

3. A compound, or a pharmaceutically acceptable salt, or solvate of a compound or salt, of Formula (I):

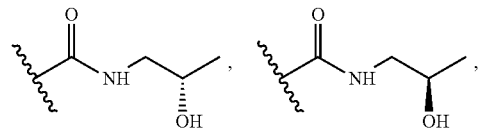

(I)

wherein:

$R^1$ is selected from the group consisting of isobutyl, benzyl, 3-fluorobenzyl, sec-butyl, isopropyl, propyl, phenyl, 2,2,2-trifluoroethyl, neopentyl, 2-hydroxy-2-methylpropyl, tert-butyl, 4,4-difluorocyclohexyl, 2-cyano-2-methylpropyl, 1-hydroxypropan-2-yl, 4-cyanobutan-2-yl, 1-cyanopropan-2-yl, 3-hydroxy-2, 2-dimethylpropyl and 4-hydroxybutan-2-yl;

$R^2$ is selected from the group consisting of

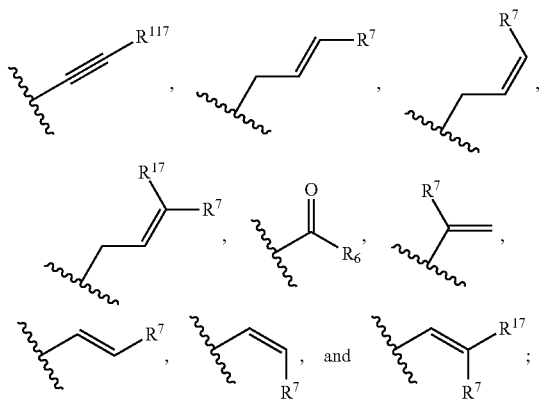

$R^6$ is methyl or chloromethyl;

each of R⁷ and R¹⁷ is independently selected from the group consisting of cyano, acetyl, aminocarbonyl, methylaminocarbonyl, ethylaminocarbonyl, methoxycarbonyl,

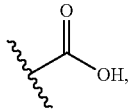

cyclopropylaminocarbonyl, cyclopropylmethylaminocarbonyl,

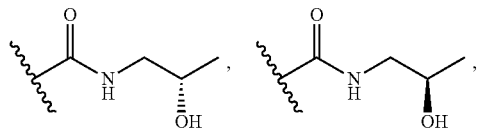

dimethylaminocarbonyl, chloro, fluoro, and methyl; and

R117 is

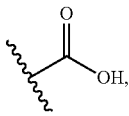

aminocarbonyl, methylaminocarbonyl, ethylaminocarbonyl or dimethylaminocarbonyl.

4. Compound of claim 3, wherein:
R¹ is selected from the group consisting of isobutyl, sec-butyl, isopropyl, propyl, phenyl, 2,2,2-trifluoroethyl, 2-cyano-2-methylpropyl, 1-hydroxypropan-2-yl, 4-cyanobutan-2-yl, 1-cyanopropan-2-yl, 3-hydroxy-2,2-dimethylpropyl, 4-hydroxybutan-2-yl, 4,4-difluorocyclohexyl and neopentyl;
R² is

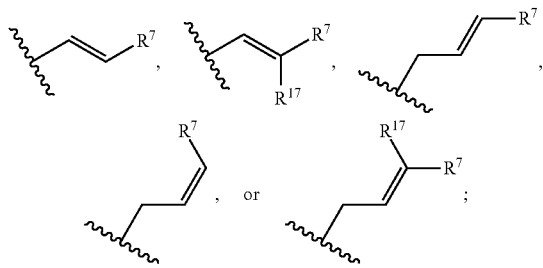

R⁷ is selected from the group consisting of cyano, aminocarbonyl, methylaminocarbonyl, ethylaminocarbonyl, cyclopropylaminocarbonyl, and dimethylaminocarbonyl; and
R¹⁷ is cyano, methylaminocarbonyl, or ethylaminocarbonyl.

5. Compound of claim 4, wherein:
R¹ is isobutyl;

R² is

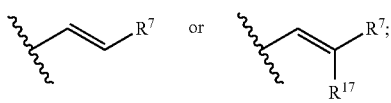

and
R⁷ is selected from the group consisting of aminocarbonyl, methylaminocarbonyl, ethylaminocarbonyl, cyclopropylaminocarbonyl, and dimethylaminocarbonyl.

6. Compound of claim 3, wherein:
R¹ is selected from the group consisting of isobutyl, 3-fluorobenzyl, phenyl, 2-hydroxy-2-methylpropyl, tert-butyl, 2-cyano-2-methylpropyl, 1-hydroxypropan-2-yl, 4-cyanobutan-2-yl, 1-cyanopropan-2-yl, 3-hydroxy-2,2-dimethylpropyl, 4,4-difluorocyclohexyl and 4-hydroxybutan-2-yl;
R² is selected from the group consisting of

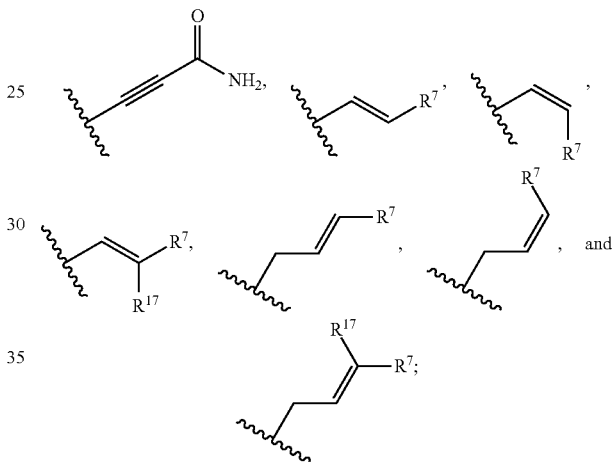

R⁷ is selected from the group consisting of cyano, acetyl, and aminocarbonyl; and
R¹⁷ is cyano, methylaminocarbonyl, or ethylaminocarbonyl.

7. Compound of claim 4, which is selected from the group consisting of:
(E)-3-(4-(sec-butoxy)-7H-pyrrolo[2,3-d]pyrimidin-5-yl)acrylamide;
(E)-3-(4-isopropoxy-7H-pyrrolo[2,3-d]pyrimidin-5-yl)acrylamide;
(E)-3-(4-propoxy-7H-pyrrolo[2,3-d]pyrimidin-5-yl)acrylamide;
(E)-3-(4-(2,2,2-trifluoroethoxy)-7H-pyrrolo[2,3-d]pyrimidin-5-yl)acrylamide;
(E)-3-(4-(neopentyloxy)-7H-pyrrolo[2,3-d]pyrimidin-5-yl)acrylamide;
3-[4-(4,4-difluoro-cyclohexyloxy)-7H-pyrrolo[2,3-d]pyrimidin-5-yl]-acrylamide;
(E)-3-(4-(2-cyano-2-methylpropoxy)-7H-pyrrolo[2,3-d]pyrimidin-5-yl) acrylamide;
(E)-3-(4-((1-hydroxypropan-2-yl)oxy)-7H-pyrrolo[2,3-d]pyrimidin-5-yl)acrylamide;
(E)-3-(4-((4-cyanobutan-2-yl)oxy)-7H-pyrrolo[2,3-d]pyrimidin-5-yl)acrylamide;
(E)-3-(4-((1-cyanopropan-2-yl)oxy)-7H-pyrrolo[2,3-d]pyrimidin-5-yl)acrylamide;
(E)-3-(4-(3-hydroxy-2,2-dimethylpropoxy)-7H-pyrrolo[2,3-d]pyrimidin-5-yl)acrylamide; and (E)-3-(4-((4-hydroxybutan-2-yl)oxy)-7H-pyrrolo[2,3-d]pyrimidin-5-yl)acrylamide.

8. Compound of claim 5, which is selected from the group consisting of:
 (E)-3-(4-isobutoxy-7H-pyrrolo[2,3-d]pyrimidin-5-yl)acrylamide;
 (E)-3-(4-isobutoxy-7H-pyrrolo[2,3-d]pyrimidin-5-yl)-N-methylacrylamide;
 (E)-N-ethyl-3-(4-isobutoxy-7H-pyrrolo[2,3-d]pyrimidin-5-yl)acrylamide;
 (E)-N-cyclopropyl-3-(4-isobutoxy-7H-pyrrolo[2,3-d]pyrimidin-5-yl)acrylamide; and
 (E)-3-(4-isobutoxy-7H-pyrrolo[2,3-d]pyrimidin-5-yl)-N,N-dimethylacrylamide.

9. Compound of claim 6, which is selected from the group consisting of:
 (Z)-3-(4-isobutoxy-7H-pyrrolo[2,3-d]pyrimidin-5-yl)acrylonitrile;
 (E)-4-(4-isobutoxy-7H-pyrrolo[2,3-d]pyrimidin-5-yl)but-3-en-2-one;
 3-(4-isobutoxy-7H-pyrrolo[2,3-d]pyrimidin-5-yl)propiolamide;
 (E)-3-(4-phenoxy-7H-pyrrolo[2,3-d]pyrimidin-5-yl)acrylamide;
 (E)-3-(4-(2-hydroxy-2-methylpropoxy)-7H-pyrrolo[2,3-d]pyrimidin-5-yl)acrylamide;
 (E)-3-(4-((3-fluorobenzyl)oxy)-7H-pyrrolo[2,3-d]pyrimidin-5-yl)acrylamide; and
 (E)-3-(4-(tert-butoxy)-7H-pyrrolo[2,3-d]pyrimidin-5-yl)acrylamide.

10. A compound, or a pharmaceutically acceptable salt, or solvate of a compound or salt, of Formula (I):

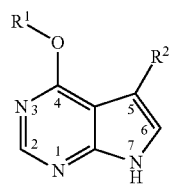

(I)

wherein:
R$^1$ is selected from the group consisting of alkyl, cycloalkyl, aryl, heterocyclylalkyl and aralkyl, wherein alkyl, cycloalkyl, aryl, heterocyclylalkyl and aralkyl are optionally substituted, on any substitutable carbon, with one or more R$^3$ radicals;
R$^2$ is selected from the group consisting of

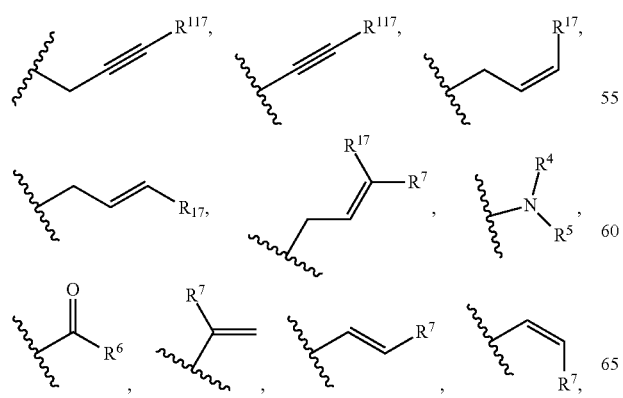

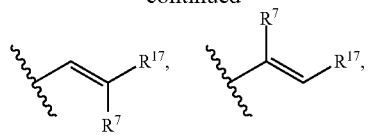

cycloalkenyl optionally substituted with one or more R$^9$ radicals, heterocycloalkenyl optionally substituted with one or more R$^{119}$ radicals, and heteroaryl optionally substituted with one or more R$^{19}$ radicals;
R$^3$ is selected from the group consisting of hydroxyl, halo, and cyano;
R$^4$ is selected from the group consisting of cyano, haloacyl, alkenylcarbonyl, hydroxyalkenylcarbonyl, aminoalkenylcarbonyl, monoalkylaminoalkenylcarbonyl, haloalkenylcarbonyl, alkynylcarbonyl, hydroxyalkynylcarbonyl and alkenylsulfonyl;
R$^5$ is H or methyl;
R$^6$ is selected from the group consisting of methyl, fluoromethyl, chloromethyl, chloroethyl, trifluoromethyl,

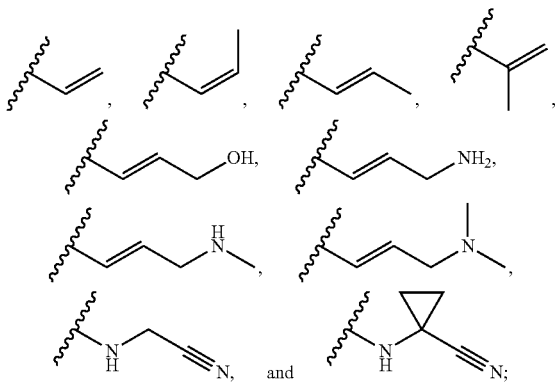

each of R$^7$ and R$^{17}$ is independently selected from the group consisting of cyano, chloro, fluoro, methyl, acetyl, ethylcarbonyl, isopropylcarbonyl, methoxycarbonyl, aminocarbonyl, methylaminocarbonyl, ethylaminocarbonyl, dimethylaminocarbonyl, benzoyl,

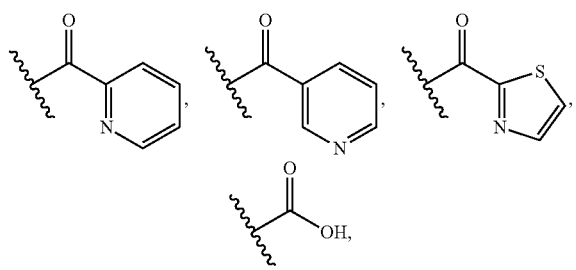

cyclopropylaminocarbonyl,

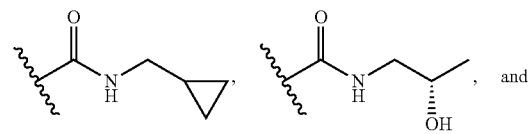

and

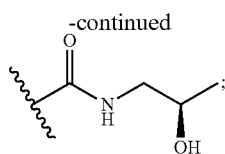

$R^{117}$ is selected from the group consisting of

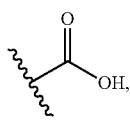

aminocarbonyl, and methylaminocarbonyl;
each of $R^9$ and $R^{119}$ is independently selected from the group consisting of alkyl, oxo, cyano, and halo; and
$R^{19}$ is selected from the group consisting of alkyl, cyano, and halo.

11. Compound of claim 10, wherein:
$R^1$ is selected from the group consisting of alkyl, cycloalkyl, aryl, and aralkyl, wherein alkyl, cycloalkyl, aryl, and aralkyl are optionally substituted, on any substitutable carbon, with one or more $R^3$ radicals;
$R^2$ is

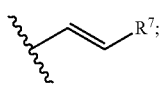

$R^3$ is selected from the group consisting of hydroxyl, fluoro, and cyano; and
$R^7$ is selected from the group consisting of aminocarbonyl, methylaminocarbonyl, ethylaminocarbonyl, cyclopropylaminocarbonyl, and dimethylaminocarbonyl.

12. Compound of claim 10, wherein:
$R^1$ is selected from the group consisting of alkyl, cycloalkyl, aryl, and aralkyl, wherein alkyl, cycloalkyl, aryl, and aralkyl are optionally substituted, on any substitutable carbon, with one or more $R^3$ radicals;
$R^2$ is selected from the group consisting of

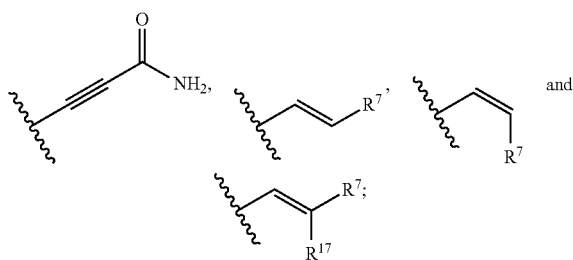

$R^3$ is selected from the group consisting of hydroxyl, fluoro, and cyano;
$R^7$ is selected from the group consisting of acetyl, cyano, aminocarbonyl, methylaminocarbonyl and ethylaminocarbonyl; and
$R^{17}$ is selected from the group consisting of cyano, methylaminocarbonyl, and ethylaminocarbonyl.

13. Compound of claim 10, wherein:
$R^1$ is selected from the group consisting of alkyl, cycloalkyl, aryl, and aralkyl, wherein alkyl, cycloalkyl, aryl, and aralkyl are optionally substituted, on any substitutable carbon, with one or more $R^3$ radicals;
$R^2$ is selected from the group consisting of

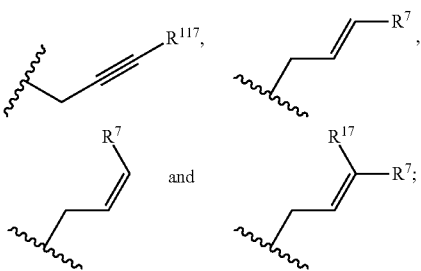

$R^3$ is selected from the group consisting of hydroxyl, fluoro, and cyano;
$R^7$ is selected from the group consisting of acetyl, cyano, aminocarbonyl, methylaminocarbonyl and ethylaminocarbonyl; and
$R^{17}$ is selected from the group consisting of cyano, methylaminocarbonyl, and ethylaminocarbonyl.

14. Compound of claim 10, wherein:
$R^1$ is selected from the group consisting of alkyl, cycloalkyl, aryl, heterocyclylalkyl and aralkyl, wherein alkyl, cycloalkyl, aryl, heterocyclylalkyl and aralkyl are optionally substituted, on any substitutable carbon, with one or more $R^3$ radicals;
$R^2$ is heteroaryl optionally substituted with one or more $R^{19}$ radicals;
$R^3$ is selected from the group consisting of hydroxyl, halo, and cyano,
$R^{19}$ is selected from the group consisting of alkyl, cyano, and halo.

15. Compound of claim 14, wherein:
$R^1$ is selected from the group consisting of alkyl, cycloalkyl, aryl, heterocyclylalkyl and aralkyl, wherein alkyl, cycloalkyl, aryl, heterocyclylalkyl and aralkyl are optionally substituted, on any substitutable carbon, with one or more $R^3$ radicals;
$R^2$ is selected from the group consisting of

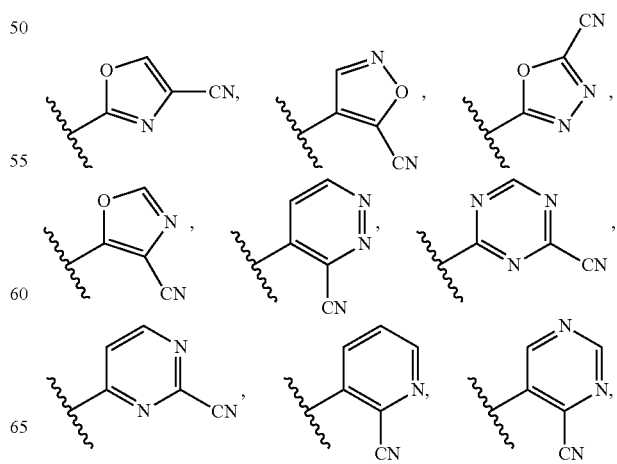

-continued

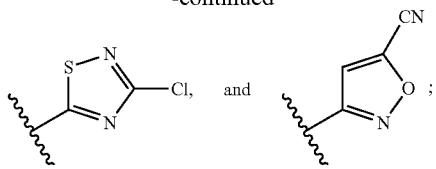

and
R³ is selected from the group consisting of hydroxyl, halo, and cyano.

16. Compound of claim 10, wherein:
R¹ is selected from the group consisting of alkyl, cycloalkyl, aryl, heterocyclylalkyl and aralkyl, wherein alkyl, cycloalkyl, aryl, heterocyclylalkyl and aralkyl are optionally substituted, on any substitutable carbon, with one or more R³ radicals;
R² is

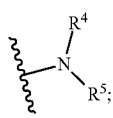

R³ is selected from the group consisting of hydroxyl, halo, and cyano;
R⁴ is selected from the group consisting of cyano, haloacyl, alkenylcarbonyl, hydroxyalkenylcarbonyl, aminoalkenylcarbonyl, monoalkylaminoalkenylcarbonyl, haloalkenylcarbonyl, alkynylcarbonyl, hydroxyalkynylcarbonyl and alkenylsulfonyl; and
R⁵ is H or methyl.

17. Compound of claim 10, wherein:
R¹ is selected from the group consisting of alkyl, cycloalkyl, aryl, heterocyclylalkyl and aralkyl, wherein alkyl, cycloalkyl, aryl, heterocyclylalkyl or aralkyl is optionally substituted, on any substitutable carbon, with one or more R³ radicals;
R² is

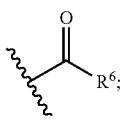

R³ is selected from the group consisting of hydroxyl, halo, and cyano; and
R⁶ is selected from the group consisting of methyl, fluoromethyl, chloromethyl, chloroethyl, trifluoromethyl,

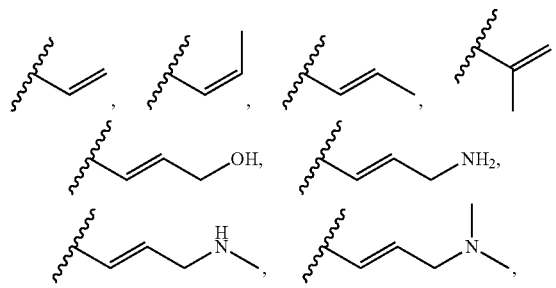

-continued

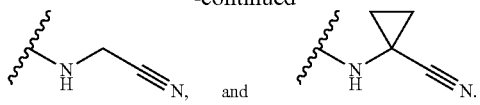

18. Compound of claim 10, wherein:
R¹ is selected from the group consisting of alkyl, cycloalkyl, aryl, heterocyclylalkyl and aralkyl, wherein alkyl, cycloalkyl, aryl, heterocyclylalkyl and aralkyl are optionally substituted, on any substitutable carbon, with one or more R³ radicals;
R² is

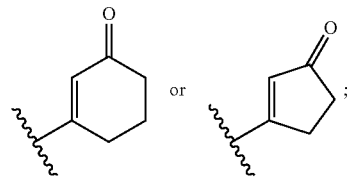 [SMILES: *C1=CC(=O)CCC1 ; *C1=CC(=O)CC1]

and
R³ is selected from the group consisting of hydroxyl, halo, and cyano.

19. Compound of claim 10, wherein:
R¹ is selected from the group consisting of alkyl, cycloalkyl, aryl, heterocyclylalkyl and aralkyl, wherein alkyl, cycloalkyl, aryl, heterocyclylalkyl and aralkyl are optionally substituted, on any substitutable carbon, with one or more R³ radicals;
R² is

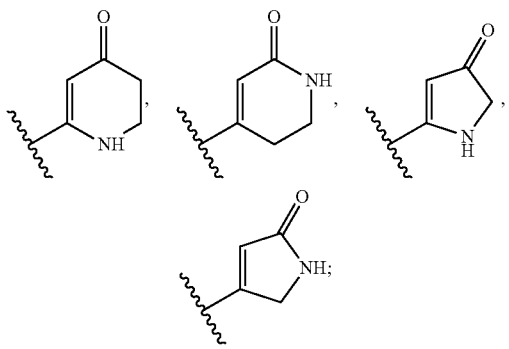

and
R³ is selected from the group consisting of hydroxyl, halo, and cyano.

20. Compound of claim 11, which is selected from the group consisting of:
(E)-3-(4-isopropoxy-7H-pyrrolo[2,3-d]pyrimidin-5-yl)-N-methylacrylamide;
(E)-N-ethyl-3-(4-isopropoxy-7H-pyrrolo[2,3-d]pyrimidin-5-yl)acrylamide;
(E)-3-(4-isopropoxy-7H-pyrrolo[2,3-d]pyrimidin-5-yl)-N,N-dimethylacrylamide;
(E)-N-cyclopropyl-3-(4-isopropoxy-7H-pyrrolo[2,3-d]pyrimidin-5-yl)acrylamide;
(E)-N-methyl-3-(4-(neopentyloxy)-7H-pyrrolo[2,3-d]pyrimidin-5-yl)acrylamide;
(E)-N-ethyl-3-(4-(neopentyloxy)-7H-pyrrolo[2,3-d]pyrimidin-5-yl)acrylamide;

(E)-N,N-dimethyl-3-(4-(neopentyloxy)-7H-pyrrolo[2,3-d]pyrimidin-5-yl)acrylamide;
(E)-N-cyclopropyl-3-(4-(neopentyloxy)-7H-pyrrolo[2,3-d]pyrimidin-5-yl)acrylamide;
(E)-3-(4-(2-hydroxy-2-methylpropoxy)-7H-pyrrolo[2,3-d]pyrimidin-5-yl)-N-methylacrylamide;
(E)-N-ethyl-3-(4-(2-hydroxy-2-methylpropoxy)-7H-pyrrolo[2,3-d]pyrimidin-5-yl)acrylamide;
(E)-3-(4-(2-hydroxy-2-methylpropoxy)-7H-pyrrolo[2,3-d]pyrimidin-5-yl)-N,N-dimethylacrylamide; and
(E)-N-cyclopropyl-3-(4-(2-hydroxy-2-methylpropoxy)-7H-pyrrolo[2,3-d]pyrimidin-5-yl)acrylamide.

21. Compound of claim 13, which is selected from the group consisting of:
(E)-4-(4-isopropoxy-7H-pyrrolo[2,3-d]pyrimidin-5-yl)but-2-enamide;
(E)-4-(4-isopropoxy-7H-pyrrolo[2,3-d]pyrimidin-5-yl)-N-methylbut-2-enamide;
(E)-5-(4-isopropoxy-7H-pyrrolo[2,3-d]pyrimidin-5-yl)pent-3-en-2-one;
(E)-4-(4-isopropoxy-7H-pyrrolo[2,3-d]pyrimidin-5-yl)but-2-enenitrile;
(Z)-4-(4-isopropoxy-7H-pyrrolo[2,3-d]pyrimidin-5-yl)but-2-enenitrile;
2-(2-(4-isopropoxy-7H-pyrrolo[2,3-d]pyrimidin-5-yl)ethylidene)malononitrile;
(E)-2-cyano-4-(4-isopropoxy-7H-pyrrolo[2,3-d]pyrimidin-5-yl)but-2-enamide; and
4-(4-isopropoxy-7H-pyrrolo[2,3-d]pyrimidin-5-yl)but-2-ynamide.

22. Compound of claim 16, wherein the compound is 2-chloro-1-(4-isopropoxy-7H-pyrrolo[2,3-d]pyrimidin-5-yl)ethanone.

23. A pharmaceutical composition comprising a therapeutically effective amount of a compound of claim 1 or a pharmaceutically acceptable salt thereof, and a pharmaceutically acceptable carrier.

24. The pharmaceutical composition of claim 23, further comprising a therapeutically effective amount of an active pharmaceutical ingredient selected from the group consisting of an anti-cancer drug, anti-proliferative agent and an anti-inflammatory drug.

* * * * *